US009498526B2

(12) United States Patent
Jiang et al.

(10) Patent No.: US 9,498,526 B2
(45) Date of Patent: *Nov. 22, 2016

(54) HUMAN ROTAVIRUS VACCINE STRAINS AND DIAGNOSTICS

(71) Applicant: The United States of America as represented by the Secretary of the Department of Health and Human Services, Bethesda, MD (US)

(72) Inventors: Baoming Jiang, Duluth, GA (US); Roger I. Glass, Atlanta, GA (US); Yuhuan Wang, Lilburn, GA (US); Jon Gentsch, Atlanta, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,663

(22) Filed: Aug. 18, 2014

(65) Prior Publication Data

US 2015/0079122 A1 Mar. 19, 2015

Related U.S. Application Data

(63) Continuation of application No. 13/320,095, filed as application No. PCT/US2010/034537 on May 12, 2012, now Pat. No. 8,822,192.

(60) Provisional application No. 61/177,393, filed on May 12, 2009.

(51) Int. Cl.

| | |
|---|---|
| ***A61K 39/12*** | (2006.01) |
| ***A61K 39/15*** | (2006.01) |
| ***C07K 16/10*** | (2006.01) |
| ***C07K 14/005*** | (2006.01) |
| ***C12N 7/00*** | (2006.01) |
| *A61K 39/00* | (2006.01) |

(52) U.S. Cl.

CPC ............... *A61K 39/15* (2013.01); *A61K 39/12* (2013.01); *C07K 14/005* (2013.01); *C07K 16/10* (2013.01); *C12N 7/00* (2013.01); *A61K 2039/5252* (2013.01); *A61K 2039/5254* (2013.01); *A61K 2039/54* (2013.01); *A61K 2039/545* (2013.01); *A61K 2039/55505* (2013.01); *C12N 2720/12334* (2013.01); *C12N 2720/12361* (2013.01)

(58) Field of Classification Search

None

See application file for complete search history.

(56) References Cited

U.S. PATENT DOCUMENTS

| | | | |
|---|---|---|---|
| 5,474,773 A | 12/1995 | Ward | |
| 5,626,851 A | 5/1997 | Clark et al. | |
| 5,695,767 A | 12/1997 | Ward | |
| 5,750,109 A | 5/1998 | Clark et al. | |
| 5,773,009 A | 6/1998 | Glass et al. | |
| 6,113,910 A | 9/2000 | Clark et al. | |
| 6,290,968 B1 | 9/2001 | Clark et al. | |
| 6,506,385 B1 | 1/2003 | Poston et al. | |
| 6,616,931 B1 | 9/2003 | Burke et al. | |
| 6,673,355 B1 | 1/2004 | Estes et al. | |
| 6,780,630 B1 | 8/2004 | Estes et al. | |
| 7,150,984 B2 | 12/2006 | Hoshino et al. | |
| 8,822,192 B2 * | 9/2014 | Jiang ...................... | A61K 39/15 424/215.1 |
| 2002/0058043 A1 | 5/2002 | Hoshino et al. | |
| 2003/0166139 A1 | 9/2003 | Choi et al. | |
| 2004/0009187 A1 | 1/2004 | Choi et al. | |
| 2005/0048083 A1 | 3/2005 | Colau et al. | |
| 2007/0276130 A1 | 11/2007 | Dormitzer et al. | |

FOREIGN PATENT DOCUMENTS

| | | |
|---|---|---|
| CA | 2379196 | 2/2001 |
| WO | WO-96/01651 | 1/1996 |
| WO | WO-0006196 | 2/2000 |
| WO | WO-2004/009115 | 1/2004 |
| WO | WO-2006/087205 | 8/2006 |
| WO | WO-2007008905 | 1/2007 |
| WO | WO-2009032913 | 3/2009 |

OTHER PUBLICATIONS

Lytle and Sagripanti, J. Virology, 2005, 79(22):14244-14252.*

Moe et al., Archives of Virology, 1982, 72:179-186.*

Bernstein, D. et al., Second-Year Follow-up Evaluation of Live, Attenuated Human Rotavirus Vaccine 89-12 in Healthy Infants, *The Journal of infectious Diseases*, 186: 1487-9, Nov. 15, 2002.

Crawford, S. et al., Characterization of Virus-Like Particles Produced by the Expression of Rotavirus Capsid Proteins in Insect Cells, *Journal of Virology*, 68(9): 5945-52, Sep. 1994.

Esona, M. et al., Molecular characterization of human rotavirus vaccine strain CDC-9 during sequential passages in Vero cells, *Human Vaccines*, 6(3): 247-53, 2009.

(Continued)

*Primary Examiner* — Stacy B Chen

(74) *Attorney, Agent, or Firm* — Dinsmore & Shohl LLP

(57) ABSTRACT

A vaccine composition and method of vaccination are provided useful for immunizing a subject against a rotavirus. The vaccines include rotavirus strains CDC-9 and CDC-66, fragments thereof, homologues thereof, or combinations thereof. Inventive vaccines may include a fragment of CDC-9, CDC-66, homologues thereof, or combinations thereof. Methods of inducing an immunological response are provided by administering an inventive vaccine.

9 Claims, 7 Drawing Sheets

(56) References Cited

OTHER PUBLICATIONS

Gentsch, J. et al., Serotype Diversity and Reassortment between Human and Animal Rotavirus Strains: Implications for Rotavirus Vaccine Programs, *Journal of Infectious Diseases*, Suppl. 1, 192: S146-159, 2005.
Gentsch, J. et al., G and P Types of Circulating Rotavirus Strains in the United States during 1996-2005: Nine Years of Prevaccine Data, *Journal of Infectious Diseases*, 200: S99-105,2009.
Gerna, G. et al., Rapid Serotyping of Human Rotavirus Strains by Solid-Phase Immune Electronic Microscopy, *Journal of Clinical Microbiology*, 19(2): 273-78, Feb. 1984.
Glass, R., New Hope for Defeating Rotavirus, *Scientific American*, 294: 46-55, 2006.
Glass, R. et al., Rotavirus vaccines: past, present, and future, *Archives de pediatrie*, 12: 844-47, 2005.
Glass, R. et al., Rotavirus vaccines: current prospects and future challenges, *The Lancet*, 368: 323-32, 2006.
Jiang, B., Information for Keystone Meeting, Keystone Symposia: Malnutrition, Gut-microbial Interactions for Mucosal Immunity to Vaccines, New Delhi, India, Nov. 2011.
Jiang, B. et al., Immunogenicity of a thermally inactivated rotavirus vaccine in mice, Human Vaccines, 4(2): 143-47, Mar./Apr. 2008.
Jiang, B. et al., Inactivated rotavirus vaccines: A priority for accelerated vaccine development, Vaccine, 26: 6754-58, 2008.
Jiang, B., Should we consider non live-oral rotavirus vaccines?, Presented at the 9th International Rotavirus Symposium, Johannesburg, South Africa, Aug. 2010 (abstract).
Jiang, B. et al., Inactivated Rotavirus Vaccine: An Update and Pathway Forward, The 6th International Conference on Vaccines for Enteric Diseases, Cannes, France, Sep. 2011 (abstract).
Jiang, B., Vaccination against rotavirus using microneedles, Skin Vaccination Summit, Washington, D.C., Oct. 2011 (abstract).
Jiang, B. et al., The Role of Serum Antibodies in the Protection against Rotavirus Disease: An Overview, *Clinical Infectious Diseases*, 34(10): 1351-61, May 15, 2002.
Jiang, B. et al., Synthesis of Rotavirus-Like Particles in Insect Cells: Comparative and Quantitative Analysis, *Biotechnology and Bioengineering*, 60(3): 369-74, Nov. 5, 1998.
Jiang, B. et al., Heterotypic protection from rotavirus infection in mice vaccinated with viruslike particles, *Vaccine*, 17: 1005-13, 1999.
Jiang, B. et al., Rotavirus vaccines for global use, *Human Vaccines*, 6(5): 1-3, May 2010.
Jiang, B. et al., Parenteral Rotavirus Vaccines, Chinese Journal of Vaccines and Immunization, 11: 77-79, 2005.
Jiang, B. et al., Dose sparing of and enhanced immune response to inactivated rotavirus vaccine by skin vaccination using microneedles in mice, presented at Microneedles 2012, Cork, Ireland, May 2012 (Abstract).
Kapikian, Z., A rotavirus vaccine for prevention of severe diarrhoea of infants and young children: development, utilization and withdrawal, Novaritis Found Symp, 238: 153-71, 2001 (Abstract).
Leite, J. et al., Rotavirus G and P types circulating in Brazil: characterization by RT-PCR, probe hybridization, and sequence analysis, Arch Virol, 141(12): 2365-74, 1996 (Abstract).
Linhares, A. et al., Efficacy and safety of an oral live attenuated human rotavirus vaccine against rotavirus gastroenteritis during the first 2 years of life in Latin American infants: a randomised, double-blind, placebo-controlled phase III study, The Lancet, 371(9619): 1181-89, Apr. 5, 2008.
Mascarenhas, J. et al., Rotavirus G Serotypes and P□, G Genotypes Identified in Cases of Reinfection Among Children Participating in a Trial with Rhesus-human Reassortant Tetravalent Vaccine (RRV-TV) in Belem, Brazil, *Journal of Tropical Pediatrics*, 48(2): 93-97, 2002 (Abstract).
Moon, S. et al., Inhibitory Effect of Breast Milk on Infectivity of Live Oral Rotavirus Vaccines, The Pediatric Infectious Disease Journal, 29(10): 919-23, Oct. 2010.
O'Mahony, J. et al., VP4 and VP7 genotyping of rotavirus samples recovered from infected children in Ireland over a 3-year period, J Clin Microbiol, 37(6): 1699-1703, Jun. 1999 (Abstract).
Patel, M. et al., Oral Rotavirus Vaccines: How Well Will They Work Where They are Needed Most?, *Journal of Infectious Diseases*, 200 (Supp 1), S39-48, 2009.
Phua, K. et al., Evaluation of RIX4414, a live, attenuated rotavirus vaccine, in a randomized, double-blind, placebo-controlled phase 2 trial involving 2464 Singaporean infants, *J Infect Dis*, 192, Suppl 1: S1-5, Sep. 1, 2005 (Abstract).
Pichichero, E. et al., A comparative evaluation of the safety and immunogenicity of a single dose of unbuffered oral rhesus rotavirus serotype 3, rhesus/human reassortant serotypes 1,2 and 4 and combined (tetravalent) vaccines in healthy infants, *Vaccine*, 11(7): 747-53, 1993 (Abstract).
Piec, T. et al., Sequence comparison of the VP7 of serotype G2 rotaviruses from diverse geographical locations, DNA Seq, 9(5-6): 369-73, 1998.
Ruiz-Palacios, G. et al., Safety and Efficacy of an Attenuated Vaccine against Severe Rotavirus Gastroenteritis, 354(1): 11-22, Jan. 5, 2006.
Santos, N. et al., Global distribution of rotavirus serotypes/genotypes and its implication for the development and implementation of an effective rotavirus vaccine, Reviews in Medical Virology, 15(1): 29-56, 2005.
Vesikari, T. et al., Safety and Efficacy of a Pentavalent Human-Bovine (WC3) Reassortment Rotavirus Vaccine, The New England Journal of Medicine, 354: 23-33, Jan. 5, 2006.
Wang, Y. et al., Dose sparing of and enhanced immune response to inactivated rotavirus vaccine by skin vaccination using a microneedle patch in mice, The 6th International Conference on Vaccines for Enteric Diseases, Cannes, France, Sep. 2011 (Abstract).
Wang, Y. et al., Inactivated rotavirus vaccine induces protective immunity in gnotobiotic piglets, Vaccine, 28, S432-36, 2010.
Westerman, L. et al., Serum IgG mediates mucosal immunity against rotavirus infection, PNAS, 102(20): 7268-73, May 17, 2005.
Xu, J. et al., Serum Antibody Responses in Children with Rotavirus Diarrhea Can Serve as Proxy for Protection, Clinical and Diagnostic Laboratory Immunology, 12(2): 273-79, Feb. 2005.
Zeng, C. et al., Characterization and Replicase Activity of Double-Layered and Single-Layered Rotavirus-Like Particles Expressed from Baculovirus Recombinants, Journal of Virology, 70(5): 2736-42, May 1996.
(author unknown) Suspension of rotavirus vaccine after reports of intussusception—United States, 1999, Centers for Disease Control and Prevention (CDC), Erratum in MMWR Morb Mortal Wkly Rep, 53(37): 879, Sep. 24, 2004.
(author unknown) Erratum in MMWR Morb Mortal Wkly Rpt, 53(37): 786-9, Sep. 3, 2004, Suspension of rotavirus vaccine after reports of intussusception—United States, 1999 (Abstract).

* cited by examiner

HUMAN ROTAVIRUS VACCINE STRAINS AND DIAGNOSTICS

REFERENCE TO RELATED APPLICATIONS

This application is a continuation of U.S. patent application Ser. No. 13/320,095, filed Nov. 11, 2011, now U.S. Pat. No. 8,822,192 which is a U.S. national stage application of PCT/US2010/034537, filed May 12, 2010, which claims priority from U.S. Provisional Application No. 61/177,393 filed May 12, 2009, the entire content of all of which is incorporated herein by reference.

GOVERNMENT SPONSORSHIP

This invention was made by the Centers for Disease Control and Prevention, an agency of the United States Government.

FIELD OF THE INVENTION

The present invention relates generally to virus vaccine strains as well as vaccine compositions and methods relating thereto. More specifically, the present invention relates to human rotavirus A vaccine strains, vaccine compositions and methods of use to induce an immunological response against rotavirus A in a subject.

BACKGROUND OF THE INVENTION

Of the various enteric pathogenic viruses causing severe diarrhea in children, rotavirus is the most common causing an average of 611,000 deaths per year. Virtually all children are infected by rotavirus by age 5. The virus is believed to be highly contagious and has been described as a "democratic" virus since the infection affects no particular socio-economic or geographic group disproportionately. While the majority of children having access to adequate supportive and palliative medical care survive infection with no significant long-term consequences, the number of deaths associated with severe diarrhea, vomiting, dehydration and shock is unacceptable and requires preventative intervention if possible.

Rotavirus A is an icosahedral virus in the family Reoviridae with a distinct hub-and-spoke morphology. Particular rotaviruses are classified by group, subgroup and serotype according to properties characteristic of the viral capsid proteins. Rotavirus particles contain 3 protein layers surrounding the viral genome which consists of 11 segments of double-stranded RNA, each segment encoding a protein. The viral proteins include structural proteins called VPs and nonstructural proteins designated NSPs. A number of the structural proteins are particularly important in eliciting an immune response in a host since these proteins are present on the outermost surface of the viral particles. In particular the proteins VP7 and VP4 both figure prominently in host immune response and therefore have also played a central role in development of rotavirus vaccines.

Variants of VP7 and VP4 structural proteins characterize distinct rotavirus A serotypes. In particular, variants of human VP7 are identified as "G" serotypes including at least serotypes G1, G2, G3, G4, as well as the less common G5, G6, G8, G9, G10, G11, G12, G13 and G14. Variants of the VP4 structural protein are identified as "P" serotypes including P1A, P1B, P2A, P3, P4, P5, P6 and P8. Because intact rotaviruses are characterized by both a VP7 protein and a VP4 protein, individual virus serotypes are named according to the identity of the variant of these two proteins contained in the particular virus. For example, a common rotavirus A contains both G1 and P[8] variants of VP7 and VP4, respectively. The G1, P[8] serotype of rotavirus A is one of the most common forms of the virus which cause disease worldwide. The G1 serotype of rotavirus A is the most common serotype associated with human disease worldwide. A number of vaccines have been developed which use rotavirus A G1 strains with the goal of developing immunity in a host against rotavirus A G1 strains as well as rotavirus A strains having other serotypes. However, this approach has been limited by important differences between the G1 and G2 serotypes. In particular, rotavirus A G2 strains are derived from a different lineage than most other rotavirus strains. This is demonstrated by nucleic acid hybridization experiments showing that labeled transcripts of the 11 gene segments of G2 strains, also known as the DS-1 genogroup, do not hybridize with corresponding nucleic acids from the strains known as the Wa genogroup of rotavirus A which includes G1, G3, G4, and G9. The lack of hybridization of these homologous genes indicates that differences in the encoded proteins, such as the outer capsid proteins VP4 and VP7 and inner capsid protein VP6, are substantial. These genetic differences support the observations that individuals infected or immunized using a G1 strain are less likely to show cross protection against G2 strains than other strains of the Wa genogroup.

In addition, to the common G1 and G2 rotavirus A strains, a diversity of human rotavirus types is increasingly recognized as contributing to acute severe diarrhea disease worldwide. This diversity underscores the need for robust vaccines capable of generating immunity against several strains. Recently, the United States Food and Drug Administration suspended the use of the ROTARIX vaccine citing contaminants in its preparation. Thus, the number of available vaccines for rotavirus is declining at a time when infections remain a serious worldwide problem. Another vaccine, RotaTeq®, appears safe and effective in preventing diarrhea among children in middle and high income countries and are currently licensed and recommended for use in infants throughout the world. However, the efficacy of this vaccine is reduced in low income countries of Africa and Asia.

Thus, there is a continuing need for vaccines against human rotavirus A of both common and less common types.

SUMMARY OF THE INVENTION

Figure 1A:
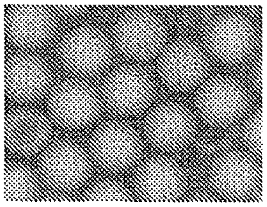
FIG. 1A is a xerographic image of an electron micrograph showing intact isolated rotavirus A virions identified as strain CDC-9, having serotype P[8], G1.

A vaccine composition is provided including one or more isolated rotavirus strains illustratively strain CDC-9 or CDC-66 in combination with a pharmaceutically acceptable carrier. An inventive vaccine optionally includes an adjuvant.

The CDC-9 or CDC-66 strains in an inventive vaccine are optionally live attenuated rotavirus or inactivated rotavirus.

It is appreciated that an inventive vaccine optionally includes at least two isolated rotavirus strains. The at least two isolated rotavirus strains each independently have a G group serotype of G1, G2, G3, G4, G5, G6, G7, G8, G9, G10, G11, G12, G13 or G14. Optionally, the at least two isolated rotavirus strains each independently have a P group serotype of P1A, P1B, P2A, P3, P4, P5, P6, P8, P11, or P12.

An inventive vaccine is optionally administered parenterally or orally.

An isolated rotavirus strain is also provided that is illustratively CDC-9 or CDC-66 strain.

An inventive vaccine is provided that includes a pharmaceutically acceptable carrier admixed with an isolated rotavirus strain characterized as having a G1 group serotype and an isolated rotavirus strain characterized as having a G2 group serotype. The G1 or G2 group serotype strains optionally each independently have a P group serotype of P1A, P1B, P2A, P3, P4, P5, P6, P8, P11 or P12. In some embodiments the human rotavirus strain characterized as having a G1 group serotype is CDC-9, or the human rotavirus strain characterized as having a G2 group serotype is CDC-66.

A method of inducing an immunological response to a rotavirus in a subject is provided including administering a vaccine composition including a pharmaceutically acceptable carrier admixed with an isolated human rotavirus strain of CDC-9 or CDC-66.

A method of inducing an immunological response to a rotavirus in a subject is provided including administering a vaccine composition including a pharmaceutically acceptable carrier admixed with an isolated human rotavirus strain characterized as having a G1 group serotype and an isolated human rotavirus strain characterized as having a G2 group serotype.

Also provided is a vaccine including a pharmaceutically acceptable carrier admixed with a portion of an isolated human rotavirus. The isolated human rotavirus portion is a peptide or polypeptide including an amino acid sequence of SEQ ID No. 2; SEQ ID No. 5; SEQ ID No. 8; SEQ ID No. 11; SEQ ID No. 14; SEQ ID No. 17; SEQ ID No. 20; SEQ ID No. 23; SEQ ID No. 26; SEQ ID No. 29; SEQ ID No. 32; SEQ ID No. 3; SEQ ID No. 6; SEQ ID No. 9; SEQ ID No. 12; SEQ ID No. 15; is SEQ ID No. 18; SEQ ID No. 21; SEQ ID No. 24; SEQ ID No. 27; SEQ ID No. 30; SEQ ID No. 33; SEQ ID No. 71; SEQ ID No. 77; SEQ ID No. 83; SEQ ID No. 89; SEQ ID No. 95; SEQ ID No. 101; SEQ ID No. 107; SEQ ID No. 113; SEQ ID No. 119; SEQ ID No. 125; SEQ ID No. 131; SEQ ID No. 72; SEQ ID No. 78; SEQ ID No. 84; SEQ ID No. 90; SEQ ID No. 96; SEQ ID No. 102; SEQ ID No. 108; SEQ ID No. 114; SEQ ID No. 120; SEQ ID No. 126; SEQ ID No. 132; a homolog thereof or a fragment thereof

DETAILED DESCRIPTION OF THE PREFERRED EMBODIMENTS

Novel isolated human rotavirus A strains, vaccines including human rotavirus A strains, vaccines including a human rotavirus A polypeptide and/or an immunogenic fragment thereof, anti-rotavirus A antibodies and methods for vaccinating humans against rotavirus A disease are provided according to embodiments of the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press; 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975); the contents of each of which are incorporated herein by reference.

Human Rotaviruses

Novel human rotavirus A strains of the present invention are illustratively identified as CDC-9 and CDC-66, fragments thereof or homologues thereof.

The CDC-9 rotavirus A strain was isolated from a fecal specimen of a 5-month boy in Providence, R.I. Human rotavirus strain CDC-9 was characterized by RT-PCR using G and P type-specific primers. RT-PCR analysis indicates that isolated strain CDC-9 is a strain having a genotype P[8], G1. Particular characteristics of CDC-9, its identification, isolation, and passages in Vero cells are described by Esona, M D, et al., *Human Vaccines,* 2010; 6:1-7, the entire contents of which are incorporated herein by reference.

Following isolation from the fecal sample, isolated rotavirus strain CDC-9 was adapted to grow in MA104 cells that were prepared and frozen before 1980 and have complete documentation. The CDC-9 strain was then adapted to grow in Vero cells qualified for vaccine production. CDC-9 was purified by performing 3 rounds of limiting dilution and after amplification in Vero cells, was further purified by performing 3 rounds of plaque assays. The isolated strain CDC-9 was passaged 7 and 38 times in MA104 and Vero cells, respectively (total 45 passages). The adaptation and all passages are done using standard operation procedures and certified raw materials and reagents and under the Good Laboratory Practice Guidelines. Unlike other reference or laboratory strains, the isolated strain CDC-9 has complete passage history and documentation.

The titer of passaged human rotavirus strain CDC-9 is about $10^7$ ffu/ml.

Isolated human rotavirus strain CDC-9 was studied by electron microscopy using CDC-9 virions isolated from the medium of infected Vero cell cultures. FIG. 1A shows an electron micrograph of isolated CDC-9 virions. The micrograph shows the virions to have the morphology typical of human rotavirus A virions.

Figure 2:
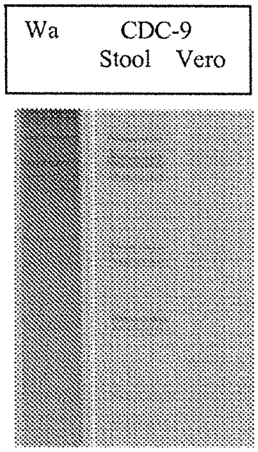
FIG. 2 shows a xerographic reproduction of an image of a polyacrylamide gel illustrating RNA profiles of rotavirus A strain CDC-9 isolated from a stool sample (S) and Vero cells (V) and showing typical long (CDC-9) RNA electropherotypes for the rotavirus strain.

Isolated human rotavirus strain CDC-9 was further examined using polyacrylamide gel electrophoresis of RNA isolated from the strain. As shown in FIG. 2, CDC-9 has a typical long RNA electropherotype and the RNA profiles of both the original isolate from the stool and the Vero passaged rotavirus are identical. Also shown in FIG. 2 is a standard for comparison including an RNA profile of a Wa genogroup human rotavirus.

Isolated human rotavirus strain CDC-9 in stool and Vero cells (passage 27) was analyzed by sequence analysis of entire genome.

CDC9 amino acid sequences of proteins encoded by nucleic acids isolated from a stool sample: CDC9 NSP1 aa—stool is SEQ ID No. 2; CDC9 NSP 2 aa—stool is SEQ ID No. 5; CDC9 NSP 3 aa—stool is SEQ ID No. 8; CDC9 NSP 4 aa—stool is SEQ ID No. 11; CDC9 NSP 5 aa—stool is SEQ ID No. 14; CDC9 VP1 aa—stool is SEQ ID No. 17; CDC9 VP 2 aa—stool is SEQ ID No. 20; CDC9 VP 3 aa—stool is SEQ ID No. 23; CDC9 VP 4 aa—stool is SEQ ID No. 26; CDC9 VP 6 aa—stool is SEQ ID No. 29; and CDC9 VP 7 aa—stool is SEQ ID No. 32.

CDC9 nucleotide sequences of nucleic acids isolated from a stool sample: CDC9 NSP1 nt—stool is SEQ ID No. 35; CDC9 NSP 2 nt—stool is SEQ ID No. 38; CDC9 NSP 3 nt—stool is SEQ ID No. 41; CDC9 NSP 4 nt—stool is SEQ ID No. 44; CDC9 NSP 5 nt—stool is SEQ ID No. 47; CDC9 VP1 nt—stool is SEQ ID No. 50; CDC9 VP 2 nt—stool is SEQ ID No. 53; CDC9 VP 3 nt—stool is SEQ ID No. 56; CDC9 VP 4 nt—stool is SEQ ID No. 59; CDC9 VP 6 nt—stool is SEQ ID No. 62; and CDC9 VP 7 nt—stool is SEQ ID No. 65.

CDC9 amino acid sequences of proteins encoded by nucleic acids isolated from CDC9 rotavirus at passage 27 isolated from Vero cells: CDC9 NSP1 aa—Vero is SEQ ID No. 3; CDC9 NSP 2 aa—Vero is SEQ ID No. 6; CDC9 NSP 3 aa—Vero is SEQ ID No. 9; CDC9 NSP 4 aa—Vero is SEQ ID No. 12; CDC9 NSP 5 aa—Vero is SEQ ID No. 15; CDC9 VP1 aa—Vero is SEQ ID No. 18; CDC9 VP 2 aa—Vero is SEQ ID No. 21; CDC9 VP 3 aa—Vero is SEQ ID No. 24; CDC9 VP 4 aa—Vero is SEQ ID No. 27; CDC9 VP 6 aa—Vero is SEQ ID No. 30; and CDC9 VP 7 aa—Vero is SEQ ID No. 33.

CDC9 nucleotide sequences of nucleic acids isolated from CDC9 rotavirus at passage 27 isolated from Vero cells: CDC9 NSP1 nt—Vero is SEQ ID No. 36; CDC9 NSP 2 nt—Vero is SEQ ID No. 39; CDC9 NSP 3 nt—Vero is SEQ ID No. 42; CDC9 NSP 4 nt—Vero is SEQ ID No. 45; CDC9 NSP 5 nt—Vero is SEQ ID No. 48; CDC9 VP1 nt—Vero is SEQ ID No. 51; CDC9 VP 2 nt—Vero is SEQ ID No. 54; CDC9 VP 3 nt—Vero is SEQ ID No. 57; CDC9 VP 4 nt—Vero is SEQ ID No. 60; CDC9 VP 6 nt—Vero is SEQ ID No. 63; and CDC9 VP 7 nt—Vero is SEQ ID No. 66.

Nucleotide and amino acid sequences of entire genome from CDC-9 rotavirus isolated from stool and infected culture were compared with amino acid and nucleotide sequences of entire genome from reference KU or other G1P8 strains of rotavirus A, as shown herein.

Additionally, as shown in Table 2, CDC-9 genes (except for segment 3) share high sequence identity with the corresponding genes of the prototype P[8],G1 human KU strain.

TABLE 2

Percentages of nucleotide (NT) and deduced amino acid (AA) identity of rotavirus vaccine strain CDC-9 gene segments compared with cognate gene sequences of prototype rotavirus strain KU.

| | CDC-9 | |
|---|---|---|
| Gene | % NT | % AA |
| VP1 | 88 | 96 |
| VP2 | 95 | 98 |
| VP3 | 77 | 80 |
| VP4 | 91 | 94 |
| VP6 | 91 | 98 |
| VP7 | 93 | 96 |
| NSP1 | 83 | 81 |
| NSP2 | 90 | 94 |
| NSP3 | 93 | 95 |
| NSP4 | 93 | 94 |
| NSP5 | 93 | 94 |

In addition, changes in nt and aa sequences of entire genome of CDC-9 strain from stool to passage 27 in Vero cells have been documented, as shown in Table 3.

TABLE 3

Changes of nt and aa in genes of CDC-9 from stool to passage 27 in Vero cells

| Gene segment | # of nt changes | nt position | # of aa changes | aa position |
|---|---|---|---|---|
| NSP1 | 1 | 396 A→G | 1 | 122 Q→R |
| NSP2 | 0 | | 0 | |
| NSP3 | 0 | | 0 | |
| NSP4 | 0 | 0 | 0 | |

TABLE 3-continued

| Changes of nt and aa in genes of CDC-9 from stool to passage 27 in Vero cells | | | | |
|---|---|---|---|---|
| Gene segment | # of nt changes | nt position | # of aa changes | aa position |
| NSP5 | 1 | 155C→T | 1 | 45 A→I |
| VP1 | 0 | | 0 | |
| VP2 | 0 | | 0 | |
| VP3 (DS-1) | 0 | | 0 | |
| VP4 | 6 | 161G→A, 1001C→T, 1101G→A, 1162G→C, 1171A→C, 2025T→C | 5 | 51G→D, 331S→F, 364M→I, 385D→H, 388I→L |
| VP6 | 1 | 325C→T | 1 | 101A→V |
| VP7 | 1 | 678G→A | 0 | |
| Total: | 10 | | 8 | |

Isolated rotavirus CDC-9 in Vero cells is a reassortant that has all (except segment 3) genes from a KU-like strain. CDC-9 has a segment 3 derived from a DS-1 like strain as CDC-9 VP3 shares a high identity with the cognate gene of DS-1 strain. This reassortment might have occurred during natural infection or when G1P8 and G2P4 rotaviruses in the fecal specimen were adapted and passaged in cell culture. Rotavirus VP3 has been described to possess guanylyltransferase and may be involved in viral replication and morphogenesis.

The CDC-66 rotavirus A strain was isolated from a fecal specimen of an 11-month girl in Providence, R.I. Human rotavirus strain CDC-66 was characterized by RT-PCR using G and P type-specific primers. RT-PCR analysis indicates that isolated strain CDC-66 is a strain having a serotype P[4], G2.

Following isolation from the fecal sample, isolated rotavirus strain CDC-66 was adapted to grow in MA104 cells that were prepared and frozen before 1980 and have complete passage history and documentation. The CDC-66 strain was then adapted to grow in Vero cells qualified for vaccine production. CDC-66 was purified by performing 3 rounds of limiting dilution and after amplification in Vero cells, was further purified by performing 3 rounds of plaque assays. The isolated strain CDC-66 was passaged 5 and 40 times in MA104 and Vero cells, respectively (total 45 passages). The adaptation and all passages are done using standard operation procedures and certified raw materials and reagents and under the Good Laboratory Practice Guidelines. Unlike other reference and laboratory strains, the isolated strain CDC-66 has complete passage history and documentation.

The titer of passaged human rotavirus strain CDC-66 is about $10^7$ pfu/ml.

Figure 1B:
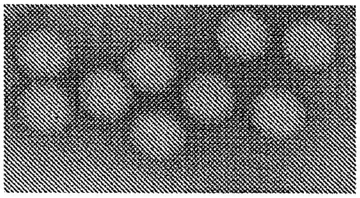
FIG. 1B is a xerographic image of an electron micrograph showing intact isolated rotavirus A virions identified as strain CDC-66, having serotype P[4], G2.

Isolated human rotavirus strain CDC-66 was studied by electron microscopy using CDC-66 virions isolated from the medium of infected Vero cell cultures. FIG. 1B shows an electron micrograph of isolated CDC-66 virions. The micrograph shows the virions to have the morphology typical of human rotavirus virions.

Figure 3:
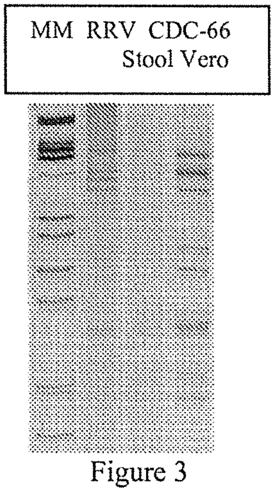
FIG. 3 shows a xerographic reproduction of an image of a polyacrylamide gel illustrating RNA profiles of the rotavirus A strain CDC-66 isolated from a stool sample and Vero cells and showing typical short RNA electropherotypes for this rotavirus strain.

Isolated human rotavirus strain CDC-66 was further examined using polyacrylamide gel electrophoresis of RNA isolated from the strain. As shown in FIG. 3, CDC-66 has a typical short RNA electropherotype and the RNA profiles of both the original isolate from the stool and the Vero passaged rotavirus are identical. Also shown in FIG. 3 are standards for comparison including a DNA molecular weight marker III (Roche) in the far left lane and an RNA profile of rhesus rotavirus, RRV.

Isolated human rotavirus strain CDC-66 in stool and Vero cells (passage 27) was analyzed by sequence analysis of entire genome.

CDC66 amino acid sequences of proteins encoded by nucleic acids isolated from a stool sample: CDC66 NSP1 aa—stool is SEQ ID No. 71; CDC66 NSP 2 aa—stool is SEQ ID No. 77; CDC66 NSP 3 aa—stool is SEQ ID No. 83; CDC66 NSP 4 aa—stool is SEQ ID No. 89; CDC66 NSP 5 aa—stool is SEQ ID No. 95; CDC66 VP1 aa—stool is SEQ ID No. 101; CDC66 VP 2 aa—stool is SEQ ID No. 107; CDC66 VP 3 aa—stool is SEQ ID No. 113; CDC66 VP 4 aa—stool is SEQ ID No. 119; CDC66 VP 6 aa—stool is SEQ ID No. 125; and CDC66 VP 7 aa—stool is SEQ ID No. 131.

CDC-66 nucleotide sequences of proteins encoded by nucleic acids isolated from a stool sample: CDC66 NSP1 nt—stool is SEQ ID No. 68; CDC66 NSP 2 nt—stool is SEQ ID No. 74; CDC66 NSP 3 nt—stool is SEQ ID No. 80; CDC66 NSP 4 nt—stool is SEQ ID No. 86; CDC66 NSP 5 nt—stool is SEQ ID No. 92; CDC66 VP1 nt—stool is SEQ ID No. 98; CDC66 VP 2 nt—stool is SEQ ID No. 104; CDC66 VP 3 nt—stool is SEQ ID No. 110; CDC66 VP 4 nt—stool is SEQ ID No. 116; CDC66 VP 6 nt—stool is SEQ ID No. 122; and CDC66 VP 7 nt—stool is SEQ ID No. 128.

CDC-66 amino acid sequences of proteins encoded by nucleic acids isolated at passage 27 isolated from Vero cells: CDC66 NSP1 aa—Vero is SEQ ID No. 72; CDC66 NSP 2 aa—Vero is SEQ ID No. 78; CDC66 NSP 3 aa—Vero is SEQ ID No. 84; CDC66 NSP 4 aa—Vero is SEQ ID No. 90; CDC66 NSP 5 aa—Vero is SEQ ID No. 96; CDC66 VP1 aa—Vero is SEQ ID No. 102; CDC66 VP 2 aa—Vero is SEQ ID No. 108; CDC66 VP 3 aa—Vero is SEQ ID No. 114; CDC66 VP 4 aa—Vero is SEQ ID No. 120; CDC66 VP 6 aa—Vero is SEQ ID No. 126; and CDC66 VP 7 aa—Vero is SEQ ID No. 132.

CDC-66 nucleotide sequences of proteins encoded by nucleic acids isolated at passage 27 isolated from Vero cells: CDC66 NSP1 nt—Vero is SEQ ID No. 69; CDC66 NSP 2 nt—Vero is SEQ ID No. 75; CDC66 NSP 3 nt—Vero is SEQ ID No. 81; CDC66 NSP 4 nt—Vero is SEQ ID No. 87; CDC66 NSP 5 nt—Vero is SEQ ID No. 93; CDC66 VP1 nt—Vero is SEQ ID No. 99; CDC66 VP 2 nt—Vero is SEQ ID No. 105; CDC66 VP 3 nt—Vero is SEQ ID No. 111; CDC66 VP 4 nt—Vero is SEQ ID No. 117; CDC66 VP 6 nt—Vero is SEQ ID No. 123; and CDC66 VP 7 nt—Vero is SEQ ID No. 129.

Entire amino acid and nucleotide sequences from CDC-66 rotavirus isolated from stool and Vero cells are compared with entire amino acid and nucleotide sequences of a strain of rotavirus A considered to be the closest related known rotavirus A, human rotavirus DS-1 strain or another closely related strain, as shown herein.

As shown in Table 4, CDC-66 genes share high sequence identity with the corresponding genes of the prototype P[4],G2 strain DS-1.

Table 4. Percentages of nucleotide (NT) and deduced amino acid (AA) identity of rotavirus vaccine strain CDC-66 genome compared with genome sequence of prototype rotavirus strain DS-1.

TABLE 4

| Gene | nt % | aa % |
|---|---|---|
| VP1 | 90.85 | 97.24 |
| VP2 | 94.11 | 98.86 |
| VP3 | 92.9 | 95.69 |
| VP4 | 94.02 | 96.52 |
| VP6 | 87.98 | 98.74 |
| VP7 | 93.88 | 96.32 |
| NSP1 | 93.12 | 93.21 |
| NSP2 | 86.89 | 93.99 |
| NSP3 | 95.31 | 97.12 |
| NSP4 | 94.76 | 95.43 |
| NSP5 | 92.57 | 96.5 |

Changes in nt and aa sequences of entire genome of CDC-66 strain from stool to the passage in Vero cells have been documented, as shown in Table 5.

TABLE 5

| Changes of nt and aa in genes of CDC-66 from stool to passage 27 in Vero cells | | |
|---|---|---|
| Gene | nt change | aa change |
| NSP1 | none | none |
| NSP2 | 470 C→T | 142 H → Y |
| NSP3 | none | none |
| NSP4 | none | none |
| NSP5 | 126 T→C, 199 A→G | 60 I→V |
| VP1 | 440 A→G | 141 N→S |
| VP2 | none | none |
| VP3 | 760 T→C, 1143 T→C, 1882 A→G | 365 L→S |
| VP4 | 770C→A, 1109T→C, 1162G→A, 1184A→G | 254T→K, 367V→A, 385D→N, 392E→G |
| VP6 | none | none |
| VP7 | none | none |

Vaccines

Vaccines and methods for their use to induce active immunity and protection against rotavirus induced illness in a subject are provided according to the present invention.

In particular embodiments, vaccine compositions for enhancing immunological protection against a rotavirus-mediated disease in a subject are provided according to the present invention which includes a human rotavirus strain admixed with a pharmaceutically acceptable carrier.

The term "vaccine composition" is used herein to refers to a composition including a biological agent capable of inducing an immune response in a subject inoculated with the vaccine composition. In particular embodiments, the biological agent is a live attenuated and/or inactive rotavirus. In further embodiments, the biological agent is an antigenic portion of a rotavirus.

In particular embodiments, a human rotavirus strain included in a vaccine composition of the present invention is CDC-9 or CDC-66. Combinations of these human rotavirus strains are optionally included in vaccine compositions of the present invention. Additionally, a human rotavirus strain other than CDC-9 or CDC-66 is optionally included in a vaccine composition of the present invention.

In particular embodiments of a vaccine composition according to the present invention, at least two rotavirus strains are included. The two or more rotavirus strains each independently have a G1, G2, G3, G4, G5, G6, G7, G8, G9, G10, G11, G12, G13 or G14 G serotype. Thus, for example, at least one of CDC-9 or CDC-66 is present in a vaccine composition of the present invention along with at least a second human rotavirus strain which has a G1, G2, G3, G4, G5, G6, G7, G8, G9, G10, G11, G12, G13 or 014 G serotype.

Each of the at least two rotavirus strains included in a vaccine composition has a P serotype which is P1A, P1B, P2A, P3, P4, P5, P6, P8, P11, or P12 in particular embodiments.

A vaccine composition for enhancing immunological protection against a rotavirus-mediated disease in a subject includes a first human rotavirus strain characterized as having a G1 serotype and a second human rotavirus strain characterized as having a G2 serotype in particular embodiments of a vaccine composition of the present invention. Each of the two rotavirus strains independently has a P group serotype which is P1A, P1B, P2A, P3, P4, P5, P6, P8, P11 or P12.

In some embodiments, the human rotavirus strain having a G1 serotype is CDC-9.

In some embodiments, the human rotavirus strain having a G2 serotype is CDC-66.

Combinations of human rotavirus strains in particular embodiments of a vaccine composition of the present invention include CDC-9 and CDC-66.

A human rotavirus strain included in a vaccine composition according to the present invention is a live attenuated rotavirus or an inactivated rotavirus. The choice of live attenuated rotavirus or inactivated rotavirus depends on factors such as route of vaccine composition administration.

In a particular embodiment, a vaccine composition including a human rotavirus A strain CDC-9, and/or CDC-66, one or more rotavirus A CDC-9, and/or CDC-66 polypeptides and/or an immunogenic fragment of one or more rotavirus A CDC-9, and/or CDC-66 polypeptides, stimulates generation of neutralizing antibodies to a rotavirus A CDC-9, and/or CDC-66 strain.

Vaccine compositions are provided according to embodiments of the present invention which include one or more rotavirus A polypeptides and/or an immunogenic fragment of one or more rotavirus A polypeptides. In particular embodiments of an inventive vaccine composition, a CDC-9, and/or CDC-66 polypeptide, a homolog thereof, and/or an immunogenic fragment thereof is included.

The term "homolog" refers to a polypeptide characterized by amino acid sequence homology to a reference CDC-9 or CDC-66 rotavirus A polypeptide.

CDC-9 Sequences

Accordingly, the present invention provides a virus including an NSP1 having SEQ ID NO: 2 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 2. Further, the present invention provides a virus including an NSP1 having SEQ ID NO: 3 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 3.

The present invention provides a virus including an NSP2 having SEQ ID NO: 5 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 5.

The present invention provides a virus including an NSP3 having SEQ ID NO: 8 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 8.

The present invention provides a virus including an NSP4 having SEQ ID NO: 11 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 11.

The present invention provides a virus including an NSP5 having SEQ ID NO: 14 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 14. Further, the present invention provides a virus including an NSP5 having SEQ ID NO: 15 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 15.

Accordingly, the present invention provides a virus including a VP1 having SEQ ID NO: 17 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 17.

The present invention provides a virus including a VP2 having SEQ ID NO: 20 or a homolog having an amino acid sequence that is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 20.

The present invention provides a virus including a VP3 having SEQ ID NO: 23 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 23.

The present invention provides a virus including a VP4 having SEQ ID NO: 26 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 26. Further, the present invention provides a virus including an VP4 having SEQ ID NO: 27 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 27.

The present invention provides a virus including a VP6 having SEQ ID NO: 29 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 29. Further, the present invention provides a virus including an VP6 having SEQ ID NO: 30 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 30.

The present invention provides a virus including a VP7 having SEQ ID NO: 32 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 32.

CDC-66 Sequences

The present invention provides a virus including an NSP 1 having SEQ ID NO: 71 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 71.

The present invention provides a virus including an NSP2 having SEQ ID NO: 77 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 77. Further, the present invention provides a virus including an NSP2 having SEQ ID NO: 78 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 78.

The present invention provides a virus including an NSP3 having SEQ ID NO: 83 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 83.

The present invention provides a virus including an NSP4 having SEQ ID NO: 89 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 89.

The present invention provides a virus including an NSP5 having SEQ ID NO: 95 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 95. Further, the present invention provides a virus including an NSP5 having SEQ ID NO: 96 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 96.

Accordingly, the present invention provides a virus including a VP1 having SEQ ID NO: 101 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 101. Further, the present invention provides a virus including an VP 1 having SEQ ID NO: 102 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 102.

The present invention provides a virus including a VP2 having SEQ ID NO: 107 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 107.

The present invention provides a virus including a VP3 having SEQ ID NO: 113 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 113. Further, the present invention provides a virus including an VP3 having SEQ ID NO: 114 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 114.

The present invention provides a virus including a VP4 having SEQ ID NO: 119 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 119. Further, the present invention provides a virus including an VP4 having SEQ ID NO: 120 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 120.

The present invention provides a virus including a VP6 having SEQ ID NO: 125 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 125.

The present invention provides a virus including a VP7 having SEQ ID NO: 131 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 131.

The present invention provides an isolated or purified NSP1, NSP2, NSP3, NSP4, NSP5, VP1, VP2, VP3, VP4, VP6, or VP7. The term "purified" or "isolated" as used herein, is intended to refer to a composition, isolatable from other components, wherein the compositions is purified to any degree relative to its naturally-obtainable state, i.e., in this case, relative to its purity within a cell, relative to is purity within a virion, or relative to its purity within an infective organism. An isolated composition, therefore, also refers to a protein, peptide, nucleic acid, or oligonucleotide, substantially free from the environment in which it may naturally occur.

It is recognized that numerous variants, analogues, or homologues are within the scope of the present invention including amino acid substitutions, alterations, modifications, or other amino acid changes that increase, decrease, or do not alter the function or immunogenic propensity of the inventive immunogen or vaccine. It is further appreciated that the inventive sequences are optionally modified by the addition of one or more amino acids, sugars, nucleotides, pendent groups, fluorophores, lumiphores, radioactive molecules, lipids, fatty acids, derivatives thereof, or other groups known in the art. Illustratively, an inventive immunogen is conjugated to a protein. Optionally, an inventive immunogen is conjugated to a protein that promotes the immunogenicity of an immunogen, illustratively, keyhole limpet hemocyanin (KLH), bovine serum albumin (BSA), or modifications thereof, as well as BLUE CARRIER immunogenic protein from Thermo Scientific, Rockford, Ill. Other sources of natural or artificial immunogenic protein conjugates are known in the art. Optionally, an inventive immunogen is conjugated to an antibody. Optionally, an inventive immunogen is conjugated to other regions of G-protein that may or may not also contain epitopes.

In some embodiments, the NSP1 has SEQ ID NO: 2 or SEQ ID No. 3, or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 2 or to SEQ ID No. 3. In a further embodiment, the NSP1 has SEQ ID NO: 71 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 71.

The present invention provides an isolated or purified NSP2. In one embodiment, the NSP2 has SEQ ID NO: 5 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 5. In a further embodiment, the NSP2 has SEQ ID NO: 77 or SEQ ID NO: 78 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 77 or SEQ ID NO: 78.

The present invention provides an isolated or purified NSP3. In one embodiment, the NSP3 has SEQ ID NO: 8 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 8. In a further embodiment, the NSP3 has SEQ ID NO: 83 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 83.

The present invention provides an isolated or purified NSP4. In one embodiment, the NSP4 has SEQ ID NO: 11 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 11. In a further embodiment, the NSP4 has SEQ ID NO: 89 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 89

The present invention provides an isolated or purified NSP5. In one embodiment, the NSP5 has SEQ ID NO: 14 or SEQ ID NO. 15 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 14 or SEQ ID NO. 15. In a further embodiment, the NSP5 has SEQ ID NO: 95 or SEQ ID NO: 96 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 95 or SEQ ID NO: 96.

The present invention provides an isolated or purified VP1. In one embodiment, the VP1 has SEQ ID NO: 17 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 17. In a further embodiment, the VP1 has SEQ ID NO: 101 or SEQ ID NO. 102 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 101 or SEQ ID NO. 102.

The present invention provides an isolated or purified VP2. In one embodiment, the VP2 has SEQ ID NO: 20 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 20. In a further embodiment, the VP2 has SEQ ID NO: 107 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 107.

The present invention provides an isolated or purified VP3. In one embodiment, the VP3 has SEQ ID NO: 23 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 23. In a further embodiment, the VP3 has SEQ ID NO: 113 or SEQ ID NO. 114 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 113 or SEQ ID NO. 114.

The present invention provides an isolated or purified VP4. In one embodiment, the VP4 has SEQ ID NO: 26 or SEQ ID NO. 27 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 26 or SEQ ID NO. 27. In a further embodiment, the VP4 has SEQ ID NO: 119 or SEQ ID NO. 120 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 119 or SEQ ID NO. 120.

The present invention provides an isolated or purified VP6. In one embodiment, the VP6 has SEQ ID NO: 29 or SEQ ID NO. 30 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 29 or SEQ ID NO. 30. In a further embodiment, the VP6 has SEQ ID NO: 125 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 125.

The present invention provides an isolated or purified VP7. In one embodiment, the VP7 has SEQ ID NO: 32 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 32. In a further embodiment, the VP7 has SEQ ID NO: 131 or is a homolog having an amino acid sequence that is greater than 97%, greater than 98% or greater than 99% identical to SEQ ID NO: 131.

An isolated or purified nucleic acid encoding an above-described protein or fragment thereof is provided according to embodiments of the present invention. Optionally, the isolated or purified nucleic acid encoding an above-described protein or fragment thereof is included in a vector.

A nucleic acid encoding NSP1 includes the nucleotide sequence of SEQ ID NO: 35; SEQ ID NO: 36; SEQ ID NO: 68 or a fragment thereof encoding at least nine contiguous amino acids. A nucleic acid encoding NSP2 includes the nucleotide sequence of SEQ ID NO: 38; SEQ ID NO: 74; SEQ ID NO: 75; or a fragment thereof encoding at least nine contiguous amino acids. A nucleic acid encoding NSP3 includes the nucleotide sequence of SEQ ID NO: 41; SEQ ID NO: 80; or a fragment thereof encoding at least nine contiguous amino acids. A nucleic acid encoding NSP4 includes the nucleotide sequence of SEQ ID NO: 44; SEQ ID NO: 86; or a fragment thereof encoding at least nine contiguous amino acids. A nucleic acid encoding NSP5 includes the nucleotide sequence of SEQ ID NO: 47; SEQ ID NO: 48; SEQ ID NO: 92; SEQ ID NO: 93; or a fragment thereof encoding at least nine contiguous amino acids. A nucleic acid encoding VP1 includes the nucleotide sequence of SEQ ID NO: 50; SEQ ID NO: 98; SEQ ID NO: 99; or a fragment thereof encoding at least nine contiguous amino acids. A nucleic acid encoding VP2 includes the nucleotide sequence of SEQ ID NO: 53; SEQ ID NO: 104; or a fragment thereof encoding at least nine contiguous amino acids. A nucleic acid encoding VP3 includes the nucleotide sequence of SEQ ID NO: 23; SEQ ID NO: 110; SEQ ID NO: 111; or a fragment thereof encoding at least nine contiguous amino acids. A nucleic acid encoding VP4 includes the nucleotide sequence of SEQ ID NO: 59; SEQ ID NO: 60; SEQ ID NO: 116; SEQ ID NO: 117; or a fragment thereof encoding at least nine contiguous amino acids. A nucleic acid encoding VP6 includes the nucleotide sequence of SEQ ID NO: 62; SEQ ID NO: 63; SEQ ID NO: 122; or a fragment thereof encoding at least nine contiguous amino acids. A nucleic acid encoding VP7 includes the nucleotide sequence of SEQ ID NO: 65; SEQ ID NO: 128; SEQ ID NO: 129; or a fragment thereof encoding at least nine contiguous amino acids.

One of skill in the art will appreciate that, due to the degeneracy of the genetic code, a particular polypeptide or fragment thereof can be encoded by more than one nucleic acid sequence.

Mutations can be introduced using standard molecular biology techniques, such as site-directed mutagenesis and PCR-mediated mutagenesis. One of skill in the art will recognize that one or more amino acid mutations can be introduced without altering the functional properties of rotavirus polypeptides. For example, one or more amino acid substitutions, additions, or deletions can be made without altering the functional properties of rotavirus polypeptides. It is also appreciated that several mutations optionally increase, decrease, or do not change the immunogenicity of an inventive polypeptide.

Conservative amino acid substitutions can be made in rotavirus polypeptides to produce homologs. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

Rotavirus particles, nucleic acids, polypeptides and fragments thereof can be produced in recombinant host cells using well-known conventional techniques. Any nucleic acid construct, which is effective in producing the encoded protein or fragment thereof in a host cell, can be used to produce rotavirus particles, rotavirus polypeptides or fragments thereof.

One of ordinary skill in the art recognizes many ways to make the inventive CDC-9 or CDC-66 viruses for use in an inventive vaccine composition or in inventive processes. Illustratively, it is common practice for one to isolate a putative rotavirus from a stool or other biological sample optionally including passaging in cell culture such as in Vero cells similar to the methods illustrated in Esona, M D, et al., *Human Vaccines,* 2010; 6:1-7; the contents of which are incorporated herein by reference. One of skill in the art regularly isolates virus strains and characterizes the genome sequence by techniques well known in the art. It is common practice for one of skill in the art to sequence a viral genome and compare the output sequence to a model sequence such as the sequences of CDC-9 of CDC-66 disclosed herein to determine whether the isolated virus has the required genetic sequence to be CDC-9, CDC-66, or homologues thereof.

One of skill in the art also knows methods of modifying a model rotavirus such as KU or DS-1 to make CDC-9 or CDC-66 viruses. One such method uses the reverse genetics approach of Komoto, S., et al., *PNAS USA,* 2006; 103:4646-4651, the contents of which are incorporated herein by reference. Briefly, each of the genes of strain KU can be isolated and amplified by taking culture fluid from infected MA104 cells, extracting the viral dsRNA and synthesizing cDNA using with avian myeloblastosis virus reverse transcriptase (Seikagaku Kogyo, Tokyo, Japan) using a starting primer. It is well within the level of skill in the art to design primers for synthesizing cDNA. Numerous free and commercially available programs for primer synthesis are known to those of skill in the art. Illustratively, primers for the KU VP4 gene are described in Komoto, S., et al., *PNAS USA,* 2006; 103:4646-4651. Modification of the sequences of KU or any other strain to those of CDC-9 or CDC-66 are illustratively accomplished by establishing the sequence modifications such as by sequence alignments. Once the nucleotide substitutions are elucidated, modifications of the cDNA can be achieved by using the QUICKCHANGE XL site-directed mutagenesis kit available from Agilent Technologies, Santa Clara, Calif. Modified gene sequences to conform to that of CDC-9, CDC-66, or homologues thereof are optionally inserted into a cell line such as COS-7 cells along with a helper virus such as KU used to serve as a base for gene insertion into new viruses. The modified viruses are subsequently isolated by known techniques. An optional iterative process is used whereby each individual gene of CDC-9 or CDC-66 is substituted for the gene of the helper virus step wise whereby the isolated substituted virus strain from the substitution of the first gene is used as a helper virus for substitution of the second gene and so on until CDC-9 or CDC-66 is created from a source strain.

Illustrative examples of helper viruses or model rotaviruses can be found at GenBank Accession Nos: (a) VP3 strains: RV161-00 (DQ490547), RV176-00 (DQ490553), DRC88 (DQ005112), DRC86 (DQ005123), TB-Chen (AY787654), DS-1 (AY277914), AU-1 (DQ490537), T152 (DQ146701), Hosokawa (DQ870491), Hochi (AY277915), Wa (AY267335), L26 (AY277918), KU (AB022767), Dhaka25-02 (DQ146651), Dhaka12-03 (DQ146662), B4633-03 (DQ146640), P0-13 (AB009631).

(b) VP7 (G1) strains: SK417 (EU839907), DH415 (EU839906), MMC82 (EU839913), Dhaka18-02 (AY631051), MMC56 (EU839911), Matlab159-02 (AY631055), ISO-4 (AY098670), Thai-2104 (DQ512982), CMH042/04 (EF199713), 417 (D16328), T73 (AF450291), TE1 (D17721), K18 (D16319), Chi-87 (DQ512998), J-4825 (DQ512989), 88H249 (AB081795), 421 (D16326), RV-4 (M64666), AU007 (AB081799), HOU8697 (U88717), Mvd9607 (AF480295), 80 (D16325), DC03 (AF183859), KU (AB222788), K2 (D16323), K8 (D16344), Egy-8 (U26374), Brz-5 (U26367), Wa (K02033), D (AB118022), C95 (L24165), T449 (M92651), DS-1 (AB118023).

(c) VP4 P[8] strains: ITO (AB008280), D (EF672570), Wa (L34161), Hochi (AB008295), Odelia (AB008296), VA70 (AJ540229), CH32 (AB008274), MO (AB008278), KU (AB222784), Wi61 (EF672619), F45 (U30716) P (EF672598), AI-39 (AB008283), 90-544 (AB008304), B4633-03 (DQ146641), Dhaka25-02 (DQ146652), SK438 (EU839955), DH402 (EU839958), DH415 (EU839955), DS-1(AB118025).

(d) NSP4 strains: Dhaka16-03 (DQ492678), 1099 (AJ236759), Dhaka12-03 (DQ146669), Dhaka25-02 (DQ146658), KU (AB022772), Wa (AF093199), RMC321 (AF541921), OSU (D88831), AU-1 (D89873), CMH120/04 (DQ923799), B4106 (AY740732), C-11 (AF144793), DRC86 (DQ005116), DRC88 (DQ005105), DS-1 (AF174305), TB-Chen (AY787650), Ch-1 (AB065287).

Each of the files and sequences at the aforementioned accession numbers are incorporated herein by reference.

Other methods, primers, isolation techniques, sequencing techniques, and characterization techniques are known to those of skill in the art and are similarly operable herein. Illustratively, one can reconstitute CDC-9 or CDC-66 viruses de novo from isolated genes such as by assembly of virus particles with captured genes illustratively by the techniques of or modifications of Gonzalez, S A, and Affranchino, J L, J. Gen. Virol., 1995; 76:2357-2360, the contents of which are incorporated herein by reference.

Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Short Protocols in Molecular Biology, Wiley, 2002; and S. J. Higgins and B. D. Hames (Eds.), Protein Expression: A Practical Approach, Oxford University Press, USA, 1999.

Illustratively, a nucleic acid molecule encoding one or more rotavirus polypeptides and/or rotavirus polypeptide fragments is operably linked to regulatory sequences that control transcriptional expression in an expression vector. The expression vector is introduced into a host cell and the produced rotavirus particles, one or more rotavirus polypeptides and/or rotavirus polypeptide fragments can then be isolated. Illustrative constructs include operably linking a rotavirus nucleic acid molecule into plasmid pT7 by first amplifying the nucleic acid molecule using primers including a T7 promoter sequence and ligating the amplified nucleic acids into the T7 expression vector pX8dT as described by Schnell, M J, et al., EMBO J, 1994; 13:4195-4203, the contents of which are incorporated herein by reference.

Non-limiting examples of regulatory sequences that control transcriptional expression in an expression vector illustratively include a promoter, an enhancer, a splicing signal, a transcription start site, a transcription termination signal, a polyadenylation signal, an internal ribosome entry site (IRES) and combinations of these or other regulatory sequences.

Expression vectors include, but are not limited to, viral vectors and bacterial vectors used to express a desired protein. Non-limiting examples of expression vectors include bacterial plasmids, bacteriophage, adenovirus, adeno-associated virus, herpes virus, vaccinia virus and lentivirus.

A host cell for expression of polypeptides and fragments thereof can be prokaryotic or eukaryotic, such as bacterial, plant, insect, fungus, yeast, and mammalian cells.

An expression vector is introduced into a host cell using well-known techniques such as infection or transfection, including calcium phosphate transfection, liposome-mediated transfection, electroporation and sonoporation.

In addition to recombinant methodology, chemical synthetic techniques can be used to produce polypeptides and fragments thereof. For example, solid phase synthesis, solution phase synthesis, partial solid phase synthesis or fragment condensation can be used.

The term "isolated" as used herein refers to a substance that has been separated from other cellular components associated with the substance in nature or when recombinantly produced not intended to be associated with the substance and that may interfere with use of the substance in therapeutic, prophylactic, diagnostic, research or other uses. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

Percent identity is determined by comparison of amino acid or nucleic acid sequences, including a reference rotavirus A amino acid or nucleic acid sequence and a putative homologue amino acid or nucleic acid sequence. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis. and publicly available from the National Center for Biotechnology Information.

Rotavirus A CDC-9, and/or CDC-66 polypeptides, a homolog thereof, and/or an immunogenic fragment thereof may be prepared by any of various methods, including isolation of virus particles from sources such as cultured cells or patient samples, isolation of one or more polypeptides and/or one or more polypeptide fragments from viral particles, recombinant production of viral polypeptides, fragments and/or viral particles, including intact and virus-like particles, and/or by chemical synthetic techniques. Methods of isolation of virus particles, virus polypeptides and/or one or more virus polypeptide fragments, recombinant production of virus polypeptides, virus polypeptide fragments and/or virus particles are described in detail herein, in references cited herein, and are known to those of skill in the art.

An antigen may be made more immunogenic if desired by linkage to a carrier molecule such bovine serum albumin or keyhole limpet hemocyanin and/or by use of an adjuvant. Carrier linkage may be accomplished by any of various techniques, illustratively including, but not limited to, conjugation and expression of a fusion protein.

Recombinantly expressed polypeptides or peptides may be tagged to allow for easier isolation. For instance, such polypeptides and peptides are optionally tagged illustratively, Fc-tagged, 6×HIS-tagged, FLAG-tagged, or by other tag suitable for isolation of a tagged polypeptide.

Vaccine Formulation

In particular embodiments of the invention, a rotavirus A strain for inclusion in a vaccine composition of the present invention is prepared by standard methods typically used for preparation of live or inactivated rotavirus. For example, generally a compatible cell type is inoculated with a rotavirus strain and the cells are maintained under conditions which allow for viral replication and production of infectious particles.

A particular example of a cell type which permits rotavirus infection, replication and particle production is a mammalian cell line such as a Vero cell line.

Rotavirus particles are harvested, typically from cell culture supernatant for inclusion in a vaccine composition. The rotavirus particles may be isolated from the cell culture supernatant, for example by filtration and/or centrifugation. The isolated rotavirus particles are optionally lyophilized, such as for later resuspension in a pharmaceutically acceptable carrier.

The term "pharmaceutically acceptable carrier" refers to a carrier which is substantially non-toxic to a subject and substantially inert to the rotavirus included in a vaccine composition. A pharmaceutically acceptable carrier is a solid, liquid or gel in form and is typically sterile and pyrogen free.

A vaccine composition of the present invention may be in any form suitable for administration to a subject.

A vaccine composition is administered by any suitable route of administration including oral and parenteral such as intravenous, intradermal, intramuscular, mucosal, nasal, or subcutaneous routes of administration.

For example, a vaccine composition for parenteral administration may be formulated as an injectable liquid including a rotavirus and a pharmaceutically acceptable carrier. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

A solid dosage form for administration or for suspension in a liquid prior to administration illustratively includes capsules, tablets, powders, and granules. In such solid dosage forms, a rotavirus is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and *acacia*; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include rotavirus and a pharmaceutically acceptable carrier formulated as an emulsion, solution, suspension, syrup, or elixir. A liquid dosage form of a vaccine composition of the present invention may include a wetting agent, an emulsifying agent, a suspending agent, a sweetener, a flavoring, or a perfuming agent.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004, throughout and in chapter 16; A. R. Gennaro, Remington: The Science and Practice of Pharmacy, Lippincott Williams & Wilkins, $21^{st}$ ed., 2005, particularly chapter 89; and J. G. Hardman et al., Goodman & Gilman's The Pharmacological Basis of Therapeutics, McGraw-Hill Professional, 10th ed., 2001.

An adjuvant is optionally included in a virus composition according to embodiments of the present invention. Adjuvants are known in the art and illustratively include Freund's adjuvant, aluminum hydroxide, aluminum phosphate, aluminum oxide, saponin, dextrans such as DEAE-dextran, vegetable oils such as peanut oil, olive oil, and/or vitamin E acetate, mineral oil, bacterial lipopolysaccharides, peptidoglycans, and proteoglycans.

The term "subject" is used herein to refer to a human. Non-human animals, illustratively including other primates, cows, horses, sheep, goats, pigs, dogs, cats, birds, poultry, and rodents, are also referred to by the term subject in particular embodiments of the present invention.

The isolated rotavirus is treated to inactivate or attenuate the rotavirus. Thus, in particular embodiments a vaccine for human rotavirus includes a live attenuated human rotavirus or an inactivated human rotavirus.

The term "live attenuated rotavirus" refers to a rotavirus having the ability to infect an appropriate host or host cell and replicate and the term is used to distinguish an "inactivated" rotavirus. The term "live attenuated rotavirus" refers to a rotavirus characterized by substantially diminished virulence compared to wild type human rotavirus. The term "virulence" is used to describe the degree of pathogenicity of a rotavirus to a host cell or a host organism. Virulence is determined using any of various assays recognized in the art. For example, virulence may be assessed by exposing cultured host cells to an attenuated rotavirus and determining the number of cells which display a pathogenic response and/or the severity of pathogenic response elicited. Diminished virulence is present where an attenuated rotavirus has decreased capability to cause one or more pathogenic effects in a host cell and/or host organism.

The term "inactivated" rotavirus is used herein to refer to rotavirus that has been killed and which is therefore capable of neither replication nor infection of a host cell or host organism.

Inactivation is achieved by any of various techniques illustratively including inactivation using one or more chemical agents, thermal inactivation and/or UV light inactivation.

Chemical agents used to inactivate a rotavirus are known in the art and include such agents as ethyleneimines such as binary ethyleneimine; cross-linking aldehydes such as formaldehyde and glutaraldehyde; proteases illustratively including pronase, trypsin and/or chymotrypsin; and detergents such as octylphenol ethoxylates and alkyl trimethylammonium salts. Rotavirus may be inactivated by treatment with a base, for example by incubation of the rotavirus at a pH above pH 10.0.

Thermal inactivation may be achieved by heating at temperatures above 50° centigrade, for example.

Inactivation is assessed by techniques standard in the art, illustratively including sampling virus at various times during an inactivation procedure and observing cytopathic effects or infectivity of a sample on suitable cells, such as Vero cells.

It is appreciated that, in addition to live attenuated and inactivated rotavirus, an antigenic portion of a rotavirus is optionally included in a vaccine composition of the present invention. Thus, for example, a rotavirus-derived protein or peptide capable of inducing an immunological response in a subject is considered within the scope of the present invention. In particular, an antigenic portion of a human rotavirus strain identified as CDC-9 or CDC-66 is optionally included in a vaccine composition of the present invention.

Methods of inducing an immunological response against a rotavirus-mediated disease in a subject are provided according to embodiments of the present invention which include administering a therapeutic amount of a vaccine composition including at least one human rotavirus strain.

The phrase "therapeutically effective amount" is used herein to refer to an amount effective to induce an immunological response sufficient to prevent or ameliorate signs or symptoms of a rotavirus-mediated disease. Induction of an immunological response in a subject can be determined by any of various techniques known in the art, illustratively including detection of anti-rotavirus antibodies, measurement of anti-rotavirus antibody titer and/or lymphocyte proliferation assay. Illustrative methods for detection of anti-rotavirus antibodies are illustrated by Tsunemitsu, H, et al., *J. Clin. Microbiol.,* 1992; 30:2129-2134, the contents of which are incorporated herein by reference. Signs and symptoms of rotavirus-mediated disease may be monitored to detect induction of an immunological response to administration of a vaccine composition of the present invention in a subject. An immunological response is illustratively a reduction of clinical signs and symptoms of rotavirus-mediated disease such as reduction of the amount of virus shed in feces, reduction of the number of days on which virus is shed in feces, reduction in the number of days the subject has diarrhea, reduction in mortality, reduction in morbidity, reduction in weight loss or weight gain. An immunological response is illustratively, development of anti-rotavirus antibodies, activation of T-cells, B-cells, or other immune cells following administration of an inventive composition, or other immune responses known in the art.

In a particular embodiment, a method of inducing an immunological response against a rotavirus-mediated disease in a subject includes administering $10^4$ to $10^8$ ffu of live attenuated vaccine or 1 to 25 micrograms of inactivated virus in a typical vaccine composition.

In some embodiments, a method of inducing an immunological response against a rotavirus-mediated disease in a subject includes administering a therapeutically effective amount of a vaccine composition including a human rotavirus strain CDC-9 and/or CDC-66, polypeptide fragments thereof, homologues thereof, or combinations thereof.

In a further embodiment, a method of inducing an immunological response against a rotavirus-mediated disease in a subject includes administering a therapeutically effective amount of a vaccine composition including a G1 group serotype and a second human rotavirus strain characterized as having a G2 group serotype.

Administration of a vaccine composition according to a method of the present invention includes administration of one or more doses of a vaccine composition to a subject at one time in particular embodiments. Alternatively, two or more doses of a vaccine composition are administered at time intervals of days, weeks, or years. A suitable schedule for administration of vaccine composition doses depends on several factors including age and health status of the subject, type of vaccine composition used and route of administration, for example. One of skill in the art is able to readily determine a dose and schedule of administration to be administered to a particular subject.

Embodiments of inventive compositions and methods are illustrated in the following examples. These examples are provided for illustrative purposes and are not considered limitations on the scope of inventive compositions and methods.

EXAMPLES

Example 1

Adaptation and Passaging

One ml of a 10% virus suspension in DMEM is supplemented with neomycin in a 1.7 ml sterile low bind tube, mixed well and then centrifuged for 10 min at 3,000 rpm in an Eppendorf micro centrifuge. The supernatant is transferred to a new tube and centrifuged for 10 min at 10,000 rpm (8,000×g). The clarified supernatant is sterilized by passing though a 0.45 micron pore filter. The supernatant is tested by EIA (Rotaclone; Meridian Biosciences) and if OD value is >1.0, store it at 4° C. before use for infection. Stool extraction and Rotaclone testing can be done the day before infection.

The culture medium is removed from cell monolayers in individual roller tubes. Each roller tube is washed with 2 ml of maintenance medium, then 2 ml maintenance medium is added to each tube and incubated at 37° C. in a rolling apparatus until virus inoculum is ready.

An aliquot of 0.5 ml of supernatant is transferred to a sterile tube and 1 microliter of $CaCl_2$ stock (300 grams per liter) is added to make a final concentration of 800 micrograms per milliliter. The tube is incubated at room temperature for 30 min before adding 3 microliters of porcine trypsin stock (2.5 milligrams per milliliter)—final concentration of 15 micrograms per milliliter. The mixture is incubated for 60 min at 37° C. The same volume of MEM is treated in the same way as a mock inoculum. Separate pipette tips are used for pipetting virus suspension and trypsin solutions. All pipetting of virus should be done within the biological safety cabinet.

Medium is removed from each roller tube and 0.2 to 0.3 milliliter of trypsinized virus suspension or mock inoculums is added to each roller tube using separate sterile pipette. The caps are tightened and the tubes incubated at 37° C. on a roller tube apparatus located in an incubator. After 2 hrs incubation, inoculum is removed using a 1 ml pipette and washed gently with 2 ml maintenance medium.

Two milliliters of maintenance medium containing various concentrations (10, 20 or 30 micrograms per ml depending on strain) of trypsin is added into each tube and incubated for 2 hours at 37° C. on a roller tube apparatus located in an incubator.

The cells are observed daily for cytopathic effect (CPE), harvested at day 4 and stored at −70° C. The cells are subjected to freeze-thaw two times before the next passage.

The freeze-thawed cell lysates are treated with $CaCl_2$ and trypsin as described above and subsequent passages are performed as above. The cells are subjected to freeze-thaw at least once and assayed for rotavirus antigen by Rotaclone kit or virus titer is determined by FFA assays.

Example 2

Production and Purification of Rotavirus Strains

Production of rotavirus is accomplished by use of large scale production roller bottles. Briefly described, Vero cells are cultured in Dulbecco's Modified Eagle Medium supplemented with 5% fetal bovine serum (Invitrogen Corp., Grand Island, N.Y.) and 50 micrograms/milliliter of neomycin (Sigma Corp., St. Louis, Mo.). Confluent monolayers of Vero cells in roller bottles are infected with a particular rotavirus strain at a multiplicity of infection of 0.1.

Rotavirus obtained by large scale production is purified according to standard operating procedures. Briefly described, rotavirus is harvested from infected cultures of Vero cells at four days post-infection. Triple-layered rotavirus particles are purified from supernatants by centrifugation through 40% sucrose cushions in TNC buffer for 2 hours at 106,750×g using an SW32Ti rotor and then through isopycnic centrifugations in CsCl gradients for 17 hours at 111,160 g using an SW40Ti rotor. Rotavirus particles may also be purified using sucrose gradients. TNC buffer is 10 mM Tris, pH 8.0, 140 mM NaCl, and 10 mM $CaCl_2$. Purified rotavirus particles are resuspended in diluent buffer which is Hanks Balanced Salt Solution with $CaCl_2$ and $MgCl_2$, obtained from Invitrogen Corp., Grand Island, N.Y., supplemented with 10% sorbitol (Sigma Corp., St. Louis, Mo.). The resuspended isolated rotavirus is stored at −70° C. until it is inactivated and administered to a subject in this example.

Purified rotavirus is analyzed for purity and identity by any of various techniques, illustratively including SDS-PAGE followed by Coomassie blue staining, western blot using a rotavirus-specific antibody and/or electron microscopy. In addition, purity and identity of purified rotavirus strains is accomplished by identification of particular structural viral proteins.

Figure 4A:
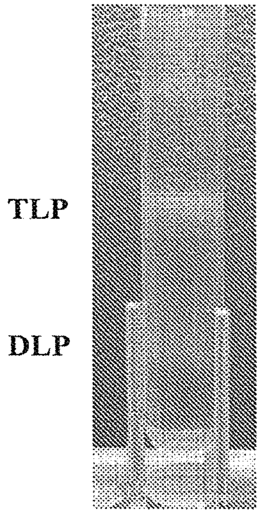
FIG. 4A shows bands of CsCl purified rotavirus particles of rotavirus A strain CDC-9.
Figure 4B:
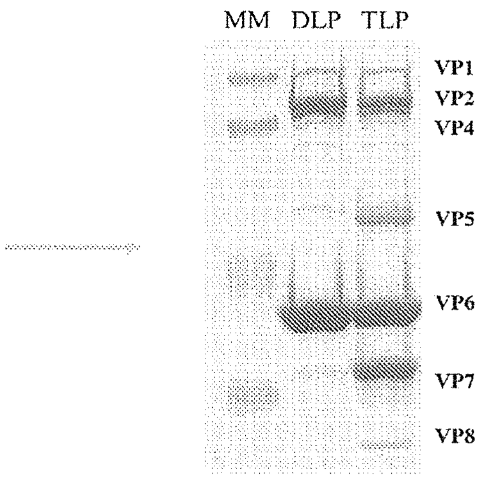
FIG. 4B shows identified structural viral proteins of rotavirus A strain CDC-9 analyzed by SDS-PAGE in comparison to molecular weight markers.

FIG. 4A shows CsCl purified rotavirus of strain CDC-9. FIG. 4B shows identified structural viral proteins of double- and triple-layered CDC-9 analyzed by SDS-PAGE in comparison to molecular weight markers.

Example 3

Immunogenicity of Inactivated Rotavirus (IRV)

Immunogenicity of rotavirus strains is tested in a mouse model. Purified killed rotavirus particles are administered intramuscularly to mice without an adjuvant. Animals are immunized with amounts of killed rotavirus protein in the range between 2 and 20 micrograms.

Immunogenicity is assayed by measuring immunoglobulin titers including IgM, IgA and IgG in blood samples obtained at various times after administration. Neutralizing antibody titers are measured by microneutralization assay as described in detail in Jiang, B., Vaccine, 17:1005-1013, 1999, the contents of which are incorporated herein by reference. Briefly described, mouse sera are serially diluted two-fold in duplicate wells and incubated with trypsin-inactivated RRV rotavirus. Activated rotavirus or similarly treated serum-free MEM medium is incubated in the absence of mouse serum and serve as positive and negative controls, respectively. MA104 cells in MEM medium supplemented with a final concentration of 10 micrograms/milliliter trypsin and 0.5% chick serum, obtained from Invitrogen Corp., Grand Island, N.Y., are added to each well. After incubation at 37° C. for 18 hours, cells are fixed with formalin. Rotavirus antigens in MA104 cells are detected by incubating cells with rabbit anti-RRV hyperimmune serum, HRP-labeled anti-rabbit IgG, and then tetramethyl benzidine. Neutralizing antibody titer in a serum is defined as the reciprocal of the highest dilution giving a 70% reduction in absorbance value compared to that in the virus control.

Figure 5A:
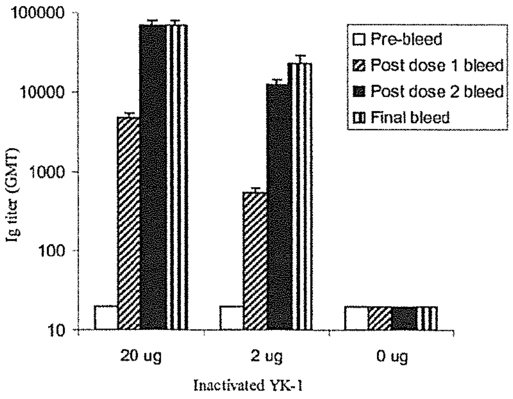
FIG. 5A is a bar graph showing total antibody titers in response to thermally inactivated rotavirus in control and vaccinated mice.
Figure 5B:
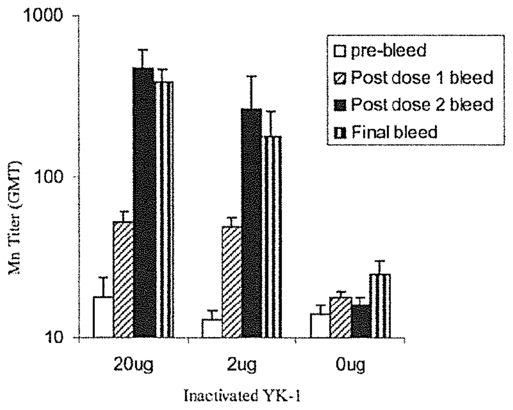
FIG. 5B is a bar graph showing neutralizing antibody titers in response to thermally inactivated rotavirus in control and vaccinated mice.

Antibody titers in mice injected with killed purified rotavirus particles are compared with antibody titers in control mice. Antibody titers in control mice are typically less than 100. FIGS. 5A and 5B illustrate total antibody and neutralizing antibody titers in control and vaccinated mice. Total serum antibody (FIG. 5A) and neutralizing antibody (FIG. 5B) responses to thermally inactivated rotavirus in mice. Mice are vaccinated I.M. twice with killed YK-1 and rotavirus-specific total (IgA, IgG, and IgM) and neutralizing antibodies are determined by EIA as described. For total antibody, each serum specimen is tested at an initial dilution of 1:100. Pre-bleed serum specimens have no detectable antibody at this dilution. A value of 20 is used for determining geometric mean titers and illustration. Neutralizing antibody is tested at an initial dilution of 1:20. Antibody titers are expressed as the geometric means for each group (n=7 or 6). Error bars represent 1 standard error.

Example 4

Adjuvant

In a further example, $Al(OH)_3$ is added as an adjutant to rotavirus particles in a vaccine administered to mice. Animals are immunized intramuscularly once with 2 micrograms or 0.2 micrograms of killed purified rotavirus particles in the presence or absence of 600 micrograms $Al(OH)_3$. AlOH dramatically enhances total antibody titers in mice at both concentrations of rotavirus administered. No antibody titers (less than 100 dilutions) are detected in control mice immunized with 600 micrograms of $Al(OH)_3$.

Figure 6:
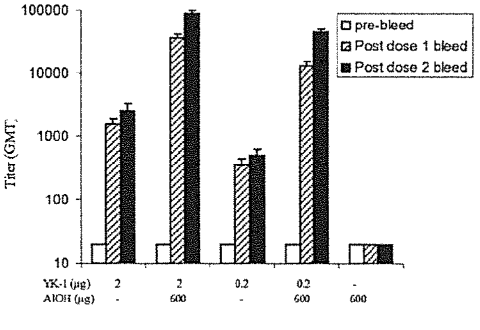
FIG. 6 is a bar graph showing total serum antibody responses to thermally inactivated rotavirus formulated with $Al(OH)_3$ in control and vaccinated mice.

FIG. 6 is a bar graph showing total serum antibody responses to thermally inactivated rotavirus formulated with $Al(OH)_3$ in control and vaccinated mice. Mice are vaccinated I.M. once with killed YK-1 in the absence or presence of $Al(OH)_3$ and rotavirus-specific total (IgA, IgG, and IgM) antibodies are determined by EIA as described. For total antibody, each serum specimen is tested at an initial dilution of 1:100. Pre-bleed serum specimens have no detectable antibody at this dilution. A value of 20 is used for determining geometric mean titers and illustration. Antibody titers are expressed as the geometric means for each group (n=6). Error bars represent 1 standard error.

Example 5

Gnotobiotic Piglet Model

A gnotobiotic piglet model of rotavirus disease is used. This piglet model allows testing under defined conditions avoiding problems of environment exposure of animals and using disease as the outcome variable. This model also allows testing of an inactivated rotavirus vaccine having a G1 serotype against a homotypic Wa challenge. Gnotobiotic piglets are the best current animal model for infection and disease with human rotavirus strains. (See Saif L J, et al., *Archives of Virology,* 1996; 12:S153-61; and Iosef C, et al., Vaccine, 2002; 20:1741-53; the contents of each of which are incorporated herein by reference.)

Thirteen infant gnotobiotic piglets are selected and randomly assigned to 4 groups as indicated in Table 6.

TABLE 6

| Piglet Study Design | | | |
|---|---|---|---|
| Group Name | Number of Piglets in Group | CDC-9 Antigen (micrograms) | Aluminum phosphate (micrograms) |
| AA | 4 | 0 | 750 |
| BB | 4 | 75 | 0 |
| CC | 3 | 75 | 750 |
| DD | 2 | 0 (buffer) | 0 (buffer) |

Each group of animals indicated in Table 6 is kept in separate isolators. Animals in groups BB and CC are vaccinated intramuscularly 3 times with an inactivated rotavirus vaccine without or with an adjuvant, respectively. The vaccine formulation in this example includes 75 micrograms of killed purified CDC-9 rotavirus in diluent mixed with 750 micrograms of aluminum phosphate. Animals in groups AA and DD are vaccinated with 750 micrograms of aluminum phosphate and buffer, respectively, in the same manner. Antigen adsorption is determined by the Bradford method which showed that about 50% of the antigen was bound to aluminum phosphate. Both bound and unbound antigen was injected in these immunizations.

Figure 7A:
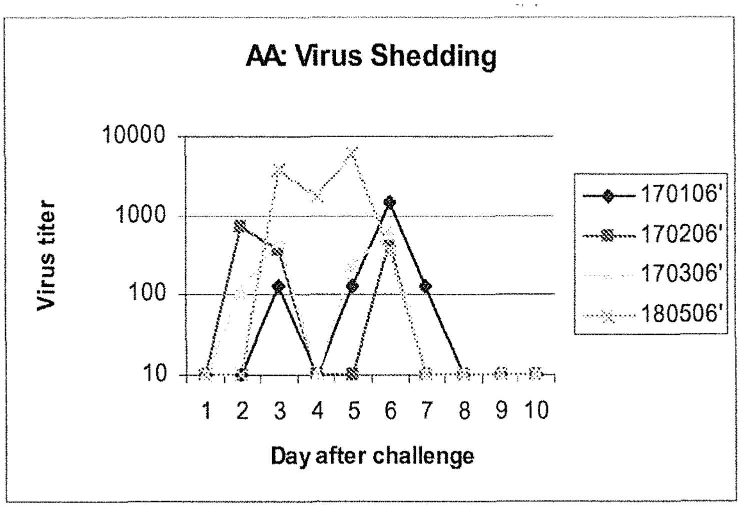
FIG. 7A shows virus shedding in fecal samples of piglets vaccinated with no antigen and with 750 micrograms of aluminum phosphate in 4 animals.
Figure 7B:
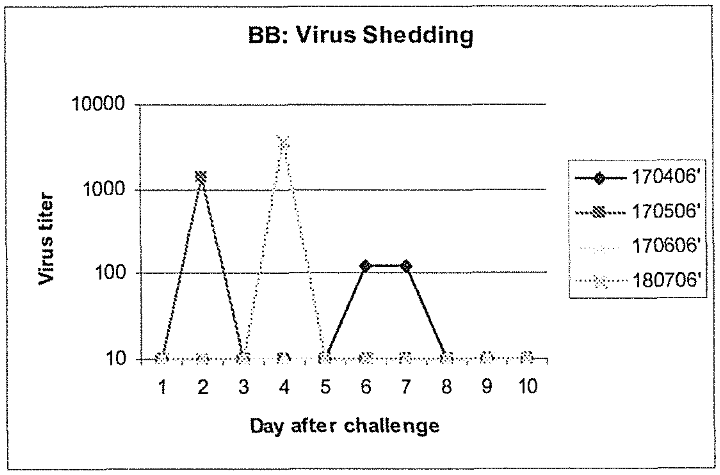
FIG. 7B shows virus shedding in fecal samples from piglets immunized with antigen and no adjuvant.
Figure 7C:
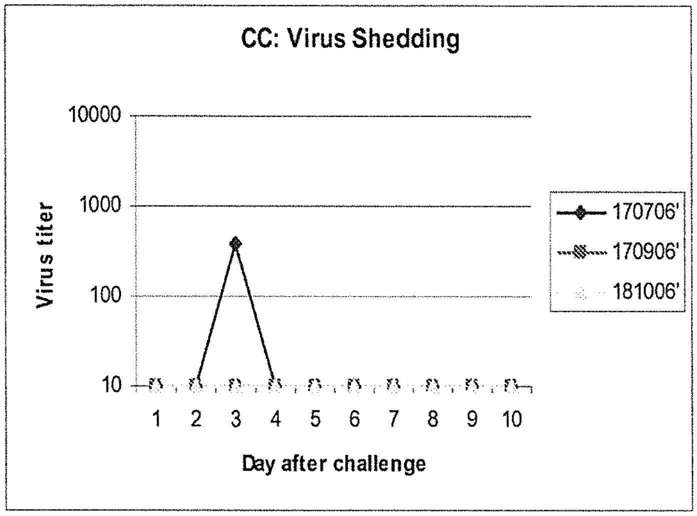
FIG. 7C shows virus shedding in fecal samples of piglets immunized with antigen and adjuvant.
Figure 7D:
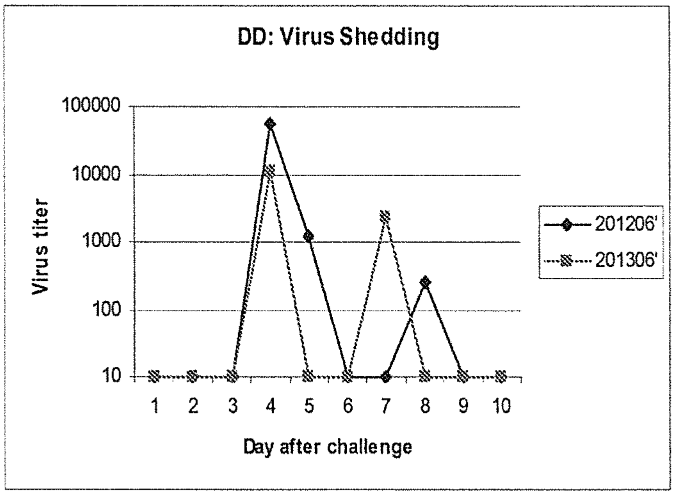
FIG. 7D shows virus shedding measured in fecal samples of piglets immunized with buffer only.

As shown in Table 6, piglets are immunized with a vaccine formulation including no antigen and 750 micrograms of aluminum phosphate; 75 micrograms of antigen and no aluminum phosphate; 75 micrograms of antigen and 750 micrograms of aluminum phosphate; or no antigen and no aluminum phosphate, that is buffer alone. Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days. FIG. 7A shows virus shedding in fecal samples of piglets vaccinated with no antigen and with 750 micrograms of aluminum phosphate in 4 animals. FIG. 7B shows virus shedding in fecal samples from piglets immunized with antigen and no adjuvant. FIG. 7C shows virus shedding in fecal samples of piglets immunized with antigen and adjuvant. FIG. 7D shows virus shedding measured in fecal samples of piglets immunized with buffer only. These illustrate that piglets that are mock vaccinated with aluminum phosphate only or diluent buffer only all shed rotavirus up to 5 days and at high titer. By contrast, piglets that are vaccinated with inactivated rotavirus without aluminum phosphate are partially protected, as evidenced by a shortened 1-day shedding or a delayed and reduced shedding. Of the 3 piglets that are vaccinated with inactivated rotavirus and aluminum phosphate, 2 are completely protected and 1 has only a short, 1-day, reduced shedding. Thus, these results show effectiveness of vaccine formulation according to embodiments of the present invention.

Example 6

Gnotobiotic Piglet Model-II

To repeat the experiment above, eleven infant gnotobiotic piglets are selected and randomly assigned to 2 groups as indicated in Table 7.

TABLE 7

| Piglet Study Design | | | |
|---|---|---|---|
| Group Name | Number of Piglets in Group | CDC-9 Antigen (micrograms) | aluminum phosphate (micrograms) |
| GG | 5 | 0 | 600 |
| HH | 6 | 50 | 600 |

As shown in Table 7, and as described by Wang, Y, et al., Inactivated rotavirus vaccine induces protective immunity in gnotobiotic piglets, in press, the contents of which are incorporated herein by reference, piglets are immunized with a vaccine formulation including no antigen and 600 micrograms of aluminum phosphate or 50 micrograms of antigen and 600 micrograms of aluminum phosphate. Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days.

Figure 8A:
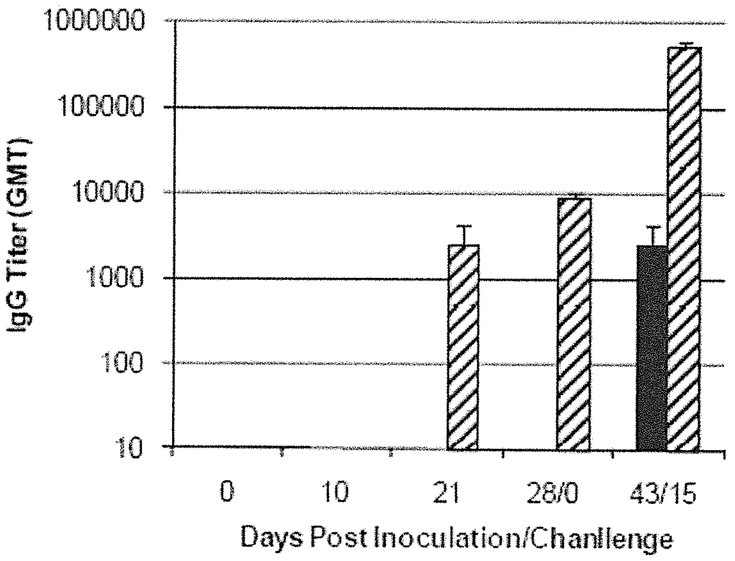
FIG. 8A is a bar graph showing rotavirus specific IgG antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars)
Figure 8B:
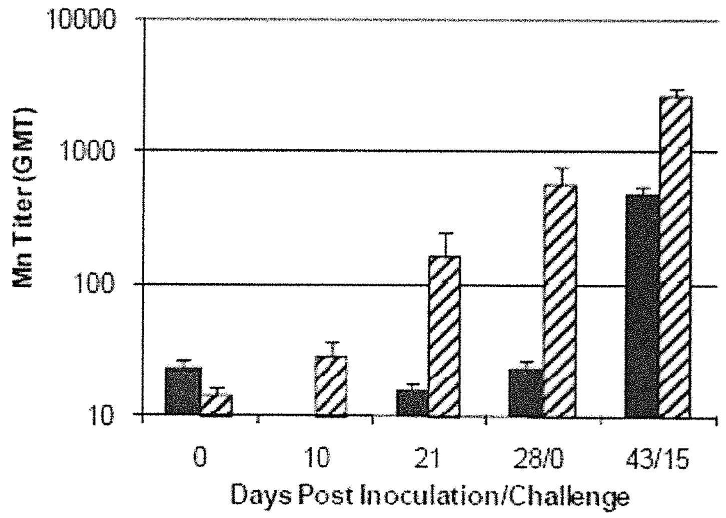
FIG. 8B is a bar graph showing neutralizing antibody response in sera of piglets vaccinated with no antigen and with 600 micrograms of aluminum phosphate or piglets vaccinated with 50 micrograms of antigen and with 600 micrograms of aluminum phosphate.

FIG. 8A shows the level of rotavirus specific IgG antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars). FIG. 8B shows neutralizing antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars). Piglets vaccinated with antigen develop significant levels of serum IgG. Oral challenge with rotavirus further enhances the serum IgG levels. The levels of neutralizing activity are significantly higher in piglets vaccinated with 50 micrograms of antigen and with 600 micrograms of aluminum phosphate than mock immunized animals.

Figure 9A:
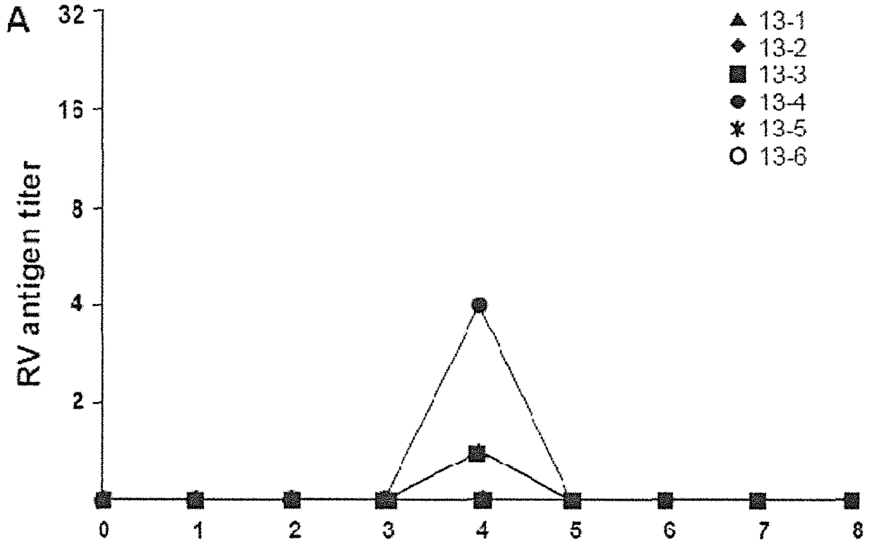
FIG. 9A shows virus shedding in fecal samples of piglets vaccinated with no antigen and with 600 micrograms of aluminum phosphate.
Figure 9B:
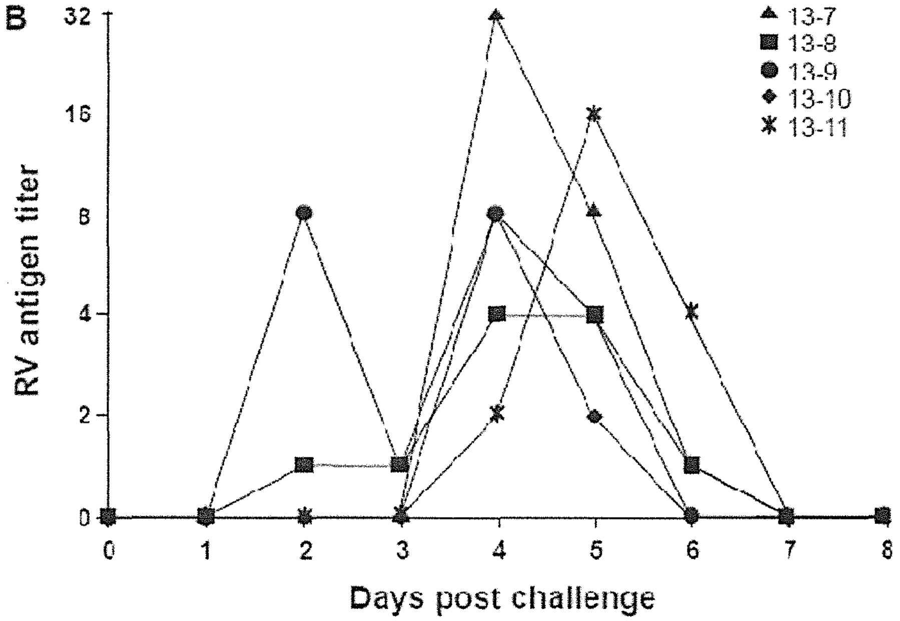
FIG. 9B shows virus shedding in fecal samples of piglets vaccinated with 50 micrograms of antigen and with 600 micrograms of aluminum phosphate.

FIG. 9A shows virus shedding in fecal samples of piglets vaccinated with 50 micrograms of antigen and with 600 micrograms of aluminum phosphate. FIG. 9B shows virus shedding in fecal samples of piglets vaccinated with no antigen and with 600 micrograms of aluminum phosphate. These figures illustrate that piglets that are mock vaccinated with aluminum phosphate only or diluent buffer only all shed rotavirus up to 5 days and at high titer. By contrast, piglets that are vaccinated with inactivated rotavirus and aluminum phosphate are protected from shedding.

These results show effectiveness of vaccine formulation according to embodiments of the present invention and confirm the results in first piglet experiment. These results clearly demonstrate that IRV formulated with alum is highly immunogenic and protective against infection in piglets and consequently establish proof of concept for inactivated rotavirus vaccine.

Example 7

Gnotobiotic Piglet Model-III—Immunization with CDC-66

To repeat the experiment above using CDC-66 rotavirus, eleven infant gnotobiotic piglets are selected and randomly assigned to 2 groups as indicated in Table 8.

TABLE 8

Piglet Study Design

| Group Name | Number of Piglets in Group | CDC-66 Antigen (micrograms) | aluminum phosphate (micrograms) |
|---|---|---|---|
| GG | 5 | 0 | 600 |
| HH | 6 | 50 | 600 |

As shown in Table 7, piglets are immunized with a vaccine formulation including no antigen and 600 micrograms of aluminum phosphate or 50 micrograms of antigen and 600 micrograms of aluminum phosphate ($AlPO_4$). Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent DS-1 rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days.

Piglets vaccinated with antigen develop significant levels of serum IgG. Oral challenge with rotavirus further enhances the serum IgG levels. The levels of neutralizing activity are significantly higher in piglets vaccinated with 50 micrograms of CDC-66 antigen and with 600 micrograms of aluminum phosphate than mock immunized animals.

Piglets that are mock vaccinated with aluminum phosphate only or diluent buffer only all shed rotavirus up to 5 days and at high titer. By contrast, piglets that are vaccinated with inactivated rotavirus CDC-66 and aluminum phosphate are protected from shedding.

These results show effectiveness of vaccine formulation according to embodiments of the present invention and confirm the results in first piglet experiment. These results clearly demonstrate that IRV formulated with alum is highly immunogenic and protective against infection in piglets and consequently establish proof of concept for inactivated rotavirus vaccine.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A vaccine composition for inducing an immunological response against a rotavirus in a subject, comprising:

a pharmaceutically acceptable carrier admixed with an isolated rotavirus strain of CDC-9 or CDC-66 inactivated by inactivation treatment comprising UV light treatment; and an adjuvant in an amount that increases immunogenicity of the isolated rotavirus strain.

2. The vaccine composition of claim 1, comprising at least two isolated rotavirus strains, wherein the adjuvant increases immunogenicity of the at least two isolated rotavirus strains.

3. The vaccine composition of claim 2, wherein the at least two isolated rotavirus strains each independently have a G group serotype of G1, G2, G3, G4, G5, G6, G7, G8, G9, G10, G11, G12, G13 or G14.

4. The vaccine composition of claim 2, wherein the at least two isolated rotavirus strains each independently have a P group serotype of P1A, P1B, P2A, P3, P4, P5, P6, P8, P11 or P12.

5. The vaccine composition of claim 1, formulated for parenteral administration to a subject.

6. The vaccine composition of claim 1, formulated for oral administration to a subject.

7. A method of inducing an immunological response to a rotavirus in a subject, comprising:

administering a vaccine composition according to claim 1.

8. An immunogenic composition for inducing an immunological response against a rotavirus in a subject, comprising:

a pharmaceutically acceptable carrier admixed with an isolated rotavirus strain of CDC-9 or CDC-66 inactivated by inactivation treatment comprising UV light treatment; and an adjuvant in an amount that increases immunogenicity of the isolated rotavirus strain.

9. The immunogenic composition of claim 8 comprising at least two isolated rotavirus strains, wherein the adjuvant increases immunogenicity of the at least two isolated rotavirus strains.

* * * * *

UNITED STATES PATENT AND TRADEMARK OFFICE

CERTIFICATE OF CORRECTION

PATENT NO. : 9,498,526 B2
APPLICATION NO. : 14/461663
DATED : November 22, 2016
INVENTOR(S) : Baoming Jiang et al.

It is certified that error appears in the above-identified patent and that said Letters Patent is hereby corrected as shown below:

On the Title Page

(63) Related U.S. Application Data: Lines 2-3: replace "May 12, 2012" with --May 12, 2010--.

Signed and Sealed this
Fourteenth Day of February, 2017

Michelle K. Lee
*Director of the United States Patent and Trademark Office*

SEQUENCE LISTING

```
<160> NUMBER OF SEQ ID NOS: 132

<210> SEQ ID NO 1
<211> LENGTH: 486
<212> TYPE: PRT
<213> ORGANISM: Human rotavirus

<400> SEQUENCE: 1

Met Ala Thr Phe Lys Asp Ala Cys Tyr Tyr Tyr Lys Arg Ile Asn Lys
1               5                   10                  15

Leu Asn His Ala Val Leu Lys Leu Gly Val Asn Asp Thr Trp Arg Pro
            20                  25                  30

Ser Pro Pro Thr Lys Tyr Lys Gly Trp Cys Leu Asp Cys Cys Gln His
        35                  40                  45

Thr Asp Leu Thr Tyr Cys Arg Gly Cys Thr Met Tyr His Val Cys Gln
    50                  55                  60

Trp Cys Ser Gln Tyr Asp Arg Cys Phe Leu Asp Asn Gln Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
            100                 105                 110

Val Asp Lys Phe Ile Ser Ser Thr Arg Gln His Lys Cys Arg Asn Glu
        115                 120                 125

Cys Met Thr Gln Trp Tyr Asn His Leu Leu Met Pro Ile Thr Leu Gln
    130                 135                 140
```

-continued

```
Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
            180                 185                 190

Arg Met Ser Phe Leu Pro Val Ala Leu Gln Gln Glu Tyr Ala Leu Arg
        195                 200                 205

Tyr Phe Ser Lys Ser Arg Phe Ile Ser Glu Lys Arg Lys Cys Ile Ser
    210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Thr Tyr Phe Asn Val
            260                 265                 270

Leu Lys Thr Ser His Ile Glu Phe Tyr Ser Ile Ser Thr Arg Cys Arg
        275                 280                 285

Met Phe Thr Gln His Lys Leu Lys Ile Ala Ser Lys His Ile Lys Pro
    290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ser Asn Ile Gly His Cys Ser Ser Gln Glu Lys Ile
        355                 360                 365

Tyr Glu His Ile Lys Asp Val Leu Asp Val Cys Asp Asp Glu Lys Trp
    370                 375                 380

Lys Met Ala Val Ala Glu Ile Phe Asn Cys Leu Glu Pro Val Glu Leu
385                 390                 395                 400

Asp Thr Val Lys Tyr Val Leu Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Ile Met Lys Ser Ile Ile Tyr Glu Trp Phe
        435                 440                 445

Asp Ile Arg Tyr Met Arg Asn Thr Pro Met Thr Thr Phe Thr Val Asp
    450                 455                 460

Lys Leu Arg Gln Leu Cys Thr Gly Val Lys Thr Val Asp Tyr Asp Ser
465                 470                 475                 480

Gly Ile Ser Asp Val Glu
                485


<210> SEQ ID NO 2
<211> LENGTH: 486
<212> TYPE: PRT
<213> ORGANISM: Human rotavirus

<400> SEQUENCE: 2

Met Ala Thr Phe Lys Asp Ala Cys Tyr Tyr Tyr Lys Arg Ile Asn Lys
1               5                   10                  15

Leu Asn His Ala Val Leu Lys Leu Gly Val Asn Asp Thr Trp Arg Pro
            20                  25                  30
```

-continued

```
Ser Pro Pro Thr Lys Tyr Lys Gly Trp Cys Leu Asp Cys Cys Gln His
        35                  40                  45

Thr Asp Leu Thr Tyr Cys Arg Gly Cys Thr Met Tyr His Val Cys Gln
    50                  55                  60

Trp Cys Ser Gln Tyr Asp Arg Cys Phe Leu Asp Ser Gln Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
            100                 105                 110

Val Asp Lys Phe Ile Ser Ser Thr Arg Gln His Lys Cys Arg Asn Glu
        115                 120                 125

Cys Met Thr Gln Trp Tyr Asn His Leu Leu Met Pro Ile Thr Leu Gln
    130                 135                 140

Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
            180                 185                 190

Arg Met Ser Phe Leu Pro Val Ala Leu Gln Gln Glu Tyr Ala Leu Arg
        195                 200                 205

Tyr Phe Ser Lys Ser Arg Phe Ile Ser Glu Lys Arg Lys Cys Ile Ser
    210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Thr Tyr Phe Asn Val
            260                 265                 270

Leu Lys Thr Ser His Ile Glu Phe Tyr Ser Ile Ser Thr Arg Cys Arg
        275                 280                 285

Met Phe Thr Gln His Lys Leu Lys Ile Ala Ser Lys His Ile Lys Pro
    290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ser Asn Ile Gly His Cys Ser Ser Gln Glu Lys Ile
        355                 360                 365

Tyr Glu His Ile Lys Asp Val Leu Asp Val Cys Asp Asp Glu Lys Trp
    370                 375                 380

Lys Met Ala Val Ala Glu Ile Phe Asn Cys Leu Gly Pro Val Glu Leu
385                 390                 395                 400

Asp Thr Val Lys Tyr Val Met Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Ile Met Lys Ser Ile Ile Tyr Glu Trp Phe
        435                 440                 445
```

```
Asp Ile Arg Tyr Met Arg Asn Thr Pro Met Thr Thr Phe Thr Val Asp
    450                 455                 460

Lys Leu Arg Gln Leu Cys Thr Gly Met Lys Thr Val Asp Tyr Asp Ser
465                 470                 475                 480

Gly Ile Ser Asp Val Glu
                485


<210> SEQ ID NO 3
<211> LENGTH: 486
<212> TYPE: PRT
<213> ORGANISM: Human rotavirus

<400> SEQUENCE: 3

Met Ala Thr Phe Lys Asp Ala Cys Tyr Tyr Tyr Lys Arg Ile Asn Lys
1               5                   10                  15

Leu Asn His Ala Val Leu Lys Leu Gly Val Asn Asp Thr Trp Arg Pro
            20                  25                  30

Ser Pro Pro Thr Lys Tyr Lys Gly Trp Cys Leu Asp Cys Cys Gln His
        35                  40                  45

Thr Asp Leu Thr Tyr Cys Arg Gly Cys Thr Met Tyr His Val Cys Gln
    50                  55                  60

Trp Cys Ser Gln Tyr Asp Arg Cys Phe Leu Asp Ser Gln Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
            100                 105                 110

Val Asp Lys Phe Ile Ser Ser Thr Arg Arg His Lys Cys Arg Asn Glu
        115                 120                 125

Cys Met Thr Gln Trp Tyr Asn His Leu Leu Met Pro Ile Thr Leu Gln
    130                 135                 140

Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
            180                 185                 190

Arg Met Ser Phe Leu Pro Val Ala Leu Gln Gln Glu Tyr Ala Leu Arg
        195                 200                 205

Tyr Phe Ser Lys Ser Arg Phe Ile Ser Glu Lys Arg Lys Cys Ile Ser
    210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Thr Tyr Phe Asn Val
            260                 265                 270

Leu Lys Thr Ser His Ile Glu Phe Tyr Ser Ile Ser Thr Arg Cys Arg
        275                 280                 285

Met Phe Thr Gln His Lys Leu Lys Ile Ala Ser Lys His Ile Lys Pro
    290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335
```

```
Arg Ile Lys Lys Ile Tyr Asp Asn Ile Phe Asn Phe Leu Arg Ala Leu
            340                 345                 350

Val Lys Ser Asn Ser Asn Ile Gly His Cys Ser Ser Gln Glu Lys Ile
        355                 360                 365

Tyr Glu His Ile Lys Asp Val Leu Asp Val Cys Asp Asp Glu Lys Trp
    370                 375                 380

Lys Met Ala Val Ala Glu Ile Phe Asn Cys Leu Gly Pro Val Glu Leu
385                 390                 395                 400

Asp Thr Val Lys Tyr Val Met Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Ile Met Lys Ser Ile Ile Tyr Glu Trp Phe
        435                 440                 445

Asp Ile Arg Tyr Met Arg Asn Thr Pro Met Thr Thr Phe Thr Val Asp
    450                 455                 460

Lys Leu Arg Gln Leu Cys Thr Gly Met Lys Thr Val Asp Tyr Asp Ser
465                 470                 475                 480

Gly Ile Ser Asp Val Glu
                485


<210> SEQ ID NO 4
<211> LENGTH: 317
<212> TYPE: PRT
<213> ORGANISM: Human rotavirus

<400> SEQUENCE: 4

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Ile
        35                  40                  45

Tyr Gly Ile Ala Pro Pro Pro Gln Phe Lys Lys Arg Tyr Asn Thr Asn
    50                  55                  60

Asp Asn Ser Arg Gly Met Asn Tyr Glu Thr Pro Met Leu Ile Lys Val
65                  70                  75                  80

Ala Ile Leu Ile Cys Glu Ala Leu Asn Ser Ile Lys Val Thr Gln Ser
                85                  90                  95

Asp Val Ala Asn Val Leu Ser Arg Val Val Ser Val Arg His Leu Glu
            100                 105                 110

Asn Leu Val Leu Arg Lys Glu Asn His Gln Asp Val Leu Phe His Ser
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Val Ala Phe Thr Met Trp Lys Leu Thr Tyr Leu Asp His Lys Leu
                165                 170                 175

Met Pro Ile Leu Asp Gln Asn Phe Ile Glu Tyr Lys Ile Thr Met Asn
            180                 185                 190

Glu Asp Lys Pro Ile Ser Asp Val His Val Lys Glu Leu Ile Ala Glu
        195                 200                 205

Leu Arg Trp Gln Tyr Asn Arg Phe Ala Val Ile Thr His Gly Lys Gly
```

```
    210                 215                 220

His Tyr Arg Val Val Lys Tyr Ser Ser Val Ala Asn His Ala Asp Arg
225                 230                 235                 240

Val Phe Ala Thr Tyr Lys Asn Asn Ala Lys Ser Gly Asn Val Ile Asp
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Phe Thr Leu Asp Val Cys Lys Lys Leu
        275                 280                 285

Leu Phe Gln Lys Met Lys Gln Glu Arg Asn Pro Phe Lys Gly Leu Ser
    290                 295                 300

Thr Asp Arg Lys Met Asp Glu Val Ser Arg Ile Gly Ile
305                 310                 315


<210> SEQ ID NO 5
<211> LENGTH: 317
<212> TYPE: PRT
<213> ORGANISM: Human rotavirus

<400> SEQUENCE: 5

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Val
        35                  40                  45

Tyr Gly Ile Ala Pro Pro Pro Gln Phe Arg Lys Arg Tyr Asn Thr Ser
    50                  55                  60

Asp Asn Ser Arg Gly Met Asn Tyr Glu Thr Ile Met Phe Asn Lys Val
65                  70                  75                  80

Ala Ile Leu Ile Cys Glu Ala Leu Asn Ser Ile Lys Val Thr Gln Ser
                85                  90                  95

Glu Val Ala Asn Val Leu Ser Arg Val Val Ser Val Arg His Leu Glu
            100                 105                 110

Asn Leu Val Leu Arg Lys Glu Asn His Gln Asp Val Leu Phe His Ser
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Asp His Lys Leu
                165                 170                 175

Met Pro Ile Leu Asp Gln Asn Phe Ile Glu Tyr Lys Ile Thr Leu Asn
            180                 185                 190

Glu Asp Lys Pro Ile Ser Asp Val Cys Val Lys Glu Leu Val Ala Glu
        195                 200                 205

Leu Arg Trp Gln Tyr Asn Arg Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Phe Ala Thr Tyr Lys Asn Asn Ala Lys Ser Gly Asn Thr Thr Asp
                245                 250                 255

Phe Asn Leu Leu Asp Gln Arg Ile Ile Trp Gln Asn Trp Tyr Ala Phe
            260                 265                 270
```

-continued

Thr Ser Ser Met Lys Gln Gly Asn Thr Ile Asp Val Cys Lys Lys Leu
275 280 285

Leu Phe Gln Lys Met Lys Gln Glu Lys Asn Pro Phe Lys Gly Leu Ser
290 295 300

Thr Asp Arg Lys Met Asp Glu Val Ser His Val Gly Ile
305 310 315

<210> SEQ ID NO 6
<211> LENGTH: 317
<212> TYPE: PRT
<213> ORGANISM: Human rotavirus

<400> SEQUENCE: 6

Met Ala Glu Leu Ala Cys Phe Cys Tyr Pro His Leu Glu Asn Asp Ser
1 5 10 15

Tyr Lys Phe Ile Pro Phe Asn Asn Leu Ala Ile Lys Cys Met Leu Thr
20 25 30

Ala Lys Val Asp Lys Lys Asp Gln Asp Lys Phe Tyr Asn Ser Ile Val
35 40 45

Tyr Gly Ile Ala Pro Pro Pro Gln Phe Arg Lys Arg Tyr Asn Thr Ser
50 55 60

Asp Asn Ser Arg Gly Met Asn Tyr Glu Thr Ile Met Phe Asn Lys Val
65 70 75 80

Ala Ile Leu Ile Cys Glu Ala Leu Asn Ser Ile Lys Val Thr Gln Ser
85 90 95

Glu Val Ala Asn Val Leu Ser Arg Val Val Ser Val Arg His Leu Glu
100 105 110

Asn Leu Val Leu Arg Lys Glu Asn His Gln Asp Val Leu Phe His Ser
115 120 125

Lys Glu Leu Leu Leu Lys Ser Val Leu Ile Ala Ile Gly Gln Ser Lys
130 135 140

Glu Ile Glu Thr Thr Ala Thr Ala Glu Gly Gly Glu Ile Val Phe Gln
145 150 155 160

Asn Ala Ala Phe Thr Met Trp Lys Leu Thr Tyr Leu Asp His Lys Leu
165 170 175

Met Pro Ile Leu Asp Gln Asn Phe Ile Glu Tyr Lys Ile Thr Leu Asn
180 185 190

Glu Asp Lys Pro Ile Ser Asp Val Cys Val Lys Glu Leu Val Ala Glu
195 200 205

Leu Arg Trp Gln Tyr Asn Arg Phe Ala Val Ile Thr His Gly Lys Gly
210 215 220

His Tyr Arg Val Val Lys Tyr Ser Ser Val Ala Asn His Ala Asp Arg
225 230 235 240

Val Phe Ala Thr Tyr Lys Asn Asn Ala Lys Ser Gly Asn Thr Thr Asp
245 250 255

Phe Asn Leu Leu Asp Gln Arg Ile Ile Trp Gln Asn Trp Tyr Ala Phe
260 265 270

Thr Ser Ser Met Lys Gln Gly Asn Thr Ile Asp Val Cys Lys Lys Leu
275 280 285

Leu Phe Gln Lys Met Lys Gln Glu Lys Asn Pro Phe Lys Gly Leu Ser
290 295 300

Thr Asp Arg Lys Met Asp Glu Val Ser His Val Gly Ile
305 310 315

<210> SEQ ID NO 7

-continued

```
<211> LENGTH: 310
<212> TYPE: PRT
<213> ORGANISM: Human rotavirus

<400> SEQUENCE: 7

Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30

Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Gly Pro Ala Cys Asn Glu Lys Phe Gly Ser Ala Ile Arg
65                  70                  75                  80

Asn Arg Asn Trp Met Ile Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Thr Arg Leu Met Lys Asp Lys Leu
    130                 135                 140

Glu Arg Gly Glu Val Glu Val Asp Asp Ser Tyr Val Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Asn Glu Lys Tyr Asn Ala Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Val Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Thr Asp Val Glu Gln Gln Leu Asn Ser Ile Asp Leu Ile Asn Pro Ile
            260                 265                 270

Gly Ala Ile Asp Asp Ile Glu Ser Leu Ile Arg Asn Leu Ile Gln Asp
        275                 280                 285

Tyr Asp Arg Thr Phe Leu Met Leu Lys Gly Leu Leu Lys Gln Cys Asn
    290                 295                 300

Tyr Glu Tyr Ala Tyr Glu
305                 310


<210> SEQ ID NO 8
<211> LENGTH: 310
<212> TYPE: PRT
<213> ORGANISM: Human rotavirus

<400> SEQUENCE: 8

Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30
```

```
Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Asp Gln Ala Leu Asn Gly Lys Phe Gly Ser Ala Ile Arg
65                  70                  75                  80

Asn Arg Asn Trp Met Thr Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Thr Lys Leu Met Lys Asp Lys Ile
    130                 135                 140

Glu Arg Gly Glu Val Glu Val Asp Asp Ser Tyr Ile Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Thr Glu Lys Tyr Asn Thr Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Thr Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Val Arg Asn Leu Val Gln Asp
        275                 280                 285

Tyr Asp Arg Thr Phe Leu Met Leu Lys Gly Leu Leu Lys Gln Cys Asn
    290                 295                 300

Tyr Glu Tyr Val Tyr Glu
305                 310
```

<210> SEQ ID NO 9
<211> LENGTH: 310
<212> TYPE: PRT
<213> ORGANISM: Human rotavirus

<400> SEQUENCE: 9

```
Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30

Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Asp Gln Ala Leu Asn Gly Lys Phe Gly Ser Ala Ile Arg
65                  70                  75                  80

Asn Arg Asn Trp Met Thr Asp Ser Lys Thr Val Ala Lys Leu Asp Glu
```

```
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Thr Lys Leu Met Lys Asp Lys Ile
    130                 135                 140

Glu Arg Gly Glu Val Glu Val Asp Asp Ser Tyr Ile Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Thr Glu Lys Tyr Asn Thr Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Thr Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Val Arg Asn Leu Val Gln Asp
        275                 280                 285

Tyr Asp Arg Thr Phe Leu Met Leu Lys Gly Leu Leu Lys Gln Cys Asn
    290                 295                 300

Tyr Glu Tyr Val Tyr Glu
305                 310


<210> SEQ ID NO 10
<211> LENGTH: 175
<212> TYPE: PRT
<213> ORGANISM: Human rotavirus

<400> SEQUENCE: 10

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Thr Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Ile Val Thr Ile Ile Asn Thr Leu Leu
65                  70                  75                  80

Arg Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Ser Ile His Asp Asn Leu Ile Thr Arg Ser Val Asp Val Ile Asp Met
    130                 135                 140
```

```
Ser Lys Glu Phe Asn Gln Lys Asn Ile Lys Thr Leu Asp Glu Trp Glu
145                 150                 155                 160

Ser Gly Arg Asn Pro Tyr Glu Pro Ser Glu Val Thr Ala Ser Met
                165                 170                 175


<210> SEQ ID NO 11
<211> LENGTH: 175
<212> TYPE: PRT
<213> ORGANISM: Human rotavirus

<400> SEQUENCE: 11

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Ile Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile Tyr Asp Asn Leu Ile Thr Arg Pro Val Asp Ile Val Asp Met
    130                 135                 140

Thr Lys Glu Phe Asn Gln Lys Asn Ile Lys Thr Leu Asp Glu Trp Glu
145                 150                 155                 160

Ser Gly Lys Asn Pro Tyr Glu Pro Ile Glu Val Thr Ala Ser Met
                165                 170                 175


<210> SEQ ID NO 12
<211> LENGTH: 175
<212> TYPE: PRT
<213> ORGANISM: Human rotavirus

<400> SEQUENCE: 12

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Ile Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125
```

Arg Ile Tyr Asp Asn Leu Ile Thr Arg Pro Val Asp Ile Val Asp Met
    130                 135                 140

Thr Lys Glu Phe Asn Gln Lys Asn Ile Lys Thr Leu Asp Glu Trp Glu
145                 150                 155                 160

Ser Gly Lys Asn Pro Tyr Glu Pro Ile Glu Val Thr Ala Ser Met
                165                 170                 175

<210> SEQ ID NO 13
<211> LENGTH: 197
<212> TYPE: PRT
<213> ORGANISM: Human rotavirus

<400> SEQUENCE: 13

Met Ser Leu Ser Ile Asp Val Thr Ser Leu Pro Ser Ile Ser Ser Ser
1               5                   10                  15

Ile Phe Lys Asn Glu Ser Ser Ser Thr Thr Ser Thr Leu Ser Gly Lys
            20                  25                  30

Ser Ile Gly Arg Asn Glu Gln Tyr Val Ser Pro Asp Ile Asp Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Met Asp Phe Ser Leu
            100                 105                 110

Asn Lys Gly Ile Asn Val Ser Ala Ser Leu Asp Ser Cys Val Ser Ile
        115                 120                 125

Ser Thr Asn Gln Lys Lys Glu Lys Ser Lys Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Asp Gly Lys Cys Lys Asn Cys Lys Tyr Lys
                165                 170                 175

Lys Lys Tyr Phe Ala Leu Arg Met Arg Met Lys Gln Val Ala Met Gln
            180                 185                 190

Leu Ile Glu Asp Leu
        195

<210> SEQ ID NO 14
<211> LENGTH: 197
<212> TYPE: PRT
<213> ORGANISM: Human rotavirus

<400> SEQUENCE: 14

Met Ser Leu Ser Ile Asp Val Thr Ser Leu Pro Ser Ile Ser Ser Ser
1               5                   10                  15

Ile Phe Lys Asn Glu Ser Ser Ser Thr Thr Ser Thr Leu Ser Gly Lys
            20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

```
Val Lys Thr Asn Ala Asp Ala Gly Val Ser Met Asp Ser Ser Thr Gln
                85                  90                  95

Ser Arg Pro Ser Ser Asn Val Gly Cys Asp Gln Leu Asp Phe Ser Leu
            100                 105                 110

Thr Lys Gly Ile Asn Val Ser Ala Asn Leu Asp Ser Cys Ile Ser Ile
        115                 120                 125

Ser Thr Asp His Lys Lys Glu Lys Ser Lys Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Asp Gly Lys Cys Lys Asn Cys Lys Tyr Lys
                165                 170                 175

Lys Lys Tyr Phe Ala Leu Arg Met Arg Met Lys Arg Val Ala Met Gln
            180                 185                 190

Leu Ile Glu Asp Leu
        195


<210> SEQ ID NO 15
<211> LENGTH: 197
<212> TYPE: PRT
<213> ORGANISM: Human rotavirus

<400> SEQUENCE: 15

Met Ser Leu Ser Ile Asp Val Thr Ser Leu Pro Ser Ile Ser Ser Ser
1               5                   10                  15

Ile Phe Lys Asn Glu Ser Ser Ser Thr Thr Ser Thr Leu Ser Gly Lys
            20                  25                  30

Ser Ile Gly Arg Ser Glu Gln Tyr Ile Ser Pro Asp Val Glu Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Leu Asp Phe Ser Leu
            100                 105                 110

Thr Lys Gly Ile Asn Val Ser Ala Asn Leu Asp Ser Cys Ile Ser Ile
        115                 120                 125

Ser Thr Asp His Lys Lys Glu Lys Ser Lys Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Asp Gly Lys Cys Lys Asn Cys Lys Tyr Lys
                165                 170                 175

Lys Lys Tyr Phe Ala Leu Arg Met Arg Met Lys Arg Val Ala Met Gln
            180                 185                 190

Leu Ile Glu Asp Leu
        195


<210> SEQ ID NO 16
<211> LENGTH: 1088
<212> TYPE: PRT
<213> ORGANISM: Human rotavirus

<400> SEQUENCE: 16
```

-continued

```
Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Thr Arg Cys Ile Glu Phe His Ala Lys Cys Val Asp Asn
        35                  40                  45

Ser Lys Lys Gly Leu Ser Leu Lys Pro Leu Phe Glu Glu Tyr Lys Asp
    50                  55                  60

Val Thr Asp Asn Ala Thr Leu Leu Ser Ile Leu Ser Tyr Ser Tyr Asp
65                  70                  75                  80

Lys Tyr Asn Ala Val Glu Arg Lys Leu Val Ser Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Ile Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Thr Phe Asp Glu Leu
        275                 280                 285

Gln Glu Met Ile Asn Asn Met Lys Lys Ile Gly Leu Val Asp Ile Pro
    290                 295                 300

Arg Met Ile Gln Glu Trp Leu Ile Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Lys Asp Val Asp Asp Glu Met Tyr Asn Glu Tyr Thr Met Leu Ile Arg
        355                 360                 365

Asp Glu Ile Val Lys Met Leu Glu Ile Pro Val Lys His Asp Asp His
    370                 375                 380

Leu Leu Arg Asp Ser Glu Leu Ala Gly Leu Leu Ser Met Ser Ser Ala
385                 390                 395                 400

Ser Asn Gly Glu Ser Arg Gln Ile Lys Phe Gly Arg Lys Thr Ile Phe
                405                 410                 415

Ser Thr Lys Lys Asn Met His Val Met Asp Asp Ile Ala His Gly Lys
```

-continued

```
            420                 425                 430

Tyr Thr Pro Gly Val Ile Pro Pro Val Asn Val Asp Lys Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Leu Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Ser
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Met
    530                 535                 540

Leu Ser Asn Met Thr Asn Asp Pro Lys Val Val Gln Ala Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Asn Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ala Asn Lys Tyr Ser Phe Ile Thr Lys
    610                 615                 620

Ile Ile Arg Val Ser Gly Asp Asp Asn Tyr Ala Val Leu Gln Phe Asn
625                 630                 635                 640

Thr Asp Leu Thr Lys Gln Met Ile Gln Asp Val Ser Asn Asp Val Arg
                645                 650                 655

Tyr Ile Tyr Phe Arg Met Asn Ala Lys Val Lys Ala Leu Val Ser Thr
            660                 665                 670

Val Gly Ile Glu Ile Ala Lys Arg Tyr Leu Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Ile Leu Thr Lys Ile
                725                 730                 735

Ile Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Ser Lys Leu Ser
                805                 810                 815

Asp Gln Leu Leu Val Ser Lys Asn Val Ile Val Ser Lys Gly Ile Ala
            820                 825                 830

Val Thr Glu Lys Ala Lys Leu Asn Ser Tyr Ala Pro Ile Tyr Leu Glu
        835                 840                 845
```

Lys Arg Arg Ala Gln Ile Ser Ala Leu Leu Thr Met Leu Gln Lys Pro
    850                 855                 860

Val Ser Phe Lys Ser Asn Lys Asn Thr Ile Asn Glu Ile Leu Arg Asp
865                 870                 875                 880

Ile Lys Pro Phe Phe Val Thr Thr Glu Asp Asn Leu Pro Ile Gln Tyr
                885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
        915                 920                 925

Ser Ile Ser Lys Leu Ile Ser Lys Tyr Ser Val Tyr Lys Pro Ser Ile
    930                 935                 940

Glu Glu Leu Tyr Lys Val Ile Ser Leu Arg Glu Gln Glu Ile Gln Leu
945                 950                 955                 960

Tyr Leu Val Ser Leu Gly Val Pro Leu Val Asp Ala Ser Ala Tyr Val
                965                 970                 975

Ala Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Ile Ile Asn Tyr Ala  Ile Lys Asn Arg Ala  Trp Ile Ser
    1040                1045                1050

Val Phe  Cys Asn Tyr Pro Lys  Ser Glu Met Ile Lys  Leu Trp Lys
    1055                1060                1065

Lys Met  Trp Ser Ile Thr Ala  Leu Arg Ser Pro Tyr  Thr Ser Ala
    1070                1075                1080

Asn Phe  Phe Gln Asp
    1085

<210> SEQ ID NO 17
<211> LENGTH: 1088
<212> TYPE: PRT
<213> ORGANISM: Human rotavirus

<400> SEQUENCE: 17

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Lys Arg Cys Ile Glu Phe His Ala Lys Cys Val Asp Ser
        35                  40                  45

Ser Lys Lys Gly Met Ser Leu Lys Pro Leu Phe Glu Glu Tyr Lys Asp
    50                  55                  60

Val Ile Asp Asn Ala Thr Leu Leu Ser Ile Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser

-continued

```
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Ile Leu Ser Tyr Ser Asn Arg Ser Thr Leu
225                 230                 235                 240

Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Ile Phe Asp Glu Leu
        275                 280                 285

Gln Glu Met Ile Asp Asn Met Lys Lys Val Gly Leu Val Asp Ile Pro
    290                 295                 300

Arg Met Ile Gln Glu Trp Leu Val Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Glu Asp Val Asp Gly Glu Met Tyr Asn Glu Tyr Thr Met Leu Ile Arg
        355                 360                 365

Asp Glu Ile Val Lys Met Leu Glu Val Pro Val Lys His Asp Asp His
    370                 375                 380

Leu Leu Arg Asp Ser Glu Leu Ala Gly Leu Leu Ser Met Ser Ser Ala
385                 390                 395                 400

Ser Asn Gly Glu Ser Arg Gln Leu Lys Phe Gly Leu Lys Thr Ile Phe
                405                 410                 415

Ser Thr Lys Lys Asn Met His Val Met Asp Asp Ile Ala His Gly Arg
            420                 425                 430

Tyr Thr Pro Gly Ile Ile Pro Pro Val Asn Val Asp Arg Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ser Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Ser
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Met
    530                 535                 540
```

-continued

```
Leu Ser Asn Met Thr Asn Asp Pro Lys Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ala Asn Lys Tyr Ser Phe Ile Thr Lys
    610                 615                 620

Ile Ile Arg Val Asp Gly Asp Asp Asn Tyr Ala Val Leu Gln Phe Asn
625                 630                 635                 640

Thr Asp Val Thr Lys Gln Met Val Gln Asp Val Ser Asn Asp Val Arg
                645                 650                 655

His Ile Tyr Ser Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Ile Leu Thr Lys Ile
                725                 730                 735

Ile Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Asn Lys Leu Ser
                805                 810                 815

Asp Gln Leu Leu Ile Ser Lys Asn Val Ile Val Ser Lys Gly Ile Ala
            820                 825                 830

Val Thr Glu Lys Ala Lys Leu Asn Ser Tyr Ala Pro Val Tyr Leu Glu
        835                 840                 845

Lys Arg Arg Ala Gln Ile Ser Ala Leu Leu Thr Met Leu Gln Lys Pro
    850                 855                 860

Val Ser Phe Lys Ser Asn Lys Ile Thr Ile Asn Asp Ile Leu Arg Asp
865                 870                 875                 880

Ile Lys Pro Phe Phe Val Thr Ser Glu Ala Asn Leu Pro Ile Gln Tyr
                885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
        915                 920                 925

Ser Ile Ser Lys Leu Ile Ser Lys Tyr Ser Val Tyr Lys Pro Ser Ile
    930                 935                 940

Glu Glu Leu Tyr Lys Val Ile Ser Leu Arg Glu Gln Glu Ile Gln Leu
945                 950                 955                 960
```

-continued

```
Tyr Leu Val Ser Leu Gly Val Pro Pro Val Asp Ala Gly Thr Tyr Val
                965                 970                 975

Gly Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
        995                 1000                 1005

Phe Asn  Ser Pro Asp Leu Glu  Lys Leu Ile Arg Ile  Pro Phe Lys
    1010                 1015                 1020

Gly Lys  Ile Pro Ala Val Thr  Phe Ile Leu His Leu  Tyr Ala Lys
    1025                 1030                 1035

Leu Glu  Ile Ile Asn His Ala  Ile Lys Asn Gly Ala  Trp Ile Ser
    1040                 1045                 1050

Leu Phe  Cys Asn Tyr Pro Lys  Ser Glu Met Ile Lys  Leu Trp Lys
    1055                 1060                 1065

Lys Met  Trp Asn Ile Thr Ala  Leu Arg Ser Pro Tyr  Thr Ser Ala
    1070                 1075                 1080

Asn Phe  Phe Gln Asp
    1085


<210> SEQ ID NO 18
<211> LENGTH: 1088
<212> TYPE: PRT
<213> ORGANISM: Human rotavirus

<400> SEQUENCE: 18

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Lys Arg Cys Ile Glu Phe His Ala Lys Cys Val Asp Ser
        35                  40                  45

Ser Lys Lys Gly Met Ser Leu Lys Pro Leu Phe Glu Glu Tyr Lys Asp
    50                  55                  60

Val Ile Asp Asn Ala Thr Leu Leu Ser Ile Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Ile Leu Ser Tyr Ser Asn Arg Ser Thr Leu
225                 230                 235                 240
```

-continued

```
Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Ile Phe Asp Glu Leu
        275                 280                 285

Gln Glu Met Ile Asp Asn Met Lys Lys Val Gly Leu Val Asp Ile Pro
    290                 295                 300

Arg Met Ile Gln Glu Trp Leu Val Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Glu Asp Val Asp Gly Glu Met Tyr Asn Glu Tyr Thr Met Leu Ile Arg
        355                 360                 365

Asp Glu Ile Val Lys Met Leu Glu Val Pro Val Lys His Asp Asp His
    370                 375                 380

Leu Leu Arg Asp Ser Glu Leu Ala Gly Leu Leu Ser Met Ser Ser Ala
385                 390                 395                 400

Ser Asn Gly Glu Ser Arg Gln Leu Lys Phe Gly Leu Lys Thr Ile Phe
                405                 410                 415

Ser Thr Lys Lys Asn Met His Val Met Asp Asp Ile Ala His Gly Arg
            420                 425                 430

Tyr Thr Pro Gly Ile Ile Pro Pro Val Asn Val Asp Arg Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ser Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Ser
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Met
    530                 535                 540

Leu Ser Asn Met Thr Asn Asp Pro Lys Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ala Asn Lys Tyr Ser Phe Ile Thr Lys
    610                 615                 620

Ile Ile Arg Val Asp Gly Asp Asp Asn Tyr Ala Val Leu Gln Phe Asn
625                 630                 635                 640

Thr Asp Val Thr Lys Gln Met Val Gln Asp Val Ser Asn Asp Val Arg
                645                 650                 655
```

```
His Ile Tyr Ser Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Ile Leu Thr Lys Ile
                725                 730                 735

Ile Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Asn Lys Leu Ser
                805                 810                 815

Asp Gln Leu Leu Ile Ser Lys Asn Val Ile Val Ser Lys Gly Ile Ala
            820                 825                 830

Val Thr Glu Lys Ala Lys Leu Asn Ser Tyr Ala Pro Val Tyr Leu Glu
        835                 840                 845

Lys Arg Arg Ala Gln Ile Ser Ala Leu Leu Thr Met Leu Gln Lys Pro
    850                 855                 860

Val Ser Phe Lys Ser Asn Lys Ile Thr Ile Asn Asp Ile Leu Arg Asp
865                 870                 875                 880

Ile Lys Pro Phe Phe Val Thr Ser Glu Ala Asn Leu Pro Ile Gln Tyr
                885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
        915                 920                 925

Ser Ile Ser Lys Leu Ile Ser Lys Tyr Ser Val Tyr Lys Pro Ser Ile
    930                 935                 940

Glu Glu Leu Tyr Lys Val Ile Ser Leu Arg Glu Gln Glu Ile Gln Leu
945                 950                 955                 960

Tyr Leu Val Ser Leu Gly Val Pro Pro Val Asp Ala Gly Thr Tyr Val
                965                 970                 975

Gly Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Ile Ile Asn His Ala  Ile Lys Asn Gly Ala  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ala  Leu Arg Ser Pro Tyr  Thr Ser Ala
```

1070 1075 1080

Asn Phe Phe Gln Asp
1085

<210> SEQ ID NO 19
<211> LENGTH: 900
<212> TYPE: PRT
<213> ORGANISM: Human rotavirus

<400> SEQUENCE: 19

Met Ala Tyr Arg Lys Arg Gly Thr Lys Arg Glu Asp Leu Pro Gln Gln
1 5 10 15

Asn Glu Arg Leu Gln Glu Lys Glu Ile Glu Asn Asn Ile Asp Val Thr
20 25 30

Met Glu Asn Lys Asn Lys Asn Ile Asn Lys Asn Asn Asn Lys Asn Asn
35 40 45

Asn Arg Lys Gln Gln Leu Ser Asp Lys Val Leu Leu Gln Lys Glu Glu
50 55 60

Ile Ile Thr Asp Val Gln Asp Asp Ile Lys Ile Thr Asp Glu Val Lys
65 70 75 80

Lys Ser Ser Lys Glu Glu Ser Lys Gln Leu Leu Glu Ile Leu Lys Thr
85 90 95

Lys Glu Asp His Gln Lys Glu Val Gln Tyr Glu Ile Leu Gln Lys Thr
100 105 110

Ile Pro Thr Phe Glu Pro Lys Glu Ser Ile Leu Lys Lys Leu Glu Asp
115 120 125

Ile Arg Pro Glu Gln Ala Lys Lys Gln Met Lys Leu Phe Arg Ile Phe
130 135 140

Glu Pro Arg Gln Leu Pro Ile Tyr Arg Ala Asn Gly Glu Lys Glu Leu
145 150 155 160

Arg Asn Arg Trp Tyr Trp Lys Leu Lys Lys Asp Thr Leu Pro Asp Gly
165 170 175

Asp Tyr Asp Val Arg Glu Tyr Phe Leu Asn Leu Tyr Asp Gln Ile Leu
180 185 190

Ile Glu Met Pro Asp Tyr Leu Leu Leu Lys Asp Met Ala Val Glu Asn
195 200 205

Lys Asn Ser Arg Asp Ala Gly Lys Val Val Asp Ser Glu Thr Ala Ser
210 215 220

Ile Cys Asp Ala Ile Phe Gln Asp Glu Glu Thr Glu Gly Val Ile Arg
225 230 235 240

Arg Phe Ile Ala Asp Met Arg Gln Gln Ile Gln Ala Asp Arg Asn Ile
245 250 255

Val Asn Tyr Pro Ser Ile Leu His Pro Ile Asp His Ala Phe Asn Glu
260 265 270

Tyr Phe Leu Asn His Gln Leu Val Glu Pro Leu Asn Asn Asp Ile Ile
275 280 285

Phe Asn Tyr Ile Pro Glu Arg Ile Arg Asn Asp Val Asn Tyr Ile Leu
290 295 300

Asn Met Asp Met Asn Leu Pro Ser Thr Ala Arg Tyr Ile Arg Pro Asn
305 310 315 320

Leu Leu Gln Asp Arg Leu Asn Leu His Asp Asn Phe Glu Ser Leu Trp
325 330 335

Asp Thr Ile Thr Thr Ser Asn Tyr Ile Leu Ala Arg Ser Val Val Pro
340 345 350

-continued

```
Asp Leu Lys Glu Lys Glu Leu Val Ser Thr Glu Ala Gln Ile Gln Lys
        355                 360                 365

Met Ser Gln Asp Leu Gln Leu Glu Ala Leu Thr Ile Gln Ser Glu Thr
    370                 375                 380

Gln Phe Leu Ala Gly Ile Asn Ser Gln Ala Ala Asn Asp Cys Phe Lys
385                 390                 395                 400

Thr Leu Ile Ala Ala Met Leu Ser Gln Arg Thr Met Ser Leu Asp Phe
                405                 410                 415

Val Thr Thr Asn Tyr Met Ser Leu Ile Ser Gly Met Trp Leu Leu Thr
            420                 425                 430

Val Ile Pro Asn Asp Met Phe Leu Arg Glu Ser Leu Val Ala Cys Glu
        435                 440                 445

Leu Ala Ile Ile Asn Thr Ile Val Tyr Pro Ala Phe Gly Met Gln Arg
    450                 455                 460

Met His Tyr Arg Asn Gly Asp Pro Gln Thr Pro Phe Gln Ile Ala Glu
465                 470                 475                 480

Gln Gln Ile Gln Asn Phe Gln Val Ala Asn Trp Leu His Phe Ile Asn
                485                 490                 495

Asn Asn Arg Phe Arg Gln Val Val Ile Asp Gly Val Leu Asn Gln Thr
            500                 505                 510

Leu Asn Asp Asn Ile Arg Asn Gly Gln Val Ile Asn Gln Leu Met Glu
        515                 520                 525

Ala Leu Met Gln Leu Ser Arg Gln Gln Phe Pro Thr Met Pro Val Asp
    530                 535                 540

Tyr Lys Arg Ser Ile Gln Arg Gly Ile Leu Leu Leu Ser Asn Arg Leu
545                 550                 555                 560

Gly Gln Leu Val Asp Leu Thr Arg Leu Leu Ser Tyr Asn Tyr Glu Thr
                565                 570                 575

Leu Met Ala Cys Ile Thr Met Asn Met Gln His Val Gln Thr Leu Thr
            580                 585                 590

Thr Glu Arg Leu Gln Leu Thr Ser Val Thr Ser Leu Cys Met Leu Ile
        595                 600                 605

Gly Asn Thr Thr Val Ile Pro Ser Pro Gln Thr Leu Phe His Tyr Tyr
    610                 615                 620

Asn Ile Asn Val Asn Phe His Ser Asn Tyr Asn Glu Arg Ile Asn Asp
625                 630                 635                 640

Ala Val Ala Ile Ile Thr Ala Ala Asn Arg Leu Asn Leu Tyr Gln Lys
                645                 650                 655

Lys Met Lys Ser Ile Val Glu Asp Phe Leu Lys Arg Leu Gln Ile Phe
            660                 665                 670

Asp Val Pro Arg Val Pro Asp Asp Gln Met Tyr Arg Leu Arg Asp Arg
        675                 680                 685

Leu Arg Leu Leu Pro Val Glu Arg Arg Arg Leu Asp Ile Phe Asn Leu
    690                 695                 700

Ile Leu Met Asn Met Glu Gln Ile Glu Arg Ala Ser Asp Lys Ile Ala
705                 710                 715                 720

Gln Gly Val Ile Ile Ala Tyr Arg Asp Met Gln Leu Glu Arg Asp Glu
                725                 730                 735

Met Tyr Gly Phe Val Asn Ile Ala Arg Asn Leu Asp Gly Tyr Gln Gln
            740                 745                 750

Ile Asn Leu Glu Glu Leu Met Arg Thr Gly Asp Tyr Gly Gln Ile Thr
        755                 760                 765

Thr Met Leu Leu Asn Asn Gln Pro Val Ala Leu Val Gly Ala Leu Pro
```

770 775 780

Phe Val Thr Asp Ser Ser Val Ile Ser Leu Ile Ala Lys Leu Asp Ala
785 790 795 800

Thr Val Phe Ala Gln Ile Val Lys Leu Arg Lys Val Asp Thr Leu Lys
805 810 815

Pro Ile Leu Tyr Lys Ile Asn Ser Asp Ser Asn Asp Phe Tyr Leu Val
820 825 830

Ala Asn Tyr Asp Trp Ile Pro Thr Ser Thr Thr Lys Val Tyr Lys Gln
835 840 845

Val Pro Gln Pro Phe Asp Phe Arg Ala Ser Met His Met Leu Thr Ser
850 855 860

Asn Leu Thr Phe Thr Val Tyr Ser Asp Leu Leu Ser Phe Val Ser Ala
865 870 875 880

Asp Thr Val Glu Pro Ile Asn Ala Ile Ala Phe Asp Asn Met Arg Ile
885 890 895

Met Asn Glu Leu
900

<210> SEQ ID NO 20
<211> LENGTH: 900
<212> TYPE: PRT
<213> ORGANISM: Human rotavirus

<400> SEQUENCE: 20

Met Ala Tyr Arg Lys Arg Gly Thr Lys Arg Glu Asp Leu Pro Gln Gln
1 5 10 15

Asn Glu Arg Leu Gln Glu Lys Glu Ile Glu Asn Asn Ile Asp Val Thr
20 25 30

Met Glu Asn Lys Asn Lys Asn Ile Asn Lys Asn Asn Asn Arg Asn Asn
35 40 45

Asn Arg Lys Gln Gln Leu Ser Asp Lys Val Leu Ser Gln Lys Glu Glu
50 55 60

Ile Ile Thr Asp Val Gln Asp Asp Ile Lys Ile Thr Asp Glu Val Lys
65 70 75 80

Lys Ser Ser Lys Glu Glu Ser Lys Gln Leu Leu Glu Ile Leu Lys Thr
85 90 95

Lys Glu Asp His Gln Lys Glu Val Gln Tyr Glu Ile Leu Gln Lys Thr
100 105 110

Ile Pro Thr Phe Glu Pro Lys Glu Ser Ile Leu Lys Lys Leu Glu Asp
115 120 125

Ile Arg Pro Glu Gln Ala Lys Lys Gln Met Lys Leu Phe Arg Ile Phe
130 135 140

Glu Pro Arg Gln Leu Pro Ile Tyr Arg Ala Asn Gly Glu Lys Glu Leu
145 150 155 160

Arg Asn Arg Trp Tyr Trp Lys Leu Lys Lys Asp Thr Leu Pro Asp Gly
165 170 175

Asp Tyr Asp Val Arg Glu Tyr Phe Leu Asn Leu Tyr Asp Gln Ile Leu
180 185 190

Ile Glu Met Pro Asp Tyr Leu Leu Leu Lys Asp Met Ala Val Glu Asn
195 200 205

Lys Asn Ser Arg Asp Ala Gly Lys Val Val Asp Ser Glu Thr Ala Ser
210 215 220

Ile Cys Asp Ala Ile Phe Gln Asp Glu Glu Thr Glu Gly Val Ile Arg
225 230 235 240

-continued

```
Arg Phe Ile Ala Asp Met Arg Gln Gln Ile Gln Ala Asp Arg Asn Ile
                245                 250                 255

Val Asn Tyr Pro Ser Ile Leu His Pro Ile Asp His Ala Phe Asn Glu
            260                 265                 270

Tyr Phe Leu Asn His Gln Leu Val Glu Pro Leu Asn Asn Asp Ile Ile
        275                 280                 285

Phe Asn Tyr Ile Pro Glu Arg Ile Arg Asn Asp Val Asn Tyr Ile Leu
    290                 295                 300

Asn Met Asp Met Asn Leu Pro Ser Thr Ala Arg Tyr Ile Arg Pro Asn
305                 310                 315                 320

Leu Leu Gln Asp Arg Leu Asn Leu His Asp Asn Phe Glu Ser Leu Trp
                325                 330                 335

Asp Thr Ile Thr Thr Ser Asn Tyr Ile Leu Ala Arg Ser Val Val Pro
            340                 345                 350

Asp Leu Lys Glu Lys Glu Leu Val Ser Thr Glu Ala Gln Ile Gln Lys
        355                 360                 365

Met Ser Gln Asp Leu Gln Leu Glu Ala Leu Thr Ile Gln Ser Glu Thr
    370                 375                 380

Gln Phe Leu Ala Gly Ile Asn Ser Gln Ala Ala Asn Asp Cys Phe Lys
385                 390                 395                 400

Thr Leu Ile Ala Ala Met Leu Ser Gln Arg Thr Met Ser Leu Asp Phe
                405                 410                 415

Val Thr Thr Asn Tyr Met Ser Leu Ile Ser Gly Met Trp Leu Leu Thr
            420                 425                 430

Val Ile Pro Asn Asp Met Phe Leu Arg Glu Ser Leu Val Ala Cys Glu
        435                 440                 445

Leu Ala Ile Ile Asn Thr Ile Val Tyr Pro Ala Phe Gly Met Gln Arg
    450                 455                 460

Met His Tyr Arg Asn Gly Asp Pro Gln Thr Pro Phe Gln Ile Ala Glu
465                 470                 475                 480

Gln Gln Ile Gln Asn Phe Gln Val Ala Asn Trp Leu His Phe Ile Asn
                485                 490                 495

Asn Asn Arg Phe Arg Gln Val Val Ile Asp Gly Val Leu Asn Gln Thr
            500                 505                 510

Leu Asn Asp Asn Ile Arg Asn Gly Gln Val Ile Asn Gln Leu Met Glu
        515                 520                 525

Ala Leu Met Gln Leu Ser Arg Gln Gln Phe Pro Thr Met Pro Val Asp
    530                 535                 540

Tyr Lys Arg Ser Ile Gln Arg Gly Ile Leu Leu Leu Ser Asn Arg Leu
545                 550                 555                 560

Gly Gln Leu Val Asp Leu Thr Arg Leu Leu Ser Tyr Asn Tyr Glu Thr
                565                 570                 575

Leu Met Ala Cys Ile Thr Met Asn Met Gln His Val Gln Thr Leu Thr
            580                 585                 590

Thr Glu Arg Leu Gln Leu Thr Ser Val Thr Ser Leu Cys Met Leu Ile
        595                 600                 605

Gly Asn Thr Thr Val Ile Pro Ser Pro Gln Thr Leu Phe His Tyr Tyr
    610                 615                 620

Asn Val Asn Val Asn Phe His Ser Asn Tyr Asn Glu Arg Ile Asn Asp
625                 630                 635                 640

Ala Val Ala Ile Ile Thr Ala Ala Asn Arg Leu Asn Leu Tyr Gln Lys
                645                 650                 655

Lys Met Lys Ser Ile Val Glu Asp Phe Leu Lys Arg Leu Gln Ile Phe
```

660 665 670

Asp Val Pro Arg Val Pro Asp Asp Gln Met Tyr Arg Leu Arg Asp Arg
675 680 685

Leu Arg Leu Leu Pro Val Glu Arg Arg Arg Leu Asp Ile Phe Asn Leu
690 695 700

Ile Leu Met Asn Met Glu Gln Ile Glu Arg Ala Ser Asp Lys Ile Ala
705 710 715 720

Gln Gly Val Ile Ile Ala Tyr Arg Asp Met Gln Leu Glu Arg Asp Glu
725 730 735

Met Tyr Gly Phe Val Asn Ile Ala Arg Asn Leu Asp Gly Tyr Gln Gln
740 745 750

Ile Asn Leu Glu Glu Leu Met Arg Thr Gly Asp Tyr Gly Gln Ile Thr
755 760 765

Thr Met Leu Leu Asn Asn Gln Pro Val Ala Leu Val Gly Ala Leu Pro
770 775 780

Phe Val Thr Asp Ser Ser Val Ile Ser Leu Ile Ala Lys Leu Asp Ala
785 790 795 800

Thr Val Phe Ala Gln Ile Val Lys Leu Arg Lys Val Asp Thr Leu Lys
805 810 815

Pro Ile Leu Tyr Lys Ile Asn Ser Asp Ser Asn Asp Phe Tyr Leu Val
820 825 830

Ala Asn Tyr Asp Trp Ile Pro Thr Ser Thr Thr Lys Val Tyr Lys Gln
835 840 845

Val Pro Gln Pro Phe Asp Phe Arg Ala Ser Met His Met Leu Thr Ser
850 855 860

Asn Leu Thr Phe Thr Val Tyr Ser Asp Leu Leu Ser Phe Val Ser Ala
865 870 875 880

Asp Thr Val Glu Pro Ile Asn Ala Ile Ala Phe Asp Asn Met Arg Ile
885 890 895

Met Asn Glu Leu
900

<210> SEQ ID NO 21
<211> LENGTH: 900
<212> TYPE: PRT
<213> ORGANISM: Human rotavirus

<400> SEQUENCE: 21

Met Ala Tyr Arg Lys Arg Gly Thr Lys Arg Glu Asp Leu Pro Gln Gln
1 5 10 15

Asn Glu Arg Leu Gln Glu Lys Glu Ile Glu Asn Asn Ile Asp Val Thr
20 25 30

Met Glu Asn Lys Asn Lys Asn Ile Asn Lys Asn Asn Asn Arg Asn Asn
35 40 45

Asn Arg Lys Gln Gln Leu Ser Asp Lys Val Leu Ser Gln Lys Glu Glu
50 55 60

Ile Ile Thr Asp Val Gln Asp Asp Ile Lys Ile Thr Asp Glu Val Lys
65 70 75 80

Lys Ser Ser Lys Glu Glu Ser Lys Gln Leu Leu Glu Ile Leu Lys Thr
85 90 95

Lys Glu Asp His Gln Lys Glu Val Gln Tyr Glu Ile Leu Gln Lys Thr
100 105 110

Ile Pro Thr Phe Glu Pro Lys Glu Ser Ile Leu Lys Lys Leu Glu Asp
115 120 125

```
Ile Arg Pro Glu Gln Ala Lys Lys Gln Met Lys Leu Phe Arg Ile Phe
    130                 135                 140

Glu Pro Arg Gln Leu Pro Ile Tyr Arg Ala Asn Gly Glu Lys Glu Leu
145                 150                 155                 160

Arg Asn Arg Trp Tyr Trp Lys Leu Lys Lys Asp Thr Leu Pro Asp Gly
                165                 170                 175

Asp Tyr Asp Val Arg Glu Tyr Phe Leu Asn Leu Tyr Asp Gln Ile Leu
            180                 185                 190

Ile Glu Met Pro Asp Tyr Leu Leu Leu Lys Asp Met Ala Val Glu Asn
        195                 200                 205

Lys Asn Ser Arg Asp Ala Gly Lys Val Val Asp Ser Glu Thr Ala Ser
    210                 215                 220

Ile Cys Asp Ala Ile Phe Gln Asp Glu Glu Thr Glu Gly Val Ile Arg
225                 230                 235                 240

Arg Phe Ile Ala Asp Met Arg Gln Gln Ile Gln Ala Asp Arg Asn Ile
                245                 250                 255

Val Asn Tyr Pro Ser Ile Leu His Pro Ile Asp His Ala Phe Asn Glu
            260                 265                 270

Tyr Phe Leu Asn His Gln Leu Val Glu Pro Leu Asn Asn Asp Ile Ile
        275                 280                 285

Phe Asn Tyr Ile Pro Glu Arg Ile Arg Asn Asp Val Asn Tyr Ile Leu
    290                 295                 300

Asn Met Asp Met Asn Leu Pro Ser Thr Ala Arg Tyr Ile Arg Pro Asn
305                 310                 315                 320

Leu Leu Gln Asp Arg Leu Asn Leu His Asp Asn Phe Glu Ser Leu Trp
                325                 330                 335

Asp Thr Ile Thr Thr Ser Asn Tyr Ile Leu Ala Arg Ser Val Val Pro
            340                 345                 350

Asp Leu Lys Glu Lys Glu Leu Val Ser Thr Glu Ala Gln Ile Gln Lys
        355                 360                 365

Met Ser Gln Asp Leu Gln Leu Glu Ala Leu Thr Ile Gln Ser Glu Thr
    370                 375                 380

Gln Phe Leu Ala Gly Ile Asn Ser Gln Ala Ala Asn Asp Cys Phe Lys
385                 390                 395                 400

Thr Leu Ile Ala Ala Met Leu Ser Gln Arg Thr Met Ser Leu Asp Phe
                405                 410                 415

Val Thr Thr Asn Tyr Met Ser Leu Ile Ser Gly Met Trp Leu Leu Thr
            420                 425                 430

Val Ile Pro Asn Asp Met Phe Leu Arg Glu Ser Leu Val Ala Cys Glu
        435                 440                 445

Leu Ala Ile Ile Asn Thr Ile Val Tyr Pro Ala Phe Gly Met Gln Arg
    450                 455                 460

Met His Tyr Arg Asn Gly Asp Pro Gln Thr Pro Phe Gln Ile Ala Glu
465                 470                 475                 480

Gln Gln Ile Gln Asn Phe Gln Val Ala Asn Trp Leu His Phe Ile Asn
                485                 490                 495

Asn Asn Arg Phe Arg Gln Val Val Ile Asp Gly Val Leu Asn Gln Thr
            500                 505                 510

Leu Asn Asp Asn Ile Arg Asn Gly Gln Val Ile Asn Gln Leu Met Glu
        515                 520                 525

Ala Leu Met Gln Leu Ser Arg Gln Gln Phe Pro Thr Met Pro Val Asp
    530                 535                 540

Tyr Lys Arg Ser Ile Gln Arg Gly Ile Leu Leu Leu Ser Asn Arg Leu
```

-continued 545 550 555 560

Gly Gln Leu Val Asp Leu Thr Arg Leu Leu Ser Tyr Asn Tyr Glu Thr
565 570 575

Leu Met Ala Cys Ile Thr Met Asn Met Gln His Val Gln Thr Leu Thr
580 585 590

Thr Glu Arg Leu Gln Leu Thr Ser Val Thr Ser Leu Cys Met Leu Ile
595 600 605

Gly Asn Thr Thr Val Ile Pro Ser Pro Gln Thr Leu Phe His Tyr Tyr
610 615 620

Asn Val Asn Val Asn Phe His Ser Asn Tyr Asn Glu Arg Ile Asn Asp
625 630 635 640

Ala Val Ala Ile Ile Thr Ala Ala Asn Arg Leu Asn Leu Tyr Gln Lys
645 650 655

Lys Met Lys Ser Ile Val Glu Asp Phe Leu Lys Arg Leu Gln Ile Phe
660 665 670

Asp Val Pro Arg Val Pro Asp Asp Gln Met Tyr Arg Leu Arg Asp Arg
675 680 685

Leu Arg Leu Leu Pro Val Glu Arg Arg Arg Leu Asp Ile Phe Asn Leu
690 695 700

Ile Leu Met Asn Met Glu Gln Ile Glu Arg Ala Ser Asp Lys Ile Ala
705 710 715 720

Gln Gly Val Ile Ile Ala Tyr Arg Asp Met Gln Leu Glu Arg Asp Glu
725 730 735

Met Tyr Gly Phe Val Asn Ile Ala Arg Asn Leu Asp Gly Tyr Gln Gln
740 745 750

Ile Asn Leu Glu Glu Leu Met Arg Thr Gly Asp Tyr Gly Gln Ile Thr
755 760 765

Thr Met Leu Leu Asn Asn Gln Pro Val Ala Leu Val Gly Ala Leu Pro
770 775 780

Phe Val Thr Asp Ser Ser Val Ile Ser Leu Ile Ala Lys Leu Asp Ala
785 790 795 800

Thr Val Phe Ala Gln Ile Val Lys Leu Arg Lys Val Asp Thr Leu Lys
805 810 815

Pro Ile Leu Tyr Lys Ile Asn Ser Asp Ser Asn Asp Phe Tyr Leu Val
820 825 830

Ala Asn Tyr Asp Trp Ile Pro Thr Ser Thr Thr Lys Val Tyr Lys Gln
835 840 845

Val Pro Gln Pro Phe Asp Phe Arg Ala Ser Met His Met Leu Thr Ser
850 855 860

Asn Leu Thr Phe Thr Val Tyr Ser Asp Leu Leu Ser Phe Val Ser Ala
865 870 875 880

Asp Thr Val Glu Pro Ile Asn Ala Ile Ala Phe Asp Asn Met Arg Ile
885 890 895

Met Asn Glu Leu
900

<210> SEQ ID NO 22
<211> LENGTH: 835
<212> TYPE: PRT
<213> ORGANISM: Human rotavirus

<400> SEQUENCE: 22

Met Lys Val Leu Ala Leu Arg His Ser Val Ala Gln Ile Tyr Ala Asp
1 5 10 15

```
Thr Gln Val Tyr Thr His Asp Asp Ser Lys Asp Asp Tyr Glu Asn Ala
            20                  25                  30

Phe Leu Ile Ser Asn Leu Thr Thr His Asn Ile Leu Tyr Leu Asn Tyr
        35                  40                  45

Ser Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Asp Tyr Ser Tyr
                85                  90                  95

Tyr Ala Asn Asn Glu Ile Arg Thr Asp Gln Tyr Trp Val Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Val Ile Ile Glu Tyr Ile Tyr Ser
145                 150                 155                 160

Asn Glu Leu Asp Phe Gln Asn Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Val Gly Pro Arg Asn Glu Ser Met Phe Thr Phe Leu Asp His Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Met Tyr His Glu Lys Pro Ile Ile Tyr Met Ile Gly Ser Ala
        275                 280                 285

Pro Ser Tyr Trp Ile Tyr Asp Val Lys Gln Tyr Ser Asp Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Asn Met Asp Trp Lys Glu
            340                 345                 350

Trp Arg Lys Val Val Glu Gly Gln Thr Ala Asp Asn Leu His Ile Ala
        355                 360                 365

Tyr Lys Tyr Leu Ser Thr Gly Lys Ala Lys Ile Cys Cys Val Lys Met
    370                 375                 380

Thr Ala Met Asp Val Glu Leu Pro Ile Ser Ala Lys Leu Leu His His
385                 390                 395                 400

Pro Thr Thr Glu Ile Arg Ser Glu Phe Tyr Leu Met Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
```

```
        435                 440                 445

Lys Leu Lys Thr Leu Lys Asn Glu Tyr Val Ile Ala Leu Tyr Ala Leu
    450                 455                 460

Ser Asn Asp Leu Asn Asn Arg Glu Asp Val Val Lys Leu Ile Asn Asn
465                 470                 475                 480

Gln Lys Arg Ala Leu Ile Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Met Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Lys Val
        675                 680                 685

Tyr Ser Ile Thr Tyr Ala Asp Asp Pro Asn Tyr Phe Ile Gly Ile Lys
    690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Ala Ile Ala
                725                 730                 735

Ile Leu Lys Lys Phe Lys Asn Glu Leu Phe Gly Met Asp Ile Thr Thr
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asp Thr Val Phe Asp
            820                 825                 830

Met Thr Glu
        835
```

<210> SEQ ID NO 23

<211> LENGTH: 835
<212> TYPE: PRT
<213> ORGANISM: Human rotavirus

<400> SEQUENCE: 23

Met Lys Val Leu Ala Leu Arg His Ser Val Ala Gln Val Tyr Ala Asp
1 5 10 15

Thr Gln Val Tyr Thr His Asp Asp Ser Lys Asp Glu Tyr Glu Asn Ala
20 25 30

Phe Leu Ile Ser Asn Leu Thr Thr His Asn Ile Leu Tyr Leu Asn Tyr
35 40 45

Asn Val Lys Thr Leu Gln Ile Leu Asn Lys Ser Gly Ile Ala Ala Ile
50 55 60

Glu Ile Gln Lys Ile Asp Glu Leu Phe Thr Leu Ile Arg Cys Asn Phe
65 70 75 80

Thr Tyr Asp Tyr Ile Asp Asn Val Val Tyr Leu His Asp Tyr Ser Tyr
85 90 95

Tyr Thr Asn Asn Glu Ile Arg Thr Asp Gln His Trp Ile Thr Lys Thr
100 105 110

Asn Ile Glu Asp Tyr Leu Leu Pro Gly Trp Lys Leu Thr Tyr Val Gly
115 120 125

Tyr Asn Gly Ser Asp Thr Arg Gly His Tyr Asn Phe Ser Phe Arg Cys
130 135 140

Gln Asn Ala Ala Thr Asp Asp Asp Ala Ile Ile Glu Tyr Ile Tyr Ser
145 150 155 160

Asp Glu Leu Asp Phe Gln Ser Phe Ile Leu Lys Lys Ile Lys Glu Arg
165 170 175

Met Thr Thr Ser Leu Pro Ile Ala Arg Leu Ser Asn Arg Val Phe Arg
180 185 190

Asp Lys Leu Phe Lys Thr Leu Ser Val Asn His Asp Lys Val Val Asn
195 200 205

Ile Gly Pro Arg Asn Glu Ser Met Phe Thr Phe Leu Asp Tyr Pro Ser
210 215 220

Ile Lys Gln Phe Ser Asn Gly Pro Tyr Leu Val Lys Asp Thr Ile Lys
225 230 235 240

Leu Lys Gln Glu Arg Trp Leu Gly Lys Arg Leu Ser Gln Phe Asp Ile
245 250 255

Gly Gln Tyr Lys Asn Met Leu Asn Val Leu Thr Thr Leu Tyr Gln Tyr
260 265 270

Tyr Asp Ile Tyr His Glu Lys Pro Ile Val Tyr Met Ile Gly Ser Ala
275 280 285

Pro Ser Tyr Trp Ile Tyr Asp Val Lys Gln Tyr Ser Asn Leu Lys Phe
290 295 300

Glu Thr Trp Asp Pro Leu Asp Thr Pro Tyr Ser Asn Leu His His Lys
305 310 315 320

Glu Leu Phe Tyr Met Asn Asp Val Gln Lys Leu Lys Asp Asn Ser Ile
325 330 335

Leu Tyr Ile Asp Ile Arg Thr Asp Arg Gly Thr Val Asp Trp Lys Glu
340 345 350

Trp Arg Lys Ile Val Glu Arg Gln Thr Ile Asp Asn Leu His Ile Ala
355 360 365

Tyr Lys Tyr Leu Ser Thr Gly Lys Ala Lys Val Cys Cys Val Lys Met
370 375 380

Thr Ala Met Asp Leu Glu Leu Pro Ile Ser Ala Lys Leu Leu His His

-continued

```
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Thr Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Arg Val
        675                 680                 685

Tyr Ser Ile Thr Tyr Ala Asp Asp Pro Asn Tyr Phe Ile Gly Val Lys
    690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Val Thr Thr
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815
```

```
Ile Asp Ser Ile Tyr Leu Arg Lys Ile Lys Gly Asn Thr Val Phe Asp
            820                 825                 830

Met Thr Gly
        835


<210> SEQ ID NO 24
<211> LENGTH: 835
<212> TYPE: PRT
<213> ORGANISM: Human rotavirus

<400> SEQUENCE: 24

Met Lys Val Leu Ala Leu Arg His Ser Val Ala Gln Val Tyr Ala Asp
1               5                   10                  15

Thr Gln Val Tyr Thr His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Asn Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asn Val Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Val Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Met Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
```

-continued

```
            340                 345                 350

Trp Arg Lys Ile Val Glu Arg Gln Thr Ile Asp Asn Leu His Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Thr Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Arg Val
        675                 680                 685

Tyr Ser Ile Thr Tyr Ala Asp Asp Pro Asn Tyr Phe Ile Gly Val Lys
    690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Val Thr Thr
            740                 745                 750

Ser Tyr Thr Tyr Met Leu Ser Asp Glu Val Tyr Val Ala Asn Ile Ser
        755                 760                 765
```

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asn Thr Val Phe Asp
            820                 825                 830

Met Thr Gly
        835

<210> SEQ ID NO 25
<211> LENGTH: 775
<212> TYPE: PRT
<213> ORGANISM: Human rotavirus

<400> SEQUENCE: 25

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Val Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Ile
    50                  55                  60

Leu Asp Gly Pro Tyr Gln Pro Thr Thr Phe Lys Pro Leu Thr Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Val Glu Pro His Val
            100                 105                 110

Asn Pro Val Asp Arg Gln Tyr Thr Val Phe Gly Glu Asn Lys Gln Phe
        115                 120                 125

Asn Val Arg Asn Asp Ser Asp Lys Trp Lys Phe Leu Glu Met Phe Arg
    130                 135                 140

Gly Ser Ser Gln Asn Glu Phe Tyr Asn Arg Arg Thr Leu Thr Ser Asp
145                 150                 155                 160

Thr Lys Leu Val Gly Ile Leu Lys Tyr Gly Gly Arg Ile Trp Thr Phe
                165                 170                 175

His Gly Glu Thr Pro Arg Ala Thr Thr Asp Ser Ser Asn Thr Ala Asn
            180                 185                 190

Leu Asn Asp Ile Ser Ile Ile Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Lys Arg Ala Gln Val Asn Glu Asp Ile Thr Ile Ser
                245                 250                 255

Lys Thr Ser Leu Trp Lys Glu Met Gln Cys Asn Arg Asp Ile Ile Ile
            260                 265                 270

Arg Phe Lys Phe Gly Asn Ser Ile Val Lys Leu Gly Gly Leu Gly Tyr
        275                 280                 285

Lys Trp Ser Glu Ile Ser Tyr Lys Ala Ala Asn Tyr Gln Tyr Asn Tyr

-continued

```
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Thr Gly Gly Ser Tyr
    370                 375                 380

Asn Phe Ser Ile Pro Val Gly Ala Trp Pro Val Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Leu Arg Thr Arg Thr Val Asn Leu Tyr Gly
        435                 440                 445

Leu Pro Ala Ala Asn Pro Asn Asn Gly Asn Glu Tyr Tyr Glu Ile Ser
    450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Val Ser Ile Arg Ser Asn Ile Ser Thr Ile Ser Asn Trp Thr Asn
            580                 585                 590

Val Ser Asn Asp Val Ser Asn Val Thr Asn Ser Leu Ser Asp Ile Ser
        595                 600                 605

Thr Gln Thr Ser Thr Ile Ser Lys Asn Leu Arg Leu Lys Glu Met Ile
    610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Val Phe Ala Tyr Lys Ile Asp Thr Leu Asn Glu Val Pro Phe Asp Val
    690                 695                 700

Asn Lys Phe Ala Glu Leu Val Thr Asn Ser Pro Val Ile Ser Ala Ile
705                 710                 715                 720
```

```
Ile Asp Phe Lys Thr Leu Lys Asn Leu Asn Asp Asn Tyr Gly Ile Thr
                725                 730                 735

Arg Ile Glu Ala Leu Asn Leu Ile Lys Ser Asn Pro Asn Val Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775


<210> SEQ ID NO 26
<211> LENGTH: 775
<212> TYPE: PRT
<213> ORGANISM: Human rotavirus

<400> SEQUENCE: 26

Met Ala Ser Leu Ile Tyr Arg Gln Leu Leu Thr Asn Ser Tyr Ser Val
1               5                   10                  15

Asp Leu Tyr Asp Glu Ile Glu Gln Ile Gly Ser Gly Lys Thr Gln Asn
            20                  25                  30

Val Thr Ile Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Ile
    50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
            100                 105                 110

Thr Pro Val Asp Arg Gln Tyr Met Ile Phe Gly Glu Ser Lys Gln Phe
        115                 120                 125

Asn Val Ser Asn Asp Ser Asn Lys Trp Lys Phe Leu Glu Met Phe Arg
    130                 135                 140

Ser Ser Ser Gln Asn Glu Phe Tyr Asn Arg Arg Thr Leu Thr Ser Asp
145                 150                 155                 160

Thr Arg Leu Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
            180                 185                 190

Leu Asn Asn Ile Ser Ile Thr Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asp Glu Asp Ile Ile Val Ser
                245                 250                 255

Lys Thr Ser Leu Trp Lys Glu Met Gln Tyr Asn Arg Asp Ile Ile Ile
            260                 265                 270

Arg Phe Lys Phe Gly Asn Ser Ile Val Lys Met Gly Gly Leu Gly Tyr
        275                 280                 285

Lys Trp Ser Glu Ile Ser Tyr Lys Ala Ala Asn Tyr Gln Tyr Asn Tyr
    290                 295                 300

Leu Arg Asp Gly Glu Gln Val Thr Ala His Thr Thr Cys Ser Val Asn
```

-continued

```
305                 310                 315                 320

Gly Val Asn Asn Phe Ser Tyr Asn Gly Gly Ser Leu Pro Thr Asp Phe
                325                 330                 335

Gly Ile Ser Arg Tyr Glu Val Ile Lys Glu Asn Ser Tyr Val Tyr Val
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Arg Cys Thr Gly Gly Ser Tyr
    370                 375                 380

Asp Phe Ser Ile Pro Val Gly Ala Trp Pro Val Ile Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Pro Phe Ser Ile Leu Arg Thr Arg Thr Val Asn Leu Tyr Gly
        435                 440                 445

Leu Pro Ala Ala Asn Pro Asn Asn Gly Asn Glu Tyr Tyr Glu Ile Ser
    450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
            500                 505                 510

Met Ala Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Asn Val Ser Ile Arg Ser Asn Leu Ser Ala Ile Ser Asn Trp Thr Asn
            580                 585                 590

Val Ser Asn Asp Val Ser Asn Val Thr Asn Ser Leu Asn Asp Ile Ser
        595                 600                 605

Thr Gln Thr Ser Thr Ile Gly Lys Lys Leu Arg Leu Lys Glu Met Ile
    610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Phe Phe Ala Tyr Lys Ile Asn Thr Phe Asp Glu Val Pro Phe Asp Val
    690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735
```

```
Arg Thr Glu Ala Leu Asn Leu Ile Lys Ser Asn Pro Asn Met Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775


<210> SEQ ID NO 27
<211> LENGTH: 775
<212> TYPE: PRT
<213> ORGANISM: Human rotavirus

<400> SEQUENCE: 27

Met Ala Ser Leu Ile Tyr Arg Gln Leu Leu Thr Asn Ser Tyr Ser Val
1               5                   10                  15

Asp Leu Tyr Asp Glu Ile Glu Gln Ile Gly Ser Gly Lys Thr Gln Asn
            20                  25                  30

Val Thr Ile Asn Pro Gly Pro Phe Ala Gln Thr Arg Tyr Ala Pro Val
        35                  40                  45

Asn Trp Asp His Gly Glu Ile Asn Asp Ser Thr Thr Val Glu Pro Ile
    50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
            100                 105                 110

Thr Pro Val Asp Arg Gln Tyr Met Ile Phe Gly Glu Ser Lys Gln Phe
        115                 120                 125

Asn Val Ser Asn Asp Ser Asn Lys Trp Lys Phe Leu Glu Met Phe Arg
    130                 135                 140

Ser Ser Ser Gln Asn Glu Phe Tyr Asn Arg Arg Thr Leu Thr Ser Asp
145                 150                 155                 160

Thr Arg Leu Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
            180                 185                 190

Leu Asn Asn Ile Ser Ile Thr Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asp Glu Asp Ile Ile Val Ser
                245                 250                 255

Lys Thr Ser Leu Trp Lys Glu Met Gln Tyr Asn Arg Asp Ile Ile Ile
            260                 265                 270

Arg Phe Lys Phe Gly Asn Ser Ile Val Lys Met Gly Gly Leu Gly Tyr
        275                 280                 285

Lys Trp Ser Glu Ile Ser Tyr Lys Ala Ala Asn Tyr Gln Tyr Asn Tyr
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Phe Leu Pro Thr Asp Phe
```

-continued

```
                325                 330                 335

Gly Ile Ser Arg Tyr Glu Val Ile Lys Glu Asn Ser Tyr Val Tyr Val
            340                 345                 350

Asp Tyr Trp Asp Asp Ser Lys Ala Phe Arg Asn Ile Val Tyr Val Arg
        355                 360                 365

Ser Leu Ala Ala Asn Leu Asn Ser Val Arg Cys Thr Gly Gly Ser Tyr
    370                 375                 380

His Phe Ser Leu Pro Val Gly Ala Trp Pro Val Ile Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Pro Phe Ser Ile Leu Arg Thr Arg Thr Val Asn Leu Tyr Gly
        435                 440                 445

Leu Pro Ala Ala Asn Pro Asn Asn Gly Asn Glu Tyr Tyr Glu Ile Ser
    450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
            500                 505                 510

Met Ala Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Asn Val Ser Ile Arg Ser Asn Leu Ser Ala Ile Ser Asn Trp Thr Asn
            580                 585                 590

Val Ser Asn Asp Val Ser Asn Val Thr Asn Ser Leu Asn Asp Ile Ser
        595                 600                 605

Thr Gln Thr Ser Thr Ile Gly Lys Lys Leu Arg Leu Lys Glu Met Ile
    610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Phe Phe Ala Tyr Lys Ile Asn Thr Phe Asp Glu Val Pro Phe Asp Val
    690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Thr Glu Ala Leu Asn Leu Ile Lys Ser Asn Pro Asn Met Leu Arg
            740                 745                 750
```

```
Asn Phe Ile Asn Gln Asn Asn Pro Ile Ile Arg Asn Arg Ile Glu Gln
        755                 760                 765

Leu Ile Leu Gln Cys Lys Leu
    770                 775


<210> SEQ ID NO 28
<211> LENGTH: 397
<212> TYPE: PRT
<213> ORGANISM: Human rotavirus

<400> SEQUENCE: 28

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
    50                  55                  60

Leu Leu Gly Thr Thr Leu Leu Asn Leu Asp Ala Asn Tyr Val Glu Asn
65                  70                  75                  80

Ala Arg Thr Thr Ile Glu Tyr Phe Ile Asp Phe Ile Asp Asn Val Cys
                85                  90                  95

Met Asp Glu Met Ala Arg Glu Ala Gln Arg Asn Gly Val Ala Pro Gln
            100                 105                 110

Ser Glu Ala Leu Gly Lys Leu Ala Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Ser Leu Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
```

```
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 29
<211> LENGTH: 397
<212> TYPE: PRT
<213> ORGANISM: Human rotavirus

<400> SEQUENCE: 29

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
    50                  55                  60

Leu Leu Gly Thr Thr Leu Leu Asn Leu Asp Ala Asn Tyr Val Glu Thr
65                  70                  75                  80

Ala Arg Thr Thr Ile Glu Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asn Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Leu Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Ile Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320
```

```
Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 30
<211> LENGTH: 397
<212> TYPE: PRT
<213> ORGANISM: Human rotavirus

<400> SEQUENCE: 30

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
    50                  55                  60

Leu Leu Gly Thr Thr Leu Leu Asn Leu Asp Ala Asn Tyr Val Glu Thr
65                  70                  75                  80

Ala Arg Thr Thr Ile Glu Tyr Phe Ile Asp Phe Ile Asp Asn Val Cys
                85                  90                  95

Met Asp Glu Met Val Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asn Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Leu Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Ile Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300
```

```
Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 31
<211> LENGTH: 346
<212> TYPE: PRT
<213> ORGANISM: Human rotavirus

<400> SEQUENCE: 31

Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
            20                  25                  30

Ile Ile Tyr Arg Phe Leu Leu Ile Thr Val Ala Leu Phe Ala Leu Thr
        35                  40                  45

Arg Ala Gln Asn Tyr Gly Leu Asn Leu Pro Ile Thr Gly Ser Met Asp
    50                  55                  60

Thr Val Tyr Thr Asn Ser Thr Gln Glu Glu Val Phe Leu Thr Ser Thr
65                  70                  75                  80

Leu Cys Leu Tyr Tyr Pro Thr Glu Ala Ser Thr Gln Ile Asn Asp Gly
                85                  90                  95

Asp Trp Lys Asp Ser Leu Ser Gln Met Phe Leu Thr Lys Gly Trp Pro
            100                 105                 110

Thr Gly Ser Val Tyr Phe Lys Glu Tyr Ser Ser Ile Val Asp Phe Ser
        115                 120                 125

Val Asp Pro Gln Leu Tyr Cys Asp Tyr Asn Leu Val Leu Met Lys Tyr
    130                 135                 140

Asp Gln Ser Leu Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Ser Gly Glu Ser Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Val Asp Ser Phe Glu Met Val Ala Glu Asn Glu Lys Leu
    210                 215                 220

Ala Ile Val Asp Val Val Asp Gly Ile Asn His Lys Ile Asn Leu Thr
225                 230                 235                 240

Thr Thr Thr Cys Thr Ile Arg Asn Cys Lys Lys Leu Gly Pro Arg Glu
                245                 250                 255

Asn Val Ala Val Ile Gln Val Gly Gly Ser Asn Val Leu Asp Ile Thr
            260                 265                 270

Ala Asp Pro Thr Thr Asn Pro Gln Thr Glu Arg Met Met Arg Val Asn
```

```
        275                 280                 285

Trp Lys Lys Trp Trp Gln Val Phe Tyr Thr Ile Val Asp Tyr Ile Asn
    290                 295                 300

Gln Ile Val Gln Val Met Ser Lys Arg Ser Arg Ser Leu Asn Ser Ala
305                 310                 315                 320

Asp Tyr Ile Asn Gln Ile Val Gln Val Met Ser Lys Arg Ser Arg Ser
                325                 330                 335

Leu Asn Ser Ala Ala Phe Tyr Tyr Arg Val
            340                 345


<210> SEQ ID NO 32
<211> LENGTH: 346
<212> TYPE: PRT
<213> ORGANISM: Human rotavirus

<400> SEQUENCE: 32

Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
            20                  25                  30

Ile Ile Tyr Arg Phe Leu Leu Ile Phe Val Ala Leu Phe Ala Leu Thr
        35                  40                  45

Lys Ala Gln Asn Tyr Gly Leu Asn Ile Pro Ile Thr Gly Ser Met Asp
    50                  55                  60

Thr Val Tyr Ser Asn Ser Thr Arg Glu Glu Val Phe Leu Thr Ser Thr
65                  70                  75                  80

Leu Cys Leu Tyr Tyr Pro Thr Glu Ala Ser Thr Gln Ile Ser Asp Gly
                85                  90                  95

Glu Trp Lys Asp Ser Leu Ser Gln Met Phe Leu Ile Lys Gly Trp Pro
            100                 105                 110

Thr Gly Ser Val Tyr Phe Lys Glu Tyr Ser Asn Ile Val Asp Phe Ser
        115                 120                 125

Val Asp Pro Gln Leu Tyr Cys Asp Tyr Asn Leu Val Leu Met Lys Tyr
    130                 135                 140

Asp Gln Ser Leu Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Ser Gly Glu Ser Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Val Asp Ser Phe Glu Thr Val Ala Glu Asn Glu Lys Leu
    210                 215                 220

Ala Ile Val Asp Val Val Asp Gly Ile Asn His Lys Ile Asn Leu Thr
225                 230                 235                 240

Thr Thr Thr Cys Thr Ile Arg Asn Cys Lys Lys Leu Gly Pro Arg Glu
                245                 250                 255

Asn Val Ala Val Ile Gln Val Gly Gly Ala Asn Ile Leu Asp Ile Thr
            260                 265                 270

Ala Asp Pro Thr Thr Asn Pro Gln Ile Glu Arg Met Met Arg Val Asn
        275                 280                 285

Trp Lys Arg Trp Trp Gln Val Phe Tyr Thr Ile Val Asp Tyr Ile Asn
    290                 295                 300
```

-continued

Gln Ile Val Gln Val Met Ser Lys Arg Ser Arg Ser Leu Asn Ser Ala
305 310 315 320

Asp Tyr Ile Asn Gln Ile Val Gln Val Met Ser Lys Arg Ser Arg Ser
325 330 335

Leu Asn Ser Ala Ala Phe Tyr Tyr Arg Val
340 345

<210> SEQ ID NO 33
<211> LENGTH: 346
<212> TYPE: PRT
<213> ORGANISM: Human rotavirus

<400> SEQUENCE: 33

Met Tyr Gly Ile Glu Tyr Thr Thr Ile Leu Ile Phe Leu Ile Ser Ile
1 5 10 15

Ile Leu Leu Asn Tyr Ile Leu Lys Ser Val Thr Arg Ile Met Asp Tyr
20 25 30

Ile Ile Tyr Arg Phe Leu Leu Ile Phe Val Ala Leu Phe Ala Leu Thr
35 40 45

Lys Ala Gln Asn Tyr Gly Leu Asn Ile Pro Ile Thr Gly Ser Met Asp
50 55 60

Thr Val Tyr Ser Asn Ser Thr Arg Glu Glu Val Phe Leu Thr Ser Thr
65 70 75 80

Leu Cys Leu Tyr Tyr Pro Thr Glu Ala Ser Thr Gln Ile Ser Asp Gly
85 90 95

Glu Trp Lys Asp Ser Leu Ser Gln Met Phe Leu Ile Lys Gly Trp Pro
100 105 110

Thr Gly Ser Val Tyr Phe Lys Glu Tyr Ser Asn Ile Val Asp Phe Ser
115 120 125

Val Asp Pro Gln Leu Tyr Cys Asp Tyr Asn Leu Val Leu Met Lys Tyr
130 135 140

Asp Gln Ser Leu Glu Leu Asp Met Ser Glu Leu Ala Asp Leu Ile Leu
145 150 155 160

Asn Glu Trp Leu Cys Asn Pro Met Asp Ile Thr Leu Tyr Tyr Tyr Gln
165 170 175

Gln Ser Gly Glu Ser Asn Lys Trp Ile Ser Met Gly Ser Ser Cys Thr
180 185 190

Val Lys Val Cys Pro Leu Asn Thr Gln Thr Leu Gly Ile Gly Cys Gln
195 200 205

Thr Thr Asn Val Asp Ser Phe Glu Thr Val Ala Glu Asn Glu Lys Leu
210 215 220

Ala Ile Val Asp Val Val Asp Gly Ile Asn His Lys Ile Asn Leu Thr
225 230 235 240

Thr Thr Thr Cys Thr Ile Arg Asn Cys Lys Lys Leu Gly Pro Arg Glu
245 250 255

Asn Val Ala Val Ile Gln Val Gly Gly Ala Asn Ile Leu Asp Ile Thr
260 265 270

Ala Asp Pro Thr Thr Asn Pro Gln Ile Glu Arg Met Met Arg Val Asn
275 280 285

Trp Lys Arg Trp Trp Gln Val Phe Tyr Thr Ile Val Asp Tyr Ile Asn
290 295 300

Gln Ile Val Gln Val Met Ser Lys Arg Ser Arg Ser Leu Asn Ser Ala
305 310 315 320

Asp Tyr Ile Asn Gln Ile Val Gln Val Met Ser Lys Arg Ser Arg Ser
325 330 335

Leu Asn Ser Ala Ala Phe Tyr Tyr Arg Val
340 345

<210> SEQ ID NO 34
<211> LENGTH: 1566
<212> TYPE: DNA
<213> ORGANISM: Human rotavirus

<400> SEQUENCE: 34
ggcttttttt atgaaaagtc ttgtggaagc catggctact ttcaaagatg cttgttatta 60
ttataagaga attaacaaat tgaatcatgc agtcttgaag ttaggagtta atgatacatg 120
gagaccatca cctccgacca aatataaagg atggtgtctg gactgttgcc aacacactga 180
cttaacttac tgtcgaggtt gtaccatgta tcatgtatgt cagtggtgta gtcaatatga 240
tagatgcttt cttgataatc aaccacatct attgagaatg agaactttca agaatgaagt 300
gacgaaaaat gatttaatga atttaattga catgtataat atattatttc ctataaatca 360
aagaatagta gataaattta ttagtagtac aagacaacat aaatgtagaa atgaatgtat 420
gacacagtgg tataatcacc tattgatgcc aataacatta caatctctat caattgaatt 480
agatggtgat gtttattacg tatttggata ttatgatagt atgcgtgaca ttaatcaaac 540
tccattctca tttacaaatt taatagatat gtatgataag ttgctacttg ataatgtaaa 600
ttttaatcga atgtcattct taccagtagc attacaacaa gaatatgcac tcagatattt 660
ttcaaaatca aggtttatta gtgaaaagag gaaatgtatt agtgatttac atttttccac 720
taatgtaata gaaaatttac acaatccaag ttttaaaata caaattacac gtaattgtag 780
tgaattatct tctgattgga acggagcatg caaacttgtt aaagatatga gtacttattt 840
taatgtgcta aaaacatcac atattgaatt ttatagtatt tcaaccagat gtagaatgtt 900
tacgcagcat aaacttaaaa tagcatccaa acatataaaa ccaaattatg taacatcaaa 960
tcatagaaca tcagcgactg aggtgcataa ctgtaaatgg tgctcaatta ataacggtta 1020
tactgtatgg aatgatttta gaattaagaa gatatatgat aacattttca attttctacg 1080
agctttagtc aaatcaaatt ctaatattgg acattgttcg tcgcaggaaa agatatatga 1140
acatattaaa gatgttctgg atgtatgtga tgatgaaaaa tggaaaatgg cggtagcgga 1200
aatatttaat tgtttagaac cagtagaact tgatactgtt aaatatgttc tgtttaatca 1260
tgaggtaaat tgggatgtta ttaatttatt agttcagagc gttggtaaag taccacaaat 1320
actgacttta aatgacatta tcataatcat gaaatctatc atatatgagt ggtttgatat 1380
cagatatatg aggaatacac caatgactac atttacagtt gacaaattaa gacagttatg 1440
tacaggagtg aagactgttg attatgattc cggcatatct gacgttgaat aatgaaatag 1500
agatcacatt tgccaccata agactccctg cactagagta gcgcctaggc agcataaaat 1560
gtgacc 1566

<210> SEQ ID NO 35
<211> LENGTH: 1569
<212> TYPE: DNA
<213> ORGANISM: Human rotavirus

<400> SEQUENCE: 35
ggcttttttt ttgaaaagtc ttgtggaagc catggctact ttcaaagatg cttgttatta 60
ttataagaga attaacaaat tgaatcatgc agtcttgaag ttaggagtta atgatacatg 120
gagaccatca cctccgacca aatataaagg atggtgtctg gactgttgcc aacacactga 180
cttaacttac tgtcgaggtt gtaccatgta tcatgtatgt cagtggtgta gtcaatatga 240
tagatgcttt cttgatagtc aaccacatct attgagaatg agaactttca agaatgaagt 300
gacgaaaaat gatttaatga atttgattga catgtataat atattatttc ctataaatca 360
aagaatagta gacaaattta ttagtagtac aagacaacat aaatgtagaa atgaatgtat 420
gacacagtgg tataatcacc tattgatgcc aataacatta caatctctat caattgaatt 480
agatggtgat gtttattacg tatttggata ttatgatagt atgcgtgaca ttaatcaaac 540
tccattctca tttacaaatt taatagatat gtatgataag ttgctacttg ataatgtaaa 600
ttttaatcga atgtcattct taccagtagc attacaacaa gaatatgcac tcagatattt 660
ttcaaaatca aggtttatta gtgaaaagag gaaatgtatt agtgatttac atttttccac 720
taatgtaata gaaaatttac acaatccaag ttttaaaata caaattacac gtaattgtag 780
tgaattatct tctgattgga acggagcatg taaacttgtt aaagatatga gtacttattt 840
taatgtgcta aaaacatcac atattgaatt ttatagtatt tcaaccagat gtagaatgtt 900
tacgcagcat aaacttaaaa tagcatctaa acatataaaa ccaaattatg taacatcaaa 960
tcatagaaca tcagcgactg aggtgcataa ctgtaaatgg tgctcaatta ataacggtta 1020
tactgtatgg aatgatttta gaattaagaa gatatatgat aacattttca attttctacg 1080
agctttagtc aaatcaaatt ctaatattgg acattgttcg tcgcaggaaa agatatatga 1140
acatattaaa gatgttctgg atgtatgtga tgatgaaaaa tggaaaatgg cggtagcgga 1200
aatatttaat tgtttaggac cagtagaact tgatactgtt aaatatgtta tgtttaatca 1260
tgaggtaaat tgggatgtta ttaatttatt agttcagagc gttggtaaag taccacaaat 1320
actgacttta aatgacatta tcataatcat gaaatctatc atatatgagt ggtttgatat 1380
cagatatatg aggaatacac caatgactac atttacagtt gacaaattaa gacagttatg 1440
tacaggaatg aagactgttg attatgattc cggcatatct gacgttgaat aatgaaatag 1500
agatcacatt tgccaccata agactccctg cactagagta gcgcctaggc agcataaaaa 1560
agtgtgacc 1569

<210> SEQ ID NO 36
<211> LENGTH: 1569
<212> TYPE: DNA
<213> ORGANISM: Human rotavirus

<400> SEQUENCE: 36
ggcttttttt ttgaaaagtc ttgtggaagc catggctact ttcaaagatg cttgttatta 60
ttataagaga attaacaaat tgaatcatgc agtcttgaag ttaggagtta atgatacatg 120
gagaccatca cctccgacca aatataaagg atggtgtctg gactgttgcc aacacactga 180
cttaacttac tgtcgaggtt gtaccatgta tcatgtatgt cagtggtgta gtcaatatga 240
tagatgcttt cttgatagtc aaccacatct attgagaatg agaactttca agaatgaagt 300
gacgaaaaat gatttaatga atttgattga catgtataat atattatttc ctataaatca 360
aagaatagta gacaaattta ttagtagtac aagacgacat aaatgtagaa atgaatgtat 420
gacacagtgg tataatcacc tattgatgcc aataacatta caatctctat caattgaatt 480
agatggtgat gtttattacg tatttggata ttatgatagt atgcgtgaca ttaatcaaac 540
tccattctca tttacaaatt taatagatat gtatgataag ttgctacttg ataatgtaaa 600
ttttaatcga atgtcattct taccagtagc attacaacaa gaatatgcac tcagatattt 660

```
ttcaaaatca aggtttatta gtgaaaagag gaaatgtatt agtgatttac atttttccac    720

taatgtaata gaaaatttac acaatccaag ttttaaaata caaattacac gtaattgtag    780

tgaattatct tctgattgga acggagcatg taaacttgtt aaagatatga gtacttattt    840

taatgtgcta aaaacatcac atattgaatt ttatagtatt tcaaccagat gtagaatgtt    900

tacgcagcat aaacttaaaa tagcatctaa acatataaaa ccaaattatg taacatcaaa    960

tcatagaaca tcagcgactg aggtgcataa ctgtaaatgg tgctcaatta ataacggtta   1020

tactgtatgg aatgatttta gaattaagaa gatatatgat aacattttca attttctacg   1080

agctttagtc aaatcaaatt ctaatattgg acattgttcg tcgcaggaaa agatatatga   1140

acatattaaa gatgttctgg atgtatgtga tgatgaaaaa tggaaaatgg cggtagcgga   1200

aatatttaat tgtttaggac cagtagaact tgatactgtt aaatatgtta tgtttaatca   1260

tgaggtaaat tgggatgtta ttaatttatt agttcagagc gttggtaaag taccacaaat   1320

actgacttta aatgacatta tcataatcat gaaatctatc atatatgagt ggtttgatat   1380

cagatatatg aggaatacac caatgactac atttacagtt gacaaattaa gacagttatg   1440

tacaggaatg aagactgttg attatgattc cggcatatct gacgttgaat aatgaaatag   1500

agatcacatt tgccaccata agactccctg cactagagta gcgcctaggc agcataaaaa   1560

agtgtgacc                                                           1569
```

<210> SEQ ID NO 37
<211> LENGTH: 1058
<212> TYPE: DNA
<213> ORGANISM: Human rotavirus

<400> SEQUENCE: 37

```
ggcttttaaa gcgtctcagt cgccgtttga gcttacggtg tagccatggc tgagctagct     60

tgcttttgtt atcctcattt ggagaacgat agctataaat ttattccttt taataattta    120

gcaataaaat gtatgttgac agctaaagtg gacaaaaagg atcaagataa attttacaat    180

tctattattt atggaattgc gccgccgcca caatttaaaa aacgttataa tactaatgac    240

aattcaagag gtatgaatta tgaaacgcct atgttaatca aggtggccat attaatttgt    300

gaagcactta attcaattaa agttactcaa tctgatgttg ctaatgttct ttcaagagtg    360

gtttctgtta gacatttgga aaatctggtt ttaagaaaag aaaaccatca ggatgtgctg    420

tttcattcaa aagaattatt attaaaatcc gttttaatag ctattggtca atcgaaagaa    480

attgaaacta ctgctactgc tgaaggagga gaaatagtat ttcagaatgt agcttttact    540

atgtggaaat taacgtattt agatcataag ttgatgccta ttttggacca aaattttatt    600

gaatacaaaa ttacaatgaa tgaagataaa ccaatttcag atgtgcatgt taaggaactt    660

atcgctgaat tgagatggca gtataataga tttgctgtaa taacacatgg taaaggtcac    720

tatagagttg ttaaatattc atcagttgct aaccatgcag atagagtgtt tgctacatat    780

aaaaataatg ctaagagtgg taatgttatt gactttaact tattggacca aagaatcatt    840

tggcaaaatt ggtatgcatt tacatcctca atgaaacaag gtttcacgct tgatgtatgt    900

aagaaactgc tatttcaaaa gatgaaacag gagagaaacc catttaaagg actgtcaact    960

gatagaaaga tggatgaagt ctcacgtatt ggaatttaat tcgctttcga tttgagaatg   1020

atgatgacgg agcaagaata gaaagcgctt atgtgacc                           1058
```

<210> SEQ ID NO 38
<211> LENGTH: 1059

<212> TYPE: DNA
<213> ORGANISM: Human rotavirus

<400> SEQUENCE: 38
ggcttttaaa gcgtctcagt cgccgtttga gccttgcggt gtagccatgg ctgagctagc 60
ttgcttttgt tatcctcatt tggagaacga tagctataaa tttattcctt ttaataattt 120
agcaataaaa tgtatgttga cagcaaaagt agataaaaaa gatcaagata aattttataa 180
ttctattgtt tatgggattg ctccaccacc acaatttaga aaacgttata atactagtga 240
taattcgaga ggaatgaatt acgaaacaat tatgtttaat aaggtggcta tcttaatttg 300
tgaagcactt aattcgatta aagttacaca atctgaagtt gcaaatgttc tttcaagagt 360
agtttccgtt agacatttgg aaaatctagt attaaggaaa gaaaatcatc aagatgtact 420
tttccattcg aaagaactac tcttaaaatc tgtgttgata gctattggtc agtcaaaaga 480
aatcgaaact actgctactg ccgaaggagg agaaatagta tttcagaatg cagcttttac 540
tatgtggaaa ttgacgtatt tagatcataa attaatgcct attttggatc agaatttcat 600
tgaatataaa attacgttga atgaagataa accaatttca gatgtatgtg ttaaagaact 660
cgttgctgaa ttaagatggc agtataacag atttgctgta ataacacatg gtaaaggtca 720
ctatagagtt gttaaatatt catcagttgc taaccatgca gatagagtat ttgctacata 780
taagaataat gctaagagtg gtaatactac tgatttcaat ttgctagacc aaagaattat 840
ttggcaaaat tggtatgcat ttacatcttc aatgaaacaa ggtaatacaa ttgatgtatg 900
taagaaacta ctctttcaaa agatgaaaca agagaaaaat ccgttcaaag gattgtcaac 960
tgatagaaaa atggatgaag tctcacatgt tggaatttaa ttcgctttcg attcaagaat 1020
gatgatgacg aagcaagaat agaaagcgct tatgtgacc 1059

<210> SEQ ID NO 39
<211> LENGTH: 1059
<212> TYPE: DNA
<213> ORGANISM: Human rotavirus

<400> SEQUENCE: 39
ggcttttaaa gcgtctcagt cgccgtttga gccttgcggt gtagccatgg ctgagctagc 60
ttgcttttgt tatcctcatt tggagaacga tagctataaa tttattcctt ttaataattt 120
agcaataaaa tgtatgttga cagcaaaagt agataaaaaa gatcaagata aattttataa 180
ttctattgtt tatgggattg ctccaccacc acaatttaga aaacgttata atactagtga 240
taattcgaga ggaatgaatt acgaaacaat tatgtttaat aaggtggcta tcttaatttg 300
tgaagcactt aattcgatta aagttacaca atctgaagtt gcaaatgttc tttcaagagt 360
agtttccgtt agacatttgg aaaatctagt attaaggaaa gaaaatcatc aagatgtact 420
tttccattcg aaagaactac tcttaaaatc tgtgttgata gctattggtc agtcaaaaga 480
aatcgaaact actgctactg ccgaaggagg agaaatagta tttcagaatg cagcttttac 540
tatgtggaaa ttgacgtatt tagatcataa attaatgcct attttggatc agaatttcat 600
tgaatataaa attacgttga atgaagataa accaatttca gatgtatgtg ttaaagaact 660
cgttgctgaa ttaagatggc agtataacag atttgctgta ataacacatg gtaaaggtca 720
ctatagagtt gttaaatatt catcagttgc taaccatgca gatagagtat ttgctacata 780
taagaataat gctaagagtg gtaatactac tgatttcaat ttgctagacc aaagaattat 840
ttggcaaaat tggtatgcat ttacatcttc aatgaaacaa ggtaatacaa ttgatgtatg 900

-continued taagaaacta ctctttcaaa agatgaaaca agagaaaaat ccgttcaaag gattgtcaac 960
tgatagaaaa atggatgaag tctcacatgt tggaatttaa ttcgctttcg attcaagaat 1020
gatgatgacg aagcaagaat agaaagcgct tatgtgacc 1059

<210> SEQ ID NO 40
<211> LENGTH: 1075
<212> TYPE: DNA
<213> ORGANISM: Human rotavirus

<400> SEQUENCE: 40
ggcttttaat gcttttcagt ggttgctgct caagatggag tctactcagc agatggtaag 60
ttctattatt aatacttctt ttgaagctgc agttgttgct gccacttcaa cattagaatt 120
aatgggtatt caatatgatt acaatgaagt atttactaga gttaaaagta aatttgatta 180
tgtaatggat gattctggcg ttaaaaacaa ccttttgggt aaagctataa ctattgggcc 240
ggcgtgtaat gaaaagtttg gctcagcaat tagaaataga aattggatga ttgattccaa 300
aacagttgct aaattagatg aagacgtgaa taaacttaga atgacgttat cttctaaagg 360
aatcgatcaa aagatgagag tacttaatgc ttgttttagt gtaaaaagaa taccagggaa 420
atcatcatca ataatcaaat gcaccagact tatgaaggat aaactagaac gtggagaagt 480
tgaagttgat gattcatatg ttgatgagaa aatggaaatt gatactattg attggaaatc 540
tcgttatgat cagttagaaa aaagatttga gtcactaaaa caaagagtta atgagaaata 600
caatgcttgg gtacaaaaag caaagaaagt aaatgaaaat atgtactctc ttcagaatgt 660
catttcacaa cagcaaaacc aaatagcaga tcttcaacaa tattgtaata aattggaagt 720
tgatttgcaa ggcaaattta gttcattagt gtcgtcagtt gagtggtatc taagatctat 780
ggaactacca gatgatgtaa agactgatgt tgaacagcag ttaaattcaa ttgatttaat 840
taatcccatt ggtgctatag atgatatcga atcattgatt agaaatttaa ttcaagatta 900
tgacagaaca tttttaatgt taaaaggact tttgaagcaa tgcaactatg aatatgcata 960
tgagtagtca cataatttaa aaatattaac catctacaca tgaccctcta tgagcacaat 1020
agttaaaagc taacactgtc aaaaacctaa atggctatag gggcgttatg tgacc 1075

<210> SEQ ID NO 41
<211> LENGTH: 1074
<212> TYPE: DNA
<213> ORGANISM: Human rotavirus

<400> SEQUENCE: 41
ggcttttaat gcttttcagt ggttgctgct caagatggag tctactcagc agatggtaag 60
ctctattatt aacacttctt ttgaagctgc agttgttgct gccacttcaa cattagaatt 120
aatgggtatt caatatgatt acaatgaagt atttactaga gttaaaagta aatttgatta 180
tgtaatggat gactctggtg ttaaaaataa tcttttgggt aaagctataa ctattgacca 240
ggcgttaaat ggaaagtttg gctcagctat tagaaataga aattggatga ctgactctaa 300
aacggttgct aaattggatg aagacgtaaa taaacttaga atgacattgt cttctaaagg 360
aatcgaccaa aagatgagag tacttaatgc ttgttttagt gtgaaaagaa taccaggaaa 420
atcatcatca ataattaagt gcactaaact catgaaggat aaaatagaac gtggggaagt 480
tgaggttgat gattcatata ttgatgagaa aatggaaatt gataccattg attggaaatc 540
tcgttatgac caattagaaa aaagatttga gtcactaaaa caaagagtta ctgagaaata 600
caatacttgg gtacaaaaag cgaagaaagt aaatgagaat atgtactctc ttcagaatgt 660
catttcacaa cagcagaatc aaatagcaga tcttcaacaa tattgtaata aattggaaac 720
tgacttgcaa ggcaaattca gttcattagt gtcatcagtt gagtggtatt taagatctat 780
ggaattacca gatgatgtaa agaatgatat tgaacagcag ttaaattcaa ttgatttaat 840
taatcccatt aatgctatag atgatatcga atcattggtt agaaatttag ttcaggatta 900
tgatagaaca tttttaatgc taaagggact gttgaagcaa tgcaactatg aatatgtata 960
tgaatagtca cataattaaa atcattaacc atctacacat gaccctctat gagcacaata 1020
gttaaaagct aacactgtca aaaacctaaa tggctatagg ggcgttatgt gacc 1074

<210> SEQ ID NO 42
<211> LENGTH: 1074
<212> TYPE: DNA
<213> ORGANISM: Human rotavirus

<400> SEQUENCE: 42
ggcttttaat gcttttcagt ggttgctgct caagatggag tctactcagc agatggtaag 60
ctctattatt aacacttctt ttgaagctgc agttgttgct gccacttcaa cattagaatt 120
aatgggtatt caatatgatt acaatgaagt atttactaga gttaaaagta aatttgatta 180
tgtaatggat gactctggtg ttaaaaataa tcttttgggt aaagctataa ctattgacca 240
ggcgttaaat ggaaagtttg gctcagctat tagaaataga aattggatga ctgactctaa 300
aacggttgct aaattggatg aagacgtaaa taaacttaga atgacattgt cttctaaagg 360
aatcgaccaa aagatgagag tacttaatgc ttgttttagt gtgaaaagaa taccaggaaa 420
atcatcatca ataattaagt gcactaaact catgaaggat aaaatagaac gtggggaagt 480
tgaggttgat gattcatata ttgatgagaa aatggaaatt gataccattg attggaaatc 540
tcgttatgac caattagaaa aaagatttga gtcactaaaa caaagagtta ctgagaaata 600
caatacttgg gtacaaaaag cgaagaaagt aaatgagaat atgtactctc ttcagaatgt 660
catttcacaa cagcagaatc aaatagcaga tcttcaacaa tattgtaata aattggaaac 720
tgacttgcaa ggcaaattca gttcattagt gtcatcagtt gagtggtatt taagatctat 780
ggaattacca gatgatgtaa agaatgatat tgaacagcag ttaaattcaa ttgatttaat 840
taatcccatt aatgctatag atgatatcga atcattggtt agaaatttag ttcaggatta 900
tgatagaaca tttttaatgc taaagggact gttgaagcaa tgcaactatg aatatgtata 960
tgaatagtca cataattaaa atcattaacc atctacacat gaccctctat gagcacaata 1020
gttaaaagct aacactgtca aaaacctaaa tggctatagg ggcgttatgt gacc 1074

<210> SEQ ID NO 43
<211> LENGTH: 750
<212> TYPE: DNA
<213> ORGANISM: Human rotavirus

<400> SEQUENCE: 43
ggcttttaaa agttctgttc cgagagagcg cgtgcggaaa gatggataag cttgccgacc 60
tcaactacac attgagtgta atcactctaa tgaatgacac attgcattct ataattcagg 120
atcctggaat ggcgtatttt acatatattg catctgttct aacagttttg ttcacattac 180
ataaagcttc aattccaacc atgaaaatag cattgaaaac atcaaaatgt tcatataaag 240
tgattaaata ttgtatagtc acgatcatta atactctttt aagattggct ggatataaag 300
agcaggttac tactaaagac gaaattgagc aacagatgga tagaattgtt aaagagatga 360
gacgtcagct ggagatgatt gataaactaa ctactcgtga aattgaacag gttgaattgc 420
ttaaaagtat acatgacaac ttgataacta gatcagttga cgttatagat atgtcgaagg 480
aattcaatca gaaaaacatc aaaacgctag atgaatggga gagtggaagg aatccatatg 540
aaccgtcaga ggtgactgca tccatgtgag aggttgagtt accgtcgtct gtcttcggaa 600
gcggcggaac tcttcaccgc aagccccatt agacctgatg attgactgag aagccacagt 660
caatcatatc gcgtgtggct cagccttaat cccgtttaac caatccagcg agtgttggac 720
gttaatggaa ggaatggtct tagtgtgacc 750

<210> SEQ ID NO 44
<211> LENGTH: 750
<212> TYPE: DNA
<213> ORGANISM: Human rotavirus

<400> SEQUENCE: 44
ggcttttaaa agttctgttc cgagagagcg cgtgcggaaa gatggataag cttgccgacc 60
tcaactacac attgagtgta atcactttaa tgaatgacac attgcattct ataattcagg 120
accctggaat ggcgtatttt ccatatattg catctgttct aacagtgttg ttcacattac 180
ataaagcttc aattccaaca atgaaaatag cattaaaaac gtcaaaatgt tcatacaaag 240
tgatcaagta ttgtatagtc acaattatta atactctttt aaaattggca ggatataaag 300
aacaagttac cactaaagac gaaattgagc aacagatgga tagaattgta aaagagatga 360
gacgtcagct ggagatgatt gataaattaa ctactcgtga aattgaacaa gttgaattgc 420
ttaaacgtat atatgacaat ttaataacta gaccagttga cattgtagat atgacgaagg 480
aatttaatca gaagaatata aaaacgctag atgagtggga gagcggaaaa aatccatatg 540
aaccgataga ggtgactgca tctatgtgag aggttgagtt gccgtcgtct gtcctcggaa 600
gcggcggaac tcttcaccgc aagccccatt ggacctgatg attgactgag aagccacagt 660
caatcatatc gcgtgtggct cagccttaat cccgtttgac caatccagcg aatgttggac 720
gttaatggaa ggaaaggtct taatgtgacc 750

<210> SEQ ID NO 45
<211> LENGTH: 750
<212> TYPE: DNA
<213> ORGANISM: Human rotavirus

<400> SEQUENCE: 45
ggcttttaaa agttctgttc cgagagagcg cgtgcggaaa gatggataag cttgccgacc 60
tcaactacac attgagtgta atcactttaa tgaatgacac attgcattct ataattcagg 120
accctggaat ggcgtatttt ccatatattg catctgttct aacagtgttg ttcacattac 180
ataaagcttc aattccaaca atgaaaatag cattaaaaac gtcaaaatgt tcatacaaag 240
tgatcaagta ttgtatagtc acaattatta atactctttt aaaattggca ggatataaag 300
aacaagttac cactaaagac gaaattgagc aacagatgga tagaattgta aaagagatga 360
gacgtcagct ggagatgatt gataaattaa ctactcgtga aattgaacaa gttgaattgc 420
ttaaacgtat atatgacaat ttaataacta gaccagttga cattgtagat atgacgaagg 480
aatttaatca gaagaatata aaaacgctag atgagtggga gagcggaaaa aatccatatg 540
aaccgataga ggtgactgca tctatgtgag aggttgagtt gccgtcgtct gtcctcggaa 600
gcggcggaac tcttcaccgc aagccccatt ggacctgatg attgactgag aagccacagt 660
caatcatatc gcgtgtggct cagccttaat cccgtttgac caatccagcg aatgttggac 720
gttaatggaa ggaaaggtct taatgtgacc 750

<210> SEQ ID NO 46
<211> LENGTH: 664
<212> TYPE: DNA
<213> ORGANISM: Human rotavirus

<400> SEQUENCE: 46
ggcttttaaa gcgctacagt gatgtctctc agcattgacg tgacgagtct tccctcaatt 60
tcttctagca tttttaaaaa tgaatcgtct tctacaacgt caactctttc tggaaaatct 120
attggtagga acgaacagta tgtttcacca gatatcgatg cgttcaataa atacatgttg 180
tcgaagtctc cagaggatat tggaccatct gattctgctt caaacgatcc actcaccagc 240
ttttcgatta gatcgaatgc ggttaagaca aatgcagatg ctggcgtgtc tatggattca 300
tcaacacaat cacgaccttc aagcaacgtt gggtgcgatc aaatggattt ctccttaaat 360
aaaggtatta atgttagtgc tagtcttgat tcatgtgtat caatttcaac taatcaaaaa 420
aaggagaaat ctaagaagga taaaagtagg aaacactacc caagaattga agcagattct 480
gactctgagg attatgtttt ggatgattca gatagtgatg acggcaaatg taagaattgt 540
aaatataaaa agaaatattt tgcattaaga atgaggatga aacaagtcgc aatgcaattg 600
atagaagact tgtaatgtcg acctgaggac acactaggga gctccccact cccgttttgt 660
gacc 664

<210> SEQ ID NO 47
<211> LENGTH: 664
<212> TYPE: DNA
<213> ORGANISM: Human rotavirus

<400> SEQUENCE: 47
ggcttttaaa gcgctacagt gatgtctctc agcattgacg taacaagtct tccctcaatt 60
tcttctagta tctttaaaaa tgaatcgtct tctacaacgt caactctttc tggaaaatct 120
attggtagga gtgaacagta catttcacca gatgcagaag cattcaataa gtacatgttg 180
tcgaagtctc cagaggatat tggaccatct gattctgctt caaacgatcc actcaccagc 240
ttttcgatta gatcgaatgc agttaagaca aatgcagacg ctggcgtgtc tatggattca 300
tcgacacaat cacgaccttc aagcaacgtt ggatgcgatc aattggattt ctccttgacc 360
aaaggtatta atgttagtgc taatcttgat tcatgtatat caatttcaac tgatcataag 420
aaggagaaat ccaagaaaga taaaagtagg aaacactacc cgagaattga agcagattct 480
gattctgaag attatgtttt ggatgattca gatagtgatg acggtaaatg caagaattgt 540
aaatataaga aaaaatattt cgcactaaga atgaggatga agcgagtcgc aatgcaattg 600
atcgaagatt tgtaatgtca acctgagagc acactaggga gctccccact cccgttttgt 660
gacc 664

<210> SEQ ID NO 48
<211> LENGTH: 664
<212> TYPE: DNA
<213> ORGANISM: Human rotavirus

<400> SEQUENCE: 48
ggcttttaaa gcgctacagt gatgtctctc agcattgacg taacaagtct tccctcaatt 60
tcttctagta tctttaaaaa tgaatcgtct tctacaacgt caactctttc tggaaaatct 120

-continued attggtagga gtgaacagta catttcacca gatgtagaag cattcaataa gtacatgttg 180
tcgaagtctc cagaggatat tggaccatct gattctgctt caaacgatcc actcaccagc 240
ttttcgatta gatcgaatgc agttaagaca aatgcagacg ctggcgtgtc tatggattca 300
tcgacacaat cacgaccttc aagcaacgtt ggatgcgatc aattggattt ctccttgacc 360
aaaggtatta atgttagtgc taatcttgat tcatgtatat caatttcaac tgatcataag 420
aaggagaaat ccaagaaaga taaaagtagg aaacactacc cgagaattga agcagattct 480
gattctgaag attatgtttt ggatgattca gatagtgatg acggtaaatg caagaattgt 540
aaatataaga aaaaatattt cgcactaaga atgaggatga agcgagtcgc aatgcaattg 600
atcgaagatt tgtaatgtca acctgagagc acactaggga gctccccact cccgttttgt 660
gacc 664

<210> SEQ ID NO 49
<211> LENGTH: 3302
<212> TYPE: DNA
<213> ORGANISM: Human rotavirus

<400> SEQUENCE: 49
ggctattaaa gctgtacaat ggggaagtac aatctaattt tgtcagaata tttatcattc 60
gtttataatt cacaatctgc agttcaaata ccaatctatt attcttccaa ttctgaatta 120
gaaacgagat gcattgaatt tcatgccaaa tgtgttgata attcaaagaa agggttatca 180
ttaaaaccat tatttgagga atataaagat gtaacagata atgcgacttt attatccata 240
ttatcatatt cgtatgataa atataatgct gtagagcgga aattagttag ttatgctaaa 300
ggtaaaccac ttgaagctga tttaacagca aacgaacttg attatgaaaa taataaaata 360
acttctgaac tatttcagtc agccgaagaa tacactgatt cattaatgga tcccgccata 420
ttgacttcac tatcttcaaa tttaaatgca gttatgtttt ggctagaacg acattcaaac 480
gatattgctg atgcaaataa aatttataaa cgcagattag atttatttac tatagtagca 540
tctacaataa ataaatatgg ggtaccgaga cataatgaga aatacagata cgaatatgaa 600
gtaatgaaag ataaaccata ctatttagtg acttgggcta attcgtccat agaaatgctt 660
atgtcagtat tttcacatga agattatcta atagcaaaag aattgattgt tttatcatat 720
tcaaataggt cgacattagc taaattggtt tcatctccaa tgtctatatt agttgcattg 780
atagatatta atggtacatt cattacgaat gaagagttag agcttgaatt ttcagataaa 840
tatgttaaag caattgtacc tgatcagact ttcgatgaat tgcaagagat gattaataat 900
atgaaaaaaa ttggtttagt agatattcct aggatgatcc aagaatggtt aatcgattgc 960
tcattagaga aattcacgct gatgtcaaaa atttactctt ggtcattcca tgttggattt 1020
agaaagcaga aaatgattga tgcggcgtta gaccaattga agacggaata tactaaggat 1080
gtggatgatg aaatgtacaa tgaatacact atgttaatta gagatgaaat agtgaaaatg 1140
ttagaaattc cagttaaaca tgatgatcat ctacttcgtg attcagaact agctggattg 1200
ttatcaatgt catcagcttc aaatggtgaa tcaagacaaa tcaaatttgg tcgcaaaaca 1260
atattttcaa ctaagaagaa tatgcatgtg atggatgata tagcacatgg aaagtatact 1320
ccaggtgtta ttcctccagt gaacgtagat aaaccaattc cactaggtcg tagagatgtt 1380
cctggaaggc gtacgagaat tatattcata cttccatatg agtattttat tgcacaacat 1440
gctgtggtag aaaagatgct attgtatgca aaacatacta gagaatatgc ggaattctat 1500
tcacagtcaa atcaattgtt atcatacggt gatgttacga gatttttgtc cagtaactct 1560
atggttttat atacagacgt ttcacaatgg gactcgtcgc agcataacac acagccattc 1620
aggaagggaa taattatggg tctagacatg ctatctaata tgactaacga tccaaaggta 1680
gtacaagcat tgaatttata taagcaaaca caaattaacc ttatggattc atacgttcag 1740
ataccagatg gtaacgtaat caaaaagaac cagtacggag ctgtcgcttc aggagaaaaa 1800
caaactaaag cagctaattc catagctaac ttagccctta ttaaaacagt actatcaagg 1860
attgcaaata aatactcttt tataactaaa ataattagag taagtggtga tgacaattat 1920
gcagtattac aatttaatac tgacctcaca aaacagatga ttcaagatgt gtctaatgac 1980
gtgagatata tatattttag aatgaatgca aaagttaaag cactagtgtc gacagttggt 2040
attgaaatag caaaaagata cttagctgga ggaaaaatat tctttagagc tggcataaat 2100
ttattaaata atgaaaaacg tgggcagagt acgcaatggg atcaagcagc tattctatat 2160
tcaaattaca ttgttaacaa attacgagga tttgagactg atagagaatt tatattaact 2220
aaaattatac aaatgacttc cgtagccatc actggatcgc taaggttatt tccatcagaa 2280
cgagtattaa ctaccaattc aacgttcaaa gtatttgatt cagaagattt cattatagaa 2340
tatggaacaa ctgatgatga agtgtatata caaagagcat tcatgtcatt gtctagtcag 2400
aaatcgggaa tagctgatga aattgcctct tcgcaaacat ttaaaaatta tgttagtaaa 2460
ttatctgatc aattattagt atcaaaaaat gtaattgtat ctaaaggtat agcagtaacg 2520
gagaaggcta aattgaattc atacgcgcca atatatttag aaaaacgtcg tgcgcaaata 2580
tcagcgttat taaccatgtt gcagaaacca gtgtcattta aatcaaataa aaatactatt 2640
aatgaaattt tacgtgatat aaaaccattc tttgtcacta ctgaagataa tttaccaatt 2700
caatatagaa aatttatgcc tacattgcca gataatgttc aatacgtcat acaatgtata 2760
ggatcaagga catatcaaat agaagatagc ggatcgaaat cgtcaatttc aaagttaata 2820
tcaaaatatt cagtttataa accatcaatt gaagagttgt acaaagttat atctctaaga 2880
gaacaagaaa tacaattgta tttggtgtca ttaggagttc cattagttga tgcgagtgca 2940
tatgtagcat caaggatata ttcacaagat aaatataaaa tattagaatc ttatgtatat 3000
aacttactat caattaatta tggatgctat caattattcg atttcaactc tccagatcta 3060
gaaaagctta tacgaattcc ttttaaaggc aaaataccag ctgtaacgtt catattgcat 3120
ctttatgcta agttagaaat aataaattat gctataaaga atagagcttg gattagtgta 3180
ttctgtaatt atccaaaatc tgagatgatt aagttatgga agaaaatgtg gagcataaca 3240
gcactacgat cgccctatac tagtgcgaat ttctttcaag attagaacgc ttagatgtga 3300
cc 3302

<210> SEQ ID NO 50
<211> LENGTH: 3302
<212> TYPE: DNA
<213> ORGANISM: Human rotavirus

<400> SEQUENCE: 50
ggctattaaa gctgtacaat ggggaagtac aatctaatct tgtcagaata tttatcattt 60
gtttataatt cacaatctgc agttcaaata ccaatttatt attcttccaa ttcagaatta 120
gaaaaaagat gtattgagtt tcatgctaaa tgtgttgaca gttctaaaaa aggtatgtca 180
ttaaaacctt tatttgaaga gtataaagat gtaatagata atgcaacgtt actatctata 240
ttatcatatt cttatgataa atacaacgct gtggaacgta aactagtcaa ttatgctaaa 300

-continued

```
ggtaaacctt tagaggctga tttaacggca aacgagcttg attatgaaaa taacaaaata    360

acttctgaac tgtttcagtc agccgaagaa tataccgatt cattaatgga tcctgctata    420

ttaacttcat tatcttcaaa tttaaatgca gttatgtttt ggttagaacg acactcaaat    480

gacgttgctg atgcaaataa aatttataag cgtagactag atttatttac catagtggca    540

tctacaataa ataaatacgg agtacccaga cataatgaaa aatacagata tgaatacgaa    600

gtgatgaagg ataaaccgta ttacttagta acttgggcta actcatctat agaaatgctt    660

atgtcagtgt tttcacatga ggattattta atagcaaaag aattaataat cttatcatac    720

tcaaatagat caacgttagc aaaactagtt tcatctccaa tgtcaatatt agttgcatta    780

atagatatca atggtacgtt tattacgaat gaagaattgg aacttgagtt ttcggataaa    840

tatgttaagg caattgtacc tgatcaaatt ttcgatgaat tacaggaaat gattgacaat    900

atgaagaaag ttggtttagt agacatacca agaatgattc aagaatggtt agttgattgt    960

tcattagaga aatttacact gatgtcaaaa atttattctt ggtcatttca tgttggtttt   1020

agaaaacaaa aatgattgga tgcagcatta gaccaattga agacagagta cactgaagat   1080

gtagatggtg agatgtacaa tgagtataca atgttaatta gagatgaaat agttaaaatg   1140

ctagaagtac cagttaaaca tgacgatcat ctacttcgtg attcagaatt agctggattg   1200

ttatcaatgt catcagcttc aaatggtgaa tcaaggcaac ttaaatttgg tctcaaaaca   1260

atattttcaa ctaagaaaaa tatgcatgtt atggatgata ttgcacatgg aaggtatact   1320

cctggtatca ttcctccagt aaacgtagat agaccaattc cattaggtcg tagagatgtt   1380

cctggacgaa gaacaagaat tatattcata ttaccatatg aatactttat tgcgcagcac   1440

gctgtcgtag aaaaaatgtt atcatacgca aagcatacta gagagtatgc ggaattttac   1500

tcacagtcaa atcaattgct atcatacggt gatgtgacaa gattcttatc cagtaattct   1560

atggtgctat acacagacgt ttcacaatgg gattcgtcac aacataacac acagccattt   1620

agaaaaggaa taattatggg tttagatatg ttatctaata tgactaatga tccaaaagta   1680

atacaaacgc taaatttata taaacaaaca caaattaatc tcatggattc atatgttcaa   1740

atacctgatg gtaatgtaat caaaaagatt cagtatggtg ctgttgcttc aggagaaaaa   1800

caaactaagg cagctaattc tatagctaat ttggcactca ttaaaacagt attgtcaagg   1860

attgcaaata aatattcttt tataaccaaa ataatcagag ttgatggtga tgataattat   1920

gcagtactac aatttaacac cgatgtcact aaacaaatgg tccaagatgt gtcaaacgat   1980

gtgagacata tatattctag aatgaatgct aaagttaaag cattggtatc tacagtcggt   2040

attgaaatag caaaaagata tatagctgga ggaaaaatat tttttagagc tggtataaac   2100

ttattaaata atgagaagcg tggacaaagt acacaatggg atcaagcagc tattttatat   2160

tcgaactaca ttgttaacaa attacgagga tttgagactg atagagaatt tatattaact   2220

aaaattatac aaatgacatc tgtagccatt actggatcac taaggctatt tccgtcagaa   2280

cgagtgttaa ctactaattc tacattcaaa gtatttgact cagaagattt cattatagag   2340

tatggaacaa ctgacgatga agtatatata cagagagcat ttatgtcatt gtctagtcaa   2400

aagtcaggaa tagctgatga aattgcctct tcacaaacat tcaaaaatta tgttaataaa   2460

ttatctgacc aactattaat atcaaaaaac gtaattgtat ccaaaggtat agctgtaaca   2520

gaaaaagcga aattgaattc atatgcacca gtttatttag aaaaacgtcg tgcgcaaata   2580

tcagcgctat taactatgtt acagaagcca gtgtcattta aatcaaataa aattactatt   2640

aatgacattt tgcgtgacat aaaaccattt tttgttactt ctgaagccaa tttgccaatt   2700
```

caatacagaa aatttatgcc aacactacct gataacgtcc aatatgttat acaatgtata 2760
ggatcaagga cgtatcagat agaagatagt gggtcgaaat catcgatttc aaagttaata 2820
tcaaaatact cagtttacaa accatcaatt gaggaactat ataaagttat atctttacga 2880
gaacaagaaa tacagttgta tttagtttca ctaggagttc cgccagttga tgcaggcacg 2940
tacgtcgggt caagaatata ttcgcaagac aagtataaaa tattagaatc ttacgtatat 3000
aatttattat caattaatta tggatgttat caattattcg attttaattc tccagattta 3060
gagaaactta tacgaattcc ttttaaaggt aagataccag ccgtaacatt tatattacat 3120
ctctatgcaa aacttgaaat aataaatcat gccattaaga atggagcatg gattagtttg 3180
ttctgtaatt acccaaaatc tgagatgatt aaactatgga agaaaatgtg gaacataaca 3240
gcattacggt ctccctatac tagtgcgaat ttctttcaag attagagtgc ttagatgtga 3300
cc 3302

<210> SEQ ID NO 51
<211> LENGTH: 3302
<212> TYPE: DNA
<213> ORGANISM: Human rotavirus

<400> SEQUENCE: 51
ggctattaaa gctgtacaat ggggaagtac aatctaatct tgtcagaata tttatcattt 60
gtttataatt cacaatctgc agttcaaata ccaatttatt attcttccaa ttcagaatta 120
gaaaaaagat gtattgagtt tcatgctaaa tgtgttgaca gttctaaaaa aggtatgtca 180
ttaaaacctt tatttgaaga gtataaagat gtaatagata atgcaacgtt actatctata 240
ttatcatatt cttatgataa atacaacgct gtggaacgta aactagtcaa ttatgctaaa 300
ggtaaacctt tagaggctga tttaacggca aacgagcttg attatgaaaa taacaaaata 360
acttctgaac tgtttcagtc agccgaagaa tataccgatt cattaatgga tcctgctata 420
ttaacttcat tatcttcaaa tttaaatgca gttatgtttt ggttagaacg acactcaaat 480
gacgttgctg atgcaaataa aatttataag cgtagactag atttatttac catagtggca 540
tctacaataa ataaatacgg agtacccaga cataatgaaa aatacagata tgaatacgaa 600
gtgatgaagg ataaaccgta ttacttagta acttgggcta actcatctat agaaatgctt 660
atgtcagtgt tttcacatga ggattattta atagcaaaag aattaataat cttatcatac 720
tcaaatagat caacgttagc aaaactagtt tcatctccaa tgtcaatatt agttgcatta 780
atagatatca atggtacgtt tattacgaat gaagaattgg aacttgagtt ttcggataaa 840
tatgttaagg caattgtacc tgatcaaatt ttcgatgaat tacaggaaat gattgacaat 900
atgaagaaag ttggtttagt agacatacca agaatgattc aagaatggtt agttgattgt 960
tcattagaga aatttacact gatgtcaaaa atttattctt ggtcatttca tgttggtttt 1020
agaaaacaaa aaatgattga tgcagcatta gaccaattga agacagagta cactgaagat 1080
gtagatggtg agatgtacaa tgagtataca atgttaatta gagatgaaat agttaaaatg 1140
ctagaagtac cagttaaaca tgacgatcat ctacttcgtg attcagaatt agctggattg 1200
ttatcaatgt catcagcttc aaatggtgaa tcaaggcaac ttaaatttgg tctcaaaaca 1260
atattttcaa ctaagaaaaa tatgcatgtt atggatgata ttgcacatgg aaggtatact 1320
cctggtatca ttcctccagt aaacgtagat agaccaattc cattaggtcg tagagatgtt 1380
cctggacgaa gaacaagaat tatattcata ttaccatatg aatactttat tgcgcagcac 1440

```
gctgtcgtag aaaaaatgtt atcatacgca aagcatacta gagagtatgc ggaattttac   1500

tcacagtcaa atcaattgct atcatacggt gatgtgacaa gattcttatc cagtaattct   1560

atggtgctat acacagacgt ttcacaatgg gattcgtcac aacataacac acagccattt   1620

agaaaaggaa taattatggg tttagatatg ttatctaata tgactaatga tccaaaagta   1680

atacaaacgc taaatttata taaacaaaca caaattaatc tcatggattc atatgttcaa   1740

atacctgatg gtaatgtaat caaaaagatt cagtatggtg ctgttgcttc aggagaaaaa   1800

caaactaagg cagctaattc tatagctaat ttggcactca ttaaaacagt attgtcaagg   1860

attgcaaata aatattcttt tataaccaaa ataatcagag ttgatggtga tgataattat   1920

gcagtactac aatttaacac cgatgtcact aaacaaatgg tccaagatgt gtcaaacgat   1980

gtgagacata tatattctag aatgaatgct aaagttaaag cattggtatc tacagtcggt   2040

attgaaatag caaaaagata tatagctgga ggaaaaatat tttttagagc tggtataaac   2100

ttattaaata atgagaagcg tggacaaagt acacaatggg atcaagcagc tattttatat   2160

tcgaactaca ttgttaacaa attacgagga tttgagactg atagagaatt tatattaact   2220

aaaattatac aaatgacatc tgtagccatt actggatcac taaggctatt tccgtcagaa   2280

cgagtgttaa ctactaattc tacattcaaa gtatttgact cagaagattt cattatagag   2340

tatggaacaa ctgacgatga agtatatata cagagagcat ttatgtcatt gtctagtcaa   2400

aagtcaggaa tagctgatga aattgcctct tcacaaacat tcaaaaatta tgttaataaa   2460

ttatctgacc aactattaat atcaaaaaac gtaattgtat ccaaaggtat agctgtaaca   2520

gaaaaagcga aattgaattc atatgcacca gtttatttag aaaaacgtcg tgcgcaaata   2580

tcagcgctat taactatgtt acagaagcca gtgtcattta aatcaaataa aattactatt   2640

aatgacattt tgcgtgacat aaaaccattt tttgttactt ctgaagccaa tttgccaatt   2700

caatacagaa aatttatgcc aacactacct gataacgtcc aatatgttat acaatgtata   2760

ggatcaagga cgtatcagat agaagatagt gggtcgaaat catcgatttc aaagttaata   2820

tcaaaatact cagtttacaa accatcaatt gaggaactat ataaagttat atctttacga   2880

gaacaagaaa tacagttgta tttagtttca ctaggagttc cgccagttga tgcaggcacg   2940

tacgtcgggt caagaatata ttcgcaagac aagtataaaa tattagaatc ttacgtatat   3000

aatttattat caattaatta tggatgttat caattattcg attttaattc tccagattta   3060

gagaaactta tacgaattcc ttttaaaggt aagataccag ccgtaacatt tatattacat   3120

ctctatgcaa aacttgaaat aataaatcat gccattaaga atggagcatg gattagtttg   3180

ttctgtaatt acccaaaatc tgagatgatt aaactatgga agaaaatgtg gaacataaca   3240

gcattacggt ctccctatac tagtgcgaat ttctttcaag attagagtgc ttagatgtga   3300

cc                                                                  3302
```

```
<210> SEQ ID NO 52
<211> LENGTH: 2747
<212> TYPE: DNA
<213> ORGANISM: Human rotavirus

<400> SEQUENCE: 52

ggctattaaa ggctcaatgg cgtacaggaa gcgcggaact aaacgtgaag acttaccaca     60

acaaaatgaa cgtctgcaag aaaaagaaat tgaaaataat atagacgtaa ccatggaaaa    120

taaaaataaa aatattaata aaaataataa taaaaataac aatagaaagc agcaattatc    180

tgacaaagtg ttattacaaa aagaggaaat aataactgat gtacaagatg acatcaaaat    240
```

-continued

```
aactgatgaa gttaaaaaat cgtcaaaaga agagtcgaaa cagttactcg aaatattaaa    300
aacgaaagaa gatcatcaga aagaagtaca gtacgaaatt ctacaaaaaa caataccgac    360
ttttgaacca aaagaatcaa ttttgaaaaa attagaagat ataagaccag aacaagctaa    420
gaagcaaatg aaattgttta gaatatttga accaagacaa ttaccaatct accgagcaaa    480
tggtgagaaa gaattaagga atagatggta ttggaaattg aaaaaggata cgttgccaga    540
cggagattat gacgtacgcg aatatttttt aaatttatat gatcaaatac tgatagaaat    600
gccagattat ttattactaa aagatatggc tgtagaaaat aaaaactcta gggatgctgg    660
taaagttgta gattctgaga ctgcaagtat ttgtgatgcc atatttcaag atgaagagac    720
agagggagtt attagaagat ttatcgcaga tatgagacaa caaattcaag ctgatagaaa    780
tattgtcaat tatccatcaa ttttacatcc aattgaccat gcatttaatg aatatttttct   840
gaaccatcaa ttagttgaac cattgaataa cgacattatt tttaattata taccagaaag    900
aataagaaat gatgtcaact atattttgaa tatggatatg aatttaccat caacagcaag    960
atatattaga ccaaatctgt tgcaagatag actaaattta catgataatt ttgaatcatt   1020
atgggacaca ataactacat cgaattatat attagcaaga tcagtcgtgc ctgatttgaa   1080
ggaaaaagaa ttagtttcga ctgaagctca gatacagaaa atgtctcaag atttgcagct   1140
tgaagcttta acaatacaat ctgaaacgca atttctggcc ggcataaatt cacaagcagc   1200
aaatgattgt tttaaaacac tgatagcagc tatgttaagt caacgtacaa tgtcattaga   1260
ttttgtaact acgaattata tgtcacttat atctggcatg tggctattga ctgttatacc   1320
aaatgatatg tttcttcgtg agtcgctagt tgcatgcgaa ttggctataa taaacactat   1380
agtttaccca gcatttggaa tgcaaagaat gcattatagg aatggcgatc cccagactcc   1440
atttcaaata gcagagcaac aaatacaaaa ttttcaagta gctaattggt tacattttat   1500
taataataat agatttagac aagttgttat tgatggagtg ttaaatcaaa cacttaatga   1560
caacattagg aatggacaag ttattaatca attaatggaa gcattaatgc agttatctag   1620
acaacaattt ccgaccatgc cagttgatta caaaagatca atccaaagag gaatattgtt   1680
attgtctaac agattgggtc agttagttga tttaacgaga ttattatcat ataattatga   1740
aactctaatg gcttgtataa ctatgaatat gcagcatgtt caaactctca ctactgaaag   1800
attacagtta acttctgtca catctttatg tatgttaatt ggaaatacca cagtaattcc   1860
aagtccacaa acactatttc actattataa tataaatgta aattttcatt caaattataa   1920
tgaacgaatt aacgatgctg tggctatcat tacggctgct aatagactaa atttatatca   1980
gaaaaaaatg aaatcaatag ttgaggattt tttgaaaaga ttgcaaattt ttgatgtacc   2040
acgagtacca gatgatcaaa tgtacagatt gagagacaga cttagattat tgccagttga   2100
aagacgaaga cttgatatat ttaacttaat attaatgaat atggagcaga tcgaacgagc   2160
ttcagataaa attgctcaag gagtaataat tgcttataga gatatgcagc tagaaagaga   2220
tgagatgtat ggatttgtta acatcgctag gaacctcgat ggatatcaac aaatcaattt   2280
agaagagtta atgagaactg gagactatgg tcaaattact actatgctat taaacaatca   2340
gcctgtagct ttggtaggag cattaccatt tgtaacagat tcatcagtta tatcgcttat   2400
agcgaaattg gatgccacag tatttgctca aatagttaaa cttagaaaag tggacacttt   2460
aaaaccgata ttgtataaaa taaattctga ttctaatgat ttctacttag ttgcaaatta   2520
tgattggata ccgacttcaa ctacaaaagt ttataaacaa gtaccacaac cttttgattt   2580
```

-continued cagagcatca atgcatatgt taacgtctaa cttaactttt accgtttatt ctgatttact 2640
atctttcgtt tctgcagaca cggttgaacc tattaacgca attgcttttg acaatatgcg 2700
cattatgaac gaactgtaaa cgccaacccc actgtggaga tatgacc 2747

<210> SEQ ID NO 53
<211> LENGTH: 2747
<212> TYPE: DNA
<213> ORGANISM: Human rotavirus

<400> SEQUENCE: 53
ggctattaaa ggctcaatgg cgtacaggaa gcgcggaact aaacgtgaag acttaccaca 60
acaaaatgaa cgtctgcaag aaaaagaaat tgaaaataat atagacgtaa ccatggaaaa 120
taaaaataaa aatattaata aaaataataa tagaaataac aatagaaagc agcaattatc 180
tgacaaagtg ttatcacaaa aagaggaaat aataactgat gtacaagatg acatcaaaat 240
aactgatgaa gttaaaaaat cgtcaaaaga agagtcgaaa cagttactcg aaatattaaa 300
aacgaaagaa gatcatcaga aagaagtaca gtacgaaatt ctacaaaaaa caataccgac 360
ttttgaacca aaagaatcaa ttttgaaaaa attagaagat ataagaccag aacaagctaa 420
gaagcaaatg aaattgttta gaatatttga accaagacaa ttaccaatct accgagcaaa 480
tggtgagaaa gaattaagga atagatggta ttggaaattg aaaaaggata cgttgccaga 540
cggagattat gacgtacgcg aatatttttt aaatttatat gatcaaatac tgatagaaat 600
gccagattat ttattactaa aagatatggc tgtagaaaat aaaaactcta gggatgctgg 660
taaagttgta gattctgaga ctgcaagtat ttgtgatgcc atatttcaag atgaagagac 720
agagggagtt attagaagat ttatcgcaga tatgagacaa caaattcaag ctgatagaaa 780
tattgtcaat tatccatcaa ttttacatcc aattgaccat gcatttaatg aatattttct 840
gaaccatcaa ttagttgaac cattgaataa cgacattatt tttaattata taccagaaag 900
aataagaaat gatgtcaact atattttgaa tatggatatg aatttaccat caacagcaag 960
atatattaga ccaaatctgt tgcaagatag actaaattta catgataatt ttgaatcatt 1020
atgggacaca ataactacat cgaattatat attagcaaga tcagtcgtgc ctgatttgaa 1080
ggaaaaagaa ttagtttcaa ctgaagctca gatacagaaa atgtctcaag atttgcagct 1140
tgaagcttta acaatacaat ctgaaacgca atttctggcc ggcataaatt cacaagcagc 1200
aaatgattgt tttaaaacac tgatagcagc tatgttaagt caacgtacaa tgtcattaga 1260
ttttgtaact acgaattata tgtcacttat atctggcatg tggctattga ctgttatacc 1320
aaatgatatg tttcttcgtg agtcgctagt tgcatgcgaa ttggctataa taaacactat 1380
agtttaccca gcatttggaa tgcaaagaat gcattatagg aatggcgatc cccagactcc 1440
atttcaaata gcagagcaac aaatacaaaa ttttcaagta gctaattggt tacattttat 1500
taataataat agatttagac aagttgttat tgatggagtg ttaaatcaaa cacttaatga 1560
caacattagg aatggacaag ttattaatca attaatggaa gcattaatgc agttatctag 1620
acaacaattt ccgaccatgc cagttgatta caaaagatca atccaaagag gaatattgtt 1680
attgtctaac agattgggtc agttagttga tttaacgaga ttattatcat ataattatga 1740
aactctaatg gcttgtataa ctatgaatat gcaacatgtt caaactctca ctactgaaag 1800
attacagtta acttctgtca catctttatg tatgttaatt ggaaatacca cagtaattcc 1860
aagtccacaa acactatttc actattataa tgtaaatgta aattttcatt caaattataa 1920
tgaacgaatt aacgatgctg tggctatcat tacggccgct aatagactaa atttatatca 1980

-continued

```
gaaaaaaatg aaatcaatag ttgaggattt tttgaaaaga ttgcaaattt ttgatgtacc   2040

acgagtacca gatgatcaaa tgtacagatt gagagacaga cttagattat tgccagttga   2100

aagacgaaga cttgatatat ttaacttaat attaatgaat atggagcaga tcgaacgagc   2160

ttcagataaa attgctcaag gagtaataat tgcttataga gatatgcagc tagaaagaga   2220

tgagatgtat ggatttgtta acatcgctag gaacctcgat ggatatcaac aaatcaattt   2280

agaagagtta atgagaactg gagactatgg tcaaattact actatgctat taaacaatca   2340

gcctgtagct ttggtaggag cattaccatt tgtaacagat tcatcagtta tatcgcttat   2400

agcgaaattg gatgccacag tatttgctca aatagttaaa cttagaaaag tggacacttt   2460

aaaaccgata ttgtataaaa taaattctga ttctaatgat ttctacttag ttgcaaatta   2520

tgattggata ccgacttcaa ctacaaaagt ttataaacaa gtaccacaac cttttgattt   2580

cagagcatca atgcatatgt taacgtctaa cttaactttt accgtttatt ctgatttact   2640

atctttcgtt tctgcagaca cggttgaacc tattaacgca attgcttttg acaatatgcg   2700

cattatgaac gaactgtaaa cgccaacccc actgtggaga tatgacc                 2747
```

<210> SEQ ID NO 54
<211> LENGTH: 2747
<212> TYPE: DNA
<213> ORGANISM: Human rotavirus

<400> SEQUENCE: 54

```
ggctattaaa ggctcaatgg cgtacaggaa gcgcggaact aaacgtgaag acttaccaca     60

acaaaatgaa cgtctgcaag aaaaagaaat tgaaaataat atagacgtaa ccatggaaaa    120

taaaaataaa aatattaata aaaataataa tagaaataac aatagaaagc agcaattatc    180

tgacaaagtg ttatcacaaa aagaggaaat aataactgat gtacaagatg acatcaaaat    240

aactgatgaa gttaaaaaat cgtcaaaaga agagtcgaaa cagttactcg aaatattaaa    300

aacgaaagaa gatcatcaga aagaagtaca gtacgaaatt ctacaaaaaa caataccgac    360

ttttgaacca aaagaatcaa ttttgaaaaa attagaagat ataagaccag aacaagctaa    420

gaagcaaatg aaattgttta gaatatttga accaagacaa ttaccaatct accgagcaaa    480

tggtgagaaa gaattaagga atagatggta ttggaaattg aaaaaggata cgttgccaga    540

cggagattat gacgtacgcg aatatttttt aaatttatat gatcaaatac tgatagaaat    600

gccagattat ttattactaa aagatatggc tgtagaaaat aaaaactcta gggatgctgg    660

taaagttgta gattctgaga ctgcaagtat ttgtgatgcc atatttcaag atgaagagac    720

agagggagtt attagaagat ttatcgcaga tatgagacaa caaattcaag ctgatagaaa    780

tattgtcaat tatccatcaa ttttacatcc aattgaccat gcatttaatg aatattttct    840

gaaccatcaa ttagttgaac cattgaataa cgacattatt tttaattata taccagaaag    900

aataagaaat gatgtcaact atattttgaa tatggatatg aatttaccat caacagcaag    960

atatattaga ccaaatctgt tgcaagatag actaaattta catgataatt ttgaatcatt   1020

atgggacaca ataactacat cgaattatat attagcaaga tcagtcgtgc ctgatttgaa   1080

ggaaaaagaa ttagtttcaa ctgaagctca gatacagaaa atgtctcaag atttgcagct   1140

tgaagcttta acaatacaat ctgaaacgca atttctggcc ggcataaatt cacaagcagc   1200

aaatgattgt tttaaaacac tgatagcagc tatgttaagt caacgtacaa tgtcattaga   1260

ttttgtaact acgaattata tgtcacttat atctggcatg tggctattga ctgttatacc   1320
```

```
aaatgatatg tttcttcgtg agtcgctagt tgcatgcgaa ttggctataa taaacactat   1380

agtttaccca gcatttggaa tgcaaagaat gcattatagg aatggcgatc cccagactcc   1440

atttcaaata gcagagcaac aaatacaaaa ttttcaagta gctaattggt tacattttat   1500

taataataat agatttagac aagttgttat tgatggagtg ttaaatcaaa cacttaatga   1560

caacattagg aatggacaag ttattaatca attaatggaa gcattaatgc agttatctag   1620

acaacaattt ccgaccatgc cagttgatta caaaagatca atccaaagag gaatattgtt   1680

attgtctaac agattgggtc agttagttga tttaacgaga ttattatcat ataattatga   1740

aactctaatg gcttgtataa ctatgaatat gcaacatgtt caaactctca ctactgaaag   1800

attacagtta acttctgtca catctttatg tatgttaatt ggaaatacca cagtaattcc   1860

aagtccacaa acactatttc actattataa tgtaaatgta aattttcatt caaattataa   1920

tgaacgaatt aacgatgctg tggctatcat tacggccgct aatagactaa atttatatca   1980

gaaaaaaatg aaatcaatag ttgaggattt tttgaaaaga ttgcaaattt ttgatgtacc   2040

acgagtacca gatgatcaaa tgtacagatt gagagacaga cttagattat tgccagttga   2100

aagacgaaga cttgatatat ttaacttaat attaatgaat atggagcaga tcgaacgagc   2160

ttcagataaa attgctcaag gagtaataat tgcttataga gatatgcagc tagaaagaga   2220

tgagatgtat ggatttgtta acatcgctag gaacctcgat ggatatcaac aaatcaattt   2280

agaagagtta atgagaactg gagactatgg tcaaattact actatgctat taaacaatca   2340

gcctgtagct ttggtaggag cattaccatt tgtaacagat tcatcagtta tatcgcttat   2400

agcgaaattg gatgccacag tatttgctca aatagttaaa cttagaaaag tggacacttt   2460

aaaaccgata ttgtataaaa taaattctga ttctaatgat ttctacttag ttgcaaatta   2520

tgattggata ccgacttcaa ctacaaaagt ttataaacaa gtaccacaac cttttgattt   2580

cagagcatca atgcatatgt taacgtctaa cttaactttt accgtttatt ctgatttact   2640

atctttcgtt tctgcagaca cggttgaacc tattaacgca attgcttttg acaatatgcg   2700

cattatgaac gaactgtaaa cgccaacccc actgtggaga tatgacc                 2747
```

<210> SEQ ID NO 55
<211> LENGTH: 2591
<212> TYPE: DNA
<213> ORGANISM: Human rotavirus

<400> SEQUENCE: 55

```
ggctattaaa gcagtactag tagtgtgttt tacctctgat ggtgtaaaca tgaaagtatt     60

agctttaaga catagtgtgg ctcagatata tgcagatact caggtgtaca cacatgatga    120

ctctaaagat gattatgaaa atgcgttctt aatttctaat ctcactacac ataatatatt    180

atatttaaat tatagtgtaa aaacactgca aatattgaat aaatccggta tagctgcaat    240

agagatacag aagatagatg agttattcac gctaattaga tgtaatttta catacgacta    300

tattgatgac gttgtctatt tacatgatta ttcatattat gctaataatg aaatacggac    360

tgaccaatat tgggtaacca agacaaatat agaagactat ctattaccag gatggaaatt    420

gacatatgtt ggatacaatg gaagtgatac gagaggacat tataattttt cttttagatg    480

tcagaatgca gctacagatg atgatgtaat aatagagtat atctattcaa atgaattaga    540

cttccagaac tttatactca aaaagattaa agaaaggatg acaacatcac taccaatagc    600

aagactttca aatcgcgtat ttagagataa attatttaaa acgttgtcag taaatcatga    660

taaagtagtt aatgttggac ctagaaatga atctatgttt actttttag accatccatc    720
```

```
aataaaacaa ttctctaatg gaccatattt ggttaaagat acaattaaac tcaaacaaga    780
gagatggctt ggtaaaagat tatcacagtt tgacattggt caatataaga atatgttaaa    840
tgtattaacg actttatatc aatattacga tatgtatcat gaaaaaccaa ttatatatat    900
gataggatca gcgccctcgt attggatata tgatgtcaaa cagtactctg acttgaaatt    960
tgagacatgg gatccactag atacaccata ttctaattta catcataagg aattatttta   1020
cataaatgac gtgcaaaaac ttaaagataa ttcgatacta tatatagata taagaacaga   1080
tagaggaaat atggactgga aggaatggcg aaaagtggtg gaagggcaaa ctgctgacaa   1140
tttacatatt gcatataaat atctatctac aggaaaagct aagatatgtt gtgttaaaat   1200
gaccgctatg gatgtagaat taccaatatc tgcaaaactg cttcaccatc caactacaga   1260
aattagatca gagttttatt taatgatgga tatatgggac tccaaaaata ttaaaagatt   1320
cataccaaaa ggtgtattat actcatatat aaacaataca attactgaaa acgtatttat   1380
acaacaacct tttaagttga aaacattgaa aaatgaatat gtaatagcac tttatgcttt   1440
atcaaatgat cttaacaata gagaagatgt ggtaaaacta atcaataatc agaaaagagc   1500
gttaataacg gtgagaatta acaatacatt taaagatgaa ccgaaagtcg gatttaaaaa   1560
catttacgat tggacatttt tgccaacgga ttttgagatg aatggatcaa taattacctc   1620
atatgatgga tgtctaggta tttttggttt atcaatatca ctagcttcaa aaccaaccgg   1680
taataatcat ttattcattt taagtggtac ggacaagtat tttaaattgg atcaattcgc   1740
aaatcatatg agtatatcac gacgatcaca tcagatacga ttttctgagt cagccacttc   1800
atactcggga tacattttta gagatttgtc taataataat ttcaatttaa taggtacgaa   1860
tgtagagaat tcagtatccg gacacgtata taatgcattg atttattata gatataatta   1920
ctcatttgac cttaaacgat ggatatactt acattcaaca ggtaaagcta gcattgaagg   1980
tggtaagtat tatgaacatg ctccaataga attaatttat gcatgcaggt cagcaagaga   2040
attcgcgaaa ttgcaagatg atttaacagt attaagatat tcaaatgaga tagaaaacta   2100
tatcaataaa gtttatagta taacatacgc cgacgaccct aattacttta ttggaattaa   2160
gtttaaaaat attccttaca agtataacgt taaagtacca catctcacat ttggcgtgtt   2220
aaatatttct gaacagatgt taccagatgc aatagcaatt ttaaagaaat ttaagaatga   2280
actatttgga atggacataa caacgagtta tacatatatg ttatctgatg aggtgtatgt   2340
agcaaatata agtggtgtac tatcaacata tttcaaaatt tacaacgcgt tttataaaga   2400
acaaattaca tttggacagt caagaatgtt tattccccat gtaacgttga gttttagtaa   2460
tgagaaaaca gtgagaatag acactacaaa attgtacata gattccattt atctaagaaa   2520
aataaaaggt gacacagtgt ttgatatgac tgagtgagct aaaaacttaa cacactagtc   2580
atgatgtgac c                                                        2591
```

<210> SEQ ID NO 56
<211> LENGTH: 2591
<212> TYPE: DNA
<213> ORGANISM: Human rotavirus

<400> SEQUENCE: 56

```
ggctattaaa gcagtaccag tagtgtgttt tacctctgat ggtgtaaaca tgaaagtatt     60
agctttaaga catagtgtgg ctcaggtgta tgcagacact caggtgtaca cacatgatga    120
ttctaaagat gagtatgaga acgcattctt aatttctaat ctcactacac ataatatatt    180
```

-continued

```
atatttaaat tataatgtaa aaacgctaca gatattaaat aaatctggta tagctgcaat    240
agagatacag aagatagatg aattattcac gttaattaga tgtaacttta catatgatta    300
cattgataat gttgtttact tacatgacta ttcatattat actaataatg aaatacggac    360
tgaccaacat tggataacca agacaaatat agaagattat ttattaccag gatggaagct    420
gacatacgtt ggatacaatg gaagtgatac gcgcggacat tataattttt catttagatg    480
tcaaaatgca gctacagatg atgatgcaat aatagagtat atctattcag atgaattaga    540
cttccagagt tttatactca agaagattaa agaaaggatg acaacatcac taccaatagc    600
aagactttca aatcgtgtat ttagagataa gttatttaaa acgttatcag taaatcatga    660
taaagtagtt aatattgggc ccagaaatga atctatgttt actttttag actatccatc    720
aataaaacag ttctcgaatg gaccgtattt agttaaagat acaattaaac tcaaacaaga    780
gagatggctt ggtaaaagat tatcacagtt tgatattggt caatataaga atatgctaaa    840
tgtattaacg actttgtatc aatattacga tatatatcat gaaaaaccaa tcgtatatat    900
gataggatca gcgccttcgt attggatata tgacgtcaaa cagtattcta acttgaaatt    960
tgaaacgtgg gatccactag atacaccata ctctaattta catcataagg aattatttta   1020
catgaatgac gtgcaaaaac ttaaagataa ttcaatacta tatatagata taagaacaga   1080
tagaggaact gtagactgga aggaatggcg aaaaatagta gaaaggcaaa ctattgacaa   1140
tttgcatatt gcatacaaat atctatctac agggaaagct aaggtatgtt gcgttaaaat   1200
gaccgccatg gatttagaat taccaatatc tgcaaaattg cttcaccatc caactacaga   1260
gattagatca gagttttatc tagtgatgga tatatgggac tctaaaaata ttaaaagatt   1320
cataccaaaa ggtgtattat actcatatat aaacaataca attactgaaa acgtattcat   1380
acaacaacct tttaagttga aaacattgaa aaatgaatat ataatagcac tttatgcttt   1440
atcaaatgat tttaacaaca gagaagatgt ggtgaaacta attaataatc agaaaaaagc   1500
gttaatgaca gtgagaatta ataatacgtt taaagacgaa ccaaaagtcg gatttaaaaa   1560
catttacgat tggacatttc taccaacgga ttttgaaact aatggatcaa taattacttc   1620
atatgatggg tgtctaggta tctttggttt atcaatatcg ctagcttcaa aaccaactgg   1680
taataatcat ttgttcattt taagtggaac agacaagtat tttaaattgg atcaatttgc   1740
aaatcatatg agcatatcac gacgatcaca tcagatacga ttttcggagt cagccacttc   1800
atattcggga tatattttta gggatttgtc taataataat ttcaatttaa taggtacgaa   1860
tgtagagaat tcagtatccg gacacgtgta taatgcattg atttattata gatataatta   1920
ttcatttgac cttaaacgat ggatatactt acattcaaca ggcaaagcta gtattgaagg   1980
tggtaagtat tatgaacacg ctccaattga attgatttat gcatgcagat cagcgagaga   2040
atttgcgaaa ctgcaagatg atttaacggt attaagatat tcaaatgaga tagaaaacta   2100
tatcaacaga gtttatagca taacatacgc cgacgatcct aattacttta ttggagttaa   2160
gtttaaaaat attccttata agtataacgt taaagtacca catctcacat ttggcgtgtt   2220
aaatatttct gaacaaatgc taccagatgt aataacgatt ttaaagagat ttaagaatga   2280
gttatttgga atggaagtaa caacgagtta tacgtacatg ttatctgatg aggtgtatgt   2340
agcaaatata agtggtgtac tatcaacata tttcaaaatt tataatgcgt tttataaaga   2400
gcaaatcaca tttggacagt caagaatgtt tattcctcat gtaacgttga gttttagtaa   2460
tgagaaaacg gtgagaatag acactacaaa actgtacata gattctattt acttaagaaa   2520
aataaaaggt aacacggtgt ttgatatgac tgggtgagct aaaaacttaa cacactagtc   2580
```

atgatgtgac c 2591

<210> SEQ ID NO 57
<211> LENGTH: 2591
<212> TYPE: DNA
<213> ORGANISM: Human rotavirus

<400> SEQUENCE: 57
ggctattaaa gcagtaccag tagtgtgttt tacctctgat ggtgtaaaca tgaaagtatt 60
agctttaaga catagtgtgg ctcaggtgta tgcagacact caggtgtaca cacatgatga 120
ttctaaagat gagtatgaga acgcattctt aatttctaat ctcactacac ataatatatt 180
atatttaaat tataatgtaa aaacgctaca gatattaaat aaatctggta tagctgcaat 240
agagatacag aagatagatg aattattcac gttaattaga tgtaacttta catatgatta 300
cattgataat gttgtttact tacatgacta ttcatattat actaataatg aaatacggac 360
tgaccaacat tggataacca agacaaatat agaagattat ttattaccag gatggaagct 420
gacatacgtt ggatacaatg gaagtgatac gcgcggacat tataattttt catttagatg 480
tcaaaatgca gctacagatg atgatgcaat aatagagtat atctattcag atgaattaga 540
cttccagagt tttatactca agaagattaa agaaaggatg acaacatcac taccaatagc 600
aagactttca aatcgtgtat ttagagataa gttatttaaa acgttatcag taaatcatga 660
taaagtagtt aatattgggc ccagaaatga atctatgttt actttttag actatccatc 720
aataaaacag ttctcgaatg gaccgtattt agttaaagat acaattaaac tcaaacaaga 780
gagatggctt ggtaaaagat tatcacagtt tgatattggt caatataaga atatgctaaa 840
tgtattaacg actttgtatc aatattacga tatatatcat gaaaaaccaa tcgtatatat 900
gataggatca gcgccttcgt attggatata tgacgtcaaa cagtattcta acttgaaatt 960
tgaaacgtgg gatccactag atacaccata ctctaattta catcataagg aattatttta 1020
catgaatgac gtgcaaaaac ttaaagataa ttcaatacta tatatagata taagaacaga 1080
tagaggaact gtagactgga aggaatggcg aaaaatagta gaaaggcaaa ctattgacaa 1140
tttgcatatt gcatacaaat atctatctac agggaaagct aaggtatgtt gcgttaaaat 1200
gaccgccatg gatttagaat taccaatatc tgcaaaattg cttcaccatc caactacaga 1260
gattagatca gagttttatc tagtgatgga tatatgggac tctaaaaata ttaaaagatt 1320
cataccaaaa ggtgtattat actcatatat aaacaataca attactgaaa acgtattcat 1380
acaacaacct tttaagttga aacattgaa aaatgaatat ataatagcac tttatgcttt 1440
atcaaatgat tttaacaaca gagaagatgt ggtgaaacta attaataatc agaaaaaagc 1500
gttaatgaca gtgagaatta ataatacgtt taaagacgaa ccaaaagtcg gatttaaaaa 1560
catttacgat tggacatttc taccaacgga ttttgaaact aatggatcaa taattacttc 1620
atatgatggg tgtctaggta tctttggttt atcaatatcg ctagcttcaa aaccaactgg 1680
taataatcat ttgttcattt taagtggaac agacaagtat tttaaattgg atcaatttgc 1740
aaatcatatg agcatatcac gacgatcaca tcagatacga ttttcggagt cagccacttc 1800
atattcggga tatattttta gggatttgtc taataataat ttcaatttaa taggtacgaa 1860
tgtagagaat tcagtatccg gacacgtgta taatgcattg atttattata gatataatta 1920
ttcatttgac cttaaacgat ggatatactt acattcaaca ggcaaagcta gtattgaagg 1980
tggtaagtat tatgaacacg ctccaattga attgatttat gcatgcagat cagcgagaga 2040

```
atttgcgaaa ctgcaagatg atttaacggt attaagatat tcaaatgaga tagaaaacta   2100

tatcaacaga gtttatagca taacatacgc cgacgatcct aattacttta ttggagttaa   2160

gtttaaaaat attccttata agtataacgt taaagtacca catctcacat ttggcgtgtt   2220

aaatatttct gaacaaatgc taccagatgt aataacgatt ttaaagagat ttaagaatga   2280

gttatttgga atggaagtaa caacgagtta tacgtacatg ttatctgatg aggtgtatgt   2340

agcaaatata agtggtgtac tatcaacata tttcaaaatt tataatgcgt tttataaaga   2400

gcaaatcaca tttggacagt caagaatgtt tattcctcat gtaacgttga gttttagtaa   2460

tgagaaaacg gtgagaatag acactacaaa actgtacata gattctattt acttaagaaa   2520

aataaaaggt aacacggtgt ttgatatgac tgggtgagct aaaaacttaa cacactagtc   2580

aagatgtgac c                                                        2591
```

<210> SEQ ID NO 58
<211> LENGTH: 2359
<212> TYPE: DNA
<213> ORGANISM: Human rotavirus

<400> SEQUENCE: 58

```
ggctataaaa tggcttcgct catttataga cagcttctca ctaattcata ttcagtagat     60

ttacatgatg aaatagagca aattgggtca gaaaaaactc aaaacgtaac tgtaaatcca    120

ggtccatttg cccaaactag atatgctcca gtaaattggg gtcatggaga gataaatgat    180

tcaaccacag tagaaccaat tttagatggt ccttatcagc ctactacatt taaaccactt    240

actgattatt ggatacttat taactcaaat acaaatggag tggtatacga gagtacgaat    300

aatagtgact tttggactgc agtcgttgct gttgaaccgc acgttaatcc agtagataga    360

caatatactg tatttggtga aaataaacaa tttaatgtaa gaaatgattc agataaatgg    420

aagtttttag aaatgtttag aggcagtagt caaaatgaat tttataatag acgtacacta    480

acttctgata ctaaactcgt aggaatatta aaatatggtg gaaggatatg gacatttcat    540

ggtgaaacac cgagagctac tactgatagc tcaaatactg caaatttaaa cgatatatca    600

attataatac attcagaatt ttatattatc ccaaggtccc aagaatctaa gtgtaatgaa    660

tatattaaca atggtttgcc accaattcaa aatactagaa atgtagtacc attatcatta    720

tcatctagat ccatacagta taaaagagca caagttaatg aagatattac aatttcaaaa    780

acctcattat ggaaagaaat gcaatgtaat agggatatta taattagatt taaatttggt    840

aatagtattg taaaactggg gggactaggt tataaatggt ccgaaatatc atataaagca    900

gcaaattatc aatataatta tctacgtgat ggcgaacaag taactgcaca tactacttgc    960

tcagtaaatg gagtaaataa ttttagctac aacggaggat ctttacctac tgattttagt   1020

gtctcaaggt atgaagttat taaagaaaat tcttatgtat atgtagatta ttgggatgat   1080

tcaaaagcat ttagaaatat ggtatatgtc agatcattag cagctaattt gaactcagtg   1140

aaatgtacag gtggaagtta taactttagt atacctgtag gtgcatggcc agtcatgaat   1200

ggaggcgctg tttcgttgca ttttgctgga gttacattat ctacgcaatt cacagatttc   1260

gtatcattga attcactacg atttagattt agtttgacag tggatgagcc atctttttca   1320

atattgagaa cacgtacggt gaatttgtac ggattaccag ctgcaaatcc aaataatgga   1380

aatgaatact atgaaatatc aggaaggttt tcgctcattt ctttagttcc aactaatgat   1440

gattatcaga ctccaattat gaattcagta acagtaagac aagatttaga acgtcaactt   1500

actgatttac gagaggaatt taattcatta tcacaagaaa tagctatgtc acaattaatt   1560
```

gatttagcgt tattaccttt agatatgttt tctatgtttt caggaattaa aagtacaatt 1620
gatttgacta aatcaatggc aactagtgta atgaaaaaat ttagaaaatc aaaattagct 1680
acatcaattt cagaaatgac taattcattg tcagacgcag catcatcagc atcaagaagc 1740
gtttctatca gatcgaatat atccacaatt tcgaattgga ctaatgtttc aaatgatgta 1800
tcaaatgtga ctaattcgtt gagtgatatt tcaacacaaa cgtctacaat cagtaagaac 1860
cttagattaa aagaaatgat tactcaaact gaaggaatga gttttgatga tatttcagcg 1920
gcagtattaa aaacaaaaat agatatgtct actcaaattg gaaagaatac tttacccgat 1980
atagtcacag aggcatctga gaaatttatt ccaaaacgat cgtatcgaat attgaaagat 2040
gatgaagtaa tggaaattaa tactgaaggg aaagtctttg catataaaat cgacacactt 2100
aatgaagtgc catttgatgt aaataaattt gctgaacttg taacaaattc tccagttata 2160
tcagcaataa tcgattttaa aacattaaaa aatttgaatg ataattatgg aattactcga 2220
atagaagcat taaatttaat taaatcgaat ccaaatgtat tacgtaattt cattaaccaa 2280
aataatccaa ttataaggaa tagaattgaa cagctaattc tacaatgtaa attgtgagaa 2340
cgctattgag gatgtgacc 2359

<210> SEQ ID NO 59
<211> LENGTH: 2359
<212> TYPE: DNA
<213> ORGANISM: Human rotavirus

<400> SEQUENCE: 59
ggctataaaa tggcttcgct catttataga cagcttctca ctaattcata ttcagtagat 60
ttatatgatg aaatagagca aattggatca ggaaaaactc agaatgtaac cataaatccg 120
ggtccatttg cacagactag atatgctcca gtcaattggg gtcatggaga gataaatgat 180
tcgactacag tagaaccaat tttagacggt ccttatcagc caactacatt tactccacct 240
aacgattatt ggatacttat taattcaaat acaaatggag tggtatatga aagtacaaat 300
aatagtgact tttggactgc agtcgttgct attgaaccgc atgtcacccc agtagataga 360
caatatatga tatttggtga aagtaaacaa tttaatgtga gtaacgattc aaataaatgg 420
aagtttttag aaatgttcag aagcagtagt caaaatgaat tttataatag acgtacatta 480
acttctgaca ccagacttgt aggaatatta aaatatggtg gaagagtatg gacatttcat 540
ggtgaaacac caagagctac tactgacagt tcaagtactg caaatttaaa taatatatca 600
attacaattc attcagaatt ttacattatt ccaaggtccc aggaatctaa atgcaatgaa 660
tatattaata atggtctgcc accaattcaa aatactagaa atgtagttcc attaccatta 720
tcatctagat cgatacagta taagagagca caagttgatg aagacattat agtttcaaaa 780
acttcattat ggaaagaaat gcagtataat agggatatta taattagatt taaatttggt 840
aatagtattg taaagatggg aggactaggt tataaatggt ctgaaatatc atataaggca 900
gcaaattatc aatataatta tttacgtgac ggtgaacaag taaccgcaca caccacttgt 960
tcagtaaatg gagtgaacaa ttttagctat aatggagggt ccctacccac tgattttggt 1020
atttcaaggt atgaagttat taaagaaaat tcttatgtat atgtagacta ttgggatgat 1080
tcaaaagcat ttagaaatat ggtatatgtt agatcattag cagctaattt aaattcagtg 1140
agatgtacag gtggaagtta tgatttcagt ataccagtag gtgcatggcc agtaataaat 1200
ggtggcgctg tttcgttgca ttttgccgga gttacattat ccacgcaatt tactgatttt 1260
gtatcattga attcattacg atttagattt agtttgacag ttgatgaacc acctttctca 1320
atattgagaa cacgtacagt gaatttgtat ggattaccag ccgctaatcc gaataatgga 1380
aatgaatact acgaaatatc aggaaggttt tcactcattt ctttagttcc gactaatgat 1440
gattatcaga ctccaattat gaattcagtg acggtaagac aagatttaga gcgccaactt 1500
actgatttac gggaagaatt taactcattg tcacaagaaa tagctatggc acaattgatt 1560
gatttagcac tgttgcctct agatatgttt tccatgtttt caggaattaa aagtacaatt 1620
gatttaacta aatcaatggc gactagtgta atgaagaaat ttagaaaatc aaaattagct 1680
acatcaattt cagaaatgac taattcattg tcagatgctg cttcatcagc atcaagaaac 1740
gtttctatta gatcgaattt atctgcgatt tcaaattgga ctaatgtttc aaatgatgtg 1800
tcaaacgtaa ctaattcatt aaatgatatt tcaacacaaa catctacaat tggtaagaaa 1860
cttagattaa aagaaatgat tactcaaact gaaggaatga gctttgatga catttcagca 1920
gctgtactaa aaacaaaaat agatatgtct actcaaattg gaaaaaatac tttacctgat 1980
atagttacag aagcatctga gaaatttatt ccaaaacgat catatcgaat attaaaggat 2040
gatgaagtaa tggaaattaa tactgaagga aaattctttg catacaaaat taatacattt 2100
gatgaagttc cattcgatgt aaacaaattc gctgaactag taacagattc tccagttata 2160
tcagcgataa tcgattttaa gacattgaaa aatttaaatg ataattatgg aatcactcgg 2220
acagaagcgt taaatttaat taagtcgaat ccaaatatgt tacgtaattt cattaatcaa 2280
aataatccaa ttataaggaa tagaattgaa cagttaatac tacaatgtaa attgtgagaa 2340
cgctattgag gatgtgacc 2359

<210> SEQ ID NO 60
<211> LENGTH: 2359
<212> TYPE: DNA
<213> ORGANISM: Human rotavirus

<400> SEQUENCE: 60
ggctataaaa tggcttcgct catttataga cagcttctca ctaattcata ttcagtagat 60
ttatatgatg aaatagagca aattggatca ggaaaaactc agaatgtaac cataaatccg 120
ggtccatttg cacagactag atatgctcca gtcaattggg atcatggaga gataaatgat 180
tcgactacag tagaaccaat tttagacggt ccttatcagc caactacatt tactccacct 240
aacgattatt ggatacttat taattcaaat acaaatggag tggtatatga aagtacaaat 300
aatagtgact tttggactgc agtcgttgct attgaaccgc atgtcacccc agtagataga 360
caatatatga tatttggtga aagtaaacaa tttaatgtga gtaacgattc aaataaatgg 420
aagtttttag aaatgttcag aagcagtagt caaaatgaat tttataatag acgtacatta 480
acttctgaca ccagacttgt aggaatatta aaatatggtg gaagagtatg gacatttcat 540
ggtgaaacac caagagctac tactgacagt tcaagtactg caaatttaaa taatatatca 600
attacaattc attcagaatt ttacattatt ccaaggtccc aggaatctaa atgcaatgaa 660
tatattaata atggtctgcc accaattcaa aatactagaa atgtagttcc attaccatta 720
tcatctagat cgatacagta taagagagca caagttgatg aagacattat agtttcaaaa 780
acttcattat ggaaagaaat gcagtataat agggatatta taattagatt taaatttggt 840
aatagtattg taaagatggg aggactaggt tataaatggt ctgaaatatc atataaggca 900
gcaaattatc aatataatta tttacgtgac ggtgaacaag taaccgcaca caccacttgt 960
tcagtaaatg gagtgaacaa ttttagctat aatggagggt tcctacccac tgattttggt 1020
atttcaaggt atgaagttat taaagaaaat tcttatgtat atgtagacta ttgggatgat 1080
tcaaaagcat ttagaaatat agtatatgtt agatcattag cagctaattt aaattcagtg 1140
agatgtacag gtggaagtta tcatttcagt ctaccagtag gtgcatggcc agtaataaat 1200
ggtggcgctg tttcgttgca ttttgccgga gttacattat ccacgcaatt tactgatttt 1260
gtatcattga attcattacg atttagattt agtttgacag ttgatgaacc acctttctca 1320
atattgagaa cacgtacagt gaatttgtat ggattaccag ccgctaatcc gaataatgga 1380
aatgaatact acgaaatatc aggaaggttt tcactcattt ctttagttcc gactaatgat 1440
gattatcaga ctccaattat gaattcagtg acggtaagac aagatttaga gcgccaactt 1500
actgatttac gggaagaatt taactcattg tcacaagaaa tagctatggc acaattgatt 1560
gatttagcac tgttgcctct agatatgttt tccatgtttt caggaattaa aagtacaatt 1620
gatttaacta aatcaatggc gactagtgta atgaagaaat ttagaaaatc aaaattagct 1680
acatcaattt cagaaatgac taattcattg tcagatgctg cttcatcagc atcaagaaac 1740
gtttctatta gatcgaattt atctgcgatt tcaaattgga ctaatgtttc aaatgatgtg 1800
tcaaacgtaa ctaattcatt aaatgatatt tcaacacaaa catctacaat tggtaagaaa 1860
cttagattaa aagaaatgat tactcaaact gaaggaatga gctttgatga catttcagca 1920
gctgtactaa aaacaaaaat agatatgtct actcaaattg gaaaaaatac tttacctgat 1980
atagttacag aagcatctga gaaatttatt ccaaaacgat cataccgaat attaaaggat 2040
gatgaagtaa tggaaattaa tactgaagga aaattctttg catacaaaat taatacattt 2100
gatgaagttc cattcgatgt aaacaaattc gctgaactag taacagattc tccagttata 2160
tcagcgataa tcgattttaa gacattgaaa aatttaaatg ataattatgg aatcactcgg 2220
acagaagcgt taaatttaat taagtcgaat ccaaatatgt tacgtaattt cattaatcaa 2280
aataatccaa ttataaggaa tagaattgaa cagttaatac tacaatgtaa attgtgagaa 2340
cgctattgag gatgtgacc 2359

<210> SEQ ID NO 61
<211> LENGTH: 1356
<212> TYPE: DNA
<213> ORGANISM: Human rotavirus

<400> SEQUENCE: 61
ggctttaaaa cgaagtcttc gacatggagg ttctgtactc actgtcaaaa actcttaaag 60
atgctaggga caaaattgtt gaaggtacat tatattctaa tgttagcgat ctcattcaac 120
aattcaatca aatgatagta actatgaatg gaaatgactt tcaaactgga ggaattggta 180
atttacctat taggaattgg actttcgatt ttggtctatt aggtacaaca cttttaaatt 240
tagacgctaa ttacgttgag aatgctagaa ctacaattga atattttatt gattttattg 300
ataatgtatg tatggatgaa atggcaagag aagctcaaag aaatggagta gctccacaat 360
ccgaagcatt ggggaagtta gcaggtatta aattcaaaag aataaatttt gataattcat 420
ctgaatatat agaaaattgg aacttacaaa ataggaggca gcgtaccgga tttgtttttc 480
ataaacctaa tatatttcca tactcagctt cattcacttt aaatagatct caaccaatgc 540
atgacaattt gatgggaact atgtggctta atgctggatc agaaattcag gtagctggat 600
ttgattattc atgcgctata aatgcaccag caaacataca gcaatttgaa catattgtcc 660
agcttagacg tgcgctaact acagctacta taactttatt gcctgatgca gagagattca 720
gttttccaag agttattaat tcagctgatg gcgcgactac atggtttttt aatccagtca 780
ttttaagacc gaataatgtt gaagtagaat ttttgttgaa tggacaaatt atcaatacat 840
atcaagctag atttggcact attattgcaa gaaatttcga tacgattcgg tcattattcc 900
agttaatgcg tccaccaaat atgacgccag ctgttaatgc actgtttccg caagcacaac 960
cttttcaaca tcatgcaaca gttggactta cattacgtat tgaatctgca gtttgtgaat 1020
cagtgcttgc ggatgctaat gagactctat tggcgaatgt gaccgcagta cgtcaagagt 1080
atgctatacc agttggtcca gtatttccac caggcatgaa ttggactgaa ttaattacta 1140
actattcacc atctagagaa gataatttac aacgtgtttt tacggtagct tccattagaa 1200
gcatgttgat taagtgagga ccagactaag catctggtat ccaatcttag ttagcatgta 1260
gctacatcaa gtcattcaga ctcttcaagt aaggacatga tttcatgttc gctacgtaga 1320
gtaactgtct gaatgatgta gtgagaggat gtgacc 1356

<210> SEQ ID NO 62
<211> LENGTH: 1356
<212> TYPE: DNA
<213> ORGANISM: Human rotavirus

<400> SEQUENCE: 62
ggctttaaaa cgaagtcttc gacatggagg ttctgtattc attgtcaaaa actcttaaag 60
atgctaggga taagattgtt gaaggtacat tatattctaa tgttagcgat cttattcagc 120
aatttaatca aatgatagta accatgaacg gaaatgactt tcaaactgga ggaattggca 180
atttacccat tagaaattgg acatttgact ttggcctact aggtactacg cttttaaatc 240
ttgatgctaa ttatgttgag actgctagaa ctacgatcga gtattttatt gatttcattg 300
ataatgtatg tatggatgaa atggcaagag agtctcaaag aaatggagta gctccacaat 360
ctgaggcatt gagaaagcta gccggtatta aatttaaaag aataaacttt aataattcat 420
cagaatatat agaaaattgg aatttacaaa atagaagaca acgtactgga tttgtttttc 480
ataaacctaa tatatttcca tactcagcgt catttacttt aaatagatct caaccaatgc 540
atgataattt aatgggaacc atgtggctta atgctggatc agaaattcaa gtagctggat 600
ttgactattc gtgtgctcta aatgctccag caaatattca gcaatttgaa catattgtcc 660
agctaaggcg tgcgctaact acagctacta taactttgtt acctgatgca gaaagattta 720
gttttccaag agttattaat tcagcagatg gcgcaactac atggttcttt aatccaatca 780
tcctaagacc aaacaatgta gaagtagaat tttactgaa tggacaaatt attaatacat 840
atcaagctag atttggcact attgtcgcaa gaaattttga tacaattcgc ctgtcattcc 900
aattaatgcg tccaccaaac atgacgccag ccgtaaatgc attatttccg caagcacaac 960
cttttcaaca tcatgcaaca gttggactta cgttacgtat tgagtctgca gtttgtgaat 1020
cagtgcttgc ggatgcaaat gaaactttat tggcgaatgt taccgcagta cgtcaagagt 1080
atgctatacc agttggacca gtatttccac caggcatgaa ttggactgag ctaattacta 1140
actattcacc atctagggaa gataatttgc aacgtgtctt tacagtagcc tctatcagaa 1200
gcatgttaat taagtgagga ccagactaac catctggtat ccaatcttag ttagcatgta 1260
gctatatcaa gtcattcaga ctctacaagt aaggacatgg ctccatgttc gctacgtaga 1320
gtaactgtat gaatgatgta gtgagaggat gtgacc 1356

<210> SEQ ID NO 63
<211> LENGTH: 1356

<212> TYPE: DNA
<213> ORGANISM: Human rotavirus

<400> SEQUENCE: 63

```
ggctttaaaa cgaagtcttc gacatggagg ttctgtattc attgtcaaaa actcttaaag     60
atgctaggga taagattgtt gaaggtacat tatattctaa tgttagcgat cttattcagc    120
aatttaatca aatgatagta accatgaacg gaaatgactt tcaaactgga ggaattggca    180
atttacccat tagaaattgg acatttgact ttggcctact aggtactacg cttttaaatc    240
ttgatgctaa ttatgttgag actgctagaa ctacgatcga gtattttatt gatttcattg    300
ataatgtatg tatggatgaa atggtaagag agtctcaaag aaatggagta gctccacaat    360
ctgaggcatt gagaaagcta gccggtatta aatttaaaag aataaacttt aataattcat    420
cagaatatat agaaaattgg aatttacaaa atagaagaca acgtactgga tttgtttttc    480
ataaacctaa tatatttcca tactcagcgt catttacttt aaatagatct caaccaatgc    540
atgataattt aatgggaacc atgtggctta atgctggatc agaaattcaa gtagctggat    600
ttgactattc gtgtgctcta aatgctccag caaatattca gcaatttgaa catattgtcc    660
agctaaggcg tgcgctaact acagctacta taactttgtt acctgatgca gaaagattta    720
gttttccaag agttattaat tcagcagatg gcgcaactac atggttcttt aatccaatca    780
tcctaagacc aaacaatgta gaagtagaat tttactgaa tggacaaatt attaatacat     840
atcaagctag atttggcact attgtcgcaa gaaattttga tacaattcgc ctgtcattcc    900
aattaatgcg tccaccaaac atgacgccag ccgtaaatgc attatttccg caagcacaac    960
cttttcaaca tcatgcaaca gttggactta cgttacgtat tgagtctgca gtttgtgaat   1020
cagtgcttgc ggatgcaaat gaaactttat tggcgaatgt taccgcagta cgtcaagagt   1080
atgctatacc agttggacca gtatttccac caggcatgaa ttggactgag ctaattacta   1140
actattcacc atctagggaa gataatttgc aacgtgtctt tacagtagcc tctatcagaa   1200
gcatgttaat taagtgagga ccagactaac catctggtat ccaatcttag ttagcatgta   1260
gctatatcaa gtcattcaga ctctacaagt aaggacatgg ctccatgttc gctacgtaga   1320
gtaactgtat gaatgatgta gtgagaggat gtgacc                             1356
```

<210> SEQ ID NO 64
<211> LENGTH: 1062
<212> TYPE: DNA
<213> ORGANISM: Human rotavirus

<400> SEQUENCE: 64

```
ggctttaaaa gagagaattt ccgtttggct aacggttagc tccttttaat gtatggtatt     60
gaatatacca caattctaat ctttttgata tcaatcattc tactcaacta tatattaaaa    120
tcagtgactc gaataatgga ctacattata tacagatttt tgttgattac tgtagcatta    180
tttgccttga cgagagctca gaattatgga cttaacttac caataacagg atcaatggac    240
actgtatata ccaactctac tcaagaagaa gtgttcctaa cttctacatt atgtctatat    300
tatccaactg aagcaagtac tcaaatcaat gatggtgact ggaaagactc attgtcgcaa    360
atgtttctca caaaaggttg gccaacagga tctgtttact tcaaagagta ctcaagtatt    420
gttgattttt ctgttgaccc gcaactgtat gttgattttt ccgttgaccc acaattatat    480
gaccaaagtc ttgaattaga tatgtcagag ttagctgatt taatattgaa tgaatggtta    540
tgcaacccaa tggatataac attatactat tatcaacaat cgggagaatc aaataagtgg    600
```

```
atatcgatgg gatcatcatg tactgtgaaa gtgtgtccgc tgaatacaca aacgttaggg    660

ataggttgtc aaacaacaaa cgtagactca tttgaaatgg ttgctgagaa tgagaaatta    720

gctatagtgg atgtcgttga tgggataaat cataaaataa atttaacaac tacgacatgt    780

actattcgaa attgtaagaa attaggtcca agagaaaatg tagctgtaat acaagttggt    840

ggttctaatg tattagatat aacagcagat ccaacaacta atccacaaac tgagagaatg    900

atgagagtga attggaaaaa atggtggcaa gtattttata ctatagtaga ttatattaac    960

caaattgtac aggtgatgtc caaaagatca agatcattaa attctgcggc tttttattat   1020

agagtataga tatatcttag attagaattg ttcgatgtga cc                      1062
```

<210> SEQ ID NO 65
<211> LENGTH: 1062
<212> TYPE: DNA
<213> ORGANISM: Human rotavirus

<400> SEQUENCE: 65

```
ggctttaaaa gagagaattt ccgtttggct aacggttagc tccttttaat gtatggtatt     60

gaatatacca caattctaat ctttctgata tcaatcattc tacttaacta tatattaaaa    120

tcagtgaccc gaataatgga ctacattata tatagatttt tgttaatttt tgtagcatta    180

tttgccttaa ctaaagctca gaattatgga cttaatatac caataacagg atcaatggat    240

actgtatatt ccaactctac tcgagaagaa gtatttctaa catccacatt atgtttgtac    300

tatccaactg aagcaagtac tcaaatcagt gatggtgaat ggaaagactc attatcgcaa    360

atgtttctta taaaaggttg gccaacagga tcagtctatt ttaaagagta ctcaaatatc    420

gttgattttt ccgttgaccc acaattatat tgtgattata acttagtact aatgaagtat    480

gatcaaagtc ttgaattaga tatgtcagaa ttagctgatt tgatattgaa tgaatggtta    540

tgtaatccaa tggatataac attatattat tatcagcaat cgggagaatc aaataagtgg    600

atatcaatgg gatcatcatg tactgtgaaa gtgtgtccac tgaatacaca aacgttagga    660

ataggttgtc aaacaacgaa tgtagactca tttgaaacag ttgctgagaa tgaaaaatta    720

gctatagtgg atgtcgttga tgggataaat cataaaataa atttgacaac tacaacatgt    780

actattcgaa attgtaagaa gttaggtcca agagagaatg tggctgtaat acaagttggt    840

ggcgctaata tattagacat aacagcggat ccaacaacta atccacaaat tgagagaatg    900

atgagagtga attggaaaag atggtggcaa gtgttctata ctatagtaga ttatattaat    960

cagattgtac aggtaatgtc caaaagatca agatcattaa attccgctgc gttctattat   1020

agagtataga tatatcttag attagaattg tatgatgtga cc                      1062
```

<210> SEQ ID NO 66
<211> LENGTH: 1062
<212> TYPE: DNA
<213> ORGANISM: Human rotavirus

<400> SEQUENCE: 66

```
ggctttaaaa gagagaattt ccgtttggct aacggttagc tccttttaat gtatggtatt     60

gaatatacca caattctaat ctttctgata tcaatcattc tacttaacta tatattaaaa    120

tcagtgaccc gaataatgga ctacattata tatagatttt tgttaatttt tgtagcatta    180

tttgccttaa ctaaagctca gaattatgga cttaatatac caataacagg atcaatggat    240

actgtatatt ccaactctac tcgagaagaa gtatttctaa catccacatt atgtttgtac    300

tatccaactg aagcaagtac tcaaatcagt gatggtgaat ggaaagactc attatcgcaa    360
```

atgtttctta taaaaggttg gccaacagga tcagtctatt ttaaagagta ctcaaatatc 420
gttgattttt ccgttgaccc acaattatat tgtgattata acttagtact aatgaagtat 480
gatcaaagtc ttgaattaga tatgtcagaa ttagctgatt tgatattgaa tgaatggtta 540
tgtaatccaa tggatataac attatattat tatcagcaat cgggagaatc aaataagtgg 600
atatcaatgg gatcatcatg tactgtgaaa gtgtgtccac tgaatacaca aacgttagga 660
ataggttgtc aaacaacaaa tgtagactca tttgaaacag ttgctgagaa tgaaaaatta 720
gctatagtgg atgtcgttga tgggataaat cataaaataa atttgacaac tacaacatgt 780
actattcgaa attgtaagaa gttaggtcca agagagaatg tggctgtaat acaagttggt 840
ggcgctaata tattagacat aacagcggat ccaacaacta atccacaaat tgagagaatg 900
atgagagtga attggaaaag atggtggcaa gtgttctata ctatagtaga ttatattaat 960
cagattgtac aggtaatgtc caaaagatca agatcattaa attccgctgc gttctattat 1020
agagtataga tatatcttag attagaattg tatgatgtga cc 1062

<210> SEQ ID NO 67
<211> LENGTH: 1564
<212> TYPE: DNA
<213> ORGANISM: Human rotavirus

<400> SEQUENCE: 67
ggcttttttt tgaaaagtct tgtggaagcc atggctactt ttaaagatgc ttgctatcaa 60
tataaaaaat taaacaaatt aaataatgca gttttaaagt taggagctaa tgatgtctgg 120
agaccttcta ctctaacaaa acgtaaagga tggtgcttag attgttgtca acacacggat 180
ttaacttact gccaaggatg tctaatatat cacgtttgtg aatggtgtag tcaatataac 240
agatgttttc ttgatgatga tcctcattta ctaagaatgc gaacttttag aaatgaaatc 300
acaaagagtg atttagaaaa cttaattaat atgtataata cattatttcc tataaataaa 360
aaaatagttc ataaatttgc aaacacaatt aaacagcata aatgcagaaa tgagtattca 420
acacaatggt ataatcattt cttgatgcct attacattac agtctttatc aatagaatta 480
gatggagata tatattatat atttggttat tatgacgata tgcataaaat taatcagact 540
cccttctcat tcacgaattt aattagtaaa tacgatatgt tactacttga tagtataaat 600
tttgacagaa tggcattttt accattaaca ttacaacaag agtatgcact tagatatttt 660
tcaaaatcaa gatttattac tgaaagaaga aaatgtattg aaattttaca tttttcagat 720
aatatattag ataatttaca taacccaaat tttacattac aagtgattag gaattgtagt 780
aatatgtcag ttgaatggaa taaggcgtgt aatattatta gaaatataag tgattatttc 840
gatatactaa aatcgtcaca cactgagttc tataatatat ctcctagatg tagaatgttc 900
acacaatata aattaaaaat agcatctaaa ttaattaaac caaattatgt agcatcaaat 960
cataattcct tggctactga agtacataat tgtaaatggt gttcaattaa taataactct 1020
attgtatgga atgattttag aattaaaaat gtttataatg atatatttaa ttttattaga 1080
gctttagtga aatcaaatct ttatgtggga cattgctctt cagaagaaaa gatatatgaa 1140
tctattaaag aagttctaaa cgtgtgtaaa gaaaacgaat ggaacatgtt ggtaacggaa 1200
atgttcaatc aattagaacc aataaaatta aatgagaata attacatttt attaaattat 1260
gaaataaatt ggaatgtcat gaatgtatta attaatagta tcggtaaaat accaaaaata 1320
ttaactttga gtgatgttat tttaatttta cgtataataa tatatgattg gtttgatata 1380
aggtttatga gaaacacgcc aatgactacg ttcacagtta ataaattaaa acaattatat 1440
gaaaaggata gaactgcaga acatgattcc aggatatccg atattgaatg attttaaaga 1500
aattctcgcc accatgagac tctctgcact agagtagcgc ctaggcagca ttaaaagtgt 1560
gacc 1564

<210> SEQ ID NO 68
<211> LENGTH: 1569
<212> TYPE: DNA
<213> ORGANISM: Human rotavirus

<400> SEQUENCE: 68
ggcttttttt ttgaaaagtc ttgtggaagc catggctact tttaaagatg cttgctatca 60
atataaaaaa ttaaacaaat taaataatgc agttttaaag ttaggagcta atgatgtttg 120
gagaccttct actctaacaa aacgtaaagg atggtgctta gattgttgtc aacacacgga 180
tttgacttac tgccaaggat gcttaatata tcacgtttgt gaatggtgta gtcaatatag 240
cagatgcttt cttgataatg atccgcattt actaagaatg cgaactttta gaaatgaaat 300
cacaaagagt gacttagaaa acttaattaa tatgtatgat acattatttc ctataaatca 360
aaaaatagtt aataagtttg caaacacaat taaacaacat aaatgtagaa atgagtattt 420
gatacaatgg tataatcatt ttttaatgcc aattacacta cagtctttat caatagaatt 480
agatggagat atatattata tatttggtta ctatgacgat atgcataaaa ttaatcagac 540
tcccttctca ttcacgaatt taattagtaa atatgatgta ttacttctag atagcataaa 600
ttttgacaga atggcatttt taccattaac attacagcaa gaatatgcac ttagatattt 660
ttcaaaatca agatttatta ctgaaagaag gaaatgtatt gaactttcac atttttcaga 720
taatatatta aatgatttac ataatccgaa ttttacatta caagtgatta gaaattgcag 780
caatatgtca gttgaatgga ataaagcatg taatcttatt aaaaatataa gtaattattt 840
cgatatactc aaatcgtcac atactgagtc ttataatgta tctcctagat gtagagtatt 900
cacacaatat aaattaaaaa tagcatctaa attaattaaa ccaaattatg tagcatcaaa 960
tcataattcc ttggctactg aagtacacaa ttgcaaatgg tgttcaatta ataataattc 1020
tattgtatgg actgatttca ggattaaaaa tgtttataac gatatattta attttattag 1080
ggctttagtg aaatcaaatc tttacgtggg acattgttct tcagaagaaa agatatatga 1140
atctattaag gatattttaa atgtatgtaa agaaaacgaa tggaacatgt tggtaacgga 1200
aatattcaat caattagatc caataaagct aaatgatgat agctatgttt tgttgaatta 1260
tgaaataaat tggaatgtta tgaatgtatt aattaatagt atcggtaaag taccaaaaat 1320
attaactttg agtgacgtta tttcgatttt acgtataata atatatgatt ggtttgacat 1380
aaggtttatg agaaatactc caatgactac gttcacagtt aataaattga agcaattata 1440
tgaaaaggat agaactgcag aatatgattc aggtatatcc gatgttgact aatttcagag 1500
aaattatgtt cgccaccata agactctctg cactagagta gcgcctaggc agcataaaaa 1560
agtgtgacc 1569

<210> SEQ ID NO 69
<211> LENGTH: 1569
<212> TYPE: DNA
<213> ORGANISM: Human rotavirus

<400> SEQUENCE: 69
ggcttttttt ttgaaaagtc ttgtggaagc catggctact tttaaagatg cttgctatca 60

```
atataaaaaa ttaaacaaat taaataatgc agttttaaag ttaggagcta atgatgtttg    120
gagaccttct actctaacaa aacgtaaagg atggtgctta gattgttgtc aacacacgga    180
tttgacttac tgccaaggat gcttaatata tcacgtttgt gaatggtgta gtcaatatag    240
cagatgcttt cttgataatg atccgcattt actaagaatg cgaactttta gaaatgaaat    300
cacaaagagt gacttagaaa acttaattaa tatgtatgat acattatttc ctataaatca    360
aaaaatagtt aataagtttg caaacacaat taaacaacat aaatgtagaa atgagtattt    420
gatacaatgg tataatcatt ttttaatgcc aattacacta cagtctttat caatagaatt    480
agatggagat atatattata tatttggtta ctatgacgat atgcataaaa ttaatcagac    540
tcccttctca ttcacgaatt taattagtaa atatgatgta ttacttctag atagcataaa    600
ttttgacaga atggcatttt taccattaac attacagcaa gaatatgcac ttagatattt    660
ttcaaaatca agatttatta ctgaaagaag gaaatgtatt gaactttcac atttttcaga    720
taatatatta aatgatttac ataatccgaa ttttacatta caagtgatta gaaattgcag    780
caatatgtca gttgaatgga ataaagcatg taatcttatt aaaaatataa gtaattattt    840
cgatatactc aaatcgtcac atactgagtc ttataatgta tctcctagat gtagagtatt    900
cacacaatat aaattaaaaa tagcatctaa attaattaaa ccaaattatg tagcatcaaa    960
tcataattcc ttggctactg aagtacacaa ttgcaaatgg tgttcaatta ataataattc   1020
tattgtatgg actgatttca ggattaaaaa tgtttataac gatatattta attttattag   1080
ggctttagtg aaatcaaatc tttacgtggg acattgttct tcagaagaaa agatatatga   1140
atctattaag gatattttaa atgtatgtaa agaaaacgaa tggaacatgt tggtaacgga   1200
aatattcaat caattagatc caataaagct aaatgatgat agctatgttt tgttgaatta   1260
tgaaataaat tggaatgtta tgaatgtatt aattaatagt atcggtaaag taccaaaaat   1320
attaactttg agtgacgtta tttcgatttt acgtataata atatatgatt ggtttgacat   1380
aaggtttatg agaaatactc caatgactac gttcacagtt aataaattga agcaattata   1440
tgaaaaggat agaactgcag aatatgattc aggtatatcc gatgttgact aatttcagag   1500
aaattatgtt cgccaccata agactctctg cactagagta gcgcctaggc agcataaaaa   1560
agtgtgacc                                                           1569
```

<210> SEQ ID NO 70
<211> LENGTH: 486
<212> TYPE: PRT
<213> ORGANISM: Human rotavirus

<400> SEQUENCE: 70

```
Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30

Ser Thr Leu Thr Lys Arg Lys Gly Trp Cys Leu Asp Cys Cys Gln His
        35                  40                  45

Thr Asp Leu Thr Tyr Cys Gln Gly Cys Leu Ile Tyr His Val Cys Glu
    50                  55                  60

Trp Cys Ser Gln Tyr Asn Arg Cys Phe Leu Asp Asp Asp Pro His Leu
65                  70                  75                  80

Leu Arg Met Arg Thr Phe Arg Asn Glu Ile Thr Lys Ser Asp Leu Glu
                85                  90                  95
```

```
Asn Leu Ile Asn Met Tyr Asn Thr Leu Phe Pro Ile Asn Lys Lys Ile
            100                 105                 110

Val His Lys Phe Ala Asn Thr Ile Lys Gln His Lys Cys Arg Asn Glu
        115                 120                 125

Tyr Ser Thr Gln Trp Tyr Asn His Phe Leu Met Pro Ile Thr Leu Gln
    130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Met Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Ile Leu His Phe Ser Asp Asn Ile Leu Asp Asn Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Ile Ile Arg Asn Ile Ser Asp Tyr Phe Asp Ile
            260                 265                 270

Leu Lys Ser Ser His Thr Glu Phe Tyr Asn Ile Ser Pro Arg Cys Arg
        275                 280                 285

Met Phe Thr Gln Tyr Lys Leu Lys Ile Ala Ser Lys Leu Ile Lys Pro
    290                 295                 300

Asn Tyr Val Ala Ser Asn His Asn Ser Leu Ala Thr Glu Val His Asn
305                 310                 315                 320

Cys Lys Trp Cys Ser Ile Asn Asn Asn Ser Ile Val Trp Asn Asp Phe
                325                 330                 335

Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
        355                 360                 365

Tyr Glu Ser Ile Lys Glu Val Leu Asn Val Cys Lys Glu Asn Glu Trp
    370                 375                 380

Asn Met Leu Val Thr Glu Met Phe Asn Gln Leu Glu Pro Ile Lys Leu
385                 390                 395                 400

Asn Glu Asn Asn Tyr Ile Leu Leu Asn Tyr Glu Ile Asn Trp Asn Val
                405                 410                 415

Met Asn Val Leu Ile Asn Ser Ile Gly Lys Ile Pro Lys Ile Leu Thr
            420                 425                 430

Leu Ser Asp Val Ile Leu Ile Leu Arg Ile Ile Ile Tyr Asp Trp Phe
        435                 440                 445

Asp Ile Arg Phe Met Arg Asn Thr Pro Met Thr Thr Phe Thr Val Asn
    450                 455                 460

Lys Leu Lys Gln Leu Tyr Glu Lys Asp Arg Thr Ala Glu His Asp Ser
465                 470                 475                 480

Arg Ile Ser Asp Ile Glu
                485
```

<210> SEQ ID NO 71
<211> LENGTH: 486
<212> TYPE: PRT

<213> ORGANISM: Human rotavirus

<400> SEQUENCE: 71

```
Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30

Ser Thr Leu Thr Lys Arg Lys Gly Trp Cys Leu Asp Cys Cys Gln His
        35                  40                  45

Thr Asp Leu Thr Tyr Cys Gln Gly Cys Leu Ile Tyr His Val Cys Glu
    50                  55                  60

Trp Cys Ser Gln Tyr Ser Arg Cys Phe Leu Asp Asn Asp Pro His Leu
65                  70                  75                  80

Leu Arg Met Arg Thr Phe Arg Asn Glu Ile Thr Lys Ser Asp Leu Glu
                85                  90                  95

Asn Leu Ile Asn Met Tyr Asp Thr Leu Phe Pro Ile Asn Gln Lys Ile
            100                 105                 110

Val Asn Lys Phe Ala Asn Thr Ile Lys Gln His Lys Cys Arg Asn Glu
        115                 120                 125

Tyr Leu Ile Gln Trp Tyr Asn His Phe Leu Met Pro Ile Thr Leu Gln
    130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Val Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Leu Ser His Phe Ser Asp Asn Ile Leu Asn Asp Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Leu Ile Lys Asn Ile Ser Asn Tyr Phe Asp Ile
            260                 265                 270

Leu Lys Ser Ser His Thr Glu Ser Tyr Asn Val Ser Pro Arg Cys Arg
        275                 280                 285

Val Phe Thr Gln Tyr Lys Leu Lys Ile Ala Ser Lys Leu Ile Lys Pro
    290                 295                 300

Asn Tyr Val Ala Ser Asn His Asn Ser Leu Ala Thr Glu Val His Asn
305                 310                 315                 320

Cys Lys Trp Cys Ser Ile Asn Asn Asn Ser Ile Val Trp Thr Asp Phe
                325                 330                 335

Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
        355                 360                 365

Tyr Glu Ser Ile Lys Asp Ile Leu Asn Val Cys Lys Glu Asn Glu Trp
    370                 375                 380

Asn Met Leu Val Thr Glu Ile Phe Asn Gln Leu Asp Pro Ile Lys Leu
385                 390                 395                 400
```

```
Asn Asp Asp Ser Tyr Val Leu Leu Asn Tyr Glu Ile Asn Trp Asn Val
                405                 410                 415

Met Asn Val Leu Ile Asn Ser Ile Gly Lys Val Pro Lys Ile Leu Thr
            420                 425                 430

Leu Ser Asp Val Ile Ser Ile Leu Arg Ile Ile Ile Tyr Asp Trp Phe
        435                 440                 445

Asp Ile Arg Phe Met Arg Asn Thr Pro Met Thr Thr Phe Thr Val Asn
    450                 455                 460

Lys Leu Lys Gln Leu Tyr Glu Lys Asp Arg Thr Ala Glu Tyr Asp Ser
465                 470                 475                 480

Gly Ile Ser Asp Val Asp
                485


<210> SEQ ID NO 72
<211> LENGTH: 486
<212> TYPE: PRT
<213> ORGANISM: Human rotavirus

<400> SEQUENCE: 72

Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30

Ser Thr Leu Thr Lys Arg Lys Gly Trp Cys Leu Asp Cys Cys Gln His
        35                  40                  45

Thr Asp Leu Thr Tyr Cys Gln Gly Cys Leu Ile Tyr His Val Cys Glu
    50                  55                  60

Trp Cys Ser Gln Tyr Ser Arg Cys Phe Leu Asp Asn Asp Pro His Leu
65                  70                  75                  80

Leu Arg Met Arg Thr Phe Arg Asn Glu Ile Thr Lys Ser Asp Leu Glu
                85                  90                  95

Asn Leu Ile Asn Met Tyr Asp Thr Leu Phe Pro Ile Asn Gln Lys Ile
            100                 105                 110

Val Asn Lys Phe Ala Asn Thr Ile Lys Gln His Lys Cys Arg Asn Glu
        115                 120                 125

Tyr Leu Ile Gln Trp Tyr Asn His Phe Leu Met Pro Ile Thr Leu Gln
    130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Val Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Leu Ser His Phe Ser Asp Asn Ile Leu Asn Asp Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Leu Ile Lys Asn Ile Ser Asn Tyr Phe Asp Ile
            260                 265                 270

Leu Lys Ser Ser His Thr Glu Ser Tyr Asn Val Ser Pro Arg Cys Arg
        275                 280                 285
```

Val Phe Thr Gln Tyr Lys Leu Lys Ile Ala Ser Lys Leu Ile Lys Pro
    290                 295                 300

Asn Tyr Val Ala Ser Asn His Asn Ser Leu Ala Thr Glu Val His Asn
305                 310                 315                 320

Cys Lys Trp Cys Ser Ile Asn Asn Asn Ser Ile Val Trp Thr Asp Phe
                325                 330                 335

Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
        355                 360                 365

Tyr Glu Ser Ile Lys Asp Ile Leu Asn Val Cys Lys Glu Asn Glu Trp
    370                 375                 380

Asn Met Leu Val Thr Glu Ile Phe Asn Gln Leu Asp Pro Ile Lys Leu
385                 390                 395                 400

Asn Asp Asp Ser Tyr Val Leu Leu Asn Tyr Glu Ile Asn Trp Asn Val
                405                 410                 415

Met Asn Val Leu Ile Asn Ser Ile Gly Lys Val Pro Lys Ile Leu Thr
            420                 425                 430

Leu Ser Asp Val Ile Ser Ile Leu Arg Ile Ile Ile Tyr Asp Trp Phe
        435                 440                 445

Asp Ile Arg Phe Met Arg Asn Thr Pro Met Thr Thr Phe Thr Val Asn
    450                 455                 460

Lys Leu Lys Gln Leu Tyr Glu Lys Asp Arg Thr Ala Glu Tyr Asp Ser
465                 470                 475                 480

Gly Ile Ser Asp Val Asp
                485

<210> SEQ ID NO 73
<211> LENGTH: 1059
<212> TYPE: DNA
<213> ORGANISM: Human rotavirus

<400> SEQUENCE: 73
ggcttttaaa gcgtctcagt cgccgtttga gccttgcggt gtagccatgg ctgagctagc 60
ttgcttttgt tatccccatt tggagaatga tagctataaa tttattccat ttaataattt 120
agccataaaa tgtatgttga cagcaaaagt ggataaaaaa gatcaggata aattttacaa 180
ttcaataatt tatggtattg cgccaccacc gcaatttaaa aaacgttata atacaaatga 240
caattccaga ggaatgaatt acgaaacttc aatgtttaat aaggtggcag cattaatttg 300
tgaagcatta aattcaacca aagttactca atctgatatt gctagtgtgc tctcaagagt 360
agtttctgta agacatttgg aaaacttagt attaagaaga gaaaatcatc aagacgtgtt 420
atttcattca aaagagctac tattaaaatc agtactaata gctattggtc attcgaaaga 480
aattgaaacg accgctactg ctgagggagg ggaaattgtt ttccaaaata cagcatttac 540
aatgtggaga ttgacgtatt tggagcataa attaatgcca attcttgatc caaatttcat 600
tgagtacaaa attacagtta acgaaggtaa accaatctca gaatctcata taaaagaact 660
tattgctgaa ttgcggtggc aatataataa atttgcggtg attactcatg gtaaaggtca 720
ctacagagtt gtaaagtatt catcagttgc aaatcatgcg gacagagttt acgctactta 780
caagagtaac aataagaatg gaaatatgtt ggaatttaac ctactggatc aaagaataat 840
atggcaaaat tggtatgcgt ttacgtcctc gatgaaacaa ggtaatactc tcgatacatg 900
caagaaacta ctctttcaaa aaattaagcg agaaagtaat ccgttcaagg gactgtcaac 960
tgataggaag atggatgaag tttctcaaat aggaatttaa ttcgttatcg attcaagaat 1020
gggtataacg aagtaagaat agaaagcgct tatgtgacc 1059

<210> SEQ ID NO 74
<211> LENGTH: 1059
<212> TYPE: DNA
<213> ORGANISM: Human rotavirus

<400> SEQUENCE: 74
ggcttttaaa gcgtctcagt cgccgtttga gccttgcggt gtagccatgg ctgagctagc 60
ttgcttttgc tatccccatt tggagaacga tagctataaa tttattcctt ttaacaattt 120
ggctataaaa tgtatgttga cagcaaaagt agagaaaaaa gatcaggaca aattttacaa 180
ttcgataatc tatggtattg cgccgccacc acaatttaaa aaacgctata atacaaatga 240
taactcaaga ggaatgaatt atgagactgt aatgtttaac aaggtggcgg tgctaatttg 300
tgaagcattg aattcaatta aagtcacgca gtctgatgtt gcaagtgtac tttcaagagt 360
agtttctgtg agacatcttg agaatttagt attgagaaga gaaaatcatc aggatgttct 420
ttttcactca aaagagctac tactcaaatc agttttaata gctattggtc attcaaagga 480
gattgaaacg actgccactg ctgaaggggg agaaattgtt tttcaaaatg cagcatttac 540
aatgtggaaa ttgacatatt tggaacataa actaatgcca attcttgatc aaaactttat 600
tgaatataaa attacagtaa atgaagataa accaatttca gagtcacacg taaaagaact 660
tattgctgaa ttacggtggc aatacaataa atttgcagta attacgcatg gtaaaggtca 720
ctatagagtt ataaaatact cgtcagttgc aaatcacgca gaccgagttt acgctacttt 780
taagagtaat aacaaaaacg gaggtccact agagtttaat ttgcttgacc aaagaataat 840
atggcaaaat tggtacgcat ttacgtcctc aatgaaacaa ggtaatactc ttgatgtatg 900
caaaaaacta ctcttcaaaa aaatgaaacg agaaagtaat ccatttaagg ggctgtcaac 960
tgatagaaaa atggatgaag tttctcaagt aggaatctaa ttcgttatct gtttgaaggt 1020
gggtatggca gagtaagaat agaaagcgct tatgtgacc 1059

<210> SEQ ID NO 75
<211> LENGTH: 1059
<212> TYPE: DNA
<213> ORGANISM: Human rotavirus

<400> SEQUENCE: 75
ggcttttaaa gcgtctcagt cgccgtttga gccttgcggt gtagccatgg ctgagctagc 60
ttgcttttgc tatccccatt tggagaacga tagctataaa tttattcctt ttaacaattt 120
ggctataaaa tgtatgttga cagcaaaagt agagaaaaaa gatcaggaca aattttacaa 180
ttcgataatc tatggtattg cgccgccacc acaatttaaa aaacgctata atacaaatga 240
taactcaaga ggaatgaatt atgagactgt aatgtttaac aaggtggcgg tgctaatttg 300
tgaagcattg aattcaatta aagtcacgca gtctgatgtt gcaagtgtac tttcaagagt 360
agtttctgtg agacatcttg agaatttagt attgagaaga gaaaatcatc aggatgttct 420
ttttcactca aaagagctac tactcaaatc agttttaata gctattggtt attcaaagga 480
gattgaaacg actgccactg ctgaaggggg agaaattgtt tttcaaaatg cagcatttac 540
aatgtggaaa ttgacatatt tggaacataa actaatgcca attcttgatc aaaactttat 600
tgaatataaa attacagtaa atgaagataa accaatttca gagtcacacg taaaagaact 660

-continued

```
tattgctgaa ttacggtggc aatacaataa atttgcagta attacgcatg gtaaaggtca    720

ctatagagtt ataaaatact cgtcagttgc aaatcacgca gaccgagttt acgctacttt    780

taagagtaat aacaaaaacg gaggtccact agagtttaat ttgcttgacc aaagaataat    840

atggcaaaat tggtacgcat ttacgtcctc aatgaaacaa ggtaatactc ttgatgtatg    900

caaaaaacta ctcttcaaaa aaatgaaacg agaaagtaat ccatttaagg ggctgtcaac    960

tgatagaaaa atggatgaag tttctcaagt aggaatctaa ttcgttatct gtttgaaggt   1020

gggtatggca gagtaagaat agaaagcgct tatgtgacc                          1059


<210> SEQ ID NO 76
<211> LENGTH: 316
<212> TYPE: PRT
<213> ORGANISM: Human rotavirus

<400> SEQUENCE: 76

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Ile
        35                  40                  45

Tyr Gly Ile Ala Pro Pro Pro Gln Phe Lys Lys Arg Tyr Asn Thr Asn
    50                  55                  60

Asp Asn Ser Arg Gly Met Asn Tyr Glu Thr Ser Met Phe Asn Lys Val
65                  70                  75                  80

Ala Ala Leu Ile Cys Glu Ala Leu Asn Ser Thr Lys Val Thr Gln Ser
                85                  90                  95

Asp Ile Ala Ser Val Leu Ser Arg Val Val Ser Val Arg His Leu Glu
            100                 105                 110

Asn Leu Val Leu Arg Arg Glu Asn His Gln Asp Val Leu Phe His Ser
        115                 120                 125

Lys Glu Leu Leu Leu Lys Ser Val Leu Ile Ala Ile Gly His Ser Lys
    130                 135                 140

Glu Ile Glu Thr Thr Ala Thr Ala Glu Gly Gly Glu Ile Val Phe Gln
145                 150                 155                 160

Asn Thr Ala Phe Thr Met Trp Arg Leu Thr Tyr Leu Glu His Lys Leu
                165                 170                 175

Met Pro Ile Leu Asp Pro Asn Phe Ile Glu Tyr Lys Ile Thr Val Asn
            180                 185                 190

Glu Gly Lys Pro Ile Ser Glu Ser His Ile Lys Glu Leu Ile Ala Glu
        195                 200                 205

Leu Arg Trp Gln Tyr Asn Lys Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Tyr Ala Thr Tyr Lys Ser Asn Asn Lys Asn Gly Asn Met Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Asp Thr Cys Lys Lys Leu
        275                 280                 285

Leu Phe Gln Lys Ile Lys Arg Glu Ser Asn Pro Phe Lys Gly Leu Ser
    290                 295                 300
```

Thr Asp Arg Lys Met Asp Glu Val Ser Gln Ile Gly
305 310 315

<210> SEQ ID NO 77
<211> LENGTH: 316
<212> TYPE: PRT
<213> ORGANISM: Human rotavirus

<400> SEQUENCE: 77

Met Ala Glu Leu Ala Cys Phe Cys Tyr Pro His Leu Glu Asn Asp Ser
1 5 10 15

Tyr Lys Phe Ile Pro Phe Asn Asn Leu Ala Ile Lys Cys Met Leu Thr
20 25 30

Ala Lys Val Glu Lys Lys Asp Gln Asp Lys Phe Tyr Asn Ser Ile Ile
35 40 45

Tyr Gly Ile Ala Pro Pro Pro Gln Phe Lys Lys Arg Tyr Asn Thr Asn
50 55 60

Asp Asn Ser Arg Gly Met Asn Tyr Glu Thr Val Met Phe Asn Lys Val
65 70 75 80

Ala Val Leu Ile Cys Glu Ala Leu Asn Ser Ile Lys Val Thr Gln Ser
85 90 95

Asp Val Ala Ser Val Leu Ser Arg Val Val Ser Val Arg His Leu Glu
100 105 110

Asn Leu Val Leu Arg Arg Glu Asn His Gln Asp Val Leu Phe His Ser
115 120 125

Lys Glu Leu Leu Leu Lys Ser Val Leu Ile Ala Ile Gly His Ser Lys
130 135 140

Glu Ile Glu Thr Thr Ala Thr Ala Glu Gly Gly Glu Ile Val Phe Gln
145 150 155 160

Asn Ala Ala Phe Thr Met Trp Lys Leu Thr Tyr Leu Glu His Lys Leu
165 170 175

Met Pro Ile Leu Asp Gln Asn Phe Ile Glu Tyr Lys Ile Thr Val Asn
180 185 190

Glu Asp Lys Pro Ile Ser Glu Ser His Val Lys Glu Leu Ile Ala Glu
195 200 205

Leu Arg Trp Gln Tyr Asn Lys Phe Ala Val Ile Thr His Gly Lys Gly
210 215 220

His Tyr Arg Val Ile Lys Tyr Ser Ser Val Ala Asn His Ala Asp Arg
225 230 235 240

Val Tyr Ala Thr Phe Lys Ser Asn Asn Lys Asn Gly Gly Pro Leu Glu
245 250 255

Phe Asn Leu Leu Asp Gln Arg Ile Ile Trp Gln Asn Trp Tyr Ala Phe
260 265 270

Thr Ser Ser Met Lys Gln Gly Asn Thr Leu Asp Val Cys Lys Lys Leu
275 280 285

Leu Phe Lys Lys Met Lys Arg Glu Ser Asn Pro Phe Lys Gly Leu Ser
290 295 300

Thr Asp Arg Lys Met Asp Glu Val Ser Gln Val Gly
305 310 315

<210> SEQ ID NO 78
<211> LENGTH: 316
<212> TYPE: PRT
<213> ORGANISM: Human rotavirus

<400> SEQUENCE: 78

-continued

```
Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Glu Lys Lys Asp Gln Asp Lys Phe Tyr Asn Ser Ile Ile
        35                  40                  45

Tyr Gly Ile Ala Pro Pro Pro Gln Phe Lys Lys Arg Tyr Asn Thr Asn
    50                  55                  60

Asp Asn Ser Arg Gly Met Asn Tyr Glu Thr Val Met Phe Asn Lys Val
65                  70                  75                  80

Ala Val Leu Ile Cys Glu Ala Leu Asn Ser Ile Lys Val Thr Gln Ser
                85                  90                  95

Asp Val Ala Ser Val Leu Ser Arg Val Val Ser Val Arg His Leu Glu
            100                 105                 110

Asn Leu Val Leu Arg Arg Glu Asn His Gln Asp Val Leu Phe His Ser
        115                 120                 125

Lys Glu Leu Leu Leu Lys Ser Val Leu Ile Ala Ile Gly Tyr Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Glu His Lys Leu
                165                 170                 175

Met Pro Ile Leu Asp Gln Asn Phe Ile Glu Tyr Lys Ile Thr Val Asn
            180                 185                 190

Glu Asp Lys Pro Ile Ser Glu Ser His Val Lys Glu Leu Ile Ala Glu
        195                 200                 205

Leu Arg Trp Gln Tyr Asn Lys Phe Ala Val Ile Thr His Gly Lys Gly
    210                 215                 220

His Tyr Arg Val Ile Lys Tyr Ser Ser Val Ala Asn His Ala Asp Arg
225                 230                 235                 240

Val Tyr Ala Thr Phe Lys Ser Asn Asn Lys Asn Gly Gly Pro Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Asp Val Cys Lys Lys Leu
        275                 280                 285

Leu Phe Lys Lys Met Lys Arg Glu Ser Asn Pro Phe Lys Gly Leu Ser
    290                 295                 300

Thr Asp Arg Lys Met Asp Glu Val Ser Gln Val Gly
305                 310                 315


<210> SEQ ID NO 79
<211> LENGTH: 1064
<212> TYPE: DNA
<213> ORGANISM: Human rotavirus

<400> SEQUENCE: 79

ggcttttaat gcttttcagt ggttgatgct caagatggag tctactcaac agatggcatc      60

ttctattatt aactcttctt ttgaagctgc agttgtcgct gcaacttcta cgttggagtt     120

aatgggtatt caatatgatt ataatgaagt atacactaga gttaaaagta agtttgattt     180

tgtaatggat gattctggtg ttaaaaataa tttaatgggt aaagcagcta caattgatca     240

ggctttgaat ggtaagttta gttcatctat tagaaataga aattggatga ctgattctaa     300

aactgtatca agattggatg aagatgtgaa caaacttagg ttattattat catcgaaggg     360
```

aattgatcaa aaaatgagag ttcttaatgc gtgctttagt gttaagagag tgcctggaaa 420
atcatcatct gtcattaaat gtactagact aatgaaagag aagatagaac gcggagaagt 480
cgaagtggat gatacattcg ttgaagagag aatggaaatt gacactatag attggaaatc 540
cagatatgac caacttgaaa gacgatttga gtcattaaag cagcgagtta atgaaaagta 600
caataattgg gttattaagg caaggaaagt aaatgaaaat atgaactctc ttcaaaacgt 660
tatttcgcaa cagcaagctc atatcaatga attacaaata tataataaca aactagagcg 720
tgatttacaa tcaaaaatag gatcagttat ttcatccatt gaatggtact tacggtccat 780
ggagctatca gatgacatta aatcagatat tgaacaacaa ctcaattcaa tagatcatat 840
taatccagtt aatgctttcg atgattttga gtccattctt cgtaatttaa tatctgatta 900
tgatagaatt tttattatgt ttaaaggatt gttgcagcaa agtaattaca cttatactta 960
tgagtaaaca tggtataacc atcttcacgt aaccctctat gagcacaata gttaaaagct 1020
aacactgtca aaaacctaaa tggctatagg ggcgttatgt gacc 1064

<210> SEQ ID NO 80
<211> LENGTH: 1066
<212> TYPE: DNA
<213> ORGANISM: Human rotavirus

<400> SEQUENCE: 80
ggcttttaat gcttttcagt ggttgatgct caagatggag tctactcaac agatggtatc 60
ttctattatt aactcttctt ttgaagctgc agttgtcgct gcaacttcta cattagaatt 120
aatgggtatt caatatgatt ataatgaagt atatactaga gttaaaagta agtttgattt 180
tgtaatggat gattctggcg ttaagaataa tctaataggt aaagcagcta caattgatca 240
ggctttgaat ggtaagttta gttcatctat cagaaataga aattggatga ctgattcaaa 300
aactgtagca agattagatg aagatgtgaa caaacttaga ttattattgt catcgaaagg 360
aattgatcaa aaaatgagag ttcttaatgc atgctttagt gttaagagaa tacctggaaa 420
atcgtcatcc atcattaaat gtactaggtt aatgaaagag aaaatagaac gtggagaagt 480
cgaagtggat gatgcattca ttgaagaaaa aatggaaatt gacactatag attggaaatc 540
cagatatgat caacttgaaa gacgatttga gtcgttaaaa cagcgagtta atgaaaagta 600
caataattgg gttattaagg caaggaaagt aaacgaaaac atgaactctc ttcagaatgt 660
tatttcgcaa cagcaagctc atattaatga attacaagta tataataata aactagagcg 720
tgatttacaa tcaaaaatag gatcagttat ttcatccatt gaatggtact tacggtctat 780
ggaactatca gatgacatta aatcagatat tgaacaacaa cttaattcaa tagatcatat 840
taatccagtt aatgcttttg atgattttga gtctattctt cgtaatttaa tatctgatta 900
tgatagaatt tttattatgt ttaaaggatt gttgcagcaa agtaattaca cttataccta 960
tgaataaaca tggcatatta ccatcttcac gtaaccctct atgagcacaa tagttaaaag 1020
ctaacactgt caaaaaccta aatggctata ggggcgttat gtgacc 1066

<210> SEQ ID NO 81
<211> LENGTH: 1066
<212> TYPE: DNA
<213> ORGANISM: Human rotavirus

<400> SEQUENCE: 81
ggcttttaat gcttttcagt ggttgatgct caagatggag tctactcaac agatggtatc 60

-continued

```
ttctattatt aactcttctt ttgaagctgc agttgtcgct gcaacttcta cattagaatt    120

aatgggtatt caatatgatt ataatgaagt atatactaga gttaaaagta agtttgattt    180

tgtaatggat gattctggcg ttaagaataa tctaataggt aaagcagcta caattgatca    240

ggctttgaat ggtaagttta gttcatctat cagaaataga aattggatga ctgattcaaa    300

aactgtagca agattagatg aagatgtgaa caaacttaga ttattattgt catcgaaagg    360

aattgatcaa aaaatgagag ttcttaatgc atgctttagt gttaagagaa tacctggaaa    420

atcgtcatcc atcattaaat gtactaggtt aatgaaagag aaaatagaac gtggagaagt    480

cgaagtggat gatgcattca ttgaagaaaa aatggaaatt gacactatag attggaaatc    540

cagatatgat caacttgaaa gacgatttga gtcgttaaaa cagcgagtta atgaaaagta    600

caataattgg gttattaagg caaggaaagt aaacgaaaac atgaactctc ttcagaatgt    660

tatttcgcaa cagcaagctc atattaatga attacaagta tataataata aactagagcg    720

tgatttacaa tcaaaaatag gatcagttat ttcatccatt gaatggtact tacggtctat    780

ggaactatca gatgacatta aatcagatat tgaacaacaa cttaattcaa tagatcatat    840

taatccagtt aatgcttttg atgattttga gtctattctt cgtaatttaa tatctgatta    900

tgatagaatt tttattatgt ttaaaggatt gttgcagcaa agtaattaca cttataccta    960

tgaataaaca tggcatatta ccatcttcac gtaaccctct atgagcacaa tagttaaaag   1020

ctaacactgt caaaaaccta aatggctata ggggcgttat gtgacc                  1066
```

<210> SEQ ID NO 82
<211> LENGTH: 313
<212> TYPE: PRT
<213> ORGANISM: Human rotavirus

<400> SEQUENCE: 82

```
Met Leu Lys Met Glu Ser Thr Gln Gln Met Ala Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Met
    50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ser Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Val Pro Gly Lys Ser Ser Ser Val Ile Lys Cys Thr Arg Leu Met Lys
    130                 135                 140

Glu Lys Ile Glu Arg Gly Glu Val Glu Val Asp Asp Thr Phe Val Glu
145                 150                 155                 160

Glu Arg Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
```

```
        195                 200                 205

Leu Gln Asn Val Ile Ser Gln Gln Gln Ala His Ile Asn Glu Leu Gln
    210                 215                 220

Ile Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255

Asp Ile Lys Ser Asp Ile Glu Gln Gln Leu Asn Ser Ile Asp His Ile
            260                 265                 270

Asn Pro Val Asn Ala Phe Asp Asp Phe Glu Ser Ile Leu Arg Asn Leu
        275                 280                 285

Ile Ser Asp Tyr Asp Arg Ile Phe Ile Met Phe Lys Gly Leu Leu Gln
    290                 295                 300

Gln Ser Asn Tyr Thr Tyr Thr Tyr Glu
305                 310


<210> SEQ ID NO 83
<211> LENGTH: 313
<212> TYPE: PRT
<213> ORGANISM: Human rotavirus

<400> SEQUENCE: 83

Met Leu Lys Met Glu Ser Thr Gln Gln Met Val Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Ile
    50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ala Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Ile Pro Gly Lys Ser Ser Ser Ile Ile Lys Cys Thr Arg Leu Met Lys
    130                 135                 140

Glu Lys Ile Glu Arg Gly Glu Val Glu Val Asp Asp Ala Phe Ile Glu
145                 150                 155                 160

Glu Lys Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
        195                 200                 205

Leu Gln Asn Val Ile Ser Gln Gln Gln Ala His Ile Asn Glu Leu Gln
    210                 215                 220

Val Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255
```

```
Asp Ile Lys Ser Asp Ile Glu Gln Gln Leu Asn Ser Ile Asp His Ile
            260                 265                 270

Asn Pro Val Asn Ala Phe Asp Asp Phe Glu Ser Ile Leu Arg Asn Leu
        275                 280                 285

Ile Ser Asp Tyr Asp Arg Ile Phe Ile Met Phe Lys Gly Leu Leu Gln
    290                 295                 300

Gln Ser Asn Tyr Thr Tyr Thr Tyr Glu
305                 310


<210> SEQ ID NO 84
<211> LENGTH: 313
<212> TYPE: PRT
<213> ORGANISM: Human rotavirus

<400> SEQUENCE: 84

Met Leu Lys Met Glu Ser Thr Gln Gln Met Val Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Ile
    50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ala Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Ile Pro Gly Lys Ser Ser Ser Ile Ile Lys Cys Thr Arg Leu Met Lys
    130                 135                 140

Glu Lys Ile Glu Arg Gly Glu Val Glu Val Asp Asp Ala Phe Ile Glu
145                 150                 155                 160

Glu Lys Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
        195                 200                 205

Leu Gln Asn Val Ile Ser Gln Gln Gln Ala His Ile Asn Glu Leu Gln
    210                 215                 220

Val Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255

Asp Ile Lys Ser Asp Ile Glu Gln Gln Leu Asn Ser Ile Asp His Ile
            260                 265                 270

Asn Pro Val Asn Ala Phe Asp Asp Phe Glu Ser Ile Leu Arg Asn Leu
        275                 280                 285

Ile Ser Asp Tyr Asp Arg Ile Phe Ile Met Phe Lys Gly Leu Leu Gln
    290                 295                 300

Gln Ser Asn Tyr Thr Tyr Thr Tyr Glu
305                 310
```

<210> SEQ ID NO 85
<211> LENGTH: 687
<212> TYPE: DNA
<213> ORGANISM: Human rotavirus

<400> SEQUENCE: 85
cggaaagatg gaaaagctta ccgacctcaa ttacacattg agtgtaatca ctttaatgaa 60
taatacatta cacacaatac tagaggatcc aggaatggcg tattttcctt atattgcatc 120
tgtcctgaca gttttattcg cattacacaa agcgtcaatt ccaacaatga aaatagcatt 180
gaagacgtca aaatgttcat ataaagtagt aaagtattgt attgtaacga tctttaatac 240
attactaaaa ctagcaggtt acaaagaaca aattactact aaagatgaaa tagaaaagca 300
aatggacaga gttgttaaag aaatgagacg tcaattagag atgattgata aactaactac 360
gcgtgaaatt gagcaagttg aattacttaa acgtatctac gataaattga tggtgcgatc 420
gactgacgag atagatatga caaaagaaat taatcaaaag aacgtgagaa cgctagaaga 480
gtgggagaat ggaaaaaatc cttatgaacc aaaagaagtg actgcagcaa tgtgagaggt 540
tgagctgccg tcgactgtct tcggaagcgg cggagttctt tacagtaagc tccatcagac 600
ctgatggctg gctaagaagc catagtcagc catatcgcgt gtggcttaag ccttaatccc 660
gtttaaccaa tccggtcagc accggac 687

<210> SEQ ID NO 86
<211> LENGTH: 751
<212> TYPE: DNA
<213> ORGANISM: Human rotavirus

<400> SEQUENCE: 86
ggcttttaaa agttctgttc cgagagagcg cgtgcggaaa gatggaaaag tttaccgacc 60
tcaactacac attgagtgta atcactttaa tgaatagtac attacataca atattagagg 120
atccaggaat ggcgtatttt ccttatattg catctgtcat gacagttttg tttacattac 180
acaaagcgtc aattccaaca atgaaaatag cattgaagac gtcaaaatgt tcgtataaag 240
tagtaaagta ttgtattgta acggttctta atacattatt aaagttagca ggttacaaag 300
aacaaattac tactaaagat gaaatagaaa aacaaatgga cagagtcgtt aaagaaatga 360
gacgtcagtt agagatgatt gataaactaa ctacacgtga aattgaacaa gttgaattac 420
ttaaacgcat ctacgataaa ttaatagtgc gatcgactga tgaaatagat atgacaaaag 480
aaattaatca aaagaacgta agaacgctag aagagtggga gagcgggaaa aatccttatg 540
aaccaaaaga agtgactgca gcgatgtgag aggttgagct gccgtcgact gtcttcggaa 600
gcggcggagt tctttacagt aaactccatt ggacccgatg gctggctaag aagccatagt 660
cagccatatc gcgtgtggct taagccttaa tcccgtttaa ctaatccggt cagcaccgga 720
cgttaatgga aggaaaggtc ttaatgtgac c 751

<210> SEQ ID NO 87
<211> LENGTH: 751
<212> TYPE: DNA
<213> ORGANISM: Human rotavirus

<400> SEQUENCE: 87
ggcttttaaa agttctgttc cgagagagcg cgtgcggaaa gatggaaaag tttaccgacc 60
tcaactacac attgagtgta atcactttaa tgaatagtac attacataca atattagagg 120

```
atccaggaat ggcgtatttt ccttatattg catctgtcat gacagttttg tttacattac    180

acaaagcgtc aattccaaca atgaaaatag cattgaagac gtcaaaatgt tcgtataaag    240

tagtaaagta ttgtattgta acggttctta atacattatt aaagttagca ggttacaaag    300

aacaaattac tactaaagat gaaatagaaa aacaaatgga cagagtcgtt aaagaaatga    360

gacgtcagtt agagatgatt gataaactaa ctacacgtga aattgaacaa gttgaattac    420

ttaaacgcat ctacgataaa ttaatagtgc gatcgactga tgaaatagat atgacaaaag    480

aaattaatca aaagaacgta agaacgctag aagagtggga gagcgggaaa aatccttatg    540

aaccaaaaga agtgactgca gcgatgtgag aggttgagct gccgtcgact gtcttcggaa    600

gcggcggagt tctttacagt aaactccatt ggacccgatg gctggctaag aagccatagt    660

cagccatatc gcgtgtggct taagccttaa tcccgtttaa ctaatccggt cagcaccgga    720

cgttaatgga aggaaaggtc ttaatgtgac c                                   751
```

```
<210> SEQ ID NO 88
<211> LENGTH: 175
<212> TYPE: PRT
<213> ORGANISM: Human rotavirus

<400> SEQUENCE: 88

Met Glu Lys Leu Thr Asp Leu Asn Tyr Thr Leu Ser Val Ile Thr Leu
1               5                   10                  15

Met Asn Asn Thr Leu His Thr Ile Leu Glu Asp Pro Gly Met Ala Tyr
            20                  25                  30

Phe Pro Tyr Ile Ala Ser Val Leu Thr Val Leu Phe Ala Leu His Lys
        35                  40                  45

Ala Ser Ile Pro Thr Met Lys Ile Ala Leu Lys Thr Ser Lys Cys Ser
    50                  55                  60

Tyr Lys Val Val Lys Tyr Cys Ile Val Thr Ile Phe Asn Thr Leu Leu
65                  70                  75                  80

Lys Leu Ala Gly Tyr Lys Glu Gln Ile Thr Thr Lys Asp Glu Ile Glu
                85                  90                  95

Lys Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile Tyr Asp Lys Leu Met Val Arg Ser Thr Asp Glu Ile Asp Met
    130                 135                 140

Thr Lys Glu Ile Asn Gln Lys Asn Val Arg Thr Leu Glu Glu Trp Glu
145                 150                 155                 160

Asn Gly Lys Asn Pro Tyr Glu Pro Lys Glu Val Thr Ala Ala Met
                165                 170                 175


<210> SEQ ID NO 89
<211> LENGTH: 175
<212> TYPE: PRT
<213> ORGANISM: Human rotavirus

<400> SEQUENCE: 89

Met Glu Lys Phe Thr Asp Leu Asn Tyr Thr Leu Ser Val Ile Thr Leu
1               5                   10                  15

Met Asn Ser Thr Leu His Thr Ile Leu Glu Asp Pro Gly Met Ala Tyr
            20                  25                  30

Phe Pro Tyr Ile Ala Ser Val Met Thr Val Leu Phe Thr Leu His Lys
        35                  40                  45
```

Ala Ser Ile Pro Thr Met Lys Ile Ala Leu Lys Thr Ser Lys Cys Ser
50 55 60

Tyr Lys Val Val Lys Tyr Cys Ile Val Thr Val Leu Asn Thr Leu Leu
65 70 75 80

Lys Leu Ala Gly Tyr Lys Glu Gln Ile Thr Thr Lys Asp Glu Ile Glu
85 90 95

Lys Gln Met Asp Arg Val Val Lys Glu Met Arg Arg Gln Leu Glu Met
100 105 110

Ile Asp Lys Leu Thr Thr Arg Glu Ile Glu Gln Val Glu Leu Leu Lys
115 120 125

Arg Ile Tyr Asp Lys Leu Ile Val Arg Ser Thr Asp Glu Ile Asp Met
130 135 140

Thr Lys Glu Ile Asn Gln Lys Asn Val Arg Thr Leu Glu Glu Trp Glu
145 150 155 160

Ser Gly Lys Asn Pro Tyr Glu Pro Lys Glu Val Thr Ala Ala Met
165 170 175

<210> SEQ ID NO 90
<211> LENGTH: 175
<212> TYPE: PRT
<213> ORGANISM: Human rotavirus

<400> SEQUENCE: 90

Met Glu Lys Phe Thr Asp Leu Asn Tyr Thr Leu Ser Val Ile Thr Leu
1 5 10 15

Met Asn Ser Thr Leu His Thr Ile Leu Glu Asp Pro Gly Met Ala Tyr
20 25 30

Phe Pro Tyr Ile Ala Ser Val Met Thr Val Leu Phe Thr Leu His Lys
35 40 45

Ala Ser Ile Pro Thr Met Lys Ile Ala Leu Lys Thr Ser Lys Cys Ser
50 55 60

Tyr Lys Val Val Lys Tyr Cys Ile Val Thr Val Leu Asn Thr Leu Leu
65 70 75 80

Lys Leu Ala Gly Tyr Lys Glu Gln Ile Thr Thr Lys Asp Glu Ile Glu
85 90 95

Lys Gln Met Asp Arg Val Val Lys Glu Met Arg Arg Gln Leu Glu Met
100 105 110

Ile Asp Lys Leu Thr Thr Arg Glu Ile Glu Gln Val Glu Leu Leu Lys
115 120 125

Arg Ile Tyr Asp Lys Leu Ile Val Arg Ser Thr Asp Glu Ile Asp Met
130 135 140

Thr Lys Glu Ile Asn Gln Lys Asn Val Arg Thr Leu Glu Glu Trp Glu
145 150 155 160

Ser Gly Lys Asn Pro Tyr Glu Pro Lys Glu Val Thr Ala Ala Met
165 170 175

<210> SEQ ID NO 91
<211> LENGTH: 740
<212> TYPE: DNA
<213> ORGANISM: Human rotavirus

<400> SEQUENCE: 91
atgtctctca gtattgatgt gactagtctt ccttcaattt cttcaagtgt ttataaaaat 60
gaatcgtctt caacaacgtc aactatttct ggaaaatcta ttggtaggag tgaacagtac 120
atttcaccag atgcagaagc tttcaataaa tacatgttgt caaaatctcc agaagatatt 180

```
ggaccttctg attctgcatc gaacgatcca ctcaccagct tttcgattag atcgaatgca    240

gttaagacaa atgcagatgc tggcgtgtct atggattcat cagcgcaatc acgaccatct    300

agcgacattg gatacgatca aatggatttc tccttgaata aaggtattaa atttgatgct    360

acagtggact cttcaatatc aatatctacc acatcaaaga aggagaaatc taaacaagaa    420

aacaaaaata agtataaaaa atgttaccca aaaatcgaag cagagtctga ttccgatgat    480

tacatattag atgattcaga tagcgatgat ggaaaatgta aaaattgcaa atataaaaag    540

aaatattttg cacttcgttt aagaatgaaa caagttgcaa tgcaattaat taaagattta    600

tgaaaatttt ctgattactc ttgtcattaa ttactaaata ttcactcaat gcacggataa    660

taaatgctat ctaattatat tgtatgataa ttattacaat atatactgtg ttattgaatt    720

taatgatatc ctaatgatag                                                740
```

<210> SEQ ID NO 92
<211> LENGTH: 816
<212> TYPE: DNA
<213> ORGANISM: Human rotavirus

<400> SEQUENCE: 92

```
ggcttttaaa gcgctacagt gatgtctctt agtattgacg tgactagtct tccttcaatt     60

tcttctagtg tttataaaaa tgaatcgttt tcaacaacgt caactatttc tggaaaatct    120

attggtagga gtgaacagta catttcacca gatgcagaag ccttcaataa gtacatgttg    180

tcaaaatctc cagaagatat tggaccttct gattctgcat cgaacgatcc actcaccagc    240

ttttcgatta gatcgaatgc agttaagaca aatgcagatg ctggcgtgtc tatggattca    300

tcagcacaat cacgaccatc tagcgacatt ggatacgatc aaatggattt ctccttaaat    360

aaaggtatta aaattgatgc tacaatggat tcttcaatat caatatctac cacatcaaag    420

aaggagaaat ctaaacaaga gaacaaaaat aaatataaaa aatattatcc aaaaattgaa    480

gcagaatctg attctgatga atacgtatta gatgattcag atagtgatga tggaaaatgt    540

aaaaattgca agtataaaaa gaaatatttt gcacttcgtt taagaatgaa acaagttgca    600

atgcaattga ttaaagattt gtgaaaattt tcttattact cttatcatta actgttaaat    660

atttacttaa tatacagata gtgaatgttg tttaattata ttatatgata gtattattat    720

atcgcgttat tgaatttaat aactttctaa tgagagaaga ttgatgcgtc taccctaaga    780

gatcactagg gagctcccca ctcccgtttt gtgacc                              816
```

<210> SEQ ID NO 93
<211> LENGTH: 816
<212> TYPE: DNA
<213> ORGANISM: Human rotavirus

<400> SEQUENCE: 93

```
ggcttttaaa gcgctacagt gatgtctctt agtattgacg tgactagtct tccttcaatt     60

tcttctagtg tttataaaaa tgaatcgttt tcaacaacgt caactatttc tggaaaatct    120

attggcagga gtgaacagta catttcacca gatgcagaag ccttcaataa gtacatgttg    180

tcaaaatctc cagaagatgt tggaccttct gattctgcat cgaacgatcc actcaccagc    240

ttttcgatta gatcgaatgc agttaagaca aatgcagatg ctggcgtgtc tatggattca    300

tcagcacaat cacgaccatc tagcgacatt ggatacgatc aaatggattt ctccttaaat    360

aaaggtatta aaattgatgc tacaatggat tcttcaatat caatatctac cacatcaaag    420
```

```
aaggagaaat ctaaacaaga gaacaaaaat aaatataaaa aatattatcc aaaaattgaa    480

gcagaatctg attctgatga atacgtatta gatgattcag atagtgatga tggaaaatgt    540

aaaaattgca agtataaaaa gaaatatttt gcacttcgtt taagaatgaa acaagttgca    600

atgcaattga ttaaagattt gtgaaaattt tcttattact cttatcatta actgttaaat    660

atttacttaa tatacagata gtgaatgttg tttaattata ttatatgata gtattattat    720

atcgcgttat tgaatttaat aactttctaa tgagagaaga ttgatgcgtc taccctaaga    780

gatcactagg gagctcccca ctcccgtttt gtgacc                              816
```

<210> SEQ ID NO 94
<211> LENGTH: 200
<212> TYPE: PRT
<213> ORGANISM: Human rotavirus

<400> SEQUENCE: 94

```
Met Ser Leu Ser Ile Asp Val Thr Ser Leu Pro Ser Ile Ser Ser Ser
1               5                   10                  15

Val Tyr Lys Asn Glu Ser Ser Ser Thr Thr Ser Thr Ile Ser Gly Lys
            20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Ala Gln
                85                  90                  95

Ser Arg Pro Ser Ser Asp Ile Gly Tyr Asp Gln Met Asp Phe Ser Leu
            100                 105                 110

Asn Lys Gly Ile Lys Phe Asp Ala Thr Val Asp Ser Ser Ile Ser Ile
        115                 120                 125

Ser Thr Thr Ser Lys Lys Glu Lys Ser Lys Gln Glu Asn Lys Asn Lys
    130                 135                 140

Tyr Lys Lys Cys Tyr Pro Lys Ile Glu Ala Glu Ser Asp Ser Asp Asp
145                 150                 155                 160

Tyr Ile Leu Asp Asp Ser Asp Ser Asp Asp Gly Lys Cys Lys Asn Cys
                165                 170                 175

Lys Tyr Lys Lys Lys Tyr Phe Ala Leu Arg Leu Arg Met Lys Gln Val
            180                 185                 190

Ala Met Gln Leu Ile Lys Asp Leu
        195                 200
```

<210> SEQ ID NO 95
<211> LENGTH: 200
<212> TYPE: PRT
<213> ORGANISM: Human rotavirus

<400> SEQUENCE: 95

```
Met Ser Leu Ser Ile Asp Val Thr Ser Leu Pro Ser Ile Ser Ser Ser
1               5                   10                  15

Val Tyr Lys Asn Glu Ser Phe Ser Thr Thr Ser Thr Ile Ser Gly Lys
            20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Ile Gly Pro Ser Asp
```

```
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Ala Gln
                85                  90                  95

Ser Arg Pro Ser Ser Asp Ile Gly Tyr Asp Gln Met Asp Phe Ser Leu
            100                 105                 110

Asn Lys Gly Ile Lys Ile Asp Ala Thr Met Asp Ser Ser Ile Ser Ile
        115                 120                 125

Ser Thr Thr Ser Lys Lys Glu Lys Ser Lys Gln Glu Asn Lys Asn Lys
    130                 135                 140

Tyr Lys Lys Tyr Tyr Pro Lys Ile Glu Ala Glu Ser Asp Ser Asp Glu
145                 150                 155                 160

Tyr Val Leu Asp Asp Ser Asp Ser Asp Asp Gly Lys Cys Lys Asn Cys
                165                 170                 175

Lys Tyr Lys Lys Lys Tyr Phe Ala Leu Arg Leu Arg Met Lys Gln Val
            180                 185                 190

Ala Met Gln Leu Ile Lys Asp Leu
        195                 200


<210> SEQ ID NO 96
<211> LENGTH: 200
<212> TYPE: PRT
<213> ORGANISM: Human rotavirus

<400> SEQUENCE: 96

Met Ser Leu Ser Ile Asp Val Thr Ser Leu Pro Ser Ile Ser Ser Ser
1               5                   10                  15

Val Tyr Lys Asn Glu Ser Phe Ser Thr Thr Ser Thr Ile Ser Gly Lys
            20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Val Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Ala Gln
                85                  90                  95

Ser Arg Pro Ser Ser Asp Ile Gly Tyr Asp Gln Met Asp Phe Ser Leu
            100                 105                 110

Asn Lys Gly Ile Lys Ile Asp Ala Thr Met Asp Ser Ser Ile Ser Ile
        115                 120                 125

Ser Thr Thr Ser Lys Lys Glu Lys Ser Lys Gln Glu Asn Lys Asn Lys
    130                 135                 140

Tyr Lys Lys Tyr Tyr Pro Lys Ile Glu Ala Glu Ser Asp Ser Asp Glu
145                 150                 155                 160

Tyr Val Leu Asp Asp Ser Asp Ser Asp Asp Gly Lys Cys Lys Asn Cys
                165                 170                 175

Lys Tyr Lys Lys Lys Tyr Phe Ala Leu Arg Leu Arg Met Lys Gln Val
            180                 185                 190

Ala Met Gln Leu Ile Lys Asp Leu
        195                 200


<210> SEQ ID NO 97
<211> LENGTH: 3302
```

<212> TYPE: DNA
<213> ORGANISM: Human rotavirus

<400> SEQUENCE: 97

```
ggctattaaa gctatacaat ggggaagtat aatctaatct tgtcagaata tttgtcattt     60
atatataatt cacaatctgc agttcaaatt ccaatttatt attcttccaa tagtgaatta    120
gagagtagat gcatagaatt tcattccaaa tgtttagaaa attcgaaaaa tggtttatca    180
ctgaagaaat tatttagtga atacagtgat gttattgaga atgctacatt attatcaata    240
ttatcgtact cctatgacaa gtacaacgcc gttgaacgga aattagttaa atatgcaaaa    300
agtaaaccgt tagaggcaga tttaacattg aatgaactag actatgaaaa taataaaata    360
acatctgagt tatttccaac agaagaagaa tatactgatt cattgatgga tccagcaatt    420
ctgacttcct tatcatctaa tttgaacgca gtcatgtttt ggttggaaaa acacgaaaat    480
gatactgctg aaaagcttaa aatttataag agaagattgg atttatttag tatagtagct    540
tcaactataa acaaatatgg tgtgccaaga cacaatgcaa aatatagata tgagtatgat    600
gtgatgaaag ataaaccata ttacttagta acatgggcga attcttcgat cgaaatgtta    660
atgtcagtct tttctcatga agattactta attgcaaaag aattgatagt attatcatat    720
tctaatagat caactttagc aaagttggtg tcatctccaa tgtcaatttt agtcgcttta    780
gtggatatta atggaacgtt tattacgaat gaggagttag aattagaatt ttcaaataaa    840
tatgtacgag ccatagtgcc cgatcaaaca tttgatgaac taaaacaaat gctcgataat    900
atgaggaaag ctggattggt tgacatacct aagatgatac aagactggtt agttgattgt    960
tcaattgaaa gatttccatt aatggctaaa atatactcat ggtcatttca cgttggattc   1020
agaaagcaaa aaatgttaga tgctgctcta gaccaattaa aaactgagta tacagaaaat   1080
gtagatgatg aaatgtatcg tgaatatact atgttgataa gagatgaagt tgttaagatg   1140
cttgaagaat cagtaaaaca tgacgaccat ttgttacaag attctgaatt agctggattg   1200
ctatcaatgt cgtcggcatc aaatggagaa tctagacagc ttaaatttgg cagaaagacg   1260
attttttcaa ctaaaaagaa catgcatgta atggatgata tggctaatgg aagatacact   1320
ccaggcataa ttccacctgt gaatgctgat aagccaatac cgttaggaag aagagatgta   1380
ccaggaagaa gaactaggat aatatttata ttaccatatg agtattttat agcacagcat   1440
gctgtggttg agaaaatgtt aatttatgcg aaacatacta gagaatatgc tgaattttat   1500
tcacaatcaa accagctctt atcatatggt gatgtcacac gtttcctttc caacaattct   1560
atggtattgt acacagacgt atctcaatgg gattcatctc aacataatac gcaaccattt   1620
agaaaaggaa taataatggg gttagatata ttagctaaca tgactaatga tgctagagtc   1680
atccagacac taaatctata taaacaaacg caaattaatt tgatggactc atatgttcaa   1740
ataccagatg gcaatgttat taagaaaata cagtatggag ccgtagcatc aggagaaaaa   1800
caaactaaag cagctaactc tatagcaaat ctagcattaa ttaagactgt cttatcacgt   1860
atctctaaca aatactcatt catcacaaaa ataataagag ttgacggcga tgataactat   1920
gctgtactac agtttaacac agaagtgacc aaacaaatgg ttcaagatgt atcaaatgac   1980
gtgagagaaa cttacgcacg aatgaacgct aaagtcaaag ctctagtatc cacagtagga   2040
atagaaatag ccaaaaggta tattgcagga ggaaaaatat tttttagagc cggaataaat   2100
ttacttaata atgaaaaaag aggacaaagt acgcaatggg atcaagcagc agttctttat   2160
tctaactata ttgtaaatag acttaggggt tttgagactg atagagaatt tattctaact   2220
```

```
aaaataatgc aaatgacgtc agttgctatt actggatcgt taagactttt tccctctgaa   2280
cgcgtattaa ccacaaactc tacgtttaaa gtattcgatt cagaagattt tatcatagag   2340
tatggaacaa ctgatgatga agtgtatata caaagagcat ttatgtcttt atcaagtcag   2400
aaatcaggaa tagctgatga aatatctgcg tcatcaacgt ttaaaaatta cgtgtctaaa   2460
ttatcagaac aattactttt ttcaaaaaat aatatagtat ctagaggaat agctttaact   2520
gaaaaagcga aattgaattc gtatgcacca atatcactcg agaagagacg tgcgcaaata   2580
tcagctttat taacaatgct acaaaaacca gtcactttta aatcgagcaa aataacgata   2640
aacgatatac ttaaagatat aaaaccgttt ttcacattga gtgaagcaca tttaccaatg   2700
cagtatcaaa agttcatgcc aaacttgccg gaaaacgtac aatacataat tcagtgtata   2760
gggtcaagaa cttatcagat tgaagatgat ggttcaaaat cagcaatctc ccggcttata   2820
tcaaagtatt cagtttataa accatcaatt gaggagctgt ataaagtaat ttcactacat   2880
gaaaatgaaa tacaattgta tttaatttca ctaggcatac caaaaataga tgctgataca   2940
tatgtcgggt caaagattta ttctcaagat aaatatagga tactggaatc atatgtatat   3000
aatctgttat ctatcaatta tggatgttat caattatttg actttaattc accggactta   3060
gaaaagctga ttagaatacc gttcaaagga aagataccag ctgtcacatt tatattacat   3120
ttatacgcta aattagaagt tataaactac gcgattaaga atggttcatg gataagtcta   3180
ttttgtaact acccaaaatc agaaatgata aagttatgga agaaaatgtg gaatattacg   3240
tcgttacgtt cgccatacac taatgcaaac ttctttcaag attagaacgc ttagatgtga   3300
cc                                                                  3302
```

<210> SEQ ID NO 98
<211> LENGTH: 3302
<212> TYPE: DNA
<213> ORGANISM: Human rotavirus

<400> SEQUENCE: 98

```
ggctattaaa gctgtacaat ggggaagtat aatctaatct tgtcagaata tttatcattt     60
atatataatt cacaatctgc agttcaaatt ccaatttatt attcttccaa tagtgagctg    120
gaaagtagat gtatagaatt tcattctaaa tgtctagaaa attcgaaaaa tggtctatca    180
ctgaaaaaac tattcaatga atatagcgat gtcattgaga atgctacgtt attatcaata    240
ttatcatatt cctacgacaa atataacgcc gttgaacgga aattagtaaa atatgcgaaa    300
ggtaaaccgc ttgaggcaga cctaacggtg aatgaactgg attatgaaaa taataaaata    360
acatctgagt tgtttccgac agcggaagaa tacaccgact cattgatgga tccagcaatt    420
ctaacttcct tgtcatcaaa tttaaacgca gtcatgtttt ggttagaaaa acacgaaaat    480
gatactgctg aaagatttaa gatttataaa agaagattag acttattcat tatagtagcc    540
tcaaccgtaa acaaatatgg tgtaccaaga cacaatgcaa aatatagata tgagtatgat    600
gtgatgaaag ataaaccata ttacttagtg acatgggcaa actcttctat tgaaatgcta    660
atgtcagttt tttctcatga agattattta attgcaagag aattgatagt actgtcatat    720
tctaatagat caactttggc aaaattagta tcatctccaa tgtcaatttt agttgcttta    780
gtggatatta atggaacgtt tattacgaat gaggagttag aattagagtt ttcaaataaa    840
tacgtgcgag ccgtagtacc agatcaaaca tttgatgaat taaaacagat gctagacagt    900
atgaggaaag ctggattggt tgatatacct aaaatgatac aagactggtt agttgattgt    960
tccatcgaga aatttccact aatggctaaa atatactcat ggtcgtttca tgttgggttc   1020
```

-continued

```
aggaagcaaa aaatgttaga cgctgcctta gaccaattga aaactgagta tatagaagat   1080
gtagatgacg aaatgtatcg tgaatataca atgttaataa gagatgaagt tgttaaaatg   1140
cttgaagaat cagtaaaaca tgatgaccac ctattacaag attctgaatt agctggcttg   1200
ttatcaatgt cttcagcatc gaatggagaa tcaagacagc ttaaatttgg tagaaagaca   1260
gtttttttcaa ctaaaaagaa catgcatgtt atggatgata tggctaatgg aagatataca   1320
ccaggtataa ttccacctgt aaatgctgat aaaccaatac cgttaggaag aagagatgta   1380
ccaggaagaa gaactagaat aatattcata ttgccgtatg aatattttat agcacagcat   1440
gctgtggttg agaaaatgtt aatctatgca aagcatacca gagaatacgc tgaattctat   1500
tcgcaatcaa atcaactctt atcatacggt gatgttacac gtttcctttc taataatgcg   1560
atggtgttat atacagacgt atctcaatgg gattcatctc aacataatac gcaaccgttt   1620
agaaaaggaa taataatggg attggatata ttagctaaca tgactaatga tgctaaagtt   1680
attcagacac taaatttata taaacaaaca caaattaact tgatggactc atatgttcaa   1740
ataccagatg gtaatgttat taagaaaata cagtatggag ctgtagcatc aggagagaaa   1800
caaacgaagg cagctaactc tatagcgaat ctagcactaa ttaaaacggt tttatcacgt   1860
atttctaata aatattcatt tgccacaaaa ataataagag ttgacggtga tgataactac   1920
gctgtactac aatttaatac ggaagtgact aaacaaatgg ttcaagatgt ttcgaacgat   1980
gtgagagaaa tttacgcacg aatgaatgct aaagtcaaag ctctagtatc cacggtagga   2040
atagaaatag ctaaaagata cattgcagga ggaaaaatat tctttagagc aggaataaat   2100
ttgcttaata atgaaaaaag aggacaaagt acgcaatggg atcaggcagc agttttatac   2160
tctaattaca ttgtaaatag acttagaggg tttgagactg atagagaatt tattttaact   2220
aaaataatgc aaatgacgtc tgttgctatt actgggtcgc taagactttt tccttctgaa   2280
cgtgtgttaa ctacgaattc tacatttaag gtatttgatt cagaagattt tatcatagag   2340
tatggaacaa ctgatgatga agtatatata cagagagcat ttatgtcttt gtcaagtcag   2400
agatcaggaa tagctgatga aatagctgca tcgccaacat ttaaaaatta cgtgtctaga   2460
ctatcagaac agctactttt ttcaaaaaat aatatagtat ctaaaggaat agctttgact   2520
gaaaaagcaa agttgaattc gtatgcacca atatcacttg aaaaaagacg tgcacagata   2580
tcagctttgt tgacaatgct acaaaaacca gttactttca aatcaaacaa aataacaata   2640
aatgacatac ttaaagacat taaaccattt tttacagtga gtgaagcaca tttaccaata   2700
cagtatcaaa agtttatgcc aaccttacca gaaaacgtac aatatataat tcaatgtata   2760
gggtcaagaa cttaccagat tgaagatgat ggttcaaaat cagcaatatc ccggcttata   2820
tcaaagtact cagtttataa accatcgatc gaggaactat ataaagtaat ttcattacat   2880
gagaatgaaa tacaattata tttaatttca ttaggcatac caaaaataga tgctgataca   2940
tatgttggtt caaagattta ttctcaagac aaatacagga tattggaatc atatgtatat   3000
aacctgttat ccatcaatta tggatgctat caattattcg actttaattc accggacttg   3060
gaaaaattaa ttagaatacc atttaaaggg aagataccag ctgtcacatt tatattgcat   3120
ttatatgcta aattagaagt tataaaccat gcgattaaaa atggttcatg gataagtcta   3180
ttctgtaact atccgaaatc agaaatgata aagttatgga agaaaatgtg gaacattaca   3240
tcgttacgtt caccatatac caatgcaaat ttctttcaag attagaacgc ttagatgtga   3300
cc                                                                  3302
```

<210> SEQ ID NO 99
<211> LENGTH: 3302
<212> TYPE: DNA
<213> ORGANISM: Human rotavirus

<400> SEQUENCE: 99

```
ggctattaaa gctgtacaat ggggaagtat aatctaatct tgtcagaata tttatcattt     60
atatataatt cacaatctgc agttcaaatt ccaatttatt attcttccaa tagtgagctg    120
gaaagtagat gtatagaatt tcattctaaa tgtctagaaa attcgaaaaa tggtctatca    180
ctgaaaaaac tattcaatga atatagcgat gtcattgaga atgctacgtt attatcaata    240
ttatcatatt cctacgacaa atataacgcc gttgaacgga aattagtaaa atatgcgaaa    300
ggtaaaccgc ttgaggcaga cctaacggtg aatgaactgg attatgaaaa taataaaata    360
acatctgagt tgtttccgac agcggaagaa tacaccgact cattgatgga tccagcaatt    420
ctaacttcct tgtcatcaag tttaaacgca gtcatgtttt ggttagaaaa acacgaaaat    480
gatactgctg aaagatttaa gatttataaa agaagattag acttattcat tatagtagcc    540
tcaaccgtaa acaaatatgg tgtaccaaga cataatgcaa aatatagata cgaatatgat    600
gtgatgaaag ataaaccata ttacttagtg acatgggcaa actcttctat tgaaatgcta    660
atgtcagttt tttctcatga agattattta attgcaagag aattgatagt actgtcatat    720
tctaatagat caactttggc aaaattagta tcatctccaa tgtcaatttt agttgcttta    780
gtggatatta atggaacgtt tattacgaat gaggagttag aattagagtt ttcaaataaa    840
tacgtgcgag ccgtagtacc agatcaaaca tttgatgaat taaaacagat gctagacagt    900
atgaggaaag ctggattggt tgatatacct aaaatgatac aagactggtt agttgattgt    960
tccatcgaga aatttccact aatggctaaa atatactcat ggtcgtttca tgttgggttc   1020
aggaagcaaa aaatgttaga cgctgcctta gaccaattga aaactgagta tatagaagat   1080
gtagatgacg aaatgtatcg tgaatataca atgttaataa gagatgaagt tgttaaaatg   1140
cttgaagaat cagtaaaaca tgatgaccac ctattacaag attctgaatt agctggcttg   1200
ttatcaatgt cttcagcatc gaatggagaa tcaagacagc ttaaatttgg tagaaagaca   1260
gtttttttcaa ctaaaaagaa catgcatgtt atggatgata tggctaatgg aagatataca   1320
ccaggtataa ttccacctgt aaatgctgat aaaccaatac cgttaggaag aagagatgta   1380
ccaggaagaa gaactagaat aatattcata ttgccgtatg aatattttat agcacagcat   1440
gctgtggttg agaaaatgtt aatctatgca aagcatacca gagaatacgc tgaattctat   1500
tcgcaatcaa atcaactctt atcatacggt gatgttacac gtttcctttc taataatgcg   1560
atggtgttat atacagacgt atctcaatgg gattcatctc aacataatac gcaaccgttt   1620
agaaaaggaa taataatggg attggatata ttagctaaca tgactaatga tgctaaagtt   1680
attcagacac taaatttata taaacaaaca caaattaact tgatggactc atatgttcaa   1740
ataccagatg gtaatgttat taagaaaata cagtatggag ctgtagcatc aggagagaaa   1800
caaacgaagg cagctaactc tatagcgaat ctagcactaa ttaaaacggt tttatcacgt   1860
atttctaata aatattcatt tgccacaaaa ataataagag ttgacggtga tgataactac   1920
gctgtactac aatttaatac ggaagtgact aaacaaatgg ttcaagatgt ttcgaacgat   1980
gtgagagaaa tttacgcacg aatgaatgct aaagtcaaag ctctagtatc cacggtagga   2040
atagaaatag ctaaaagata cattgcagga ggaaaaatat tctttagagc aggaataaat   2100
ttgcttaata atgaaaaaag aggacaaagt acgcaatggg atcaggcagc agttttatac   2160
```

```
tctaattaca ttgtaaatag acttagaggg tttgagactg atagagaatt tattttaact   2220

aaaataatgc aaatgacgtc tgttgctatt actgggtcgc taagactttt tccttctgaa   2280

cgtgtgttaa ctacgaattc tacatttaag gtatttgatt cagaagattt tatcatagag   2340

tatggaacaa ctgatgatga agtatatata cagagagcat ttatgtcttt gtcaagtcag   2400

agatcaggaa tagctgatga aatagctgca tcgccaacat ttaaaaatta cgtgtctaga   2460

ctatcagaac agctactttt ttcaaaaaat aatatagtat ctaaaggaat agctttgact   2520

gaaaaagcaa agttgaattc gtatgcacca atatcacttg aaaaaagacg tgcacagata   2580

tcagctttgt tgacaatgct acaaaaacca gttactttca aatcaaacaa aataacaata   2640

aatgacatac ttaaagacat taaaccattt tttacagtga gtgaagcaca tttaccaata   2700

cagtatcaaa agtttatgcc aaccttacca gaaaacgtac aatatataat tcaatgtata   2760

gggtcaagaa cttaccagat tgaagatgat ggttcaaaat cagcaatatc ccggcttata   2820

tcaaagtact cagtttataa accatcgatc gaggaactat ataaagtaat ttcattacat   2880

gagaatgaaa tacaattata tttaatttca ttaggcatac caaaaataga tgctgataca   2940

tatgttggtt caaagattta ttctcaagac aaatacagga tattggaatc atatgtatat   3000

aacctgttat ccatcaatta tggatgctat caattattcg actttaattc accggacttg   3060

gaaaaattaa ttagaatacc atttaaaggg aagataccag ctgtcacatt tatattgcat   3120

ttatatgcta aattagaagt tataaaccat gcgattaaaa atggttcatg gataagtcta   3180

ttctgtaact atccgaaatc agaaatgata aagttatgga agaaaatgtg gaacattaca   3240

tcgttacgtt caccatatac caatgcaaat ttctttcaag attagaacgc ttagatgtga   3300

cc                                                                  3302
```

<210> SEQ ID NO 100
<211> LENGTH: 1088
<212> TYPE: PRT
<213> ORGANISM: Human rotavirus

<400> SEQUENCE: 100

```
Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser
            20                  25                  30

Glu Leu Glu Ser Arg Cys Ile Glu Phe His Ser Lys Cys Leu Glu Asn
        35                  40                  45

Ser Lys Asn Gly Leu Ser Leu Lys Lys Leu Phe Ser Glu Tyr Ser Asp
    50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Ser Lys
                85                  90                  95

Pro Leu Glu Ala Asp Leu Thr Leu Asn Glu Leu Asp Tyr Glu Asn Asn
            100                 105                 110

Lys Ile Thr Ser Glu Leu Phe Pro Thr Glu Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Lys His Glu Asn Asp Thr Ala Glu Lys Leu
145                 150                 155                 160
```

-continued

```
Lys Ile Tyr Lys Arg Arg Leu Asp Leu Phe Ser Ile Val Ala Ser Thr
                165                 170                 175

Ile Asn Lys Tyr Gly Val Pro Arg His Asn Ala Lys Tyr Arg Tyr Glu
            180                 185                 190

Tyr Asp Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Val Asp
                245                 250                 255

Ile Asn Gly Thr Phe Ile Thr Asn Glu Glu Leu Glu Leu Glu Phe Ser
            260                 265                 270

Asn Lys Tyr Val Arg Ala Ile Val Pro Asp Gln Thr Phe Asp Glu Leu
        275                 280                 285

Lys Gln Met Leu Asp Asn Met Arg Lys Ala Gly Leu Val Asp Ile Pro
    290                 295                 300

Lys Met Ile Gln Asp Trp Leu Val Asp Cys Ser Ile Glu Arg Phe Pro
305                 310                 315                 320

Leu Met Ala Lys Ile Tyr Ser Trp Ser Phe His Val Gly Phe Arg Lys
                325                 330                 335

Gln Lys Met Leu Asp Ala Ala Leu Asp Gln Leu Lys Thr Glu Tyr Thr
            340                 345                 350

Glu Asn Val Asp Asp Glu Met Tyr Arg Glu Tyr Thr Met Leu Ile Arg
        355                 360                 365

Asp Glu Val Val Lys Met Leu Glu Glu Ser Val Lys His Asp Asp His
    370                 375                 380

Leu Leu Gln Asp Ser Glu Leu Ala Gly Leu Leu Ser Met Ser Ser Ala
385                 390                 395                 400

Ser Asn Gly Glu Ser Arg Gln Leu Lys Phe Gly Arg Lys Thr Ile Phe
                405                 410                 415

Ser Thr Lys Lys Asn Met His Val Met Asp Asp Met Ala Asn Gly Arg
            420                 425                 430

Tyr Thr Pro Gly Ile Ile Pro Pro Val Asn Ala Asp Lys Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ile Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Ile
    530                 535                 540

Leu Ala Asn Met Thr Asn Asp Ala Arg Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
```

-continued

```
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ser Asn Lys Tyr Ser Phe Ile Thr Lys
    610                 615                 620

Ile Ile Arg Val Asp Gly Asp Asp Asn Tyr Ala Val Leu Gln Phe Asn
625                 630                 635                 640

Thr Glu Val Thr Lys Gln Met Val Gln Asp Val Ser Asn Asp Val Arg
                645                 650                 655

Glu Thr Tyr Ala Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Val Leu Tyr Ser Asn Tyr Ile Val Asn
705                 710                 715                 720

Arg Leu Arg Gly Phe Glu Thr Asp Arg Glu Phe Ile Leu Thr Lys Ile
                725                 730                 735

Met Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ser Ala Ser Ser Thr Phe Lys Asn Tyr Val Ser Lys Leu Ser
                805                 810                 815

Glu Gln Leu Leu Phe Ser Lys Asn Asn Ile Val Ser Arg Gly Ile Ala
            820                 825                 830

Leu Thr Glu Lys Ala Lys Leu Asn Ser Tyr Ala Pro Ile Ser Leu Glu
        835                 840                 845

Lys Arg Arg Ala Gln Ile Ser Ala Leu Leu Thr Met Leu Gln Lys Pro
    850                 855                 860

Val Thr Phe Lys Ser Ser Lys Ile Thr Ile Asn Asp Ile Leu Lys Asp
865                 870                 875                 880

Ile Lys Pro Phe Phe Thr Leu Ser Glu Ala His Leu Pro Met Gln Tyr
                885                 890                 895

Gln Lys Phe Met Pro Asn Leu Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
    930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn  Tyr Gly Cys Tyr Gln  Leu Phe Asp
        995                 1000                1005
```

```
Phe Asn  Ser Pro Asp Leu Glu  Lys Leu Ile Arg Ile  Pro Phe Lys
    1010                 1015                 1020

Gly Lys  Ile Pro Ala Val Thr  Phe Ile Leu His Leu  Tyr Ala Lys
    1025                 1030                 1035

Leu Glu  Val Ile Asn Tyr Ala  Ile Lys Asn Gly Ser  Trp Ile Ser
    1040                 1045                 1050

Leu Phe  Cys Asn Tyr Pro Lys  Ser Glu Met Ile Lys  Leu Trp Lys
    1055                 1060                 1065

Lys Met  Trp Asn Ile Thr Ser  Leu Arg Ser Pro Tyr  Thr Asn Ala
    1070                 1075                 1080

Asn Phe  Phe Gln Asp
    1085


<210> SEQ ID NO 101
<211> LENGTH: 1088
<212> TYPE: PRT
<213> ORGANISM: Human rotavirus

<400> SEQUENCE: 101

Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser
            20                  25                  30

Glu Leu Glu Ser Arg Cys Ile Glu Phe His Ser Lys Cys Leu Glu Asn
        35                  40                  45

Ser Lys Asn Gly Leu Ser Leu Lys Lys Leu Phe Asn Glu Tyr Ser Asp
    50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Gly Lys
                85                  90                  95

Pro Leu Glu Ala Asp Leu Thr Val Asn Glu Leu Asp Tyr Glu Asn Asn
            100                 105                 110

Lys Ile Thr Ser Glu Leu Phe Pro Thr Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Lys His Glu Asn Asp Thr Ala Glu Arg Phe
145                 150                 155                 160

Lys Ile Tyr Lys Arg Arg Leu Asp Leu Phe Ile Ile Val Ala Ser Thr
                165                 170                 175

Val Asn Lys Tyr Gly Val Pro Arg His Asn Ala Lys Tyr Arg Tyr Glu
            180                 185                 190

Tyr Asp Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Arg Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Val Asp
                245                 250                 255

Ile Asn Gly Thr Phe Ile Thr Asn Glu Glu Leu Glu Leu Glu Phe Ser
            260                 265                 270

Asn Lys Tyr Val Arg Ala Val Val Pro Asp Gln Thr Phe Asp Glu Leu
```

-continued

```
        275                 280                 285

Lys Gln Met Leu Asp Ser Met Arg Lys Ala Gly Leu Val Asp Ile Pro
    290                 295                 300

Lys Met Ile Gln Asp Trp Leu Val Asp Cys Ser Ile Glu Lys Phe Pro
305                 310                 315                 320

Leu Met Ala Lys Ile Tyr Ser Trp Ser Phe His Val Gly Phe Arg Lys
                325                 330                 335

Gln Lys Met Leu Asp Ala Ala Leu Asp Gln Leu Lys Thr Glu Tyr Ile
            340                 345                 350

Glu Asp Val Asp Asp Glu Met Tyr Arg Glu Tyr Thr Met Leu Ile Arg
        355                 360                 365

Asp Glu Val Val Lys Met Leu Glu Glu Ser Val Lys His Asp Asp His
    370                 375                 380

Leu Leu Gln Asp Ser Glu Leu Ala Gly Leu Leu Ser Met Ser Ser Ala
385                 390                 395                 400

Ser Asn Gly Glu Ser Arg Gln Leu Lys Phe Gly Arg Lys Thr Val Phe
                405                 410                 415

Ser Thr Lys Lys Asn Met His Val Met Asp Asp Met Ala Asn Gly Arg
            420                 425                 430

Tyr Thr Pro Gly Ile Ile Pro Pro Val Asn Ala Asp Lys Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ile Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ala Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Ile
    530                 535                 540

Leu Ala Asn Met Thr Asn Asp Ala Lys Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ser Asn Lys Tyr Ser Phe Ala Thr Lys
    610                 615                 620

Ile Ile Arg Val Asp Gly Asp Asp Asn Tyr Ala Val Leu Gln Phe Asn
625                 630                 635                 640

Thr Glu Val Thr Lys Gln Met Val Gln Asp Val Ser Asn Asp Val Arg
                645                 650                 655

Glu Ile Tyr Ala Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700
```

```
Thr Gln Trp Asp Gln Ala Ala Val Leu Tyr Ser Asn Tyr Ile Val Asn
705                 710                 715                 720

Arg Leu Arg Gly Phe Glu Thr Asp Arg Glu Phe Ile Leu Thr Lys Ile
                725                 730                 735

Met Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Arg Ser Gly Ile Ala Asp
785                 790                 795                 800

Glu Ile Ala Ala Ser Pro Thr Phe Lys Asn Tyr Val Ser Arg Leu Ser
                805                 810                 815

Glu Gln Leu Leu Phe Ser Lys Asn Asn Ile Val Ser Lys Gly Ile Ala
            820                 825                 830

Leu Thr Glu Lys Ala Lys Leu Asn Ser Tyr Ala Pro Ile Ser Leu Glu
        835                 840                 845

Lys Arg Arg Ala Gln Ile Ser Ala Leu Leu Thr Met Leu Gln Lys Pro
    850                 855                 860

Val Thr Phe Lys Ser Asn Lys Ile Thr Ile Asn Asp Ile Leu Lys Asp
865                 870                 875                 880

Ile Lys Pro Phe Phe Thr Val Ser Glu Ala His Leu Pro Ile Gln Tyr
                885                 890                 895

Gln Lys Phe Met Pro Thr Leu Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
    930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Val Ile Asn His Ala  Ile Lys Asn Gly Ser  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ser  Leu Arg Ser Pro Tyr  Thr Asn Ala
    1070                1075                1080

Asn Phe  Phe Gln Asp
    1085
```

<210> SEQ ID NO 102
<211> LENGTH: 1088

<212> TYPE: PRT
<213> ORGANISM: Human rotavirus

<400> SEQUENCE: 102

```
Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser
            20                  25                  30

Glu Leu Glu Ser Arg Cys Ile Glu Phe His Ser Lys Cys Leu Glu Asn
        35                  40                  45

Ser Lys Asn Gly Leu Ser Leu Lys Lys Leu Phe Asn Glu Tyr Ser Asp
    50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Gly Lys
                85                  90                  95

Pro Leu Glu Ala Asp Leu Thr Val Asn Glu Leu Asp Tyr Glu Asn Asn
            100                 105                 110

Lys Ile Thr Ser Glu Leu Phe Pro Thr Ala Glu Glu Tyr Thr Asp Ser
        115                 120                 125

Leu Met Asp Pro Ala Ile Leu Thr Ser Leu Ser Ser Ser Leu Asn Ala
    130                 135                 140

Val Met Phe Trp Leu Glu Lys His Glu Asn Asp Thr Ala Glu Arg Phe
145                 150                 155                 160

Lys Ile Tyr Lys Arg Arg Leu Asp Leu Phe Ile Ile Val Ala Ser Thr
                165                 170                 175

Val Asn Lys Tyr Gly Val Pro Arg His Asn Ala Lys Tyr Arg Tyr Glu
            180                 185                 190

Tyr Asp Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Arg Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Val Asp
                245                 250                 255

Ile Asn Gly Thr Phe Ile Thr Asn Glu Glu Leu Glu Leu Glu Phe Ser
            260                 265                 270

Asn Lys Tyr Val Arg Ala Val Val Pro Asp Gln Thr Phe Asp Glu Leu
        275                 280                 285

Lys Gln Met Leu Asp Ser Met Arg Lys Ala Gly Leu Val Asp Ile Pro
    290                 295                 300

Lys Met Ile Gln Asp Trp Leu Val Asp Cys Ser Ile Glu Lys Phe Pro
305                 310                 315                 320

Leu Met Ala Lys Ile Tyr Ser Trp Ser Phe His Val Gly Phe Arg Lys
                325                 330                 335

Gln Lys Met Leu Asp Ala Ala Leu Asp Gln Leu Lys Thr Glu Tyr Ile
            340                 345                 350

Glu Asp Val Asp Asp Glu Met Tyr Arg Glu Tyr Thr Met Leu Ile Arg
        355                 360                 365

Asp Glu Val Val Lys Met Leu Glu Glu Ser Val Lys His Asp Asp His
    370                 375                 380

Leu Leu Gln Asp Ser Glu Leu Ala Gly Leu Leu Ser Met Ser Ser Ala
385                 390                 395                 400
```

```
Ser Asn Gly Glu Ser Arg Gln Leu Lys Phe Gly Arg Lys Thr Val Phe
                405                 410                 415

Ser Thr Lys Lys Asn Met His Val Met Asp Asp Met Ala Asn Gly Arg
            420                 425                 430

Tyr Thr Pro Gly Ile Ile Pro Pro Val Asn Ala Asp Lys Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ile Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ala Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Ile
    530                 535                 540

Leu Ala Asn Met Thr Asn Asp Ala Lys Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ser Asn Lys Tyr Ser Phe Ala Thr Lys
    610                 615                 620

Ile Ile Arg Val Asp Gly Asp Asp Asn Tyr Ala Val Leu Gln Phe Asn
625                 630                 635                 640

Thr Glu Val Thr Lys Gln Met Val Gln Asp Val Ser Asn Asp Val Arg
                645                 650                 655

Glu Ile Tyr Ala Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Val Leu Tyr Ser Asn Tyr Ile Val Asn
705                 710                 715                 720

Arg Leu Arg Gly Phe Glu Thr Asp Arg Glu Phe Ile Leu Thr Lys Ile
                725                 730                 735

Met Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Arg Ser Gly Ile Ala Asp
785                 790                 795                 800

Glu Ile Ala Ala Ser Pro Thr Phe Lys Asn Tyr Val Ser Arg Leu Ser
                805                 810                 815
```

```
Glu Gln Leu Leu Phe Ser Lys Asn Asn Ile Val Ser Lys Gly Ile Ala
            820                 825                 830

Leu Thr Glu Lys Ala Lys Leu Asn Ser Tyr Ala Pro Ile Ser Leu Glu
        835                 840                 845

Lys Arg Arg Ala Gln Ile Ser Ala Leu Leu Thr Met Leu Gln Lys Pro
    850                 855                 860

Val Thr Phe Lys Ser Asn Lys Ile Thr Ile Asn Asp Ile Leu Lys Asp
865                 870                 875                 880

Ile Lys Pro Phe Phe Thr Val Ser Glu Ala His Leu Pro Ile Gln Tyr
                885                 890                 895

Gln Lys Phe Met Pro Thr Leu Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
    930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                 1015                1020

Gly Lys  Ile Pro Ala Val Thr  Phe Ile Leu His Leu  Tyr Ala Lys
    1025                 1030                1035

Leu Glu  Val Ile Asn His Ala  Ile Lys Asn Gly Ser  Trp Ile Ser
    1040                 1045                1050

Leu Phe  Cys Asn Tyr Pro Lys  Ser Glu Met Ile Lys  Leu Trp Lys
    1055                 1060                1065

Lys Met  Trp Asn Ile Thr Ser  Leu Arg Ser Pro Tyr  Thr Asn Ala
    1070                 1075                1080

Asn Phe  Phe Gln Asp
    1085
```

<210> SEQ ID NO 103
<211> LENGTH: 2684
<212> TYPE: DNA
<213> ORGANISM: Human rotavirus

<400> SEQUENCE: 103

```
ggctattaaa ggctcaatgg cgtacaggaa acgtggagcg cgccgtgagg caaacttaaa      60

taataatgat cgaatgcagg agaaaaatga tgaaaagcaa gattcaaata aaatacaatt     120

atctgataag gtactttcga agaaagaaga aattgtaaca gatagtcatg aagaagttaa     180

aattactgat gaggtgaaaa aatcaacaaa agaagaatca aagcagttgc ttgaagtgtt     240

aaaaacaaag gaagaacatc agaaagagat acagtatgaa atattgcaga aaactatacc     300

aacatttgaa cctaaagaaa caatattgaa aaaactagag gatattaaac cagaactagc     360

gaaaaaacag actaagctat ttagaatatt tgaaccgaaa caactaccga tttatagagc     420

aaatggagaa agagagttgc gtaatagatg gtgttggaaa ttaaaaaaag ataccttacc     480

agatggagat tacgatgtga gagaatattt tctgaatctg tatgatcaag tgcttactga     540
```

```
gatgccagac tatctattat taaaagatat ggcagtcgaa aataagaact ccagagatgc    600
aggtaaggtt gttgattcag aaacggctag catatgcgac gccatttttc aagatgaaga    660
aacagaaggt gctgtcagaa gattcattgc agagatgaga cagcgtgtgc aagctgatag    720
aaatgttgtc aactatccat caatattgca tccaatagat tatgcattta atgaatactt    780
tttgcaacat caattagttg aaccattgaa taatgatata atatttaatt atataccaga    840
aaggataaga aatgatgtta attacattct caatatggat agaaatctac catcaactgc    900
cagatatata agacctaact tacttcaaga tagattaaat ttacacgata attttgaatc    960
gctatgggat acaataacca catcaaatta tatcttggca agatcaatag taccagattt   1020
aaaagaacta gtatcaactg aagcacaaat tcagaaaatg tcgcaagatt tgcaattaga   1080
agcgttaaca attcaatcag aaacacagtt tctaacgggt ataaattcac aagcagccaa   1140
cgattgcttt aaaactttaa ttgcagcaat gttaagtcaa cgtactatgt cattggactt   1200
tgtaactact aattatatgt cattaatttc aggtatgtgg ctattgacag tcataccaaa   1260
tgatatgttt ataagggagt cgttagtagc gtgccagcta gctatagtaa atacaataat   1320
ctatccagca tttggaatgc aacgcatgca ttatagaaac ggggatccac aaacaccgtt   1380
tcagatagca gaacagcaaa ttcaaaattt ccaagttgca aattggttgc attttgttaa   1440
taataatcaa tttagacagg cagttattga tggtgtattg aaccaggtat taaatgacaa   1500
tattagaagt ggtcatgtta ttaatcaact aatggaagct ttaatgcagt tgtcgcgaca   1560
acaatttcca accatgccag ttgattataa gaggtcaatt caacgtggaa tattactgtt   1620
atctaacaga cttggtcagt tagttgattt aactagatta ttagcttaca attacgagac   1680
attaatggca tgtattacaa tgaacatgca acatgttcaa actttaacaa cagaaaaatt   1740
acaattaacg tcagtcacat cattatgtat gcttattgga aacgcgactg ttataccaag   1800
tccacaaaca ttatttcatt attataacgt taatgttaat tttcattcaa attataatga   1860
gagaattaat gatgcagtag ctataataac tgctgctaat agactaaacc tatatcagaa   1920
aaaaatgaag gcaattgttg aggatttttt aaagagatta tatatttttg atgtatctag   1980
agttccggac gaccaaatgt atagattaag ggacagatta cgcttattgc cagtagaaat   2040
cagaagattg gatatcttta acctaatatt aatgaatatg gatcaaattg aacgtgcctc   2100
agataaaatt gctcaaggtg taatcattgc ttatcgtgac atgcatcttg aaagagatga   2160
gatgtacgga tatgtaaata tagctagaaa tttagacgga ttccaacaga taaatttaga   2220
ggagctaatg agatcaggtg attatgcgca aataactaac atgcttttaa ataatcaacc   2280
ggtagcattg gttggagcac ttccatttat tactgattca tcagtcatat cactaatagc   2340
aaaacttgac gctacagtgt tcgctcaaat agtcaaatta cgaaaagttg atactttaaa   2400
accaatatta tacaaaataa attcagattc aaatgacttt tatttggtag ctaactatga   2460
ttgggtgcca acttcgacta cgaaagtata caaacaggtc ccgcaacaat ttgattttag   2520
aaattcaatg catatgttaa cttcgaatct cacttttaca gtttattcag accttctcgc   2580
attcgtgtca gctgatacag tagaacctat aaatgcggtt gcgtttgaca acatgcgcat   2640
catgaacgaa ttgtagacgc caaccccact gtggagatat gacc                    2684
```

<210> SEQ ID NO 104
<211> LENGTH: 2684
<212> TYPE: DNA
<213> ORGANISM: Human rotavirus -continued

<400> SEQUENCE: 104

```
ggctattaaa ggctcaatgg cgtacaggaa acgtggagcg cgccgtgagg cgaacttaaa      60
taataatgat cgaatgcagg agaaaattga tgaaaaacaa gattcaaata aaatacaatt     120
atctgataag gtactttcga agaaagaaga agttgtaacg gatagtcatg aggaagttaa     180
agttactgat gaggtaaaaa aatcaacgaa agaagaatcg aaacaattgc ttgaagtatt     240
gaaaacaaag gaagaacatc agaaagaaat acagtatgaa atattacaaa aaactatacc     300
aacattcgaa cctaaagaga cgatattgag aaaattagag gatattaaac cagaactagc     360
gaaaaaacag actaagctat ttagaatatt tgaaccgaaa caattaccga tttatagagc     420
aaatggagag agagaattac gtaatagatg gtattggaaa ttaaaaaaag atacactacc     480
agacggagac tatgatgtga gagagtattt tctgaatttg tatgatcaag tgcttactga     540
aatgccagac tacttattat tgaaagatat ggcagtagaa aataagaact ctagggatgc     600
aggtaaagtc gttgattcag aaacggctaa tatatgcgat gccatatttc aagatgaaga     660
aacggaaggt gccgttagaa gattcattgc agaaatgaga cagcgtgtgc aagctgatag     720
aaatgttgtc aattatccat caatattaca tccaatagat tatgcattta atgaatactt     780
tttacaacat caattggttg aaccattgaa taatgatata atatttaatt atataccaga     840
aaggataaga aatgatgtta attatattct caatatggac agaaatttac catcaactgc     900
cagatatata agacctaatt tacttcaaga tagattgaat ttgcacgata attttgaatc     960
actatgggat acaataacta catcaaatta tattttggcg agatcggtag taccagattt    1020
aaaagaatta gtttcaacgg aagcacaaat tcagaaaatg tcacaagatt tgcaattaga    1080
agcattaaca attcagtcag aaacacagtt tctaacaggt ataaattcac aagcagctaa    1140
cgattgtttt aaaaccttaa ttgcagcaat gttaagtcaa cgtactatgt cattagattt    1200
tgtaactact aattatatgt cattgatttc aggtatgtgg ctattgacgg tcgtgccaaa    1260
tgatatgttt ataagggaat cattagtcgc gtgtcaacta gctatagtaa atacgataat    1320
ctatccagca tttggaatgc aacgaatgca ttatagaaac ggagatccac aaacaccgtt    1380
tcagatagca gaacagcaaa ttcaaaattt ccaagtcgca aattggttac attttgttaa    1440
taataatcaa tttagacagg cagttattga tggtgtattg aatcaggtac tgaatgacaa    1500
tattagaaat ggtcatgtta ttaatcaact gatggaagct ctaatgcagc tgtcgcgaca    1560
acaatttcca accatgccaa ttgattataa gagatcaatt caacgtggaa tattactgtt    1620
atctaacaga cttggtcagt tagttgattt aactagatta ttagcttaca attatgagac    1680
attaatggca tgcattacaa tgaacatgca acatgttcaa accttaacaa cagaaaaatt    1740
acaactaaca tcagttacat cattatgtat gcttattgga aatgcgactg ttattccaag    1800
tccacaaaca ttatttcatt attataacgt taacgttaat tttcattcaa attacaatga    1860
gagaattaat gatgcagtag ctataataac tgctgccaac agattgaatc tatatcagaa    1920
aaagatgaag gctattgttg aggatttctt aaaaagatta tacatttttg atgtatctag    1980
agttcctgac gaccaaatgt atagattaag ggatagatta cgtttattgc cagtagaaat    2040
cagaagatta gatatcttca atctaatact aatgaacatg gatcaaattg aacgtgcctc    2100
agataaaatt gctcaaggtg tgatcattgc ttatcgtgac atgcatcttg aaagagatga    2160
gatgtacgga tatgtaaata tagctagaaa tttagatgga tttcaacaga taaatctaga    2220
ggagctgatg agatcaggtg actatgcgca aataactaac atgcttttga ataatcaacc    2280
agtagcattg gttggagcac ttccatttat tactgattca tcagttatat cgctgatagc    2340
```

```
aaaacttgac gctacagtgt tcgctcaaat agttaaatta cgaaaagttg atactttaaa   2400
accaatatta tacaaaataa attcagactc aaatgacttt tatttagtag ccaattatga   2460
ttgggtgcca acttcgacta caaaagtata caaacaggtt ccgcaacagt ttgattttag   2520
aaattcaatg catatgttaa cttcgaatct tacttttacg gtttattcag atcttctcgc   2580
gttcgtatca gctgacacag tagaacctat aaatgcagtt gcatttgaca atatgcgcat   2640
catgaacgaa ttgtagacgc caaccccact gtggagatat gacc                     2684
```

<210> SEQ ID NO 105
<211> LENGTH: 2684
<212> TYPE: DNA
<213> ORGANISM: Human rotavirus

<400> SEQUENCE: 105

```
ggctattaaa ggctcaatgg cgtacaggaa acgtggagcg cgccgtgagg cgaacttaaa     60
taataatgat cgaatgcagg agaaaattga tgaaaaacaa gattcaaata aaatacaatt    120
atctgataag gtactttcga agaaagaaga agttgtaacg gatagtcatg aggaagttaa    180
agttactgat gaggtaaaaa aatcaacgaa agaagaatcg aaacaattgc ttgaagtatt    240
gaaaacaaag gaagaacatc agaaagaaat acagtatgaa atattacaaa aaactatacc    300
aacattcgaa cctaaagaga cgatattgag aaaattagag gatattaaac cagaactagc    360
gaaaaaacag actaagctat ttagaatatt tgaaccgaaa caattaccga tttatagagc    420
aaatggagag agagaattac gtaatagatg gtattggaaa ttaaaaaaag atacactacc    480
agacggagac tatgatgtga gagagtattt tctgaatttg tatgatcaag tgcttactga    540
aatgccagac tacttattat tgaaagatat ggcagtagaa aataagaact ctagggatgc    600
aggtaaagtc gttgattcag aaacggctaa tatatgcgat gccatatttc aagatgaaga    660
aacggaaggt gccgttagaa gattcattgc agaaatgaga cagcgtgtgc aagctgatag    720
aaatgttgtc aattatccat caatattaca tccaatagat tatgcattta atgaatactt    780
tttacaacat caattggttg aaccattgaa taatgatata atatttaatt atataccaga    840
aaggataaga aatgatgtta attatattct caatatggac agaaatttac catcaactgc    900
cagatatata agacctaatt tacttcaaga tagattgaat ttgcacgata attttgaatc    960
actatgggat acaataacta catcaaatta tattttggcg agatcggtag taccagattt   1020
aaaagaatta gtttcaacgg aagcacaaat tcagaaaatg tcacaagatt tgcaattaga   1080
agcattaaca attcagtcag aaacacagtt tctaacaggt ataaattcac aagcagctaa   1140
cgattgtttt aaaaccttaa ttgcagcaat gttaagtcaa cgtactatgt cattagattt   1200
tgtaactact aattatatgt cattgatttc aggtatgtgg ctattgacgg tcgtgccaaa   1260
tgatatgttt ataagggaat cattagtcgc gtgtcaacta gctatagtaa atacgataat   1320
ctatccagca tttggaatgc aacgaatgca ttatagaaac ggagatccac aaacaccgtt   1380
tcagatagca gaacagcaaa ttcaaaattt ccaagtcgca aattggttac attttgttaa   1440
taataatcaa tttagacagg cagttattga tggtgtattg aatcaggtac tgaatgacaa   1500
tattagaaat ggtcatgtta ttaatcaact gatggaagct ctaatgcagc tgtcgcgaca   1560
acaatttcca accatgccaa ttgattataa gagatcaatt caacgtggaa tattactgtt   1620
atctaacaga cttggtcagt tagttgattt aactagatta ttagcttaca attatgagac   1680
attaatggca tgcattacaa tgaacatgca acatgttcaa accttaacaa cagaaaaatt   1740
```

```
acaactaaca tcagttacat cattatgtat gcttattgga aatgcgactg ttattccaag   1800

tccacaaaca ttatttcatt attataacgt taacgttaat tttcattcaa attacaatga   1860

gagaattaat gatgcagtag ctataataac tgctgccaac agattgaatc tatatcagaa   1920

aaagatgaag gctattgttg aggatttctt aaaaagatta tacatttttg atgtatctag   1980

agttcctgac gaccaaatgt atagattaag ggatagatta cgtttattgc cagtagaaat   2040

cagaagatta gatatcttca atctaatact aatgaacatg gatcaaattg aacgtgcctc   2100

agataaaatt gctcaaggtg tgatcattgc ttatcgtgac atgcatcttg aaagagatga   2160

gatgtacgga tatgtaaata tagctagaaa tttagatgga tttcaacaga taaatctaga   2220

ggagctgatg agatcaggtg actatgcgca aataactaac atgcttttga ataatcaacc   2280

agtagcattg gttggagcac ttccatttat tactgattca tcagttatat cgctgatagc   2340

aaaacttgac gctacagtgt tcgctcaaat agttaaatta cgaaaagttg atactttaaa   2400

accaatatta tacaaaataa attcagactc aaatgacttt tatttagtag ccaattatga   2460

ttgggtgcca acttcgacta caaaagtata caaacaggtt ccgcaacagt ttgattttag   2520

aaattcaatg catatgttaa cttcgaatct tacttttacg gtttattcag atcttctcgc   2580

gttcgtatca gctgacacag tagaacctat aaatgcagtt gcatttgaca atatgcgcat   2640

catgaacgaa ttgtagacgc caaccccact gtggagatat gacc                    2684
```

<210> SEQ ID NO 106
<211> LENGTH: 879
<212> TYPE: PRT
<213> ORGANISM: Human rotavirus

<400> SEQUENCE: 106

```
Met Ala Tyr Arg Lys Arg Gly Ala Arg Arg Glu Ala Asn Leu Asn Asn
1               5                   10                  15

Asn Asp Arg Met Gln Glu Lys Asn Asp Glu Lys Gln Asp Ser Asn Lys
            20                  25                  30

Ile Gln Leu Ser Asp Lys Val Leu Ser Lys Lys Glu Glu Ile Val Thr
        35                  40                  45

Asp Ser His Glu Glu Val Lys Ile Thr Asp Glu Val Lys Lys Ser Thr
    50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Lys Lys Leu Glu Asp Ile Lys Pro
            100                 105                 110

Glu Leu Ala Lys Lys Gln Thr Lys Leu Phe Arg Ile Phe Glu Pro Lys
        115                 120                 125

Gln Leu Pro Ile Tyr Arg Ala Asn Gly Glu Arg Glu Leu Arg Asn Arg
    130                 135                 140

Trp Cys Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Ser Ile Cys Asp
        195                 200                 205
```

-continued

```
Ala Ile Phe Gln Asp Glu Glu Thr Glu Gly Ala Val Arg Arg Phe Ile
    210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
    290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Ile Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
    370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Ile Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Gln Ile Gln Asn
    450                 455                 460

Phe Gln Val Ala Asn Trp Leu His Phe Val Asn Asn Asn Gln Phe Arg
465                 470                 475                 480

Gln Ala Val Ile Asp Gly Val Leu Asn Gln Val Leu Asn Asp Asn Ile
                485                 490                 495

Arg Ser Gly His Val Ile Asn Gln Leu Met Glu Ala Leu Met Gln Leu
            500                 505                 510

Ser Arg Gln Gln Phe Pro Thr Met Pro Val Asp Tyr Lys Arg Ser Ile
        515                 520                 525

Gln Arg Gly Ile Leu Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
```

```
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
        675                 680                 685

Asp Gln Ile Glu Arg Ala Ser Asp Lys Ile Ala Gln Gly Val Ile Ile
    690                 695                 700

Ala Tyr Arg Asp Met His Leu Glu Arg Asp Glu Met Tyr Gly Tyr Val
705                 710                 715                 720

Asn Ile Ala Arg Asn Leu Asp Gly Phe Gln Gln Ile Asn Leu Glu Glu
                725                 730                 735

Leu Met Arg Ser Gly Asp Tyr Ala Gln Ile Thr Asn Met Leu Leu Asn
            740                 745                 750

Asn Gln Pro Val Ala Leu Val Gly Ala Leu Pro Phe Ile Thr Asp Ser
        755                 760                 765

Ser Val Ile Ser Leu Ile Ala Lys Leu Asp Ala Thr Val Phe Ala Gln
    770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
            820                 825                 830

Asp Phe Arg Asn Ser Met His Met Leu Thr Ser Asn Leu Thr Phe Thr
        835                 840                 845

Val Tyr Ser Asp Leu Leu Ala Phe Val Ser Ala Asp Thr Val Glu Pro
    850                 855                 860

Ile Asn Ala Val Ala Phe Asp Asn Met Arg Ile Met Asn Glu Leu
865                 870                 875


<210> SEQ ID NO 107
<211> LENGTH: 879
<212> TYPE: PRT
<213> ORGANISM: Human rotavirus

<400> SEQUENCE: 107

Met Ala Tyr Arg Lys Arg Gly Ala Arg Arg Glu Ala Asn Leu Asn Asn
1               5                   10                  15

Asn Asp Arg Met Gln Glu Lys Ile Asp Glu Lys Gln Asp Ser Asn Lys
            20                  25                  30

Ile Gln Leu Ser Asp Lys Val Leu Ser Lys Lys Glu Glu Val Val Thr
        35                  40                  45

Asp Ser His Glu Glu Val Lys Val Thr Asp Glu Val Lys Lys Ser Thr
    50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Arg Lys Leu Glu Asp Ile Lys Pro
            100                 105                 110

Glu Leu Ala Lys Lys Gln Thr Lys Leu Phe Arg Ile Phe Glu Pro Lys
        115                 120                 125
```

-continued

Gln Leu Pro Ile Tyr Arg Ala Asn Gly Glu Arg Glu Leu Arg Asn Arg
    130                 135                 140

Trp Tyr Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Asn Ile Cys Asp
        195                 200                 205

Ala Ile Phe Gln Asp Glu Glu Thr Glu Gly Ala Val Arg Arg Phe Ile
    210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
    290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Val Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
    370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Val Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Gln Ile Gln Asn
    450                 455                 460

Phe Gln Val Ala Asn Trp Leu His Phe Val Asn Asn Asn Gln Phe Arg
465                 470                 475                 480

Gln Ala Val Ile Asp Gly Val Leu Asn Gln Val Leu Asn Asp Asn Ile
                485                 490                 495

Arg Asn Gly His Val Ile Asn Gln Leu Met Glu Ala Leu Met Gln Leu
            500                 505                 510

Ser Arg Gln Gln Phe Pro Thr Met Pro Ile Asp Tyr Lys Arg Ser Ile
        515                 520                 525

Gln Arg Gly Ile Leu Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile

```
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
        675                 680                 685

Asp Gln Ile Glu Arg Ala Ser Asp Lys Ile Ala Gln Gly Val Ile Ile
    690                 695                 700

Ala Tyr Arg Asp Met His Leu Glu Arg Asp Glu Met Tyr Gly Tyr Val
705                 710                 715                 720

Asn Ile Ala Arg Asn Leu Asp Gly Phe Gln Gln Ile Asn Leu Glu Glu
                725                 730                 735

Leu Met Arg Ser Gly Asp Tyr Ala Gln Ile Thr Asn Met Leu Leu Asn
            740                 745                 750

Asn Gln Pro Val Ala Leu Val Gly Ala Leu Pro Phe Ile Thr Asp Ser
        755                 760                 765

Ser Val Ile Ser Leu Ile Ala Lys Leu Asp Ala Thr Val Phe Ala Gln
    770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
            820                 825                 830

Asp Phe Arg Asn Ser Met His Met Leu Thr Ser Asn Leu Thr Phe Thr
        835                 840                 845

Val Tyr Ser Asp Leu Leu Ala Phe Val Ser Ala Asp Thr Val Glu Pro
    850                 855                 860

Ile Asn Ala Val Ala Phe Asp Asn Met Arg Ile Met Asn Glu Leu
865                 870                 875


<210> SEQ ID NO 108
<211> LENGTH: 879
<212> TYPE: PRT
<213> ORGANISM: Human rotavirus

<400> SEQUENCE: 108

Met Ala Tyr Arg Lys Arg Gly Ala Arg Arg Glu Ala Asn Leu Asn Asn
1               5                   10                  15

Asn Asp Arg Met Gln Glu Lys Ile Asp Glu Lys Gln Asp Ser Asn Lys
            20                  25                  30

Ile Gln Leu Ser Asp Lys Val Leu Ser Lys Lys Glu Glu Val Val Thr
        35                  40                  45
```

```
Asp Ser His Glu Glu Val Lys Val Thr Asp Glu Val Lys Lys Ser Thr
    50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Arg Lys Leu Glu Asp Ile Lys Pro
            100                 105                 110

Glu Leu Ala Lys Lys Gln Thr Lys Leu Phe Arg Ile Phe Glu Pro Lys
        115                 120                 125

Gln Leu Pro Ile Tyr Arg Ala Asn Gly Glu Arg Glu Leu Arg Asn Arg
    130                 135                 140

Trp Tyr Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Asn Ile Cys Asp
        195                 200                 205

Ala Ile Phe Gln Asp Glu Glu Thr Glu Gly Ala Val Arg Arg Phe Ile
    210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
    290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Val Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
    370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Val Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Gln Ile Gln Asn
    450                 455                 460

Phe Gln Val Ala Asn Trp Leu His Phe Val Asn Asn Asn Gln Phe Arg
```

```
465                 470                 475                 480

Gln Ala Val Ile Asp Gly Val Leu Asn Gln Val Leu Asn Asp Asn Ile
                485                 490                 495

Arg Asn Gly His Val Ile Asn Gln Leu Met Glu Ala Leu Met Gln Leu
            500                 505                 510

Ser Arg Gln Gln Phe Pro Thr Met Pro Ile Asp Tyr Lys Arg Ser Ile
        515                 520                 525

Gln Arg Gly Ile Leu Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
        675                 680                 685

Asp Gln Ile Glu Arg Ala Ser Asp Lys Ile Ala Gln Gly Val Ile Ile
    690                 695                 700

Ala Tyr Arg Asp Met His Leu Glu Arg Asp Glu Met Tyr Gly Tyr Val
705                 710                 715                 720

Asn Ile Ala Arg Asn Leu Asp Gly Phe Gln Gln Ile Asn Leu Glu Glu
                725                 730                 735

Leu Met Arg Ser Gly Asp Tyr Ala Gln Ile Thr Asn Met Leu Leu Asn
            740                 745                 750

Asn Gln Pro Val Ala Leu Val Gly Ala Leu Pro Phe Ile Thr Asp Ser
        755                 760                 765

Ser Val Ile Ser Leu Ile Ala Lys Leu Asp Ala Thr Val Phe Ala Gln
    770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
            820                 825                 830

Asp Phe Arg Asn Ser Met His Met Leu Thr Ser Asn Leu Thr Phe Thr
        835                 840                 845

Val Tyr Ser Asp Leu Leu Ala Phe Val Ser Ala Asp Thr Val Glu Pro
    850                 855                 860

Ile Asn Ala Val Ala Phe Asp Asn Met Arg Ile Met Asn Glu Leu
865                 870                 875
```

<210> SEQ ID NO 109

<211> LENGTH: 2591
<212> TYPE: DNA
<213> ORGANISM: Human rotavirus

<400> SEQUENCE: 109

```
ggctattaaa gcagtactag tagtgtgttt tacctctgat ggtgtaaaca tgaaagtatt     60
agctttaaga catagtgtgg ctcagatata tgcagatact caggtgtaca cacatgatga    120
ctctaaagat gattatgaaa atgcgttctt aatttctaat ctcactacac ataatatatt    180
atatttaaat tatagtgtaa aaacactgca aatattgaat aaatccggta tagctgcaat    240
agagatacag aagatagatg agttattcac gctaattaga tgtaatttta catacgacta    300
tattgatgac gttgtctatt tacatgatta ttcatattat gctaataatg aaatacggac    360
tgaccaatat tgggtaacca agacaaatat agaagactat ctattaccag gatggaaatt    420
gacatatgtt ggatacaatg gaagtgatac gagaggacat tataattttt cttttagatg    480
tcagaatgca gctacagatg atgatgtaat aatagagtat atctattcaa atgaattaga    540
cttccagaac tttatactca aaaagattaa agaaaggatg acaacatcac taccaatagc    600
aagactttca aatcgcgtat ttagagataa attatttaaa acgttgtcag taaatcatga    660
taaagtagtt aatgttggac ctagaaatga atctatgttt actttttag accatccatc     720
aataaaacaa ttctctaatg gaccatattt ggttaaagat acaattaaac tcaaacaaga    780
gagatggctt ggtaaaagat tatcacagtt tgacattggt caatataaga atatgttaaa    840
tgtattaacg actttatatc aatattacga tatgtatcat gaaaaaccaa ttatatatat    900
gataggatca gcgccctcgt attggatata tgatgtcaaa cagtactctg acttgaaatt    960
tgagacatgg gatccactag atacaccata ttctaattta catcataagg aattatttta   1020
cataaatgac gtgcaaaaac ttaaagataa ttcgatacta tatatagata taagaacaga   1080
tagaggaaat atggactgga aggaatggcg aaaagtggtg gaagggcaaa ctgctgacaa   1140
tttacatatt gcatataaat atctatctac aggaaaagct aagatatgtt gtgttaaaat   1200
gaccgctatg gatgtagaat taccaatatc tgcaaaactg cttcaccatc caactacaga   1260
aattagatca gagttttatt taatgatgga tatatgggac tccaaaaata ttaaaagatt   1320
cataccaaaa ggtgtattat actcatatat aaacaataca attactgaaa acgtatttat   1380
acaacaacct tttaagttga aaacattgaa aaatgaatat gtaatagcac tttatgcttt   1440
atcaaatgat cttaacaata gagaagatgt ggtaaaacta atcaataatc agaaaagagc   1500
gttaataacg gtgagaatta acaatacatt taaagatgaa ccgaaagtcg gatttaaaaa   1560
catttacgat tggacatttt tgccaacgga ttttgagatg aatggatcaa taattacctc   1620
atatgatgga tgtctaggta tttttggttt atcaatatca ctagcttcaa aaccaaccgg   1680
taataatcat ttattcattt taagtggtac ggacaagtat tttaaattgg atcaattcgc   1740
aaatcatatg agtatatcac gacgatcaca tcagatacga ttttctgagt cagccacttc   1800
atactcggga tacattttta gagatttgtc taataataat ttcaatttaa taggtacgaa   1860
tgtagagaat tcagtatccg gacacgtata taatgcattg atttattata gatataatta   1920
ctcatttgac cttaaacgat ggatatactt acattcaaca ggtaaagcta gcattgaagg   1980
tggtaagtat tatgaacatg ctccaataga attaatttat gcatgcaggt cagcaagaga   2040
attcgcgaaa ttgcaagatg atttaacagt attaagatat tcaaatgaga tagaaaacta   2100
tatcaataaa gtttatagta taacatacgc cgacgaccct aattacttta ttggaattaa   2160
gtttaaaaat attccttaca agtataacgt taaagtacca catctcacat ttggcgtgtt   2220
```

aaatatttct gaacagatgt taccagatgc aatagcaatt ttaaagaaat ttaagaatga 2280
actatttgga atggacataa caacgagtta tacatatatg ttatctgatg aggtgtatgt 2340
agcaaatata agtggtgtac tatcaacata tttcaaaatt tacaacgcgt tttataaaga 2400
acaaattaca tttggacagt caagaatgtt tattccccat gtaacgttga gttttagtaa 2460
tgagaaaaca gtgagaatag acactacaaa attgtacata gattccattt atctaagaaa 2520
aataaaaggt gacacagtgt ttgatatgac tgagtgagct aaaaacttaa cacactagtc 2580
atgatgtgac c 2591

<210> SEQ ID NO 110
<211> LENGTH: 2591
<212> TYPE: DNA
<213> ORGANISM: Human rotavirus

<400> SEQUENCE: 110
ggctattaaa gcagtaccag tagtgtgttt tacctctgat ggtgtaaaca tgaaagtatt 60
agctttaaga catagtgtgg ctcaggtgta tgcagacact caggtgtaca cacatgatga 120
ttctaaagat gagtatgaga acgcattctt aatttctaat ctcaccacac ataatatatt 180
atatttaaat tataatgtaa aaacgttaca aatattaaat aaatctggta tagctgcaat 240
agagatacag aagatagatg aattattcac gttaattaga tgtaacttta catatgatta 300
cattgatgat gttgtttact tacatgacta ctcatattat actaataatg aaatacgaac 360
tgaccaacat tggataacca agacaaatat agaagattat ttattaccag gatggaagct 420
gacatacgtt ggatataatg gaagtgatac gcgcggacat tataattttt catttagatg 480
tcaaaatgcg gctacagatg atgatgcaat aatagagtat atctattcag atgaattaga 540
cttccagagt tttatactca agaagattaa agaaaggatg acaacatcac taccaatagc 600
aagactctca aatcgcgtat ttagagataa gttatttaaa acgttatcag taaatcatga 660
taaagtagtt aatattgggc ccagaaatga atctatgttt actttttttag actatccatc 720 aataaaacag ttctcaaatg gaccgtattt agttaaagat acaattaaac tcaaacaaga 780
gagatggctt ggtaaaagat tatcgcagtt tgatattggt caatataaga atatgctaaa 840
tgtattaacc actttgtatc aatattatga tatatatcat gaaaaaccaa tcatatatat 900
gataggatca gcgccttcgt attggatata tgacgtcaaa cagtattcta acttgaaatt 960
tgaaacgtgg gatccactag atacaccata ctctaattta catcataagg aattatttta 1020
cataaatgac gtgcaaaaac ttaaagataa ttcaatacta tatatagata tacgaacaga 1080
tagaggaact gtagactgga aggaatggcg aaaaatagtg gaaaggcaaa ctattgacaa 1140
cttgcgtatt gcatacaaat atctatctac agggaaagct aaagtatgtt gcgttaaaat 1200
gaccgctatg gatttagaat taccgatatc tgcaaagttg cttcaccatc caactacaga 1260
gattagatca gagttttatc tagtgatgga tatatgggac tctaaaaata ttaaaagatt 1320
cataccaaaa ggtgtattat actcgtatat aaacaataca attactgaaa acgtattcat 1380
acaacaacct tttaagttaa aaacattgaa aaacgaatat ataatagcac tttatgcttt 1440
atcaaatgat tttaacaaca gagaagatgt ggtgaaacta attaataatc agaaaaaagc 1500
gttaatgaca gtgagaatta ataatacgtt taaagatgaa ccaaaagtcg gatttaaaaa 1560
catttacgat tggacatttc taccaacgga ttttgagact aatggatcaa taattacttc 1620
atatgatggg tgtctaggta tctttggttt atcaatatcg ctagcttcaa aaccaactgg 1680

-continued taataatcat ttgttcattt taagtggaac agacaagtat tttaaactgg atcaatttgc 1740
aaatcatatg agcatatcac gacgatcaca tcaaataaga ttttcggagt cagccacttc 1800
atattcggga tatattttta gggatttgtc taataataat ttcaatttaa taggtacgaa 1860
tgtagagaat tcagtatccg gacacgtata taatgcattg atttattata gatataatta 1920
ttcatttgac cttaaacgat ggatatactt acattcaaca ggtaaagcta gtattgaagg 1980
tggtaagtat tatgaacatg ctccaattga attgatttat gcatgcagat cagcgagaga 2040
atttgcgaaa ctgcaagatg atttaacggt attaagatat tcaaatgaga tagaaaacta 2100
tattaacaaa gtttatagca taacatacgc cgatgatcct aattacttta ttggagttaa 2160
gtttaaaaat attccttata agtacaacgt taaaatacca catctcacat ttggcgtgtt 2220
aaatatttct gaacaaatgc taccagatgt aataacgatt ttaaagagat ttaaaaatga 2280
gttatttgga atggaaataa caacgagtta tacgtacatg ttatctgatg aggtgtatgt 2340
agcaaatata agtggtgtac tgtcaacata tttcaaaatt tataatgcgt tttataaaga 2400
gcaaatcaca tttggacaat caagaatgtt tattcctcat gtaacgttga gttttagtaa 2460
tgagaaaacg gtgagaatag acatcacaaa actgtacata gattctattt acttaagaaa 2520
aataaaaggt gacacggtgt ttgatatgac tgggtgagct aaaaacttaa cacactagtc 2580
atgatgtgac c 2591

<210> SEQ ID NO 111
<211> LENGTH: 2591
<212> TYPE: DNA
<213> ORGANISM: Human rotavirus

<400> SEQUENCE: 111
ggctattaaa gcagtaccag tagtgtgttt tacctctgat ggtgtaaaca tgaaagtatt 60
agctttaaga catagtgtgg ctcaggtgta tgcagacact caggtgtaca cacatgatga 120
ttctaaagat gagtatgaga acgcattctt aatttctaat ctcaccacac ataatatatt 180
atatttaaat tataatgtaa aaacgttaca aatattaaat aaatctggta tagctgcaat 240
agagatacag aagatagatg aattattcac gttaattaga tgtaacttta catatgatta 300
cattgatgat gttgtttact tacatgacta ctcatattat actaataatg aaatacgaac 360
tgaccaacat tggataacca agacaaatat agaagattat ttattaccag gatggaagct 420
gacatacgtt ggatataatg gaagtgatac gcgcggacat tataattttt catttagatg 480
tcaaaatgcg gctacagatg atgatgcaat aatagagtat atctattcag atgaattaga 540
cttccagagt tttatactca agaagattaa agaaaggatg acaacatcac taccaatagc 600
aagactctca aatcgcgtat ttagagataa gttatttaaa acgttatcag taaatcatga 660
taaagtagtt aatattgggc ccagaaatga atctatgttt actttttag actatccatc 720 aataaaacag ttctcaaatg gaccgtattt agttaaagac acaattaaac tcaaacaaga 780
gagatggctt ggtaaaagat tatcgcagtt tgatattggt caatataaga atatgctaaa 840
tgtattaacc actttgtatc aatattatga tatatatcat gaaaaaccaa tcatatatat 900
gataggatca gcgccttcgt attggatata tgacgtcaaa cagtattcta acttgaaatt 960
tgaaacgtgg gatccactag atacaccata ctctaattta catcataagg aattatttta 1020
cataaatgac gtgcaaaaac ttaaagataa ttcaatacta tatatagata tacgaacaga 1080
tagaggaact gtagactgga aggaatggcg aaaaatagtg gaaaggcaaa ctattgacaa 1140
ctcgcgtatt gcatacaaat atctatctac agggaaagct aaagtatgtt gcgttaaaat 1200

```
gaccgctatg gatttagaat taccgatatc tgcaaagttg cttcaccatc caactacaga   1260
gattagatca gagttttatc tagtgatgga tatatgggac tctaaaaata ttaaaagatt   1320
cataccaaaa ggtgtattat actcgtatat aaacaataca attactgaaa acgtattcat   1380
acaacaacct tttaagttaa aaacattgaa aaacgaatat ataatagcac tttatgcttt   1440
atcaaatgat tttaacaaca gagaagatgt ggtgaaacta attaataatc agaaaaaagc   1500
gttaatgaca gtgagaatta ataatacgtt taaagatgaa ccaaaagtcg gatttaaaaa   1560
catttacgat tggacatttc taccaacgga ttttgagact aatggatcaa taattacttc   1620
atatgatggg tgtctaggta tctttggttt atcaatatcg ctagcttcaa aaccaactgg   1680
taataatcat ttgttcattt taagtggaac agacaagtat tttaaactgg atcaatttgc   1740
aaatcatatg agcatatcac gacgatcaca tcaaataaga ttttcggagt cagccacttc   1800
atattcggga tatattttta gggatttgtc taataataat ttcaatttaa taggtacgaa   1860
tgtagagaat tcagtatccg ggcacgtata taatgcattg atttattata gatataatta   1920
ttcatttgac cttaaacgat ggatatactt acattcaaca ggtaaagcta gtattgaagg   1980
tggtaagtat tatgaacatg ctccaattga attgatttat gcatgcagat cagcgagaga   2040
atttgcgaaa ctgcaagatg atttaacggt attaagatat tcaaatgaga tagaaaacta   2100
tattaacaaa gtttatagca taacatacgc cgatgatcct aattacttta ttggagttaa   2160
gtttaaaaat attccttata agtacaacgt taaaatacca catctcacat ttggcgtgtt   2220
aaatatttct gaacaaatgc taccagatgt aataacgatt ttaaagagat ttaaaaatga   2280
gttatttgga atggaaataa caacgagtta tacgtacatg ttatctgatg aggtgtatgt   2340
agcaaatata agtggtgtac tgtcaacata tttcaaaatt tataatgcgt tttataaaga   2400
gcaaatcaca tttggacaat caagaatgtt tattcctcat gtaacgttga gttttagtaa   2460
tgagaaaacg gtgagaatag acatcacaaa actgtacata gattctattt acttaagaaa   2520
aataaaaggt gacacggtgt ttgatatgac tgggtgagct aaaaacttaa cacactagtc   2580
atgatgtgac c                                                         2591
```

<210> SEQ ID NO 112
<211> LENGTH: 835
<212> TYPE: PRT
<213> ORGANISM: Human rotavirus

<400> SEQUENCE: 112

```
Met Lys Val Leu Ala Leu Arg His Ser Val Ala Gln Ile Tyr Ala Asp
1               5                   10                  15

Thr Gln Val Tyr Thr His Asp Asp Ser Lys Asp Asp Tyr Glu Asn Ala
            20                  25                  30

Phe Leu Ile Ser Asn Leu Thr Thr His Asn Ile Leu Tyr Leu Asn Tyr
        35                  40                  45

Ser Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Asp Tyr Ser Tyr
                85                  90                  95

Tyr Ala Asn Asn Glu Ile Arg Thr Asp Gln Tyr Trp Val Thr Lys Thr
            100                 105                 110

Asn Ile Glu Asp Tyr Leu Leu Pro Gly Trp Lys Leu Thr Tyr Val Gly
```

-continued

```
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Val Ile Ile Glu Tyr Ile Tyr Ser
145                 150                 155                 160

Asn Glu Leu Asp Phe Gln Asn Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Val Gly Pro Arg Asn Glu Ser Met Phe Thr Phe Leu Asp His Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Met Tyr His Glu Lys Pro Ile Ile Tyr Met Ile Gly Ser Ala
        275                 280                 285

Pro Ser Tyr Trp Ile Tyr Asp Val Lys Gln Tyr Ser Asp Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Asn Met Asp Trp Lys Glu
            340                 345                 350

Trp Arg Lys Val Val Glu Gly Gln Thr Ala Asp Asn Leu His Ile Ala
        355                 360                 365

Tyr Lys Tyr Leu Ser Thr Gly Lys Ala Lys Ile Cys Cys Val Lys Met
    370                 375                 380

Thr Ala Met Asp Val Glu Leu Pro Ile Ser Ala Lys Leu Leu His His
385                 390                 395                 400

Pro Thr Thr Glu Ile Arg Ser Glu Phe Tyr Leu Met Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Val Ile Ala Leu Tyr Ala Leu
    450                 455                 460

Ser Asn Asp Leu Asn Asn Arg Glu Asp Val Val Lys Leu Ile Asn Asn
465                 470                 475                 480

Gln Lys Arg Ala Leu Ile Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Met Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540
```

Asn Asn His Leu Phe Ile Leu Ser Gly Thr Asp Lys Tyr Phe Lys Leu
545 550 555 560

Asp Gln Phe Ala Asn His Met Ser Ile Ser Arg Arg Ser His Gln Ile
565 570 575

Arg Phe Ser Glu Ser Ala Thr Ser Tyr Ser Gly Tyr Ile Phe Arg Asp
580 585 590

Leu Ser Asn Asn Asn Phe Asn Leu Ile Gly Thr Asn Val Glu Asn Ser
595 600 605

Val Ser Gly His Val Tyr Asn Ala Leu Ile Tyr Tyr Arg Tyr Asn Tyr
610 615 620

Ser Phe Asp Leu Lys Arg Trp Ile Tyr Leu His Ser Thr Gly Lys Ala
625 630 635 640

Ser Ile Glu Gly Gly Lys Tyr Tyr Glu His Ala Pro Ile Glu Leu Ile
645 650 655

Tyr Ala Cys Arg Ser Ala Arg Glu Phe Ala Lys Leu Gln Asp Asp Leu
660 665 670

Thr Val Leu Arg Tyr Ser Asn Glu Ile Glu Asn Tyr Ile Asn Lys Val
675 680 685

Tyr Ser Ile Thr Tyr Ala Asp Asp Pro Asn Tyr Phe Ile Gly Ile Lys
690 695 700

Phe Lys Asn Ile Pro Tyr Lys Tyr Asn Val Lys Val Pro His Leu Thr
705 710 715 720

Phe Gly Val Leu Asn Ile Ser Glu Gln Met Leu Pro Asp Ala Ile Ala
725 730 735

Ile Leu Lys Lys Phe Lys Asn Glu Leu Phe Gly Met Asp Ile Thr Thr
740 745 750

Ser Tyr Thr Tyr Met Leu Ser Asp Glu Val Tyr Val Ala Asn Ile Ser
755 760 765

Gly Val Leu Ser Thr Tyr Phe Lys Ile Tyr Asn Ala Phe Tyr Lys Glu
770 775 780

Gln Ile Thr Phe Gly Gln Ser Arg Met Phe Ile Pro His Val Thr Leu
785 790 795 800

Ser Phe Ser Asn Glu Lys Thr Val Arg Ile Asp Thr Thr Lys Leu Tyr
805 810 815

Ile Asp Ser Ile Tyr Leu Arg Lys Ile Lys Gly Asp Thr Val Phe Asp
820 825 830

Met Thr Glu
835

<210> SEQ ID NO 113
<211> LENGTH: 835
<212> TYPE: PRT
<213> ORGANISM: Human rotavirus

<400> SEQUENCE: 113

Met Lys Val Leu Ala Leu Arg His Ser Val Ala Gln Val Tyr Ala Asp
1 5 10 15

Thr Gln Val Tyr Thr His Asp Asp Ser Lys Asp Glu Tyr Glu Asn Ala
20 25 30

Phe Leu Ile Ser Asn Leu Thr Thr His Asn Ile Leu Tyr Leu Asn Tyr
35 40 45

Asn Val Lys Thr Leu Gln Ile Leu Asn Lys Ser Gly Ile Ala Ala Ile
50 55 60

Glu Ile Gln Lys Ile Asp Glu Leu Phe Thr Leu Ile Arg Cys Asn Phe

-continued

```
65                  70                  75                  80

Thr Tyr Asp Tyr Ile Asp Asp Val Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Ile Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Leu Arg Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495
```

Glu Pro Lys Val Gly Phe Lys Asn Ile Tyr Asp Trp Thr Phe Leu Pro
500 505 510

Thr Asp Phe Glu Thr Asn Gly Ser Ile Ile Thr Ser Tyr Asp Gly Cys
515 520 525

Leu Gly Ile Phe Gly Leu Ser Ile Ser Leu Ala Ser Lys Pro Thr Gly
530 535 540

Asn Asn His Leu Phe Ile Leu Ser Gly Thr Asp Lys Tyr Phe Lys Leu
545 550 555 560

Asp Gln Phe Ala Asn His Met Ser Ile Ser Arg Arg Ser His Gln Ile
565 570 575

Arg Phe Ser Glu Ser Ala Thr Ser Tyr Ser Gly Tyr Ile Phe Arg Asp
580 585 590

Leu Ser Asn Asn Asn Phe Asn Leu Ile Gly Thr Asn Val Glu Asn Ser
595 600 605

Val Ser Gly His Val Tyr Asn Ala Leu Ile Tyr Tyr Arg Tyr Asn Tyr
610 615 620

Ser Phe Asp Leu Lys Arg Trp Ile Tyr Leu His Ser Thr Gly Lys Ala
625 630 635 640

Ser Ile Glu Gly Gly Lys Tyr Tyr Glu His Ala Pro Ile Glu Leu Ile
645 650 655

Tyr Ala Cys Arg Ser Ala Arg Glu Phe Ala Lys Leu Gln Asp Asp Leu
660 665 670

Thr Val Leu Arg Tyr Ser Asn Glu Ile Glu Asn Tyr Ile Asn Lys Val
675 680 685

Tyr Ser Ile Thr Tyr Ala Asp Asp Pro Asn Tyr Phe Ile Gly Val Lys
690 695 700

Phe Lys Asn Ile Pro Tyr Lys Tyr Asn Val Lys Ile Pro His Leu Thr
705 710 715 720

Phe Gly Val Leu Asn Ile Ser Glu Gln Met Leu Pro Asp Val Ile Thr
725 730 735

Ile Leu Lys Arg Phe Lys Asn Glu Leu Phe Gly Met Glu Ile Thr Thr
740 745 750

Ser Tyr Thr Tyr Met Leu Ser Asp Glu Val Tyr Val Ala Asn Ile Ser
755 760 765

Gly Val Leu Ser Thr Tyr Phe Lys Ile Tyr Asn Ala Phe Tyr Lys Glu
770 775 780

Gln Ile Thr Phe Gly Gln Ser Arg Met Phe Ile Pro His Val Thr Leu
785 790 795 800

Ser Phe Ser Asn Glu Lys Thr Val Arg Ile Asp Ile Thr Lys Leu Tyr
805 810 815

Ile Asp Ser Ile Tyr Leu Arg Lys Ile Lys Gly Asp Thr Val Phe Asp
820 825 830

Met Thr Gly
835

<210> SEQ ID NO 114
<211> LENGTH: 835
<212> TYPE: PRT
<213> ORGANISM: Human rotavirus

<400> SEQUENCE: 114

Met Lys Val Leu Ala Leu Arg His Ser Val Ala Gln Val Tyr Ala Asp
1 5 10 15

Thr Gln Val Tyr Thr His Asp Asp Ser Lys Asp Glu Tyr Glu Asn Ala

```
            20                  25                  30

Phe Leu Ile Ser Asn Leu Thr Thr His Asn Ile Leu Tyr Leu Asn Tyr
        35                  40                  45

Asn Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Ile Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Ser Arg Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445
```

```
Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Thr Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Lys Val
        675                 680                 685

Tyr Ser Ile Thr Tyr Ala Asp Asp Pro Asn Tyr Phe Ile Gly Val Lys
    690                 695                 700

Phe Lys Asn Ile Pro Tyr Lys Tyr Asn Val Lys Ile Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Ile Thr Thr
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Ile Thr Lys Leu Tyr
                805                 810                 815

Ile Asp Ser Ile Tyr Leu Arg Lys Ile Lys Gly Asp Thr Val Phe Asp
            820                 825                 830

Met Thr Gly
        835
```

<210> SEQ ID NO 115
<211> LENGTH: 2359

<212> TYPE: DNA
<213> ORGANISM: Human rotavirus

<400> SEQUENCE: 115

```
ggctataaaa tggcttcact catttataga caacttctca ctaattcata ttcggtagac     60
ttacatgatg aaatagaaca gattggatcg gagaaaactc aaagtgtaac agtaaatcca    120
ggtccatttg cacaaaccag atacgctcca gttaattggg gtcatgggga gattaatgat    180
tcaactacag tggaaccagt tttagatggt ccttatcaac ccactacatt caaaccaccc    240
aatgattatt ggttgcttat tagttcaaat acaaatggag tagtctacga aagtacaaat    300
aataatgact tttggacagc agttatcgca gttgaaccac atgttagtca aacaaatagg    360
caatatattt tatttggtga aaataagcag tttaacgtag aaaacaattc agataaatgg    420
aaatttttcg aaatgtttaa aggtagtagt cagggtaatt tttctaatag acggactcta    480
acttctagta atagacttgt agggatgcta aaatatggtg gaagagtatg gacatttcat    540
ggtgaaacac caagagctac tactgatagt tcaaatactg cggatttaaa taatatatca    600
attataattc attcagagtt ttatattatt ccaagatccc aagaatctaa atgtaacgag    660
tatatcaata atggtttacc accaattcag aatactagaa atgtagttcc attatcttta    720
tcatccagat ctattcaata taggagagca caagttaatg aagatattac aatttcaaaa    780
acttcattat ggaaggaaat gcaatataat agagatatta taataagatt taaatttggt    840
aatagtgtta taaaactagg aggattggga tataaatggt ctgaaatatc atataaagca    900
gcgaattatc agtatagtta ttcacgtgat ggtgaacaag ttactgcaca taccacttgt    960
tcagtaaatg gagtaaacaa ttttagctat aatggaggct cactacctac tgatttcagt   1020
atttcgaggt atgaagttat taaagaaaat tcttatgtgt acatagacta ctgggatgat   1080
tcaaaagcat ttagaaatat ggtgtatgtt agatcgctag cagcaaattt aaattcagtg   1140
aaatgtacag gtgggagtta taattttaga ttgcccgtag gtaaatggcc tattatgaat   1200
ggtggtgctg tatcattaca ttttgctgga gttacattat ctacacagtt cactgatttt   1260
gtatcattaa attcactgcg atttagattc agtttaacag tagatgaacc atctttctca   1320
ataatacgaa cacgtacaat aaacttgtac ggattaccag cagctaatcc aaacaatgga   1380
aatgaatact atgaaatgtc aggaaggttt tcacttattt ctttagttca aaccaatgat   1440
gattatcaaa ctccaattat gaattcagta acagtaaggc aggatttaga acgccagctt   1500
aatgatttgc gagaagagtt taattcattg tcacaagaaa tagctatgtc acaattaatt   1560
gatttagcat tactaccttt agatatgttc tctatgtttt cgggaataaa aagcacaatt   1620
gatctaacca aatcaatggc aactagtgta atgaaaaaat ttagaaaatc gaaattagct   1680
acatcaattt cagaaatgac taattcattg tcagatgcgg cttcatcagc atcaagaagt   1740
gcttctatta gatcaaattt atctacgatt tcaaattgga ctaatacttc aaaaagtgtt   1800
tcaaatgtaa ctgactcagt aaatgatgtt tcaacacaaa catctacaat tagtaagaaa   1860
cttagattaa gagagatgat tactcaaact gaaggattga gttttgatga tatttcagca   1920
gctgtactga aaacgaaaat agatatgtcc acacaaattg gaaaaaacac tttacctgat   1980
atagttactg aagcgtctga aaaatttatt ccaaaacgat catatcgagt attaaaagat   2040
gatgaagtaa tggaaattaa tactgaagga aagtttttttg catataaagt ggatacactc   2100
aatgagatac catttgatat aaataaattc gccgaacttg tcacggattc tccagttata   2160
tcagcaataa tagactttaa gacgttaaaa aatttaaacg acaattatgg aattactcgt   2220
```

attgaagcgt ttaatttaat taaatcgaat ccaaatgtgc tacgtaattt cattaatcaa 2280
aataatccaa ttataagaaa tagaattgag cagttaattc tacaatgtaa gttgtgagaa 2340
tgtcatccag gatgtgacc 2359

<210> SEQ ID NO 116
<211> LENGTH: 2359
<212> TYPE: DNA
<213> ORGANISM: Human rotavirus

<400> SEQUENCE: 116
ggctataaaa tggcttcact catttataga caacttctca ctaattcata ttcggtagac 60
ttgcatgacg aaatagaaca gattggatcg gagaaaactc aaaatgtgac ggtaaatcca 120
ggcccatttg cacagactag atacgctcca gttaattggg gacacggaga gattaatgat 180
tcaactacag tagaaccagt tttagatggt ccttatcaac caactacatt caaaccaccc 240
aatgattatt ggctgcttat tagttcaaat acagatggag tagtctatga gagtacaaat 300
aatagtgact tttggacagc agttatcgct gttgaaccac atgtcagtca aacaaatagg 360
caatatgttt tatttggtga aaataagcag tttaacgtag aaaatagttc agataaatgg 420
aaatttttcg aaatgtttaa aggtagtagt cagagtgatt tttctaatag acggacttta 480
acctctaata ataaacttgt aggaatgcta aaatatggtg gaagagtatg gacatttcat 540
ggtgaaacac caagagctac tactgatagt tcgaatactg cggatttaaa taatatatca 600
attataattc attcagagtt ttatattatt ccaagatccc aagaatctaa atgtaatgaa 660
tatattaata atggtttacc accaattcaa aatactagaa atgtagttcc attatctcta 720
tcatccagat ctattcaata tagaagagca caagttaatg aagatattac aatttcaaaa 780
acttcattat ggaaagaaat gcaatataat agagatatta taataagatt taaatttggt 840
aatagtatca taaaattagg aggattggga tataaatggt ctgaaatatc atacaaagct 900
gcgaattatc aatatagcta ttcgcgtgat ggtgaacaag ttactgcaca taccacttgt 960
tcagtaaatg gagtaaataa ttttagctat aatggaggtt cactacctac tgatttcagt 1020
atttcgagat atgaggttat taaagaaaat tcttatgtat atatagatta ctgggatgat 1080
tcaaaagcat ttagaaatat ggtatatgtt agatcgttag cagcaaattt aaattcagtg 1140
aaatgcgtag gtggaagcta tgattttaga ttacctgtag gtgaatggcc tattatgaat 1200
ggcggtgctg tatcattaca ttttgccgga gttacattat ctacacagtt cactgatttt 1260
gtatcattga attcgctacg atttagattc agtttaacag tagatgaacc atctttctca 1320
ataatacgaa cacgtacaat gaacttatac ggattaccag cagctaatcc aaacaatgga 1380
aatgaatact atgaagtgtc aggaaggttc tcacttattt ctttagttcc aactaatgat 1440
gattatcaaa ttccaattat gaattcagta acagtaaggc aagatttaga acgtcagctt 1500
aatgatttac gagaagagtt taattcattg tcacaagaaa tagctatgtc acaattgatt 1560
gatttggcat tattaccttt agatatgttt tctatgtttt cggggataaa aagtactatt 1620
gatctgacca agtcaatggc aactagcgta atgaaaaaat ttagaaaatc aaaattagct 1680
acatcgattt cagaaatgac taattcattg tcagatgcgg cttcgtcggc atcaagaagt 1740
gcttctatta gatcaaattt atcgacaatt tcaaattggt ctgacgcttc aaaaagtgta 1800
ttaaatgtaa ctgactcagt aaatgatatt tcaacacaaa catctacaat tagtaaaaaa 1860
cttagattaa aagaaatgat tactcaaact gaaggaatta gttttgacga tatttcagca 1920
gccgtattga aaacgaaaat agatatgtcc acacaaattg gaaaaaatac cttacctgat 1980
atagttactg aagcatctga aaagtttatt ccaaaacgat catatcgagt attaaaagat 2040
gatgaagtga tggaagttaa cactgaagga aagtttttg cttataaagt ggatacactt 2100
aatgagatcc catttgatat aaataaattc gctgaacttg tgacggattc tccagttata 2160
tcagcaataa tagattttaa aacgttaaag aatttaaacg ataattatgg aattacccgc 2220
atagaagcgc ttaatttaat taaatcgaat ccgaatgtac tacgtaattt tattaatcaa 2280
aataatccaa ttataagaaa tagaattgag cagttaattc tacaatgtaa attgtgagaa 2340
cgctattgag gatgtgacc 2359

<210> SEQ ID NO 117
<211> LENGTH: 2359
<212> TYPE: DNA
<213> ORGANISM: Human rotavirus

<400> SEQUENCE: 117
ggctataaaa tggcttcact catttataga caacttctca ctaattcata ttcggtagac 60
ttgcatgacg aaatagaaca gattggatcg gagaaaactc aaaatgtgac ggtaaatcca 120
ggcccatttg cacagactag atacgctcca gttaattggg gacacggaga gattaatgat 180
tcaactacag tagaaccagt tttagatggt ccttatcaac caactacatt caaaccaccc 240
aatgattatt ggctgcttat tagttcaaat acagatggag tagtctatga gagtacaaat 300
aatagtgact tttggacagc agttatcgct gttgaaccac atgtcagtca aacaaatagg 360
caatatgttt tatttggtga aaataagcag tttaacgtag aaaatagttc agataaatgg 420
aaatttttcg aaatgtttaa aggtagtagt cagagtgatt tttctaatag acggacttta 480
acctctaata ataaacttgt aggaatgcta aaatatggtg gaagagtatg gacatttcat 540
ggtgaaacac caagagctac tactgatagt tcgaatactg cggatttaaa taatatatca 600
attataattc attcagagtt ttatattatt ccaagatccc aagaatctaa atgtaatgaa 660
tatattaata atggtttacc accaattcaa aatactagaa atgtagttcc attatctcta 720
tcatccagat ctattcaata tagaagagca caagttaatg aagatattaa aatttcaaaa 780
acttcattat ggaaagaaat gcaatataat agagatatta taataagatt taaatttggt 840
aatagtatca taaaattagg aggattggga tataaatggt ctgaaatatc atacaaagct 900
gcgaattatc aatatagcta ttcgcgtgat ggtgaacaag ttactgcaca taccacttgt 960
tcagtaaatg gagtaaataa ttttagctat aatggaggtt cactacctac tgatttcagt 1020
atttcgagat atgaggttat taaagaaaat tcttatgtat atatagatta ctgggatgat 1080
tcaaaagcat ttagaaatat ggtatatgct agatcgttag cagcaaattt aaattcagtg 1140
aaatgcgtag gtggaagcta taattttaga ttacctgtag gtggatggcc tattatgaat 1200
ggcggtgctg tatcattaca ttttgccgga gttacattat ctacacagtt cactgatttt 1260
gtatcattga attcgctacg atttagattc agtttaacag tagatgaacc atctttctca 1320
ataatacgaa cacgtacaat gaacttatac ggattaccag cagctaatcc aaacaatgga 1380
aatgaatact atgaagtgtc aggaaggttc tcacttattt ctttagttcc aactaatgat 1440
gattatcaaa ttccaattat gaattcagta acagtaaggc aagatttaga acgtcagctt 1500
aatgatttac gagaagagtt taattcattg tcacaagaaa tagctatgtc acaattgatt 1560
gatttggcat tattaccttt agatatgttt tctatgtttt cggggataaa aagtactatt 1620
gatctgacca agtcaatggc aactagcgta atgaaaaaat ttagaaaatc aaaattagct 1680

```
acatcgattt cagaaatgac taattcattg tcagatgcgg cttcgtcggc atcaagaagt   1740

gcttctatta gatcaaattt atcgacaatt tcaaattggt ctgacgcttc aaaaagtgta   1800

ttaaatgtaa ctgactcagt aaatgatatt tcaacacaaa catctacaat tagtaaaaaa   1860

cttagattaa aagaaatgat tactcaaact gaaggaatta gttttgacga tatttcagca   1920

gccgtattga aaacgaaaat agatatgtcc acacaaattg gaaaaaatac cttacctgat   1980

atagttactg aagcatctga aaagtttatt ccaaaacgat catatcgagt attaaaagat   2040

gatgaagtga tggaagttaa cactgaagga aagtttttg cttataaagt ggatacactt   2100

aatgagatcc catttgatat aaataaattc gctgaacttg tgacggattc tccagttata   2160

tcagcaataa tagattttaa aacgttaaag aatttaaacg ataattatgg aattacccgc   2220

atagaagcgc ttaatttaat taaatcgaat ccgaatgtac tacgtaattt tattaatcaa   2280

aataatccaa ttataagaaa tagaattgag cagttaattc tacaatgtaa attgtgagaa   2340

cgctattgag gatgtgacc                                                 2359
```

<210> SEQ ID NO 118
<211> LENGTH: 775
<212> TYPE: PRT
<213> ORGANISM: Human rotavirus

<400> SEQUENCE: 118

```
Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Ser
            20                  25                  30

Val Thr Val Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Val
    50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asn Gly Val Val Tyr Glu Ser Thr
                85                  90                  95

Asn Asn Asn Asp Phe Trp Thr Ala Val Ile Ala Val Glu Pro His Val
            100                 105                 110

Ser Gln Thr Asn Arg Gln Tyr Ile Leu Phe Gly Glu Asn Lys Gln Phe
        115                 120                 125

Asn Val Glu Asn Asn Ser Asp Lys Trp Lys Phe Phe Glu Met Phe Lys
    130                 135                 140

Gly Ser Ser Gln Gly Asn Phe Ser Asn Arg Arg Thr Leu Thr Ser Ser
145                 150                 155                 160

Asn Arg Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
            180                 185                 190

Leu Asn Asn Ile Ser Ile Ile Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
                245                 250                 255
```

```
Lys Thr Ser Leu Trp Lys Glu Met Gln Tyr Asn Arg Asp Ile Ile Ile
            260                 265                 270

Arg Phe Lys Phe Gly Asn Ser Val Ile Lys Leu Gly Gly Leu Gly Tyr
        275                 280                 285

Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Thr Gly Gly Ser Tyr
    370                 375                 380

Asn Phe Arg Leu Pro Val Gly Lys Trp Pro Ile Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Ile Asn Leu Tyr Gly
        435                 440                 445

Leu Pro Ala Ala Asn Pro Asn Asn Gly Asn Glu Tyr Tyr Glu Met Ser
    450                 455                 460

Gly Arg Phe Ser Leu Ile Ser Leu Val Gln Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Thr Asn
            580                 585                 590

Thr Ser Lys Ser Val Ser Asn Val Thr Asp Ser Val Asn Asp Val Ser
        595                 600                 605

Thr Gln Thr Ser Thr Ile Ser Lys Lys Leu Arg Leu Arg Glu Met Ile
    610                 615                 620

Thr Gln Thr Glu Gly Leu Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670
```

```
Arg Val Leu Lys Asp Asp Glu Val Met Glu Ile Asn Thr Glu Gly Lys
        675                 680                 685

Phe Phe Ala Tyr Lys Val Asp Thr Leu Asn Glu Ile Pro Phe Asp Ile
    690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ile Glu Ala Phe Asn Leu Ile Lys Ser Asn Pro Asn Val Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775


<210> SEQ ID NO 119
<211> LENGTH: 775
<212> TYPE: PRT
<213> ORGANISM: Human rotavirus

<400> SEQUENCE: 119

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Val Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Val
    50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asp Gly Val Val Tyr Glu Ser Thr
                85                  90                  95

Asn Asn Ser Asp Phe Trp Thr Ala Val Ile Ala Val Glu Pro His Val
            100                 105                 110

Ser Gln Thr Asn Arg Gln Tyr Val Leu Phe Gly Glu Asn Lys Gln Phe
        115                 120                 125

Asn Val Glu Asn Ser Ser Asp Lys Trp Lys Phe Phe Glu Met Phe Lys
    130                 135                 140

Gly Ser Ser Gln Ser Asp Phe Ser Asn Arg Arg Thr Leu Thr Ser Asn
145                 150                 155                 160

Asn Lys Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
            180                 185                 190

Leu Asn Asn Ile Ser Ile Ile Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
                245                 250                 255

Lys Thr Ser Leu Trp Lys Glu Met Gln Tyr Asn Arg Asp Ile Ile Ile
            260                 265                 270
```

```
Arg Phe Lys Phe Gly Asn Ser Ile Ile Lys Leu Gly Gly Leu Gly Tyr
        275                 280                 285

Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Val Gly Gly Ser Tyr
    370                 375                 380

Asp Phe Arg Leu Pro Val Gly Glu Trp Pro Ile Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Met Asn Leu Tyr Gly
        435                 440                 445

Leu Pro Ala Ala Asn Pro Asn Asn Gly Asn Glu Tyr Tyr Glu Val Ser
    450                 455                 460

Gly Arg Phe Ser Leu Ile Ser Leu Val Pro Thr Asn Asp Asp Tyr Gln
465                 470                 475                 480

Ile Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Ser Asp
            580                 585                 590

Ala Ser Lys Ser Val Leu Asn Val Thr Asp Ser Val Asn Asp Ile Ser
        595                 600                 605

Thr Gln Thr Ser Thr Ile Ser Lys Lys Leu Arg Leu Lys Glu Met Ile
    610                 615                 620

Thr Gln Thr Glu Gly Ile Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Val Asn Thr Glu Gly Lys
        675                 680                 685
```

Phe Phe Ala Tyr Lys Val Asp Thr Leu Asn Glu Ile Pro Phe Asp Ile
690 695 700

Asn Lys Phe Ala Glu Leu Val Thr Asp Ser Pro Val Ile Ser Ala Ile
705 710 715 720

Ile Asp Phe Lys Thr Leu Lys Asn Leu Asn Asp Asn Tyr Gly Ile Thr
725 730 735

Arg Ile Glu Ala Leu Asn Leu Ile Lys Ser Asn Pro Asn Val Leu Arg
740 745 750

Asn Phe Ile Asn Gln Asn Asn Pro Ile Ile Arg Asn Arg Ile Glu Gln
755 760 765

Leu Ile Leu Gln Cys Lys Leu
770 775

<210> SEQ ID NO 120
<211> LENGTH: 775
<212> TYPE: PRT
<213> ORGANISM: Human rotavirus

<400> SEQUENCE: 120

Met Ala Ser Leu Ile Tyr Arg Gln Leu Leu Thr Asn Ser Tyr Ser Val
1 5 10 15

Asp Leu His Asp Glu Ile Glu Gln Ile Gly Ser Glu Lys Thr Gln Asn
20 25 30

Val Thr Val Asn Pro Gly Pro Phe Ala Gln Thr Arg Tyr Ala Pro Val
35 40 45

Asn Trp Gly His Gly Glu Ile Asn Asp Ser Thr Thr Val Glu Pro Val
50 55 60

Leu Asp Gly Pro Tyr Gln Pro Thr Thr Phe Lys Pro Pro Asn Asp Tyr
65 70 75 80

Trp Leu Leu Ile Ser Ser Asn Thr Asp Gly Val Val Tyr Glu Ser Thr
85 90 95

Asn Asn Ser Asp Phe Trp Thr Ala Val Ile Ala Val Glu Pro His Val
100 105 110

Ser Gln Thr Asn Arg Gln Tyr Val Leu Phe Gly Glu Asn Lys Gln Phe
115 120 125

Asn Val Glu Asn Ser Ser Asp Lys Trp Lys Phe Phe Glu Met Phe Lys
130 135 140

Gly Ser Ser Gln Ser Asp Phe Ser Asn Arg Arg Thr Leu Thr Ser Asn
145 150 155 160

Asn Lys Leu Val Gly Met Leu Lys Tyr Gly Gly Arg Val Trp Thr Phe
165 170 175

His Gly Glu Thr Pro Arg Ala Thr Thr Asp Ser Ser Asn Thr Ala Asp
180 185 190

Leu Asn Asn Ile Ser Ile Ile Ile His Ser Glu Phe Tyr Ile Ile Pro
195 200 205

Arg Ser Gln Glu Ser Lys Cys Asn Glu Tyr Ile Asn Asn Gly Leu Pro
210 215 220

Pro Ile Gln Asn Thr Arg Asn Val Val Pro Leu Ser Leu Ser Ser Arg
225 230 235 240

Ser Ile Gln Tyr Arg Arg Ala Gln Val Asn Glu Asp Ile Lys Ile Ser
245 250 255

Lys Thr Ser Leu Trp Lys Glu Met Gln Tyr Asn Arg Asp Ile Ile Ile
260 265 270

Arg Phe Lys Phe Gly Asn Ser Ile Ile Lys Leu Gly Gly Leu Gly Tyr
275 280 285

-continued

```
Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Ala Arg
        355                 360                 365

Ser Leu Ala Ala Asn Leu Asn Ser Val Lys Cys Val Gly Gly Ser Tyr
    370                 375                 380

Asn Phe Arg Leu Pro Val Gly Gly Trp Pro Ile Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Met Asn Leu Tyr Gly
        435                 440                 445

Leu Pro Ala Ala Asn Pro Asn Asn Gly Asn Glu Tyr Tyr Glu Val Ser
    450                 455                 460

Gly Arg Phe Ser Leu Ile Ser Leu Val Pro Thr Asn Asp Asp Tyr Gln
465                 470                 475                 480

Ile Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Ser Asp
            580                 585                 590

Ala Ser Lys Ser Val Leu Asn Val Thr Asp Ser Val Asn Asp Ile Ser
        595                 600                 605

Thr Gln Thr Ser Thr Ile Ser Lys Lys Leu Arg Leu Lys Glu Met Ile
    610                 615                 620

Thr Gln Thr Glu Gly Ile Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Val Asn Thr Glu Gly Lys
        675                 680                 685

Phe Phe Ala Tyr Lys Val Asp Thr Leu Asn Glu Ile Pro Phe Asp Ile
    690                 695                 700
```

```
Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ile Glu Ala Leu Asn Leu Ile Lys Ser Asn Pro Asn Val Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775
```

<210> SEQ ID NO 121
<211> LENGTH: 1356
<212> TYPE: DNA
<213> ORGANISM: Human rotavirus

<400> SEQUENCE: 121

```
ggcttttaaa cgaagtcttc aacatggatg ttttatattc attatcaaaa actcttaagg     60

atgctagaga caaaattgtc gaaggcactt tatactctaa tgttagtgat ctaattcaac    120

aatttaatca aatgataatt actatgaatg ggaatgaatt tcagactgga ggaattggta    180

atctaccaac cagaaattgg agttttgatt ttggtttact tggaactacg cttttgaact    240

tagacgctaa ctatgttgaa actgcgcgta acacaattga ttattttgtt gattttgtag    300

ataacgtatg tatggatgag atggttagag aatcacaaag aaacggaatt gcaccgcagt    360

cagaatcact tagaaaacta tcaggaatta aatttaaaag aataaatttt gataattcgt    420

cggaatatat agaaaactgg aatttgcaaa atagaagaca aagaactggt tttacatttc    480

ataaaccaaa catctttcca tattcagctt catttacgtt aaatagatca caacccgcgc    540

atgataattt aatgggtacg atgtggttga atgcaggttc agagattcaa gtcgctggat    600

ttgattattc ttgcgccatc aatgcaccag ccaacataca gcaatttgaa catatagttc    660

agctccgcag agtattaacg acggctacaa taactctctt accagatgct gaaagattta    720

gttttcctag agtaattaat tcagctgatg gagcaactac atggtatttt aatccagtaa    780

tacttagacc gaataatgtc gaagtagaat ttctattgaa tggacagata ataaatactt    840

atcaggcaag atttggtaca attgtagcta gaaattttga tacaattaga ttatcatttc    900

aattaatgag accaccaaat atgaccccat cagtcgcagc acttttccct aacgcgcagc    960

catttgaaca tcatgctact gtaggcctaa cattacgaat tgaatctgca gtttgtgagt   1020

cagtgcttgc tgatgctagt gaaacaatgt tagctaatgt aacatctgtt agacaagaat   1080

atgcaatacc agttggacca gtttttccac caggtatgaa ttggactgat ttaattacta   1140

actattcacc atctagagag gataatttac aacgtgtatt tacagtagct tccattagaa   1200

gcatgcttgt taaatgagga ccgagctaat tacttggtat ccaactttga caagtatgta   1260

gctacgttaa gctgtttgaa ctctacaagt aagggtacgt ttacgtattc gctacgtaga   1320

gtaatcactc agatgacgta gtgagaggat gtgacc                            1356
```

<210> SEQ ID NO 122
<211> LENGTH: 1356
<212> TYPE: DNA
<213> ORGANISM: Human rotavirus

<400> SEQUENCE: 122

```
ggctttaaaa cgaagtcttc aacatggatg tcctgtactc cttgtcaaaa actcttaaag     60
```

atgctagaga caaaattgtc gaaggcacat tatactctaa tgtgagtgat ctaattcaac 120
aatttaacca aatgataatt actatgaatg gaaatgagtt ccaaactgga ggaattggta 180
atctaccaat tagaaattgg aattttgatt ttggattact tggaacaact ctactaaatt 240
tagacgctaa ctacgtcgaa acagcccgca acacaattga ctattttgta gattttgtag 300
acaacgtatg tatggatgaa atggttagag aatcacaaag aaatggaatt gcaccacaat 360
cagattcact tagaaaattg tcaggcatta agttcaaaag aataaatttt gataattcat 420
cggaatatat agagaactgg aatctgcaaa atagaagaca acgaacaggt tttacatttc 480
ataaaccaaa tattttccct tattcagcgt cattcacact aaatagatca caaccagctc 540
atgataactt gatgggtacg atgtggctga acgcaggatc agaaattcag gtcgctggat 600
ttgactattc gtgtgcaatt aatgcgccag ctaatacaca acaatttgag cacattgtac 660
agctccgaag agttttaact acagctacaa taacactttt accggatgca gaaagattca 720
gttttccaag agtaattaat tcagctgatg gagcaactac atggtacttt aatccagtaa 780
ttcttagacc aaacaacgtt gaagtggagt ttctactaaa cggtcagata ataaacactt 840
accaggctag atttggaaca atcgtagcta gaaattttga tacaatcaga ttgtcgttcc 900
agttgatgag accaccaaat atgacaccag cagtagcagc attatttcca aatgcgcagc 960
catttgaaca tcatgctaca gtaggactga cactgagaat tgaatctgca gtttgtgaat 1020
ctgtacttgc cgacgcaagc gagacaatgc tagcaaatgt gacatctgtt agacaagaat 1080
acgcaatacc agttggacca gtttttccac caggcatgaa ttggactgat ttgatcacta 1140
attattcacc atctagagag gataatttgc agcgtgtatt tacagtggct tccattagaa 1200
gcatgcttgt caaataaggg ccaagctaac cacttggtat ccgactttga tgagtatgta 1260
gctacgtcaa gctgtttgaa ctctgtaagt aaggatgcgt ctacgtattc gctacacaga 1320
gtaatcactc agatgatgta gtgagaggat gtgacc 1356

<210> SEQ ID NO 123
<211> LENGTH: 1356
<212> TYPE: DNA
<213> ORGANISM: Human rotavirus

<400> SEQUENCE: 123
ggctttaaaa cgaagtcttc aacatggatg tcctgtactc cttgtcaaaa actcttaaag 60
atgctagaga caaaattgtc gaaggcacat tatactctaa tgtgagtgat ctaattcaac 120
aatttaacca aatgataatt actatgaatg gaaatgagtt ccaaactgga ggaattggta 180
atctaccaat tagaaattgg aattttgatt ttggattact tggaacaact ctactaaatt 240
tagacgctaa ctacgtcgaa acagcccgca acacaattga ctattttgta gattttgtag 300
acaacgtatg tatggatgaa atggttagag aatcacaaag aaatggaatt gcaccacaat 360
cagattcact tagaaaattg tcaggcatta agttcaaaag aataaatttt gataattcat 420
cggaatatat agagaactgg aatctgcaaa atagaagaca acgaacaggt tttacatttc 480
ataaaccaaa tattttccct tattcagcgt cattcacact aaatagatca caaccagctc 540
atgataactt gatgggtacg atgtggctga acgcaggatc agaaattcag gtcgctggat 600
ttgactattc gtgtgcaatt aatgcgccag ctaatacaca acaatttgag cacattgtac 660
agctccgaag agttttaact acagctacaa taacactttt accggatgca gaaagattca 720
gttttccaag agtaattaat tcagctgatg gagcaactac atggtacttt aatccagtaa 780
ttcttagacc aaacaacgtt gaagtggagt ttctactaaa cggtcagata ataaacactt 840

```
accaggctag atttggaaca atcgtagcta gaaattttga tacaatcaga ttgtcgttcc     900

agttgatgag accaccaaat atgacaccag cagtagcagc attatttcca aatgcgcagc     960

catttgaaca tcatgctaca gtaggactga cactgagaat tgaatctgca gtttgtgaat    1020

ctgtacttgc cgacgcaagc gagacaatgc tagcaaatgt gacatctgtt agacaagaat    1080

acgcaatacc agttggacca gtttttccac caggcatgaa ttggactgat ttgatcacta    1140

attattcacc atctagagag gataatttgc agcgtgtatt tacagtggct tccattagaa    1200

gcatgcttgt caaataaggg ccaagctaac cacttggtat ccgactttga tgagtatgta    1260

gctacgtcaa gctgtttgaa ctctgtaagt aaggatgcgt ctacgtattc gctacacaga    1320

gtaatcactc agatgatgta gtgagaggat gtgacc                              1356
```

```
<210> SEQ ID NO 124
<211> LENGTH: 397
<212> TYPE: PRT
<213> ORGANISM: Human rotavirus

<400> SEQUENCE: 124

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Thr Arg Asn Trp Ser Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Glu Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
```

```
        275                 280                 285

Arg Leu Ser Phe Gln Leu Met Arg Pro Pro Asn Met Thr Pro Ser Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 125
<211> LENGTH: 397
<212> TYPE: PRT
<213> ORGANISM: Human rotavirus

<400> SEQUENCE: 125

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255
```

-continued

```
Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 126
<211> LENGTH: 397
<212> TYPE: PRT
<213> ORGANISM: Human rotavirus

<400> SEQUENCE: 126

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240
```

```
Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 127
<211> LENGTH: 1062
<212> TYPE: DNA
<213> ORGANISM: Human rotavirus

<400> SEQUENCE: 127

ggctttaaaa acgagaattt ccgtctggct agcggttagc tctttttaat gtatggtatt      60

gaatatacca caattctgac cattttaata tctatcatat tattgaatta tatattaaaa     120

actataacta atacgatgga ctacataatt ttcaggtttt tactactcat tgctttaata     180

tcaccatttg taaggacaca tgctttaata tcaccatttg taaggacaca aaattacggc     240

atgtatttac caataacggg atcactagac gctgtataca caaattcaac tagtggagaa     300

tatccagcag aagctaaaaa tgagatttca gatgatgaat gggaaaatac tctatcacaa     360

ttatttttaa ctaaaggatg gccaattgga tcagtttatt ttaaagacta caatgatatt     420

aacacatttt ctgtgaatcc acaactgtat tgtgattata atgtagtatt gatgagatat     480

gacaatacat ctgaattaga tgcatcagag ttagcagatc ttatattgaa tgaatggctg     540

tgcaatccta tggacatatc actttactat tatcaacaaa gtagcgaatc aaataaatgg     600

atatcgatgg gaacagactg cacggtaaaa gtttgtccac tcaatacaca aaccttaggc     660

attggatgca aaactacgga cgtaaacaca tttgagattg ttgcgtcgtc tgaaaaatta     720

gtaattactg acgttgtaaa tggtgttaat cataagataa atatttcaat aaatacgtgc     780

actatacgta actgtaataa attaggacca cgagaaaatg ttgctataat tcaagttggt     840

ggaccgaacg cattagatat cactgctgat ccaacaacag tcccacaagt tcaaagaatc     900

atgcgaataa attggaaaaa atggtggcaa gtattttata cagtagttga ctatattaac     960

caagttatac aagtcatgtc caaacgatca agatcattag acgcagctgc attttattat    1020

agaatttaga tatagattag attagagttg tatgatgtga cc                       1062


<210> SEQ ID NO 128
<211> LENGTH: 1062
<212> TYPE: DNA
```

<213> ORGANISM: Human rotavirus

<400> SEQUENCE: 128

```
ggctttaaaa gagagaattt ccgtctggct agcggttagc tctttttaat gtatggtatt      60
gaatatacca caattctgac cattttaata tctatcatat tattgaatta tatactaaaa     120
actataacta atacaatgga ctacataatt tttagatttt tactactcat cgctctgatg     180
tcaccatttg tgaggacaca aaattacggc atgtatttac caataacggg atcactagac     240
gctgtataca caaattcaac tagtggagaa tcatttctaa cttcaacgtt atgtttatat     300
tatccaacag aagctaaaaa tgagatttca gataatgaat gggaaaatac tctatcacaa     360
ttatttttaa ctaaaggatg gccgactggg tcagtttatt ttaaagacta caatgatatt     420
actacatttt ctatgaatcc acaactgtat tgtgattata atgtagtatt gatgcgatat     480
gataatacat ctgaattaga tgcatcggaa ttagcagatc ttatattgaa cgaatggctg     540
tgcaatccta tggatatatc actttactat tatcaacaaa atagcgaatc aaataaatgg     600
atatcgatgg gaacagactg cacggtaaaa gtttgtccac tcaatacgca aactttagga     660
attggatgca aaactacgga cgtggataca tttgagattg ttgcgtcgtc tgaaaaattg     720
gtaattactg atgttgtaaa tggtgttaat cataaaataa atatttcaat aaatacgtgc     780
actatacgta attgtaataa actaggacca cgagaaaatg ttgctataat tcaagttggt     840
ggaccgaacg cactagatat cactgctgat ccaacaacag ttccacaggt tcaaagaatt     900
atgcgagtaa attggaaaaa atggtggcaa gtgttttata cagtagttga ttatattaac     960
caaattatac aagttatgtc caaacggtca agatcattag acacggctgc tttttattat    1020
agaatttaga tataacttag attagaattg tatgatgtga cc                       1062
```

<210> SEQ ID NO 129
<211> LENGTH: 1062
<212> TYPE: DNA
<213> ORGANISM: Human rotavirus

<400> SEQUENCE: 129

```
ggctttaaaa gagagaattt ccgtctggct agcggttagc tctttttaat gtatggtatt      60
gaatatacca caattctgac cattttaata tctatcatat tattgaatta tatactaaaa     120
actataacta atacaatgga ctacataatt tttagatttt tactactcat cgctctgatg     180
tcaccatttg tgaggacaca aaattacggc atgtatttac caataacggg atcactagac     240
gctgtataca caaattcaac tagtggagaa tcatttctaa cttcaacgtt atgtttatat     300
tatccaacag aagctaaaaa tgagatttca gataatgaat gggaaaatac tctatcacaa     360
ttatttttaa ctaaaggatg gccgactggg tcagtttatt ttaaagacta caatgatatt     420
actacatttt ctatgaatcc acaactgtat tgtgattata atgtagtatt gatgcgatat     480
gataatacat ctgaattaga tgcatcggaa ttagcagatc ttatattgaa cgaatggctg     540
tgcaatccta tggatatatc actttactat tatcaacaaa atagcgaatc aaataaatgg     600
atatcgatgg gaacagactg cacggtaaaa gtttgtccac tcaatacgca aactttagga     660
attggatgca aaactacgga cgtggataca tttgagattg ttgcgtcgtc tgaaaaattg     720
gtaattactg atgttgtaaa tggtgttaat cataaaataa atatttcaat aaatacgtgc     780
actatacgta attgtaataa actaggacca cgagaaaatg ttgctataat tcaagttggt     840
ggaccgaacg cactagatat cactgctgat ccaacaacag ttccacaggt tcaaagaatt     900
atgcgagtaa attggaaaaa atggtggcaa gtgttttata cagtagttga ttatattaac     960
```

```
caaattatac aagttatgtc caaacggtca agatcattag acacggctgc tttttattat   1020

agaatttaga tataacttag attagaattg tatgatgtga cc                       1062


<210> SEQ ID NO 130
<211> LENGTH: 326
<212> TYPE: PRT
<213> ORGANISM: Human rotavirus

<400> SEQUENCE: 130

Met Tyr Gly Ile Glu Tyr Thr Thr Ile Leu Thr Ile Leu Ile Ser Ile
1               5                   10                  15

Ile Leu Leu Asn Tyr Ile Leu Lys Thr Ile Thr Asn Thr Met Asp Tyr
            20                  25                  30

Ile Ile Phe Arg Phe Leu Leu Leu Ile Ala Leu Ile Ser Pro Phe Val
        35                  40                  45

Arg Thr Gln Asn Tyr Gly Met Tyr Leu Pro Ile Thr Gly Ser Leu Asp
    50                  55                  60

Ala Val Tyr Thr Asn Ser Thr Ser Gly Glu Pro Phe Leu Thr Ser Thr
65                  70                  75                  80

Leu Cys Leu Tyr Tyr Pro Ala Glu Ala Lys Asn Glu Ile Ser Asp Asp
                85                  90                  95

Glu Trp Glu Asn Thr Leu Ser Gln Leu Phe Leu Thr Lys Gly Trp Pro
            100                 105                 110

Ile Gly Ser Val Tyr Phe Lys Asp Tyr Asn Asp Ile Asn Thr Phe Ser
        115                 120                 125

Val Asn Pro Gln Leu Tyr Cys Asp Tyr Asn Val Val Leu Met Arg Tyr
    130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Ser Ser Glu Ser Asn Lys Trp Ile Ser Met Gly Thr Asp Cys Thr
            180                 185                 190

Val Lys Val Cys Pro Leu Asn Thr Gln Thr Leu Gly Ile Gly Cys Lys
        195                 200                 205

Thr Thr Asp Val Asn Thr Phe Glu Ile Val Ala Ser Ser Glu Lys Leu
    210                 215                 220

Val Ile Thr Asp Val Val Asn Gly Val Asn His Lys Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Gly Pro Asn Ala Leu Asp Ile Thr
            260                 265                 270

Ala Asp Pro Thr Thr Val Pro Gln Val Gln Arg Ile Met Arg Ile Asn
        275                 280                 285

Trp Lys Lys Trp Trp Gln Val Phe Tyr Thr Val Val Asp Tyr Ile Asn
    290                 295                 300

Gln Val Ile Gln Val Met Ser Lys Arg Ser Arg Ser Leu Asp Ala Ala
305                 310                 315                 320

Ala Phe Tyr Tyr Arg Ile
                325


<210> SEQ ID NO 131
<211> LENGTH: 326
```

<212> TYPE: PRT
<213> ORGANISM: Human rotavirus

<400> SEQUENCE: 131

Met Tyr Gly Ile Glu Tyr Thr Thr Ile Leu Thr Ile Leu Ile Ser Ile
1 5 10 15

Ile Leu Leu Asn Tyr Ile Leu Lys Thr Ile Thr Asn Thr Met Asp Tyr
20 25 30

Ile Ile Phe Arg Phe Leu Leu Leu Ile Ala Leu Met Ser Pro Phe Val
35 40 45

Arg Thr Gln Asn Tyr Gly Met Tyr Leu Pro Ile Thr Gly Ser Leu Asp
50 55 60

Ala Val Tyr Thr Asn Ser Thr Ser Gly Glu Ser Phe Leu Thr Ser Thr
65 70 75 80

Leu Cys Leu Tyr Tyr Pro Thr Glu Ala Lys Asn Glu Ile Ser Asp Asn
85 90 95

Glu Trp Glu Asn Thr Leu Ser Gln Leu Phe Leu Thr Lys Gly Trp Pro
100 105 110

Thr Gly Ser Val Tyr Phe Lys Asp Tyr Asn Asp Ile Thr Thr Phe Ser
115 120 125

Met Asn Pro Gln Leu Tyr Cys Asp Tyr Asn Val Val Leu Met Arg Tyr
130 135 140

Asp Asn Thr Ser Glu Leu Asp Ala Ser Glu Leu Ala Asp Leu Ile Leu
145 150 155 160

Asn Glu Trp Leu Cys Asn Pro Met Asp Ile Ser Leu Tyr Tyr Tyr Gln
165 170 175

Gln Asn Ser Glu Ser Asn Lys Trp Ile Ser Met Gly Thr Asp Cys Thr
180 185 190

Val Lys Val Cys Pro Leu Asn Thr Gln Thr Leu Gly Ile Gly Cys Lys
195 200 205

Thr Thr Asp Val Asp Thr Phe Glu Ile Val Ala Ser Ser Glu Lys Leu
210 215 220

Val Ile Thr Asp Val Val Asn Gly Val Asn His Lys Ile Asn Ile Ser
225 230 235 240

Ile Asn Thr Cys Thr Ile Arg Asn Cys Asn Lys Leu Gly Pro Arg Glu
245 250 255

Asn Val Ala Ile Ile Gln Val Gly Gly Pro Asn Ala Leu Asp Ile Thr
260 265 270

Ala Asp Pro Thr Thr Val Pro Gln Val Gln Arg Ile Met Arg Val Asn
275 280 285

Trp Lys Lys Trp Trp Gln Val Phe Tyr Thr Val Val Asp Tyr Ile Asn
290 295 300

Gln Ile Ile Gln Val Met Ser Lys Arg Ser Arg Ser Leu Asp Thr Ala
305 310 315 320

Ala Phe Tyr Tyr Arg Ile
325

<210> SEQ ID NO 132
<211> LENGTH: 326
<212> TYPE: PRT
<213> ORGANISM: Human rotavirus

<400> SEQUENCE: 132

Met Tyr Gly Ile Glu Tyr Thr Thr Ile Leu Thr Ile Leu Ile Ser Ile
1 5 10 15

-continued

```
Ile Leu Leu Asn Tyr Ile Leu Lys Thr Ile Thr Asn Thr Met Asp Tyr
            20                  25                  30

Ile Ile Phe Arg Phe Leu Leu Leu Ile Ala Leu Met Ser Pro Phe Val
        35                  40                  45

Arg Thr Gln Asn Tyr Gly Met Tyr Leu Pro Ile Thr Gly Ser Leu Asp
    50                  55                  60

Ala Val Tyr Thr Asn Ser Thr Ser Gly Glu Ser Phe Leu Thr Ser Thr
65                  70                  75                  80

Leu Cys Leu Tyr Tyr Pro Thr Glu Ala Lys Asn Glu Ile Ser Asp Asn
                85                  90                  95

Glu Trp Glu Asn Thr Leu Ser Gln Leu Phe Leu Thr Lys Gly Trp Pro
            100                 105                 110

Thr Gly Ser Val Tyr Phe Lys Asp Tyr Asn Asp Ile Thr Thr Phe Ser
        115                 120                 125

Met Asn Pro Gln Leu Tyr Cys Asp Tyr Asn Val Val Leu Met Arg Tyr
    130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Asn Ser Glu Ser Asn Lys Trp Ile Ser Met Gly Thr Asp Cys Thr
            180                 185                 190

Val Lys Val Cys Pro Leu Asn Thr Gln Thr Leu Gly Ile Gly Cys Lys
        195                 200                 205

Thr Thr Asp Val Asp Thr Phe Glu Ile Val Ala Ser Ser Glu Lys Leu
    210                 215                 220

Val Ile Thr Asp Val Val Asn Gly Val Asn His Lys Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Gly Pro Asn Ala Leu Asp Ile Thr
            260                 265                 270

Ala Asp Pro Thr Thr Val Pro Gln Val Gln Arg Ile Met Arg Val Asn
        275                 280                 285

Trp Lys Lys Trp Trp Gln Val Phe Tyr Thr Val Val Asp Tyr Ile Asn
    290                 295                 300

Gln Ile Ile Gln Val Met Ser Lys Arg Ser Arg Ser Leu Asp Thr Ala
305                 310                 315                 320

Ala Phe Tyr Tyr Arg Ile
                325
```